United States Patent
Shiohara et al.

(10) Patent No.: US 7,230,031 B2
(45) Date of Patent: Jun. 12, 2007

(54) THYROID HORMONE RECEPTOR LIGAND, MEDICINAL COMPOSITIONS CONTAINING THE SAME AND USE THEREOF

(75) Inventors: Hiroaki Shiohara, Yamagata-mura (JP); Tetsuya Nakamura, Toyoshina-machi (JP); Norihiko Kikuchi, Matsumoto (JP); Tomonaga Ozawa, Matsumoto (JP); Makio Kitazawa, Matsumoto (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 320 days.

(21) Appl. No.: 10/502,737

(22) PCT Filed: Jan. 28, 2003

(86) PCT No.: PCT/JP03/00772

§ 371 (c)(1),
(2), (4) Date: Jul. 28, 2004

(87) PCT Pub. No.: WO03/064369

PCT Pub. Date: Aug. 7, 2003

(65) Prior Publication Data

US 2005/0085541 A1   Apr. 21, 2005

(30) Foreign Application Priority Data

Jan. 30, 2002   (JP) ............................. 2002-020893

(51) Int. Cl.
*A61K 31/19* (2006.01)
*C07C 303/00* (2006.01)

(52) U.S. Cl. ......................... 514/557; 560/12
(58) Field of Classification Search ................ 514/557; 560/12
See application file for complete search history.

(56) References Cited

U.S. PATENT DOCUMENTS 6,545,018 B2 *   4/2003   Chiang et al. .............. 514/307

FOREIGN PATENT DOCUMENTS

| EP | 1 033 364 A1 | 9/2000 |
|----|----|----|
| WO | WO 00/07972 | 2/2000 |
| WO | WO 00/39077 | 7/2000 |
| WO | WO 00/51971 | 9/2000 |

OTHER PUBLICATIONS

Schroeder et al. (Eur. Journ. Med. Chem., vol. 17, Issue 1, pp. 35-42).*

* cited by examiner

*Primary Examiner*—Joseph K. McKane
*Assistant Examiner*—Susannah L. Chung
(74) *Attorney, Agent, or Firm*—Sughrue Mion, PLLC

(57) ABSTRACT

The present invention provides a compound represented by general formula (I):

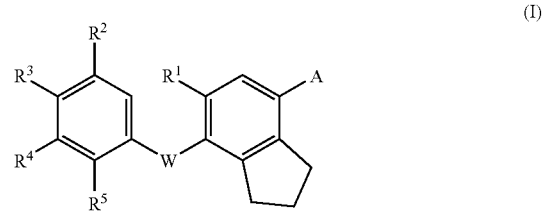

or pharmaceutically acceptable salts thereof, wherein W is O, $S(O)_m$, $CH_2$ and the like; $R^1$ is halogen, lower alkyl, halo-lower alkyl, CN and the like; $R^3$ is hydrogen and the like; $R^4$ is hydrogen, halogen, alkyl, halo-lower alkyl, substituted alkyl, aryl, aralkyl, alkoxy, substituted alkoxy, alkanoyl, aroyl, —$CONR^7(R^8)$, —$S(O)_mR^9$, —$SO_2NR^7(R^8)$ and the like; $R^5$ is hydrogen, halogen, alkyl, substituted alkyl and the like; A is —$N(R^6)CO$—$A^1$—$COR^{10}$ and the like; pharmaceutical compositions containing them and their uses, which have a high affinity to human thyroid hormone receptors, in particular human thyroid hormone receptor β.

8 Claims, No Drawings

THYROID HORMONE RECEPTOR LIGAND, MEDICINAL COMPOSITIONS CONTAINING THE SAME AND USE THEREOF

TECHNICAL FIELD

The present invention relates to novel indane derivatives which are thyroid hormone receptor ligands, pharmaceutical compositions containing them, and their uses.

BACKGROUND ART

Thyroid hormones are essential for normal growth and differentiation in mammals, and play a critical role on maintaining metabolic homeostasis. For example, thyroid hormones participate in the regulation of the metabolism of lipids, sugars, proteins and energies. Thyroid hormones also affect cardiovascular function such as heart rate, cardiac contraction, peripheral vascular resistance and the like.

A naturally occurring hormone, 3,5,3'-triiodo-L-thyronine (hereinafter referred to T3) binds to nuclear thyroid hormone receptors (hereinafter referred to TR). A complex composed of T3 and TR binds to the promoter region of T3 regulatory genes, which is referred to thyroid hormone response element, located at the upstream of target genes, and activates or suppresses the expression of the genes. Thyroid hormones exhibit the majority of actions by regulating the expression of the target genes in nucleus.

In patients with hypothyroidism, decreased body temperature, increased body weight, increased serum cholesterol, decreased cardiac functions, liver function disorders, depression, dry skins or alopecia are observed. In contrast, increased body temperature, decreased body weight, decreased serum cholesterol, tachycardia, increased stroke volume, arrhythmia or increased bone absorption are observed in patients with hyperthyroidism. As discussed above, thyroid hormones participate in the regulation of various physiological actions in vivo, and ligands having an affinity to thyroid hormone receptors have been expected to be useful as a therapeutic agent for hyperlipidemia, atherosclerosis, obesity, diabetes mellitus, arrhythmia, congestive heart failure, hypertension, depression, osteoporosis, glaucoma, skin disorders, alopecia and the like (see nonpatent literatures 1 to 17). It has been reported that the administration of a thyroid hormone ameliorated fatty liver and decreased the amount of liver fiber (see nonpatent literatures 18 to 21). It has also been demonstrated that the administration of a thyroid hormone decreased the amount of liver glutathione, and in a rat hepatocarcinogenesis model, decreased the incidence of liver cancer and suppressed metastases to lung (see nonpatent literatures 22 to 24). Accordingly, thyroid hormone receptor ligands are expected to be useful for the treatment of fatty liver, liver cirrhosis and liver cancer.

Thyroid hormones are currently used primarily as replacement therapy for patients with hypothyroidism. Further attempts to use thyroid hormones in the treatment of hyperlipidemia, obesity, depression or skin disorders have been made. However, it is reported that administering thyroid hormones at dosages more than those of replacement therapy is often accompanied with cardiac toxicities such as arrhythmia, angina, cardiac failure and the like (see nonpatent literatures 25 or 26).

Recent studies have reported that there are two major subtypes of thyroid hormone receptor (TR), TRα and TRβ, which are expressed in different ratios in different tissues (see nonpatent literature 27). Observations suggest that the TRα of the receptors contributes in a substantial way to cardiac toxicities (see nonpatent literatures 28 or 29). Accordingly, thyroid hormone receptor ligands which are selective to TRβ, would be a medicament with less cardiac toxicities.

Nonpatent Literatures:
1. Anate M. et al, "West. Afr. J. Med.", 1998, vol. 17(4), p. 248–54
2. Santalucia T. et al, "J. Mol. Biol.", 2001, vol. 314 (2), p. 195–204
3. Klein I. et al, "Am. J. Med.", 1990, vol.88 (6), p. 631–7
4. Altshuler L L. Et al, "Am. J. Psychiatry", 2001, vol. 158 (10), p. 1617–22
5. Dording CM, "Psychiatr. Clin. North. Am.", 2000, vol. 23 (4), p. 743–55
6. Kirkegaard C, "Eur. J. Endocrinol.", 1998, vol. 138, p. 1–9
7. Jamsen K, "Acta Ophthalmol. Scand.", 1996, vol. 74 (5), p. 456–60
8. Tamm E R., "J. Glaucoma", 2001, vol. 10, (4), p.329–39
9. Polansky J R. et al, "Eye", 2000, vol. 14 (Pt 3B), p.503–14
10. "N. Engl. J. Med.", 1989, vol.321 (6), p. 406–12
11. Bogazzi F. et al, "Eur. J. Endocrinol.", 2001, vol. 145 (1), p. 59–64
12. Klein I. et al, "N. Engl. J. Med.", 2001, vol. 344(7), p.501–9
13. Hamilton M A. Et al, "Am. J. Cardiol.", 1998, vol. 81 (4), p. 443–7
14. d'Amati G. et al, "J. Clin. Endocrinol. Metab.", 2001, vol. 86 (5), p. 2080–4
15. Ben-Shlomo A. et al, "Maturitas.", 2001, vol. 39 (1), p. 19–27
16. Elias A N. Et al, "J. Am. Acad. Dermatol.", 1994, vol. 31 (3 Pt 1), p. 455–8
17. Billoni N. et al, "Br. J. Dermatol.", 2000, vol. 142, p. 645–652
18. Aonuma S. et al, "Nippon Naibunpi Gakkai Zasshi", 1975, vol. 51 (1), p. 56–67
19. L'age M. et al, "J. Endocrinol. Invest.", 1980, vol. 3 (4), p. 379–83
20. Olczyk K. et al, "Endocrinologie", 1987, vol. 25 (1), p. 3–7
21. Lissoos T W. Et al, "Am. J. Physiol.", 1993, vol. 264 (6 Pt 1), p. G1090–5
22. Huang Z Z. Et al, "FASEB J.", 2001, vol. 15 (1), p. 19–21
23. Yasna C. et al, "Biochemical Pharmacology", 1993, vol. 45 (12), p. 2527–2535
24. Ledda-Columbano G M. et al, "Cancer Res.", 2000, vol. 60 (3), p. 603–9
25. "JAMA", 1972, vol. 220, p. 996–1008
26. Roti E. et al, "Endocrine Rev.", 1993, vol. 14, p. 401–423
27. Lazar M A. et al, "Endocrine Rev.", 1993, vol. 14, p. 184
28. Wikstrom L. et al, "EMBO J.", 1998, vol. 17, p. 455
29. Johansson C. et al, "Am. J. Physiol.", 1998, vol. 275, p. R640

DISCLOSURE OF THE INVENTION

The present inventors have intensively investigated novel compounds which show a high affinity to human thyroid receptors (TR) and are more preferably highly selective to TRY, and found that indane derivatives of general formula (I) have a high affinity to human thyroid hormone receptors, and surprisingly are highly selective to TRβ. Based on the findings, the present invention has been accomplished.

The present invention therefore provides a compound represented by general formula (I):

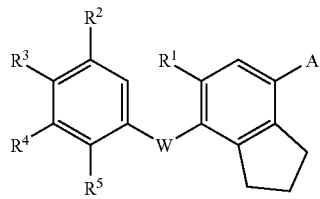

(I)

wherein

W is —O—, —S(O)$_m$—, —CH$_2$—, —CHF—, —CF$_2$—, —CH(OH)—, —CO—, —C(=CH$_2$)— or —N(R$^6$)—;

R$^1$ is a halogen atom, a lower alkyl group, a halo-lower alkyl group, a lower alkoxy group or —CN;

R$^2$ is a hydrogen atom, a halogen atom, a lower alkyl group or a lower alkoxy group;

R$^3$ is a hydroxy group or an acyloxy group;

R$^4$ is a hydrogen atom, a halogen atom, an alkyl group, a halo-lower alkyl group, a substituted alkyl group, an aryl group, an aralkyl group, an alkoxy group, a substituted alkoxy group, an alkanoyl group, an aroyl group, —CONR$^7$(R$^8$), —S(O)$_m$R$^9$ or —SO$_2$NR$^7$(R$^8$), or R$^3$ and R$^4$ are bonded together to form —NH—CH=C(R$^9$)—;

R$^5$ is a hydrogen atom, a halogen atom, an alkyl group, a substituted alkyl group, a hydroxy group, an alkoxy group a substituted alkoxy group or an aralkyloxy group, or R$^4$ and R$^5$ are bonded together to form —(CH$_2$)$_n$—;

m is 0 or an integer of 1 or 2;

n is an integer of 3 to 5;

R$^6$ is a hydrogen atom or a lower alkyl group;

each of R$^7$ and R$^8$ is independently a hydrogen atom, an alkyl group, a substituted alkyl group, a cycloalkyl group, an aryl group or a heteroaryl group, or R$^7$ and R$^8$, together with the nitrogen atom to which they are bonded, form a cyclic amine;

R$^9$ is an alkyl group, a substituted alkyl group, a cycloalkyl group, an aryl group or a heteroaryl group;

A represents a formula represented by the following formula:

(a) —N(R$^6$)CO-A$^1$—COR$^{10}$, (b) —N(R$^6$)SO$_2$—A$^2$COR$^{10}$, (c) —CON(R$^6$)—A$^2$—COR$^{10}$, (d) —X—A$^2$—COR$^{10}$, or (e) —A$^3$—Z;

R$^{10}$ is a hydroxy group, a lower alkoxy group or —NR$^{11}$(R$^{12}$);

each of R$^{11}$ and R$^{12}$ is independently a hydrogen atom, a lower alkyl group or a substituted lower alkyl group, or R$^{11}$ and R$^{12}$, together with the nitrogen atom to which they are bonded, form a cyclic amine;

X is —O—, —S(O)$_m$— or a bond;

A$^1$ is an alkylene group, an alkenylene group or a bond;

A$^2$ is an alkylene group;

A$^3$ is an alkylene group, —N(R$^6$)— or a bond;

Z is a formula represented by the following formula:

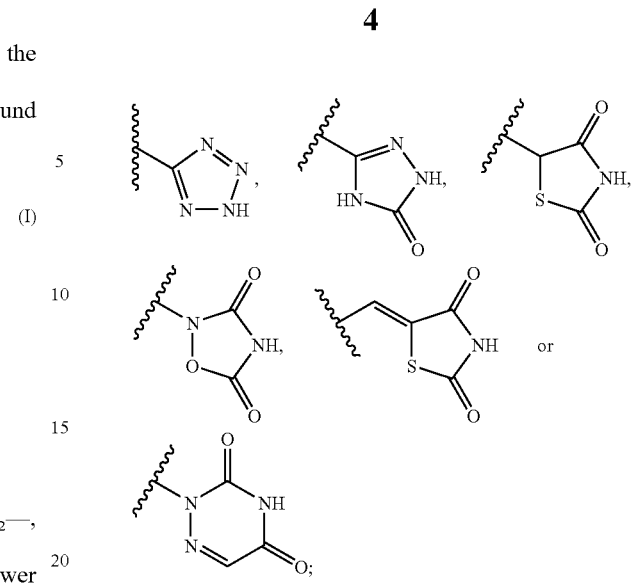

a prodrug thereof, or a pharmaceutically acceptable salt thereof.

The invention is described using the terms defined below unless otherwise specified.

The term "halogen atom" refers to a fluorine, chlorine, bromine or iodine atom.

The term "lower alkyl group" refers to a straight chained or branched alkyl group having 1 to 6 carbon atoms such as a methyl, ethyl, propyl, isopropyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl group and the like.

The term "halo-lower alkyl group" refers to a lower alkyl group substituted with the same or different 1 to 3 halogen atoms such as a trifluoromethyl, 2,2,2-trifluoroethyl group and the like.

The term "cycloalkyl group" refers to a 3 to 8 membered cyclic hydrocarbon which may be substituted with 1 to 3 groups selected independently from the group consisting of a halogen atom, a lower alkoxy, hydroxy and carbonyl group. Examples of cycloalkyl groups include a cyclopropyl, cyclobutyl, cyclopentyl, cyclohexyl, cycloheptyl, cyclooctyl, 3-fluorocyclopentyl, 3-hydroxycyclopentyl, 3-cyclopentanon-1-yl group and the like. Said cycloalkyl group includes a monocyclic, bicyclic or bridged cyclic hydrocarbon.

The term "heterocycloalkyl group" refers to a cycloalkyl group which contains a hetero atom selected from an oxygen, sulfur or nitrogen atom in the ring. Examples of heterocycloalkyl groups include a tetrahydrofuryl, tetrahydrothienyl, tetrahydropyranyl group and the like.

The term "alkyl group" refers to a straight chained or branched alkyl group having 1 to 12 carbon atoms such as a methyl, ethyl, propyl, isopropyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, heptyl octyl, nonyl group and the like.

The term "lower alkoxy group" refers to a straight chained or branched alkoxy group having 1 to 6 carbon atoms such as a methoxy, ethoxy, propoxy, isopropoxy, isobutoxy, sec-butoxy group and the like.

The term "cyclic amine" or "cyclic amino group" refers to a 5 to 7 membered saturated cyclic amine which may contains —NH—, —O—, —S— or —S(O)$_2$— in the ring such as a pyrrolidyl, piperidyl, piperazinyl, morpholinyl, thiomorpholinyl group and the like. Said cyclic amino group may be optionally substituted with 1 or 2 lower alkyl groups.

The term "substituted lower alkyl group" refers to a lower alkyl group substituted with 1 to 3 groups selected independently from the group consisting of a lower alkoxy, hydroxy, cycloalkyl, heterocycloalkyl and cyclic amino group.

The term "substituted alkyl group" refers to an alkyl group substituted with 1 to 3 groups selected independently from the group consisting of a lower alkoxy, hydroxy, cycloalkyl, heterocycloalkyl and cyclic amino group.

The term "alkoxy group" refers to a straight chained or branched alkoxy group having 1 to 12 carbon atoms such as a methoxy, ethoxy, propoxy, isopropoxy, isobutoxy, sec-butoxy, pentyloxy, hexyloxy, heptyloxy, octyloxy, decyloxy group and the like.

The term "substituted alkoxy group" refers to an alkoxy group substituted with a lower alkoxy, hydroxy, cycloalkyl or heterocycloalkyl group.

The term "aryl group" refers to an aromatic hydrocarbon group having 6 to 10 carbon atoms, the ring carbon atom of which may be optionally substituted with 1 to 3 substituents selected independently from the group consisting of a halogen atom, a lower alkyl, halo-lower alkyl, lower alkoxy and hydroxy group. Examples of aryl groups include a phenyl, 2-fluorophenyl, 3-fluorophenyl, 4-fluorophenyl, 2,4-difluorophenyl, 3,4-difluorophenyl, 2-chlorophenyl, 3-chlorophenyl, 4-chlorophenyl, 2,6-dichlorophenyl, 4-trifluoromethylphenyl, 2-methoxyphenyl, 4-methoxyphenyl, 2-hydroxyphenyl, 3-hydroxyphenyl, 4-hydroxyphenyl, 0.3-fluoro-4-methoxyphenyl, 3-fluoro-4-hydroxyphenyl, naphthyl group and the like.

The term "heteroaryl group" refers to a 5 or 6 membered monocyclic aromatic heterocycle having 1 to 5 carbon atoms and 1 to 4 heteroatoms selected independently from the group consisting of O, N and S, or a 8 to 10 membered bicyclic aromatic heterocycle-having-1 to 9-carbon atoms and 1 to 4 heteroatoms selected independently from the group consisting of O, N and S. Examples of monocyclic aromatic heterocycles include pyrrolyl, furanyl, thienyl, imidazolyl, pyrazolyl, oxazolyl, isoxazolyl, 1,2,4-oxadiazolyl, tetrazolyl, thiazolyl, isothiazolyl, 1,2,3-thiadiazolyl, triazolyl, pyridyl, pyrazinyl, pyrimidyl and pyridazinyl. Examples of bicyclic aromatic heterocycles include indolyl, indolinyl, benzofuranyl, benzothienyl, quinolyl, isoquinolyl, phthalazinyl, benzimidazolyl, benzo[1,3]dioxole and the like. The heterocycles include all position isomers such as 2-pyridyl, 3-pyridyl, 4-pyridyl. The heterocycles may be optionally substituted with 1 to 5 groups selected independently from the group consisting of a halogen atom, a lower alkyl, lower alkoxy, hydroxy and carbonyl group.

The term "aralkyl group" refers to a lower alkyl group substituted with an aryl or heteroaryl group, the lower alkyl chain of which may be optionally substituted with a hydroxy group.

The term "aralkyloxy group" refers to a group represented by (aralkyl)-O—.

The term "lower alkanoyl group" refers to a group represented by (lower alkyl)-CO—.

The term "alkanoyl group" refers to a group represented by (lower alkyl)-CO—, (halo-lower alkyl)-CO—, (substituted lower alkyl)-CO— or (aralkyl)-CO—.

The term "aroyl group" refers to a group represented by (aryl)-CO— or (heteroaryl)-CO—.

The term "acyloxy group" refers to a group represented by (alkanoyl)-O—, (aroyl)-O—, (lower alkoxy)-CO—O—, (lower alkyl)-SO$_2$—O— or (halo-lower alkyl)-SO$_2$—O—.

The term "alkylene group" refers to a bivalent saturated hydrocarbon chain having 1 to 5 carbon atoms which may be straight chained or branched. Examples of alkylene groups include —CH$_2$—, —CH$_2$CH$_2$—, —CH(CH$_3$)—, —CH$_2$CH$_2$CH$_2$—, —CH(CH$_3$)CH$_2$—, —CH$_2$CH(CH$_3$)—, —C(CH$_3$)$_2$—, —CH(CH$_2$CH$_3$)—, —CH$_2$CH$_2$CH$_2$CH$_2$— and the like.

The term "alkenylene group" refers to —CH=CH— in a cis or trans configuration.

The compounds represented by general formula (I) as described above may contain one or more asymmetric carbons. All stereoisomers in the R- or S-configuration at each of asymmetric carbons and their mixture are contemplated within the scope of the present invention. Racemic compounds, racemic mixtures, individual enantiomers and mixtures of diastereomers are also contemplated within the scope of the present invention.

The compounds represented by general formula (I) as described above may form a solvate with a pharmaceutically acceptable solvent such as water, ethanol and the like. All solvates are contemplated within the scope of the present invention.

The compounds represented by general formula (I) as described above may exist in one or more geometrical or tautomeric isomers. All geometrical or tautomeric isomers are also contemplated within the scope of the present invention.

The compounds represented by general formula (I) as described above may exist in the form of salts. Examples of such salts include acid addition salts formed with mineral acids such as hydrochloric acid, hydrobromic acid, hydroiodic acid, sulfuric acid, nitric acid, phosphoric acid and the like; acid addition salts formed with organic acids such as formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid; aspartic acid and the like; basic salts formed with inorganic bases such as lithium, sodium, potassium, calcium, magnesium and the like; basic salts formed with organic bases such as triethylamine, piperidine, morpholine, lysine and the like.

The term "prodrug" as used herein refers to a compound which can be converted into a compound represented by general formula (I) in vivo. Such prodrugs are also contemplated within the scope of the present invention. Various forms of prodrugs are well known in the art.

When a compound represented by formula (I) as described above contain a carboxylic acid as a functional group, then a prodrug may include an ester formed by the replacement of the hydrogen atom of the carboxylic acid group with the following groups: lower alkyl; lower alkanoyloxymethyl; 1-(lower alkanoyloxy)ethyl; 1-methyl-1-(lower alkanoyloxy)-ethyl; lower alkoxycarbonyloxymethyl; 1-(lower alkoxycarbonyloxy) ethyl; 1-methyl-1-(lower alkoxycarbonyloxy)ethyl; N-(lower alkoxycarbonyl) aminomethyl; 1-(N-(lower alkoxycarbonyl) amino)ethyl; 3-phthalidyl; 4-crotonolactonyl; gamma-butyro-lacton-4-yl; N,N-di(lower alkyl)amino-lower alkyl such as β-dimethylaminoethyl; carbamoyl-lower alkyl; N,N-di(lower alkyl) carbamoyl-lower alkyl; or piperidino-, pyrrolidino- or morpholino-lower alkyl.

When a compound represented by formula (I) as described above contain a hydroxy group, then a prodrug may include a compound formed by the replacement of the hydrogen atom of the hydroxy group with the following groups: lower alkanoyloxymethyl; 1-(lower alkanoyloxy)

ethyl; 1-methyl-1-(lower alkanoyloxy)ethyl; lower alkoxycarbonyloxymethyl; N-(lower alkoxycarbonyl)aminomethyl; succinoyl; lower alkanoyl; or α-amino-lower alkanoyl.

When a compound represented by formula (I) as described above contain an amino group such as —NH or —NH$_2$, then a prodrug may include a compound formed by the replacement of the hydrogen atom of the amino group with the following groups: lower alkanoyl; or lower alkoxycarbonyl.

The term "thyroid hormone receptor ligand" refers to a compound which binds to thyroid hormone receptors. Such ligands may act as an agonist, an antagonist, a partial agonist or a partial antagonist.

A preferable embodiment of general formula (I) as described above is a compound wherein W is an oxygen atom.

Another preferred embodiment of general formula (I) as described above is a compound wherein A is —N(R$^6$)CO—A$^1$—COR$^{10}$, —CON(R$^6$)—A$^2$—COR$^{10}$ or —X—A$^2$—COR$^{10}$.

A more preferable embodiment of general formula (I) as described above is a compound wherein W is an oxygen atom; and A is —N(R$^6$)CO—A$^1$—COR$^{10}$, —CON(R$^6$)—A$^2$—COR$^{10}$ or —X—A$^2$—COR$^{10}$.

An even more preferable embodiment of general formula (I) as described above is a compound wherein W is an oxygen atom; A is —N(R$^6$)CO—A$^1$—COR$^{10}$, —CON(R$^6$)—A$^2$—COR$^{10}$ or —X—A$^1$—COR$^{10}$; and R$^1$ is a halogen atom or a lower alkyl group.

Another even more preferable embodiment of general formula (I) as described above is a compound wherein W is an oxygen atom; A is —N(R$^6$)CO—A$^1$—COR$^{10}$, —CON(R$^6$)—A$^2$—COR$^{10}$ or —X—A$^2$—COR$^{10}$; and R$^2$ is a hydrogen atom.

Still another even more preferable embodiment of general formula (I) as described above is a compound wherein W is an oxygen atom; A is —N(R$^6$)CO—A$^1$—COR$^{10}$, —CON(R$^6$)—A$^2$—COR$^{10}$ or —X—A$^2$—COR$^{10}$; and R$^4$ is an alkyl group, a substituted alkyl group, an aralkyl group, an alkanoyl group or an aroyl group.

An especially preferable embodiment of general formula (I) as described above is a compound wherein W is an oxygen atom; A is —N(R$^6$)CO—A$^1$—COR$^{10}$, —CON(R$^6$)—A$^2$—COR$^{10}$ or —X—A$^2$—COR$^{10}$; and R$^1$ is a halogen atom or a lower alkyl group; R$^2$ is a hydrogen atom; and R$^4$ is an alkyl group, a substituted alkyl group, an aralkyl group, an alkanoyl group or an aroyl group.

Examples of especially preferred compounds of the present invention include:

ethyl N-[6-bromo-7-(4-hydroxy-3-isopropylphenoxy)indan-4-yl]oxamate;

N-[6-bromo-7-(4-hydroxy-3-isopropylphenoxy)indan-4-yl]malonamic acid;

ethyl N-[7-(4-hydroxy-3-isopropylphenoxy)-6-methylindan-4-yl]oxamate;

N-[7-(4-hydroxy-3-isopropylphenoxy)-6-methylindan-4-yl]malonamic acid;

N-[6-bromo-7-(4-hydroxy-5,6,7,8-tetrahydronaphthalen-1-yloxy)indan-4-yl]malonamic acid;

N-[7-(4-hydroxy-3-isopropylphenoxy)-6-methylindan-4-yl]oxamic acid;

ethyl N-[6-bromo-7-(4-hydroxy-5,6,7,8-tetrahydronaphthalen-1-yloxy)indan-4-yl]oxamate;

N-[6-bromo-7-(4-hydroxy-5,6,7,8-tetrahydronaphthalen-1-yloxy)indan-4-yl]oxamic acid;

N-(7-{3-[(4-fluorophenyl)hydroxymethyl]-4-hydroxyphenoxy}-6-methylindan-4-yl)malonamic acid;

N-[6-bromo-7-(4-hydroxy-3-isopropylphenoxy)indan-4-yl]oxamic acid;

N-(7-{3-[2-(4-fluorophenyl)ethyl]-4-hydroxyphenoxy)-6-methylindan-4-yl)oxamic acid;

N-(7-{3-[2-(3,4-difluorophenyl)ethyl]-4-hydroxyphenoxy)-6-methylindan-4-yl)malonamic acid;

N-(7-{3-[2-(4-fluorophenyl)ethyl]-4-hydroxyphenoxy}-6-methylindan-4-yl)malonamic acid;

N-{7-[3-(2-cyclohexylethyl)-4-hydroxyphenoxy]-6-methylindan-4-yl}oxamic acid;

N-{7-[3-ethyl-4-hydroxy-2-(pyridin-3-ylmethoxy) phenoxy]-6-methylindan-4-yl}malonamic acid;

N-[7-(3-ethyl-4-hydroxy-2-phenethyloxyphenoxy)-6-methylindan-4-yl]malonamic acid;

{[7-(4-hydroxy-3-isopropylphenoxy)-6-methylindan-4-carbonyl]amino}acetic acid;

N-(7-(4-hydroxy-3-[2-(3-oxocyclopentyl)ethyl]phenoxy}-6-methylindan-4-yl)oxamic acid;

N-(7-{4-hydroxy-3-[2-(4-hydroxyphenyl)ethyl]phenoxy}-6-methylindan-4-yl)malonamic acid;

N-(7-{4-hydroxy-3-[2-(2-hydroxyphenyl)ethyl]phenoxy)-6-methylindan-4-yl)malonamic acid;

ethyl N-{7-[4-hydroxy-3-(6-oxo-1,6-dihydropyridazin-3-ylmethyl)phenoxy]-6-methylindan-4-yl}oxamate;

N-{7-[4-hydroxy-3-(6-oxo-1,6-dihydropyridazin-3-ylmethyl)phenoxy]-6-methylindan-4-yl}oxamic acid;

ethyl N-[7-(4-hydroxy-3-isopropyl-2-methoxyphenoxy)-6-methylindan-4-yl]oxamate;

N-(7-[4-hydroxy-3-[2-(tetrahydrofuran-3-yl)ethyl]phenoxy}-6-methylindan-4-yl)oxamic acid;

N-(7-{3-[2-(3-fluoro-4-hydroxyphenyl)ethyl]-4-hydroxy phenoxy}-6-methylindan-4-yl)oxamic acid;

ethyl N-(7-{4-hydroxy-3-[2-(3-oxocyclopentyl)ethyl]phenoxy}-6-methylindan-4-yl)oxamate;

ethyl N-[7-(4-hydroxy-3-iodophenoxy)-6-methylindan-4-yl]oxamate;

N-[7-(4-hydroxy-3-iodophenoxy)-6-methylindan-4-yl]oxamic acid;

N-[7-(4-hydroxy-3-iodophenoxy)-6-methylindan-4-yl]malonamic acid;

ethyl N-{7-[3-(4-fluorobenzyl)-4-hydroxyphenoxy]-6-methylindan-4-yl}oxamate;

N-{7-[3-(4-fluorobenzyl)-4-hydroxyphenoxy]-6-methylindan-4-yl}oxamic acid;

N-{7-[3-(4-fluorobenzyl)-4-hydroxyphenoxy]-6-methylindan-4-yl}malonamic acid;

N-(7-[4-hydroxy-3-(tetrahydropyran-4-ylmethyl)phenoxy]-6-methylindan-4-yl)oxamic acid;

ethyl N-[7-(4-hydroxy-3-isopropylbenzyl)-6-methylindan-4-yl]oxamate;

N-[7-(4-hydroxy-3-isopropylbenzyl)-6-methylindan-4-yl]oxamic acid;

ethyl N-[7-(4-hydroxy-3-isopropylphenylsulfanyl)-6-methylindan-4-yl]oxamate;

N-[7-(4-hydroxy-3-isopropylphenylsulfanyl)-6-methylindan-4-yl]oxamic acid;

N-[7-(4-hydroxy-3-isopropyl-2-methoxyphenoxy)-6-methylindan-4-yl]oxamic acid;

N-[7-(4-hydroxy-3-isopropylbenzoyl)-6-methylindan-4-yl]malonamic acid;

ethyl N-[7-(4-hydroxy-3-trifluoromethylphenoxy)-6-methylindan-4-yl]oxamate;

N-[7-(4-hydroxy-3-trifluoromethylphenoxy)-6-methylindan-4-yl]oxamic acid;

ethyl N-[7-(4-hydroxy-3-isopropylphenoxy)-6-trifluoromethylindan-4-yl]oxamate;

N-[7-(4-hydroxy-3-isopropylphenoxy)-6-trifluoromethylindan-4-yl]oxamic acid;

ethyl N-[7-(4-hydroxy-3-isopropylphenoxy)-6-iodoindan-4-yl]oxamate;

N-[7-(4-hydroxy-3-isopropylphenoxy)-6-iodoindan-4-yl]oxamic acid;

N-[7-(4-hydroxy-3-isopropylphenoxy)-6-trifluoromethylindan-4-yl]malonamic acid;

N-[7-(4-hydroxy-3-isopropylphenoxy)-6-iodoindan-4-yl]malonamic acid;

({7-[3-(4-fluorobenzyl)-4-hydroxyphenoxy]-6-methylindan-4-carbonyl}amino)acetic acid;

{7-[3-(4-fluorobenzyl)-4-hydroxyphenoxy]-6-methylindan-4-yloxy}acetic acid; and

[7-(4-hydroxy-3-isopropylphenoxy)-6-methylindan-4-yloxy]acetic acid.

In another aspect, the present invention provides a pharmaceutical composition which comprises, as an active ingredient, a compound represented by general formula (I) as described above, a prodrug thereof, or a pharmaceutically acceptable salt thereof.

In still another aspect, the present invention provides a therapeutic or prophylactic agent for a metabolic function disorder or a disease associated with the expression of a T3 regulated gene, which comprises, as an active ingredient, a compound represented by general formula (I) as described above, a prodrug thereof, or a pharmaceutically acceptable salt thereof.

In an embodiment, the present invention provides a therapeutic or prophylactic agent for hyperlipidemia, atherosclerosis, obesity, diabetes mellitus, hypertension, fatty liver, liver cirrhosis, liver cancer, glaucoma, depression, hypothyroidism, hyperthyroidism, congestive heart failure, cardiac arrhythmia, osteoporosis, a skin disorder or alopecia, which comprises, as an active ingredient, a compound represented by general formula (I) as described above, a prodrug thereof, or a pharmaceutically acceptable salt thereof.

The skin disorder as described above includes dermal atrophy caused by steroid external preparation, psoriasis, atopic dermatitis, acne and eczema.

In a more preferable embodiment, the present invention provides a therapeutic or prophylactic agent for hyperlipidemia, atherosclerosis, obesity, diabetes mellitus, fatty liver, liver cirrhosis, liver cancer or hypothyroidism.

In still another aspect, the present invention provides a pharmaceutical combination comprising a compound represented by general formula (I) as described above or a pharmaceutically acceptable salt thereof and at least one selected from the group consisting of an antihyperlipidemic agent, an antiobesity agent, an antidiabetic agent, an antihypertensive agent and an antidepressant other than thyroid hormone receptor ligand.

In still another aspect, the present invention provides a use of a compound represented by general formula (I) as described above or a pharmaceutically acceptable salt thereof, for the manufacture of a medicament for treating or preventing a metabolic function disorder or a disease associated with the expression of a T3 regulated gene.

In still another aspect, the present invention provides a method for treating or preventing a metabolic function disorder or a disease associated with the expression of a T3 regulated gene, which comprises administering an effective amount of a compound represented by general formula (I) as described above or a pharmaceutically acceptable salt thereof.

The term "protecting group" as used herein refers to an arbitrary group which can be introduced for protecting an undesirable reaction at the phenolic hydroxy group. Examples of protecting groups include a benzyl group; a lower alkyl group such as a methyl group and the like; a lower alkoxy-lower alkyl group such as a methoxymethyl group and the like; and a tetrahydropyranyl group and the like. The introduction and removal of such protecting groups can be carried out by procedures well known to those in the art (see, for example, T. W. Green and P. G. H. Wuts, "Protective groups in organic Synthesis", 3rd edition and references described therein).

Compounds represented by general formula (I) can be prepared by methods as illustrated in the following schemes 1 to 8 and 16.

SCHEME 1

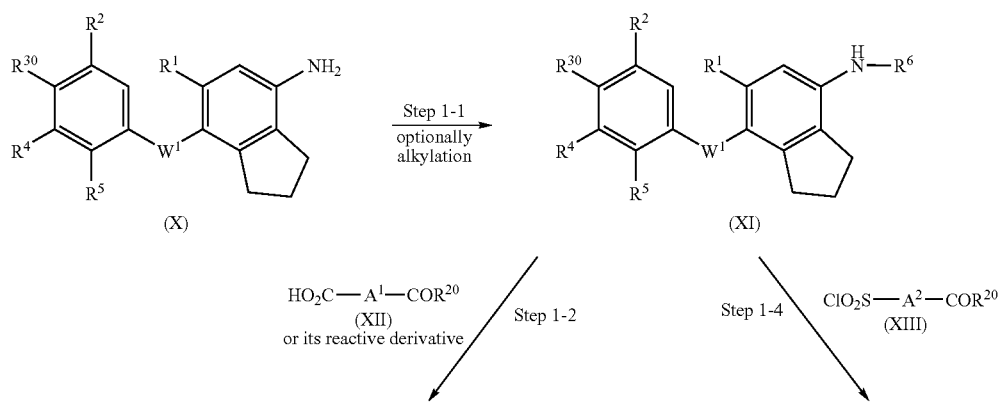

-continued

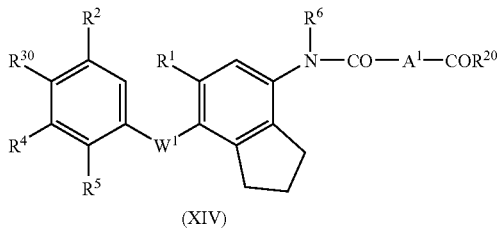

(XIV)

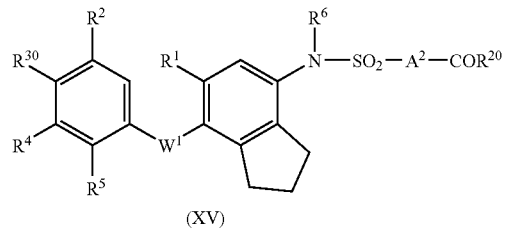

(XV)

Step 1-3
1) optionally oxidation, removal of protecting group
2) optionally hydrolysis, introduction of acyl group Step 1-5
1) optionally oxidation, removal of protecting group
2) optionally hydrolysis, introduction of acyl group

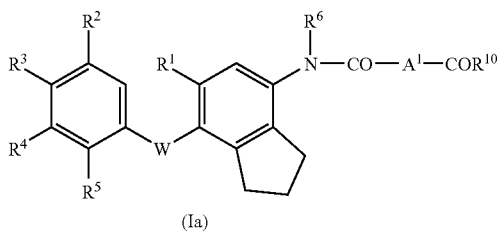

(Ia)

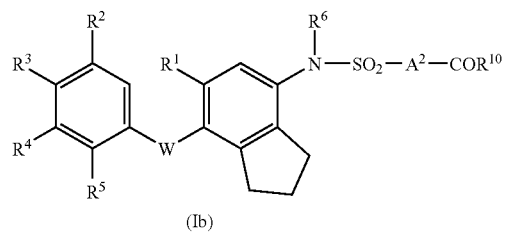

(Ib)

wherein $R^1$, $R^2$ $R^3$, $R^4$, $R^5$, $R^6$, $R^9$, $R^{10}$, $R^{11}$, $R^{12}$, $A^1$, $A^2$ and W are as defined above; $R^{20}$ is lower alkoxy or —$NR^{11}$($R^{12}$); $R^{30}$ is a hydroxy group or —O—P, or $R^{30}$ and $R^4$ are joined together to form —NH—CH=C($R^9$)— in which P represents a protecting group such as a methyl or benzyl group; $W^1$ is —O—, —S—, —N($R^6$)—, —CH$_2$—, —CHF—, —CF$_2$—, —CH(OH)—, —CO— or —C(=CH$_2$)—.

(Step 1-1)

An aminoindane derivative represented by general formula (X) is reacted, if required, with an alkylating agent in the presence of a base such as cesium carbonate, potassium carbonate, sodium hydroxide, N,N-diisopropylethylamine, triethylamine, 2,6-lutidine or the like in an inert solvent to afford a compound represented by general formula (XI). The solvent employed in the reaction includes acetonitrile, ethanol, 1,2-dimethoxyethane, tetrahydrofuran, N,N-dimethylformamide, acetone and their mixed solvent. The reaction is carried out ordinarily at 0° C. to reflux temperature. The reaction time varies depending on the starting materials employed, the solvent, the reaction temperature or the like, and is usually 1 hour to 1 day.

(Step 1-2)

The indane derivative of general formula (XI) is reacted with a compound of general formula (XII) in the presence of a condensing agent such as dicyclohexylcarbodiimide, 1-(3-dimethylaminopropyl)-3-ethylcarbodiimide hydrochloride, diethyl cyanophosphate, diphenylphosporylazide or the like in an inert solvent to afford a compound of general formula (XIV). The solvent employed in the reaction includes acetonitrile, N,N-dimethylformamide, tetrahydrofuran, methylene chloride and their mixed solvent. The reaction is carried out ordinarily at 0° C. to room temperature. The reaction time varies depending on the starting materials employed, the solvent, the reaction temperature or the like, and is usually 1 to 24 hours.

Alternatively, the compound of general formula (XIV) can be prepared by condensing compound (XI) with a reactive derivative of compound (XII) such as acid halide, mixed anhydride, ester or the like in the absence or presence of a base such as pyridine, cesium carbonate, potassium carbonate, N,N-diisopropylethylamine, triethylamine, 2,6-lutidine or the like without solvent or in an inert solvent. The solvent employed in the reaction includes acetonitrile, N,N-dimethylformamide, tetrahydrofuran, methylene chloride and their mixed solvent. The reaction is carried out ordinarily at 0° C. to room temperature. The reaction time varies depending on the starting materials employed, the solvent, the reaction temperature or the like, and is usually 20 minutes to 24 hours.

(Step 1-3)

An indane derivative represented by general formula (Ia) of the present invention can be prepared by oxidizing the sulfur atom of compound (XIV), if required, with an oxidizing agent such as m-chloroperbenzoic acid, potassium permanganate, hydrogen peroxide, peracetic acid or the like in an inert solvent such as methylene chloride, tetrahydrofuran or the like, and then, when $R^{30}$ is —O—P, removing the protecting group "P", if required, hydrolyzing an ester group, and acylating a phenolic hydroxy group according to a conventional procedure.

(Step 1-4)

The compound of general formula (XI) is reacted with a sulfonylchloride derivative of general (XIII) in the absence or presence of a base such as cesium carbonate, potassium carbonate, N,N-diisopropylethylamine, triethylamine, pyridine, 2,6-lutidine or the like in an inert solvent to afford a compound represented by general formula (XV). The solvent employed in the reaction includes acetonitrile, N,N-dimethylformamide, tetrahydrofuran, methylene chloride and their mixed solvent. The reaction is carried out ordinarily at 0° C. to room temperature. The reaction time varies depending on the starting materials employed, the solvent, the reaction temperature or the like, and is usually 20 minutes to 24 hours.

(Step 1-5)

An indane derivative represented by general formula (Ib) of the present invention can be prepared from the compound (XV) by procedures analogous to those described in step 1-3.

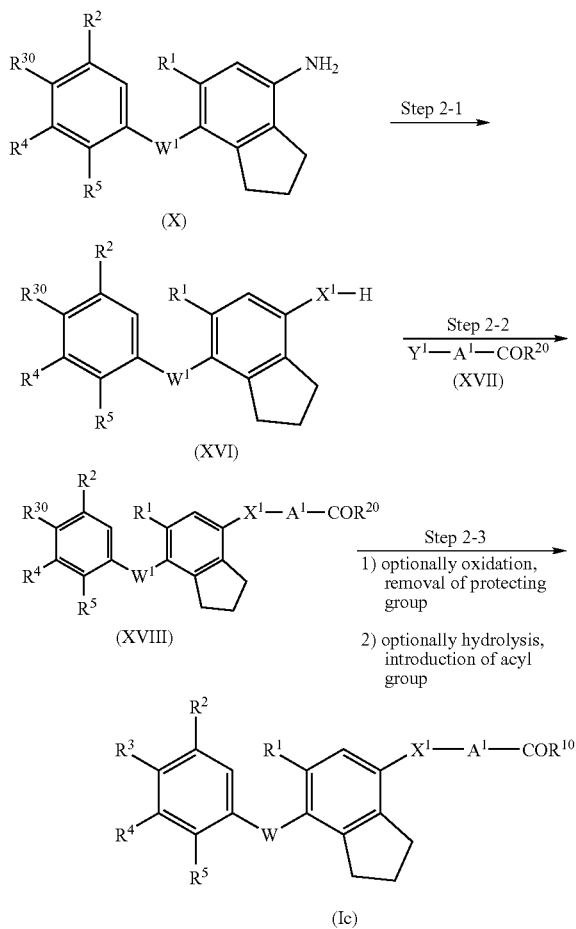

(Step 2-3)

A compound represented by general formula (Ic) of the present invention can be prepared from the compound (XVIII), if required, via oxidation, removal of a protecting group, hydrolysis or introduction of an acyl group by procedures analogous to those described in step 1-3.

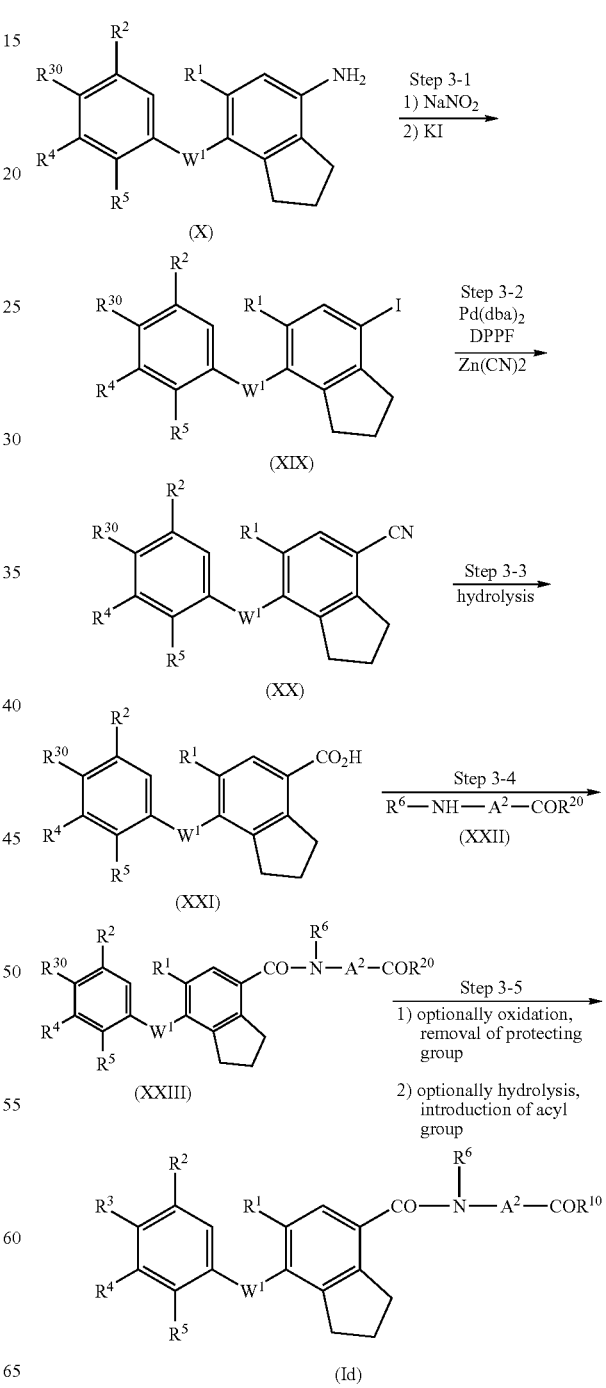

wherein $R^1$, $R^2$, $R^3$, $R^4$, $R^5$, $R^{10}$, $R^{20}$, $R^{30}$, $A^1$, $W^1$ and W are as defined above; $X^1$ is an oxygen or sulfur atom; $Y^1$ is a chlorine, bromine or iodine atom, a mesyloxy, tosyloxy group or the like.

(Step 2-1)

An aminoindane derivative of general formula (X) can be converted to a compound of general formula (XVI) according to methods as described in literatures, for example, "Tetrahedron Let." 1999, Vol.40, p.5665–5659; or "J. Med. Chem." 1995, vol.38, p.695–707.

(Step 2-2)

The compound (XVI) is reacted with an alkylating agent of general formula (XVII) in the presence of a base such as cesium carbonate, potassium carbonate, sodium hydroxide, N,N-diisopropylethylamine, triethylamine, 2,6-lutidine or the like to afford a compound represented by general formula (XVIII). The solvent employed in the reaction includes acetonitrile, ethanol, 1,2-dimethoxyethane, tetrahydrofuran, N,N-dimethyl formamide, acetone and their mixed solvent. The reaction is carried out ordinarily at 0° C. to reflux temperature. The reaction time varies depending on the starting materials employed, the solvent, the reaction temperature or the like, and is usually 1 hour to 1 day.

wherein $R^1$, $R^2$, $R^3$, $R^4$, $R^5$, $R^6$, $R^{10}$, $R^{20}$, $R^{30}$, $A^2$, $W^1$ and W are as defined above; $Pd(dba)_2$ is bis (dibenzylideneacetone)palladium, DPPF is 1,1'-bis(diphenylphosphino)ferrocene.

(Step 3-1)

An iodoindane derivative of general formula (XIX) can be prepared by diazotizing an aminoindane derivative of general formula (X) with a diazotizing reagent such as sodium nitrite or the like, then iodizing with potassium iodide. The solvent employed in the diazotization and iodization reaction includes water, toluene, acetonitrile and their mixed solvent. The diazotization reaction is ordinarily carried out at −10° C. to room temperature, and the temperature varies on depending on the starting materials employed, the solvent, the reaction temperature or the like, and is usually 10 minutes to 1 day. The iodizing reaction is ordinarily carried out at room temperature to reflux temperature, and the reaction time varies on the starting materials employed, the solvent, the reaction temperature or the like, and is usually 10 minutes to 1 day.

(Step 3-2)

The iodoindane derivative (XIX) is reacted with a cyanizing reagent such as zinc cyanide, potassium cyanide and the like in the presence of a catalyst such as bis(dibenzylideneacetone)palladium and 1,1'-bis(diphenyl phosphino)ferrocene or the like in an inert solvent to afford a cyano compound represented by general formula (XX). The solvent employed in the reaction includes 1-methyl-2-pyrrolidone, acetonitrile, N,N-dimethylformamide, toluene, dimethyl sulfoxide and their mixed solvent. The reaction is ordinarily carried out at room temperature to reflux temperature. The reaction time varies depending on the starting materials employed, the solvent, the reaction temperature or the like, and is usually 1 hour to 3 days.

(Step 3-3)

Hydrolysis of the cyano compound (XX) using alkali affords a compound represented by general formula (XXI). The solvent employed in the reaction includes methanol, ethanol, water, tetrahydrofuran and their mixed solvent. The base includes sodium hydroxide, sodium methoxide and the like. The reaction is carried out ordinarily at room temperature to reflux temperature. The reaction time varies depending on the starting materials employed, the solvent, the reaction temperature or the like, and is usually 1 to 3 hours.

(Step 3-4)

A compound represented by general formula (XXIII) can be prepared by condensing the compound (XXI) with an amine compound of general formula (XXII) by procedures analogous to those described in step 1-2.

(Step 3-5)

An indane derivative represented by general formula (Id) of the present invention can be prepared from the compound (XXIII), if required, via oxidation, removal of a protecting group, hydrolysis, or introduction of an acyl group by analogous procedures as described in step 1-3.

SCHEME 4

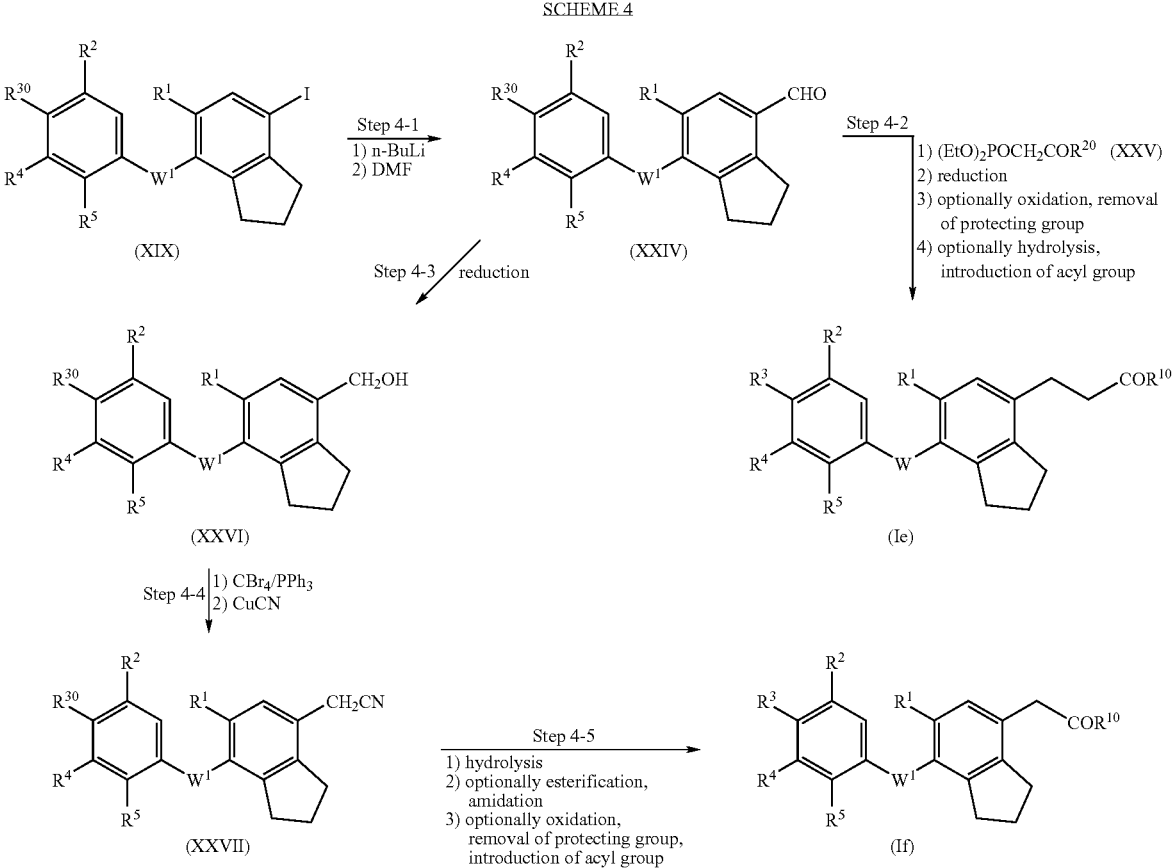

wherein $R^1$, $R^2$, $R^3$ $R^4$ $R^5$, $R^{10}$, $R^{20}$, $R^{30}$, $W^1$ and W are as defined above; DMF represents N,N-dimethylformamide; $PPh_3$ represents triphenylphosphine.

(Step 4-1)

Lithiation of an iodoindane derivative of general formula (XIX) using a lithium reagent such as n-butyllithium or the like in an inert solvent such as tetrahydrofuran or the like, and subsequent formylation using N,N-dimethylformamide afford a formyl compound represented by general formula (XXIV). The reaction is ordinarily carried out at −100° C. to room temperature. The reaction time varies depending on the starting materials employed, the solvent, the reaction temperature or the like, and is usually 1 hour to 1 day.

(Step 4-2)

The compound (XXIV) is condensed with a compound of general formula (XXV) in the presence of a base such as potassium tert-butoxide, sodium hydride or the like in an inert solvent to afford an olefin compound. The olefin compound is catalytically hydrogenated over a palladium catalyst such as palladium/carbon powder or the like under a pressure of 1 to 5 atmospheres to afford a phenylpropionic acid derivative. The solvent employed in the condensation reaction includes tetrahydrofuran, N,N-dimethylformamide, toluene, methylene chloride and their mixed solvent. The reaction is ordinarily carried out at room temperature to reflux temperature. The reaction time varies depending on the starting materials employed, the solvent, the reaction temperature or the like, and is usually 1 hour to 1 day. The solvent employed in the catalytic hydrogenation reaction includes ethyl acetate, methanol, ethanol, tetrahydrofuran, water and their mixed solvent. The reaction is ordinarily carried out at room temperature to reflux temperature. The reaction time varies depending on the starting materials employed, the solvent, the reaction temperature or the like, and is usually 1 hour to 1 day.

Thereafter, an indane derivative represented by general formula (Ie) of the present invention can be prepared from the phenylpropionic acid, if required, via oxidation, removal of a protecting group, hydrolysis, or introduction of an acyl group by procedures analogous to those described in step 1-3.

(Step 4-3)

Reduction of the formyl compound (XXIV) using a reducing reagent such as sodium borohydride or the like in a suitable solvent affords a compound represented by general formula (XXVI). The solvent employed in the reduction reaction includes a protic solvent such as methanol, ethanol etc, or a mixed solvent of such a protic solvent and tetrahydrofuran, 1,2-dimethoxyethane or the like. The reaction is ordinarily carried out at room temperature to reflux temperature. The reaction time varies depending on the starting materials employed, the solvent, the reaction temperature or the like, and is usually 15 minutes to 1 day.

(Step 4-4)

Bromination of the compound (XXVI) using triphenylphosphine and carbon tetrabromide in an inert solvent affords a bromomethylindane. The solvent employed in the reaction includes methylene chloride, chloroform and their mixed solvent. The reaction is ordinarily carried out at 0° C. to reflux temperature. The reaction time varies depending on the starting materials employed, the solvent, the reaction temperature or the like, and is usually 30 minutes to 1 day.

Cyanation of the bromomethylindane using a cyanizing reagent such as copper cyanide or the like in an inert solvent affords a compound represented by general formula (XXVII). The solvent employed in the cyanation reaction includes 1-methyl-2-pyrrolidone, acetonitrile, N,N-dimethylformamide, dimethylsulfoxide and their mixed solvent. The reaction is ordinarily carried out at 0° C. to reflux temperature. The reaction time varies depending on the starting materials employed, the solvent, the reaction temperature or the like, and is usually 1 hour to 1 day.

(Step 4-5)

The compound (XXVII) is hydrolyzed using alkali such as sodium hydroxide or the like in an inert solvent such as methanol, ethanol, water, tetrahydrofuran or the like to afford a phenylacetic acid. The phenylacetic acid can be converted to an indane derivative represented by general formula (If) of the present invention, if required, via esterification or amidation according to a conventional method, and procedures analogous to those described in step 1-3.

SCHEME 5

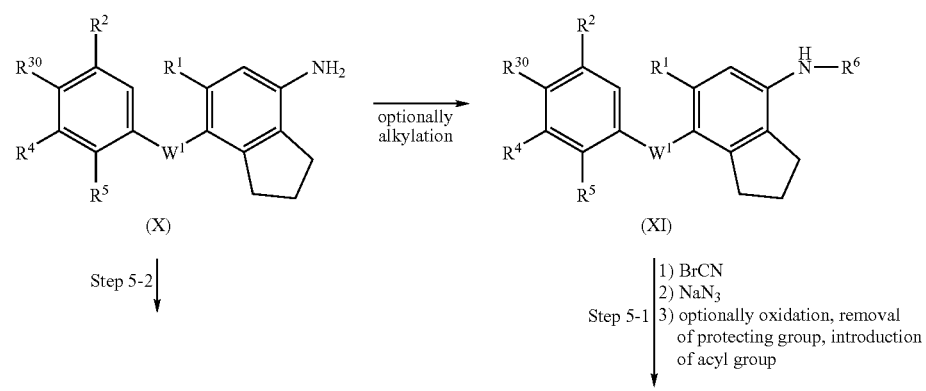

-continued

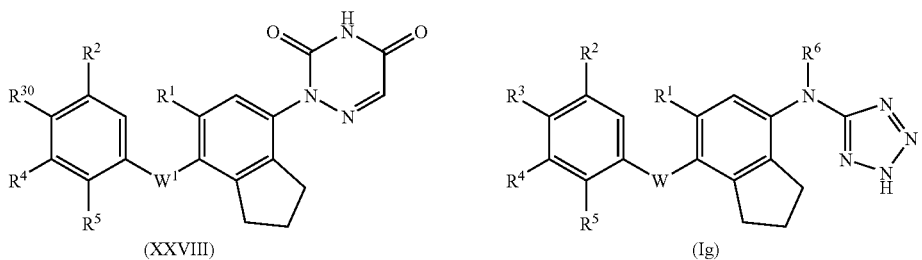

(XXVIII)

(Ig)

Step 5-3 | optionally oxidation, removal of protecting group, introduction of acyl group

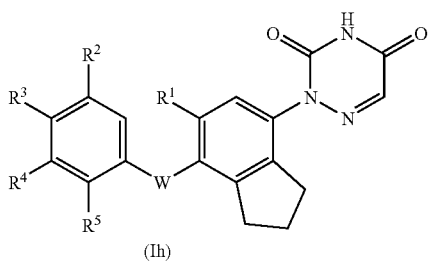

(Ih)

wherein $R^1$, $R^2$, $R^3$, $R^4$, $R^5$, $R^6$, $R^{30}$, $W^1$ and W are as defined above.

(Step 5-1)

The compound (XI) obtained in scheme 1 is reacted with bromocyanide in the presence of sodium acetate in a mixed solvent of acetic acid and water to afford a cyanamide. The cyanamide is reacted with sodium azide in the presence of ammonium chloride in N,N-dimethylforamide to afford an aminotetrazole derivative. Thereafter, the aminotetrazole can be converted to an aminotetrazole derivative represented by general formula (Ig) by procedures analogous to those described in step 1-3.

(Step 5-2)

A 6-azauracil derivative represented by general formula (XXVIII) can be prepared from compound (X) according to methods as described in literatures, for example, "J. Med. Chem." 1981, vol.24, p.1337–1342.

(Step 5-3)

Thereafter, the 6-azauracil (XXVIII) can be converted to a 6-azauracil derivative represented by general formula (Ih) by procedures analogous to those described in step 1-3.

SCHEME 6

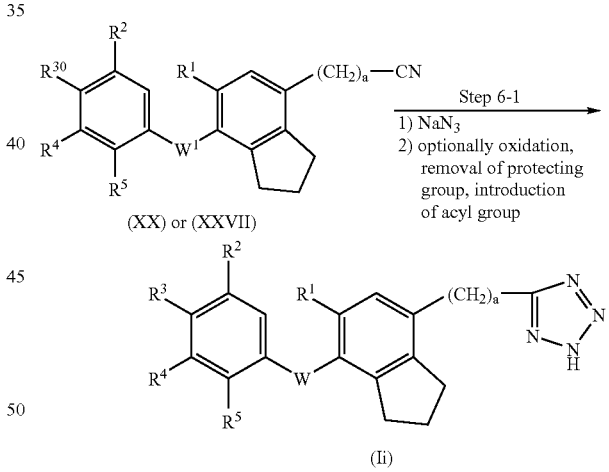

(XX) or (XXVII)

Step 6-1
1) NaN₃
2) optionally oxidation, removal of protecting group, introduction of acyl group (Ii)

wherein $R^1$, $R^2$, $R^3$, $R^4$, $R^5$, $R^{30}$, $W^1$ and W are as defined above; a is 0 or 1.

(Step 6-1)

Compound (XX) or (XXVII) is reacted with sodium azide in the presence of ammonium chloride in N,N-dimethylformamide to afford a tetrazole compound. The reaction is ordinarily carried out at 0° C. to reflux temperature. The reaction time varies depending on the starting materials employed, the solvent, the reaction temperature or the like, and is usually 1 to 24 hours. Thereafter, the tetrazole compound can be converted to a tetrazole compound represented by general formula (Ii) by procedures analogous to those described in step 1-3.

SCHEME 7

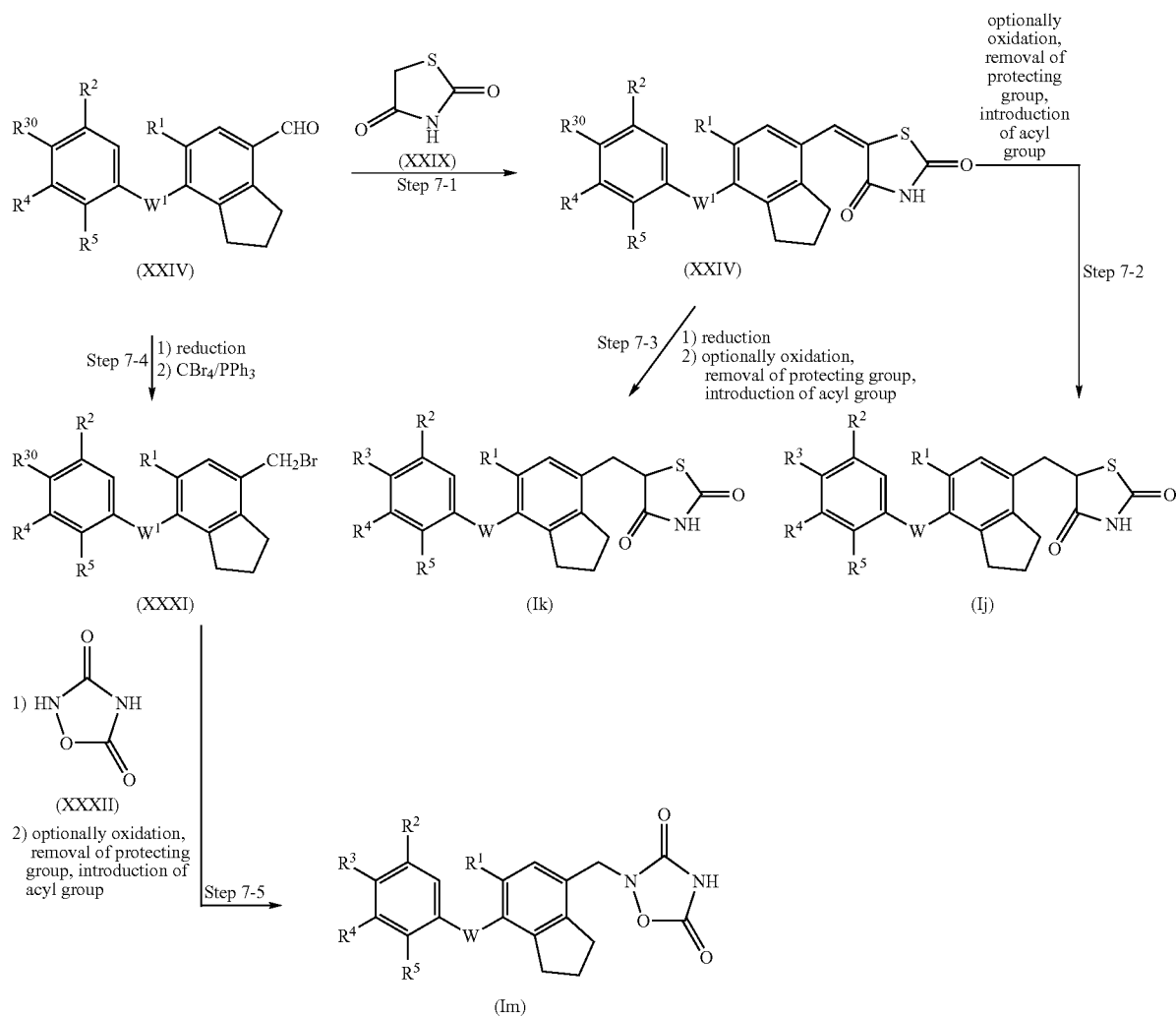

wherein $R^1$, $R^2$, $R^3$, $R^4$, $R^5$, $R^{30}$, $W^1$ and W are as defined above.

(Steps 7-1 and 7-2)

Dehydration condensation of compound (XXIV) with a 2,4-thiazolidinedione of formula (XXIX) in the presence of a catalyst such as acetic acid and pyrrolidine or the like in an inert solvent affords a compound represented by general formula (XXX). The solvent employed in the condensation reaction includes benzene, toluene, xylene and their mixed solvent. The reaction is ordinarily carried out at room temperature to reflux temperature. The reaction time varies depending on the starting materials employed, the solvent, the reaction temperature or the like, and is usually 1 hour to 1 day. The compound (XXX) can be converted to a compound represented by general formula (Ij) of the present invention by procedures analogous to those described in step 1-3.

(Step 7-3)

A compound represented by general formula (Ik) of the present invention can be prepared by catalytic hydrogenation of the compound (XXX) using a metal catalyst such as palladium/carbon powder or the like in an inert solvent such as ethyl acetate, methanol, ethanol, tetrahydrofuran, water and their mixed solvent under a pressure of 1 to 5 atmospheres, and then procedures analogous to those described in step 1-3.

(Steps 7-4 and 7-5)

A bromomethylindane (XXXI) obtained through steps 4-3 and 4-4 in scheme 4 is reacted with an oxazolidinedione of formula (XXXII) according to methods as described in literatures, for example, "Synthesis" 1991, p.265–266, in the presence of abase such as cesium carbonate, potassium carbonate, sodium carbonate, N,N-diisopropylethylamine, triethylamine, 2,6-lutidine or the like in an inert solvent such as acetonitrile, ethanol, 1,2-dimethoxyethane, tetrahydrofuran, N,N-dimethylformamide, acetone and their mixed solvent affords an oxazolidinedione derivative. Thereafter, the oxazolidinedione can be converted to an oxazolidinedione derivative represented by general formula (Im) of the present invention by procedures analogous to those described in step 1-3.

SCHEME 8

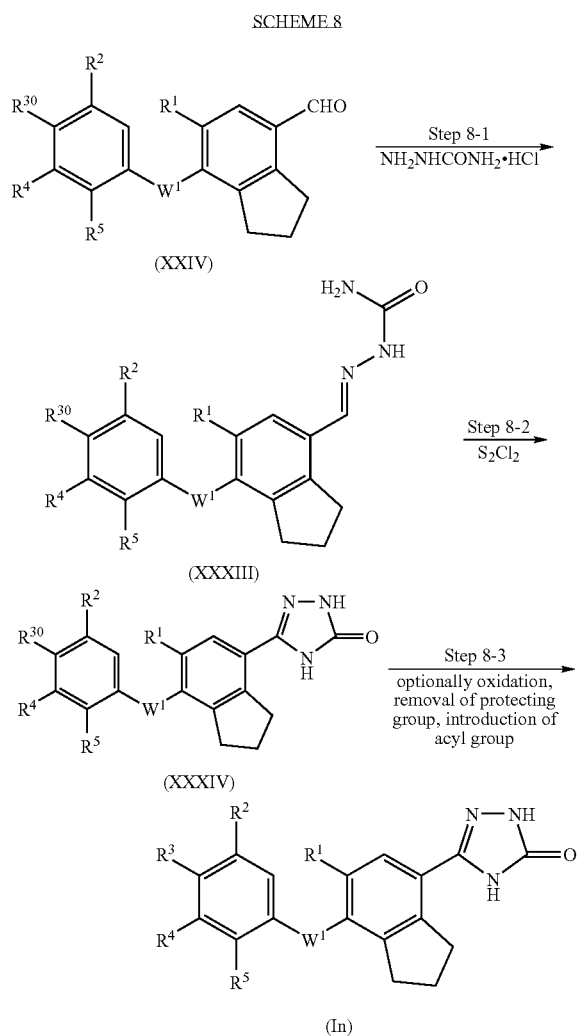

pound represented by general formula (In) of the present invention by procedures analogous to those described in step 1-3.

Of the compounds (X) employed as a starting material in schemes 1 to 3 and 5, a compound represented by general formula (Xa) wherein $W^1$ is —O—, —S— or —N($R^6$)— can be prepared by the method as illustrated in scheme 9.

SCHEME 9

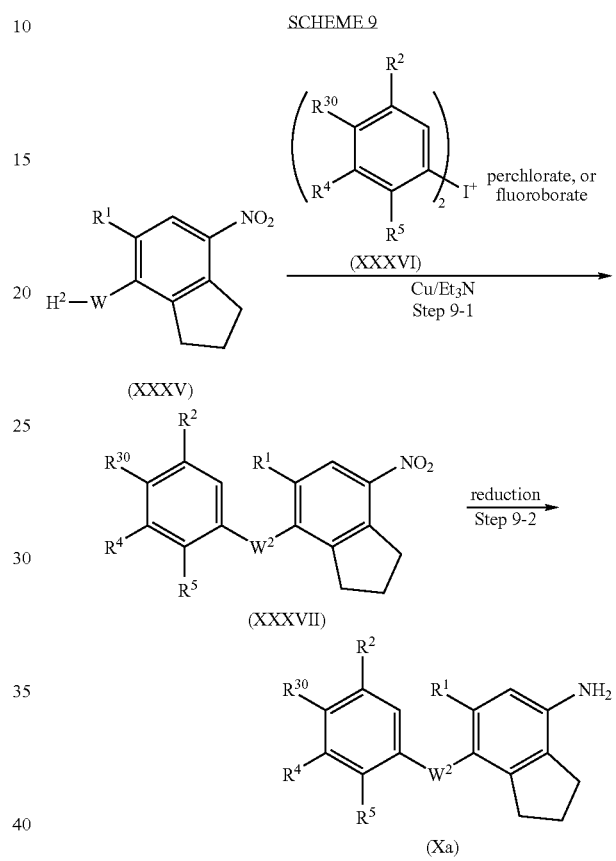

wherein $R^1$, $R^2$ $R^3$ $R^4$, $R^5$, $R^{30}$, $W^1$ and W are as defined above.

(Step 8-1)

Compound (XXIV) is reacted with semicarbazide hydrochloride in the presence of a catalyst such as sodium acetate in an inert solvent such as ethanol or the like to afford a semicarbazone compound of general formula (XXXIII). The reaction is ordinarily carried out at 0° C. to reflux temperature. The reaction time varies depending on the starting materials employed, the solvent, the reaction temperature or the like, and is usually 1 hour to 1 day.

(Steps 8-2 and 8-3)

Cyclization of the semicarbazone (XXXIII) using sulfur monochloride in an organic solvent such as a mixed solvent of ethyl acetate and acetic acid or the like affords a compound represented by general formula (XXXIV). The reaction is ordinarily carried out at room temperature to reflux temperature. The reaction time varies depending on the starting materials employed, the solvent, the reaction temperature or the like, and is usually 1 hour to 1 day. Thereafter, the compound (XXXIV) can be converted to a comwherein $R^1$, $R^2$, $R^3$, $R^5$ and $R^{30}$ are as defined above; $W^2$ is —O—, —S— or —N($R^6$)—.

(Step 9-1)

Coupling of a compound represented by general formula (XXXV) with a bis-aryl iodonium salt of general formula (XXXVI) in the presence of copper powder and a base such as N,N-diisopropylethylamine, triethylamine or the like in an inert solvent such as dichloromethane or the like affords a compound represented by general formula (XXXVII). The reaction is ordinarily carried out at 0° C. to room temperature. The reaction time varies depending on the starting materials, the solvent, the reaction temperature or the like, and is usually 6 hours to 10 days. The bis-aryl iodonium salt (XXXVI) can be prepared from a known anisole or benzyloxybenzene according to the procedure as described in "J. Med. Chem." 1995, vol.38, p.695–707.

(Step 9-2)

Catalytic hydrogenation of the compound (XXXVII) using a catalyst such as palladium/carbon powder, platinum oxide or the like in an inert solvent under a pressure of 1 to 5 atmospheres affords a compound represented by general formula (Xa). The solvent employed in the reaction includes ethyl acetate, methanol, ethanol, tetrahydrofuran, water and their mixed solvent. The reaction is ordinarily carried out at room temperature to reflux temperature. The reaction time varies depending on the starting materials employed, the solvent, the reaction temperature or the like, and is usually 1 hour to 1 day.

Of the compounds (X) employed as a starting material in schemes 1 to 3 and 5, compounds represented by general formula (Xb) and (Xc) wherein $W^1$ is —CH(OH)— or —CH$_2$— can be prepared by the method as illustrated in scheme 10.

(Step 10-2)

Catalytic hydrogenation of the compound (XXXIX) using a metal catalyst such as platinum oxide or the like in an inert solvent under a pressure of 1 to 5 atmospheres affords a compound represented by general formula (XL). The solvent employed in the reaction includes ethyl acetate, metha-

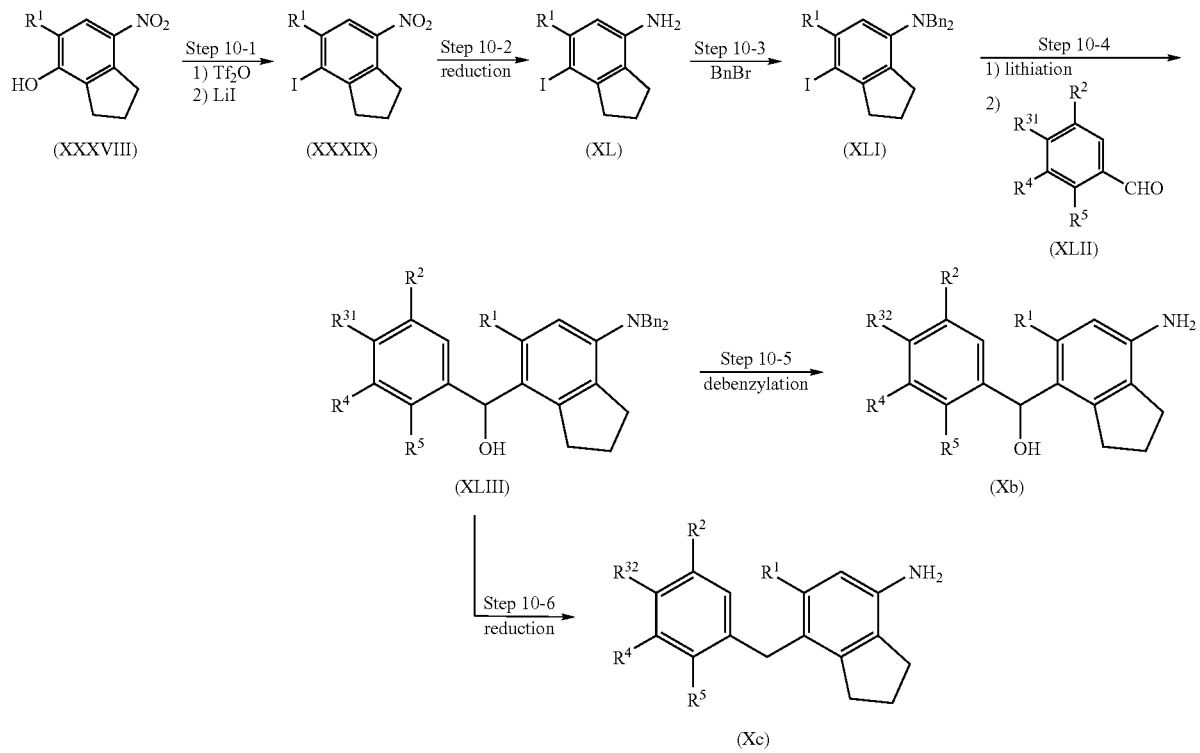

SCHEME 10 wherein $R^1$, $R^2$, $R^4$, $R^5$ and $R^{30}$ are as defined above; $R^{31}$ is a benzyl or methoxy group; $R^{32}$ is a hydroxy or methoxy group; Tf$_2$O represents trifluoromethanesulfonic anhydride; Bn represents a benzyl group.

(Step 10-1)

A compound represented by general formula (XXXVIII) is reacted with trifluoromethanesulfonic anhydride in the absence or presence of abase such as pyridine, N,N-diisopropylethylamine, triethylamine, 2,6-lutidine or the like in an inert solvent such as acetonitrile, N,N-dimethylformamide, tetrahydrofuran, methylene chloride and their mixed solvent affords a trifluoromethanesulfonic acid ester. The reaction is ordinarily carried out at −20° C. to room temperature. The reaction time varies depending on the starting materials employed, the solvent the reaction temperature or the like, and is usually 15 minutes to 1 day. The trifluoromethanesulfonic acid ester is reacted with lithium iodide in an inert solvent such as dimethylsulfoxide, 1-methyl-2-pyrrolidone, acetonitrile, N,N-dimethylformamide and their mixed solvent to afford a compound represented by general formula (XXXIX). The reaction is ordinarily carried out at room temperature to reflux temperature. The reaction time nol, ethanol, tetrahydrofuran, water and their mixed solvent. The reaction is ordinarily carried out at room temperature to reflux temperature. The reaction time varies depending on the starting materials employed, the solvent, the reaction temperature or the like, and is usually 1 hour to 1 day.

(Step 10-3)

The compound (XL) is reacted with a benzylating agent such as benzylbromide or the like in the presence of cesium carbonate, potassium carbonate, sodium hydroxide, N,N-diisopropylethyl amine, triethylamine, 2,6-lutidine or the like to afford a compound represented by general formula (XLI). The solvent employed in the reaction includes acetonitrile, ethanol, 1,2-dimethoxyethane, tetrahydrofuran, N,N-dimethylformamide, acetone and their mixed solvent. The reaction is ordinarily carried out at 0° C. to reflux temperature. The reaction time varies depending on the starting materials employed, the solvent, the reaction temperature or the like, and is usually 1 hour to 1 day.

(Step 10-4)

The compound (XLI) is lithiated with a lithium reagent such as tert-butyl lithium or the like in an inert solvent such as tetrahydrofuran or the like, and then reacted with a formyl compound of general formula (XLII) to afford a compound represented by general formula (XLIII). The reaction is ordinarily carried out at −100° C. to room temperature. The reaction time varies depending on the starting materials employed, the solvent, the reaction temperature or the like, and is usually 1 hour to 1 day.

(Step 10-5)

Catalytic hydrogenation of the compound (XLIII) using a palladium catalyst such as palladium/carbon powder or the like in an inert solvent under a pressure of 1 to 3 atmospheres affords a compound represented by general formula (Xb). The solvent employed in the reaction includes ethyl acetate, methanol, ethanol, tetrahydrofuran, water, acetic acid and their mixed solvent. The reaction is ordinarily carried out at room temperature to reflux temperature. The reaction time varies depending on the starting materials employed, the solvent, the reaction temperature or the like, and is usually 1 hour to 3 days.

(Step 10-6)

Catalytic hydrogenation of the compound (XLIII) using a metal catalyst such as platinum oxide, palladium/carbon powder or the like in an inert solvent under a pressure of 1 to 5 atmospheres affords a compound represented by general formula (Xc). The solvent employed in the reaction includes ethyl acetate, methanol, ethanol, tetrahydrofuran, water, acetic acid and their mixed solvent. Alternatively, the reaction is carried out adding a catalytic amount of an acid such as acetic acid, hydrochloric acid or the like. The reaction temperature is ordinarily room temperature to reflux temperature. The reaction time varies depending on the starting materials employed, the solvent, the reaction temperature or the like, and is usually 1 hour to 3 days.

Of the compounds (X) employed as a starting material in schemes 1 to 3 and 5, compounds represented by general formula (Xg), (Xd), (Xe) and (Xf) wherein $W^1$ is —CHF—, —CF$_2$—, —C(=O)— or —C(=CH$_2$)— can be prepared by the method as illustrated in scheme 11.

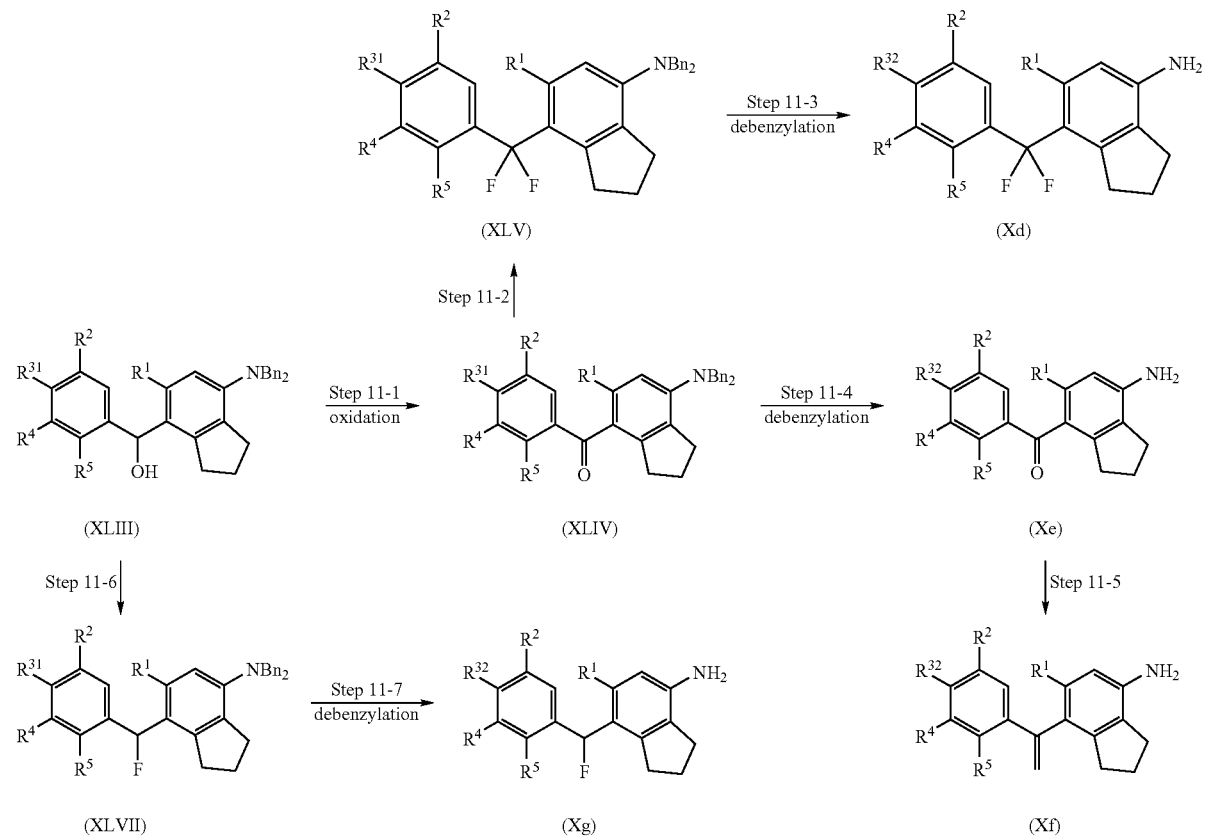

SCHEME 11 wherein $R^1$, $R^2$, $R^4$, $R^5$, $R^{31}$, $R^{32}$ and Bn are as defined above.

(Step 11-1)

Oxidation of a compound represented by general formula (XLIII) using an oxidizing reagent such as manganese dioxide or the like in an inert solvent such as methylene chloride affords a compound represented by general formula (XLIV). The reaction is ordinarily carried out at room temperature to reflux temperature. The reaction time varied depending on the starting materials employed, the solvent, the reaction temperature or the like, and is usually 1 to 72 hours.

(Steps 11-2 and 11-3)

The compound (XLIV) can be converted to a compound of general formula (XLV) according to methods as described in literatures, for example, "Tetrahedron" 1971, p.3965. A compound represented by general formula (Xd) can be prepared from the compound (XLV) by debenzylation according to procedures analogous to those described in step 10-6.

(Step 11-4)

A compound represented by general formula (Xe) can be prepared from the compound (XLIV) by debenzylation according to procedures analogous to those described in step 10-6.

(Step 11-5)

The compound of general formula (Xe) can be converted to a compound represented by general formula (Xf) according to methods as described in literatures, for example, "Synth. Commun." 1996, vol.26, p.2241–2247.

(Steps 11-6 and 11-7)

The compound (XLIII) can be converted to a compound represented by general formula (XLVII) according to methods as described in literatures, for example, "J. Fluorine Chem. 1995, vol.70, p.233–236. Thereafter, a compound represented by general formula (Xg) can be prepared from the compound (XLVII) by debenzylation according to procedures analogous to those described in step 10-6.

The compounds (XXXV) and (XXXVIII) employed as a starting material in schemes 9 and 10 can be prepared by the method as illustrated in scheme 12.

base such as pyridine, N,N-diisopropylethylamine, triethylenediamine, triethylamine, 2,6-lutidine or the like in an inert solvent to afford a compound represented by general formula (L). The solvent employed in the reaction includes acetonitrile, N,N-dimethylformamide, methylene chloride and their mixed solvent. The reaction is ordinarily carried out at 0° C. to reflux temperature. The reaction time varies depending on the starting materials, the solvent, the reaction temperature or the like, and is usually 20 minutes to 24 hours.

(Step 12-3)

The compound (L) is heated without solvent or in ah inert solvent such as dimethylsulfoxide or the like to afford a thiocarbamic acid S-ester. Hydrolysis of the thiocarbamic acid S-ester using an alkali according to a conventional method affords a compound represented by general formula (LI). In the rearrangement reaction, the reaction temperature is ordinarily 100° C. to 250° C. The reaction time varies depending on the starting materials, the solvent, the reaction temperature or the like, and is usually 1 hour to 1 day.

(Step 12-4)

A trifluoromethanesulfonic acid ester, prepared from compound (XXXVIII), is reacted with an amine of general

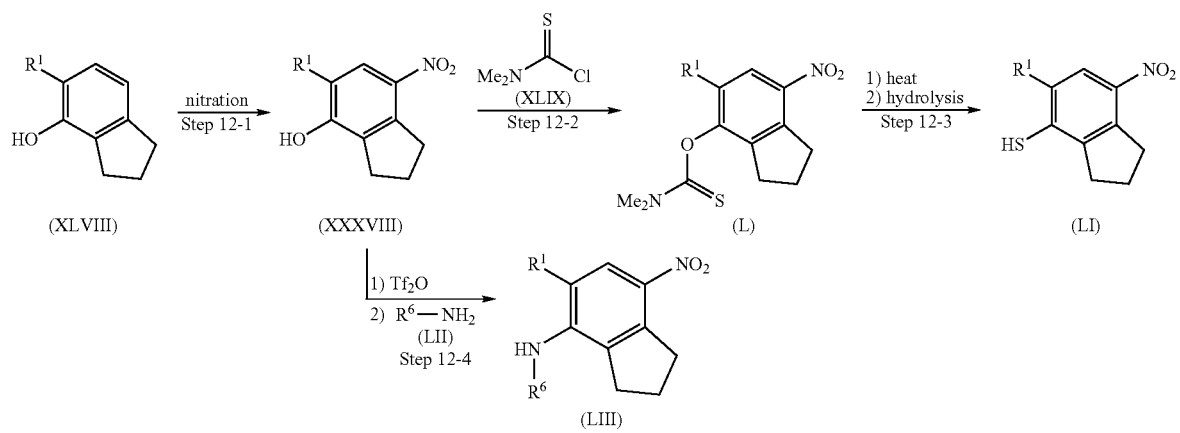

SCHEME 12 wherein $R^1$, $R^6$ and $Tf_2O$ are as defined above.

(Step 12-1)

Nitration of a compound represented by general formula (XLVIII) using a nitrating reagent such as acetic acid/nitric acid, trifluoroacetic acid/sodium nitrite, nitronium tetrafluoroborate or the like without solvent or in an inert solvent such as methylene chloride or the like affords a compound represented by general formula (XXXVIII). The reaction is ordinarily carried out at 0° C. to reflux temperature. The reaction time varies depending on the starting materials, the solvent, the reaction temperature or the like, and is usually 1 hour to 1 day.

(Step 12-2)

The compound (XXXVIII) is reacted with dimethylthiocarbamoyl chloride of formula (XLIX) in the presence of a formula (LII) in an inert solvent to afford a compound represented by general formula (LIII). The solvent employed in the reaction includes dimethylsulfoxide, 1-methyl-2-pyrrolidone, acetonitrile, N,N-dimethylformamide and their mixed solvent. The reaction is ordinarily carried out at room temperature to reflux temperature. The reaction time varies depending on the starting materials, the solvent, the reaction temperature or the like, and is usually 1 to 24 hours.

Of the compounds (XXIV) employed as an intermediate or a starting material in schemes 4, 7 and 8, a compound represented by general formula (XXIVa) wherein $W^1$ is an oxygen atom can be prepared by the method as illustrated in scheme 13.

SCHEME 13

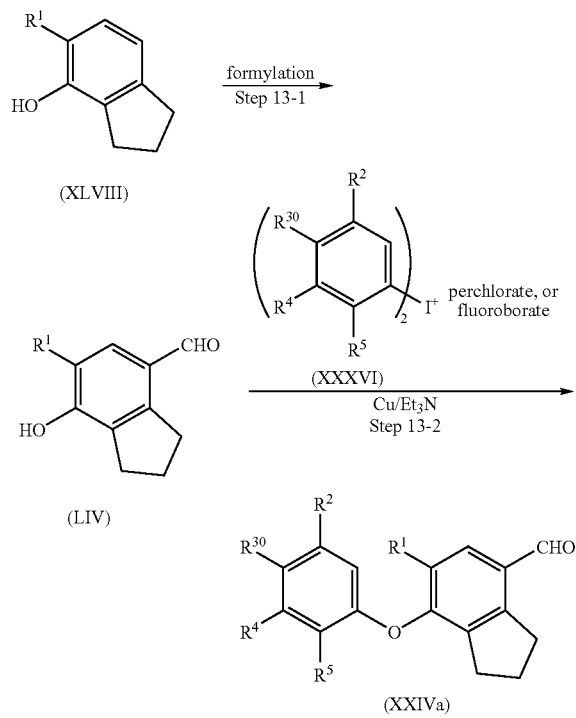

wherein $R^1$, $R^2$, $R^4$, $R^5$ and $R^{30}$ are as defined above.

(Step 13-1)

Formylation of a compound represented by general formula (XLVIII) using a formylating reagent such as chloromethyl methyl ether or the like in the presence of a Lewis acid such as titanium tetrachloride or the like in an inert solvent such as methylene chloride or the like affords a compounds represented by general formula (LIV). Alternatively, the formulation can be carried out using hexamethylenetetramine as a formulating reagent in an acidic solvent such as trifluoroacetic acid or the like. The reaction is ordinarily carried out at 0° C. to reflux temperature. The reaction time varies depending on the starting materials, the solvent, the reaction temperature or the like, and is usually 1 hour to 1 day.

(Step 13-2)

The compound (LIV) can be converted to a compound represented by general formula (XXIVa) by procedures analogous to those described in step 9-1.

Of the compounds (X) employed as a starting material in schemes 1 to 3 and 5, compoumds represented by general formula (Xh), (Xi) and (Xj) can be prepared by the method as illustrated in scheme 14.

SCHEME 14

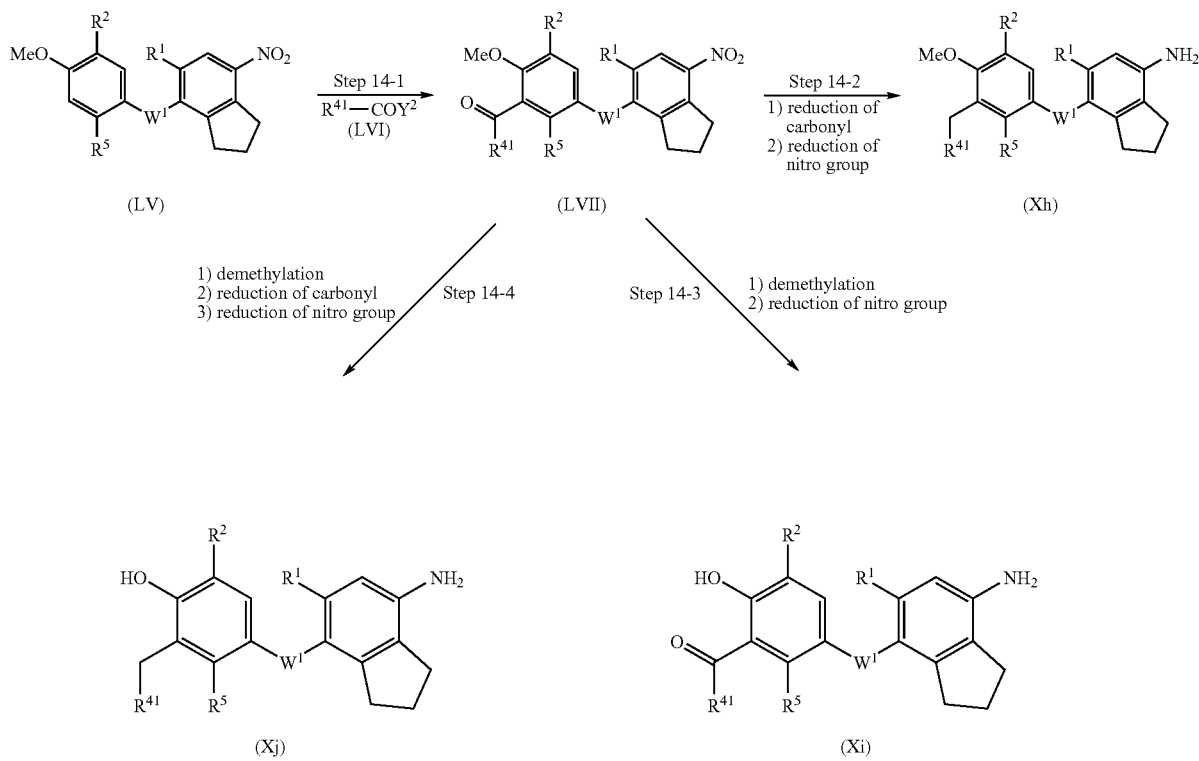

wherein $R^1$, $R^2$, $R^3$ and $W^1$ are as defined above; $R^{41}$ is an alkyl, cycloalkyl, heterocycloalkyl, substituted alkyl, aryl or heteroaryl group; $Y^2$ is a hydroxy group, a chlorine or bronine atom.

(Step 14-1)

A compound represented by general formula (LV) is reacted with a compound represented by general formulas (LVI) in the presence of a Lewis acid such as titanium tetrachloride or the like, or trifluoromethanesulfonic anhydride in an inert solvent such as methylenechloride or the like to afford a compound represented by general formula (LVII). The reaction is ordinarily carried out at 0° C. to reflux temperature. The reaction time varies depending on the starting materials, the solvent, the reaction temperature or the like, and is usually 3 hours to 3 days.

(Step 14-2)

Reduction of the carbonyl group of the compound (LVII) using triethylsilane and trifluoroacetic acid in an inert solvent such as methylene chloride or the like, and thereafter catalytic hydrogenation of the nitro group using a catalyst such as palladium/carbon powder, platinum oxide (IV), platinum/carbon powder or the like in an inert solvent under a pressure of 1 to 5 atmospheres affords a compound represented by general formula (Xh). The reaction temperature in the reduction of the carbonyl group is ordinarily 0° C. to reflux temperature. The reaction time varies depending on the starting materials, the solvent, the reaction temperature or the like, and is usually 3 hours to 3 days. The solvent employed in the catalytic hydrogenation reaction includes ethyl acetate, methanol, ethanol, tetrahydrofuran, water and their mixed solvent. The reaction is ordinarily carried out at room temperature to reflux temperature. The reaction time varies depending on the starting materials, the solvent, the reaction temperature or the like, and is usually 1 hour to 1 day.

(Step 14-3)

Demethylation of the compound (LVII) is carried out in the presence of a Lewis acid such as titanium tetrachloride or the like, or concentrated hydrobromic acid/acetic acid in an inert solvent such as methylenechloride or the like usually at room temperature to reflux temperature for 3 to 72 hours to afford a demethylated compounds. Alternatively, the demethylation is carried out using stannic tetrachloride or a boron trihalide such as boron trichloride, boron tribromide or the like in an inert solvent such as methylene chloride or the like usually at −78° C. to reflux temperature for 1 to 24 hours. Thereafter, the nitro group is reduced by procedures analogous to those described in step 14-2 to afford a compound represented by (Xi).

(Step 14-4)

A compound represented by general formula (Xj) can be prepared from the demethylated compound obtained in step 14-3 via reduction of the carbonyl and nitro group according to procedures analogous to those described in step 14-2.

Of the compounds (X) employed as a starting material in schemes 1 to 3 and 5, compounds represented by general formula (Xk), (Xm) and (Xn) can be prepared by the method as illustrated in scheme 15.

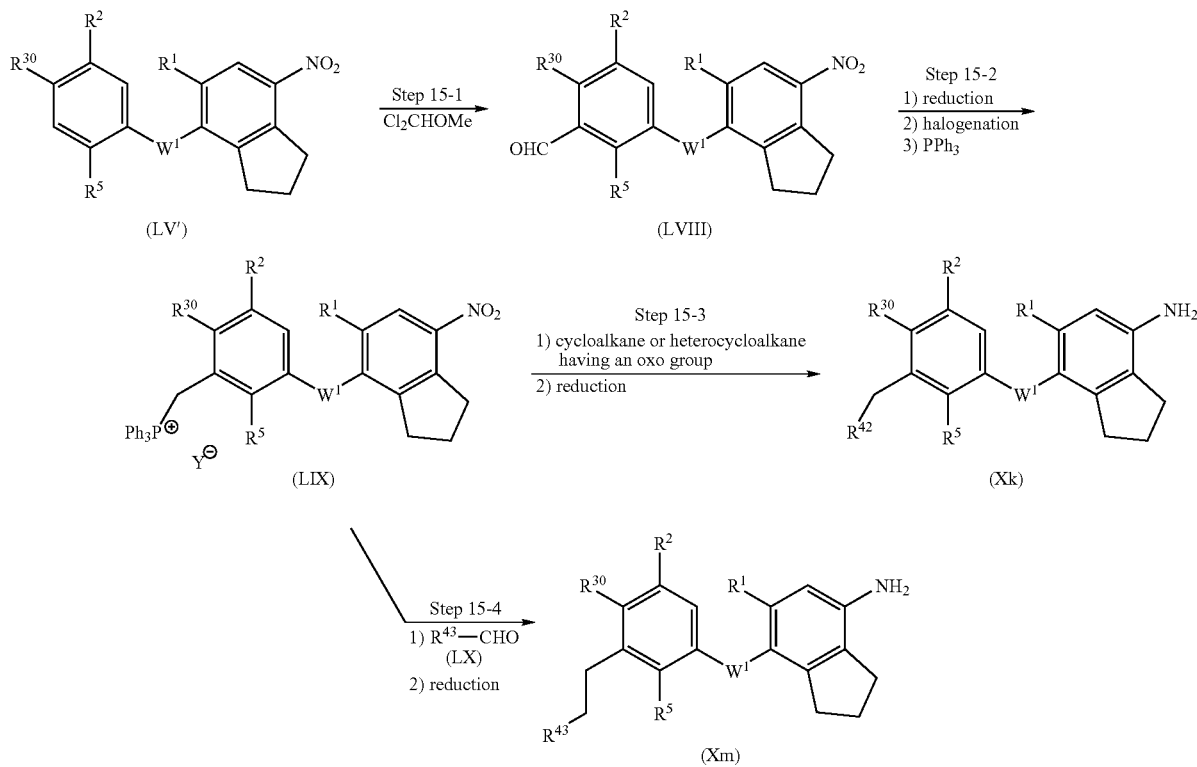

-continued

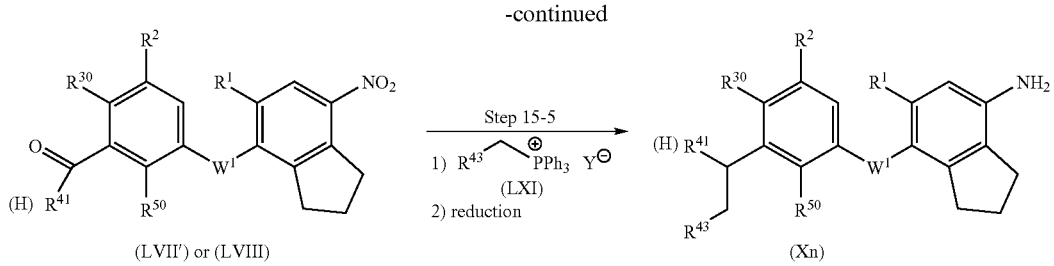

(LVII') or (LVIII) → (Xn)

wherein $R^1$, $R^2$, $R^5$, $R^{30}$, $R^{41}$, $W^1$ and $PPh_3$ are as defined above; $R^{42}$ is a cycloalkyl or heterocycloalkyl group; $R^{43}$ is an alkyl, cycloalkyl, heterocycloalkyl, substituted alkyl, aryl or heteroaryl group; Y is a chlorine, bromine or iodine atom.

(Step 15-1)

A compound represented by general formula (LV') is reacted with dichloromethyl methyl ether in the presence of a Lewis acid such as titanium tetrachloride or the like in an inert solvent such as methylene chloride or the like to afford a compound represented by general formula (LVIII). The reaction is ordinarily carried out at 0° C. to reflux temperature. The reaction time varies depending on the starting materials, the solvent, the reaction temperature or the like, and is usually 3 hours to 2 days.

(Step 15-2)

The compound (LVIII) is reduced with a reducing agent such as sodium borohydride or the like in a suitable solvent such as methanol, ethanol or the like, and the resulting alcohol is halogenated using a halogenating reagent such as thionyl chloride, tribromophosphine, triphenylphosphine/carbon tetrahalide or the like in an inert solvent such as methylene chloride, chloroform or the like to afford a benzylhalide compound. The benzylhalide compound is reacted with triphenylphosphine in an inert solvent such as toluene, xylene or the like to afford a compound represented by general formula (LIX).

(Step 15-3)

Condensation of the compound (LIX) with a cycloalkane or heterocycloalkane which contains an oxo group (carbonyl group) in the ring in the presence of a base such as potassium tert-butoxide, sodium hydride or the like in an inert solvent, and subsequent catalytic hydrogenation of the double bond and nitro group using a catalyst such as palladium/carbon powder, platinum oxide (IV), platinum/carbon powder or the like under a pressure of 1 to 5 atmospheres in an inert solvent afford a compound represented by general formula (Xk). The solvent employed in the condensation reaction includes tetrahydrofuran, N,N-dimethylformamide, toluene, methylene chloride and their mixed solvent. The reaction is ordinarily carried out at 0° C. to reflux temperature. The reaction time varies depending on the starting materials, the solvent, the reaction temperature or the like, and is usually 1 hour to 1 day. The solvent employed in the catalytic hydrogenation reaction includes ethyl acetate, methanol, ethanol, tetrahydrofuran, water and their mixed solvent. The reaction is ordinarily carried out at room temperature to reflux temperature. The reaction time varies depending on the starting materials, the solvent, the reaction temperature or the like, and is usually 1 hour to 1 day.

(Step 15-4)

A compound represented by general formula (Xm) can be prepared from the compound (LIX) and an aldehyde of general formula (LX) via condensation and catalytic hydrogenation according to procedures analogous to those described in step 15-3.

(Step 15-5)

A compound represented by general formula (Xn) can be prepared from compound (LVII') or (LVIII) and a compound of general formula (LXI) via condensation and catalytic hydrogenation according to procedures analogous to those described in step 15-3.

Of compounds represented by general formula (I), compounds represented by general formula (Iq), (Ir) and (Is) can be prepared by the method as illustrated in scheme 16.

SCHEME 16

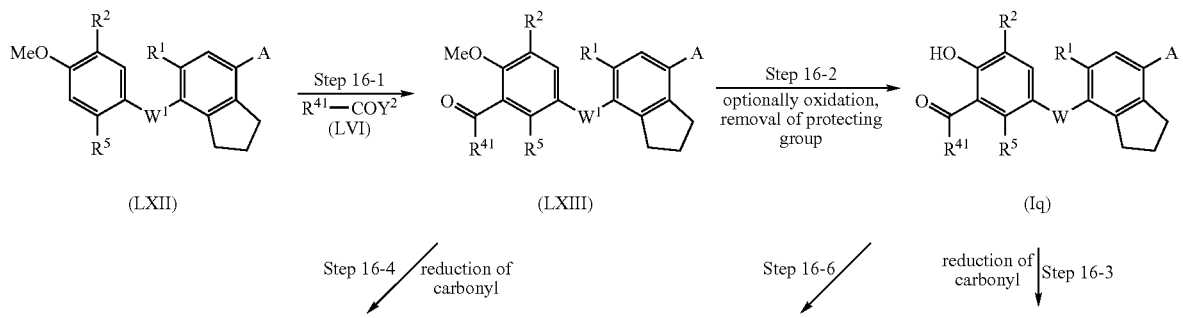

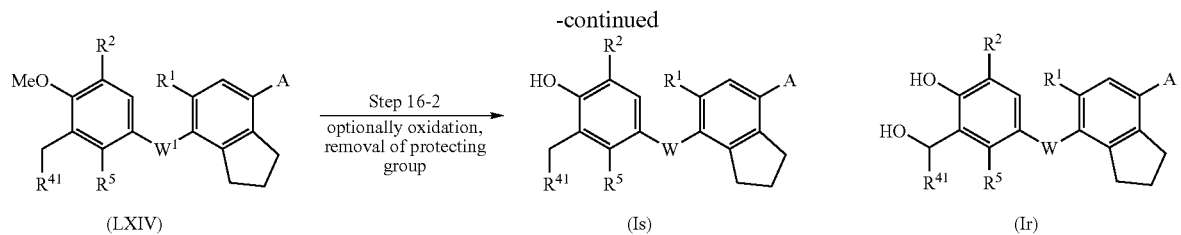

(LXIV) (Is) (Ir)

wherein A, $R^1$, $R^2$, $R^5$, $R^{41}$, $Y^2$, $W^1$ and W are as defined above.

(Steps 16-1 and 16-2)

Acylation of a compound represented by general formula (LXII) with a compound of general formula (LVI) in the presence of a Lewis acid such as titanium tetrachloride or the like, or trifluoromethanesulfonic anhydride in an inert solvent such as methylene chloride or the like affords a compound represented by general formula (LXIII). The reaction is ordinarily carried out at 0° C. to reflux temperature. The reaction time varies depending on the starting materials, the solvent, the reaction temperature or the like, and is usually 3 hours to 3 days. The compound (LXIII) can be converted to a compound represented by general formula (Iq) of the present invention, if required, via oxidation, or removal of a protecting group according to procedures analogous to those described in step 1-3.

(Step 16-3)

A compound represented by general formula (Ir) of the present invention can be prepared by reducing the compound (Iq) using a reducing reagent such as sodium borohydride, sodium triacetoxyborohydride or the like in a suitable solvent. The solvent employed in the reaction includes a protic solvent such as methanol, ethanol etc, or a mixed solvent of such a protic solvent and tetrahydrofuran, 1,2-dimethoxyethane or the like. The reaction is ordinarily carried out at room temperature to reflux temperature. The reaction time varies depending on the starting materials, the solvent, the reaction temperature or the like, and is usually 1 hour to 2 days.

(Steps 16-4 and 16-5)

Reduction of the carbonyl group of the compound (LXIII) using triethylsilane and trifluoroacetic acid in an inert solvent such as methylene chloride, and then, if required, oxidation or removal of a protecting group according to procedures analogous to those described in step 1-3 afford a compound represented by general formula (Is) of the present invention.

(Step 16-6)

Alternatively, the compound (Is) can be prepared by reducing the carbonyl group of the compound (Iq) according to procedures analogous to those described in step 16-4.

Of the compounds (X) employed as a starting material in schemes 1 to 3 and 5, a compound represented by general formula (Xo) can be prepared by the method as illustrated in scheme 17.

SCHEME 17

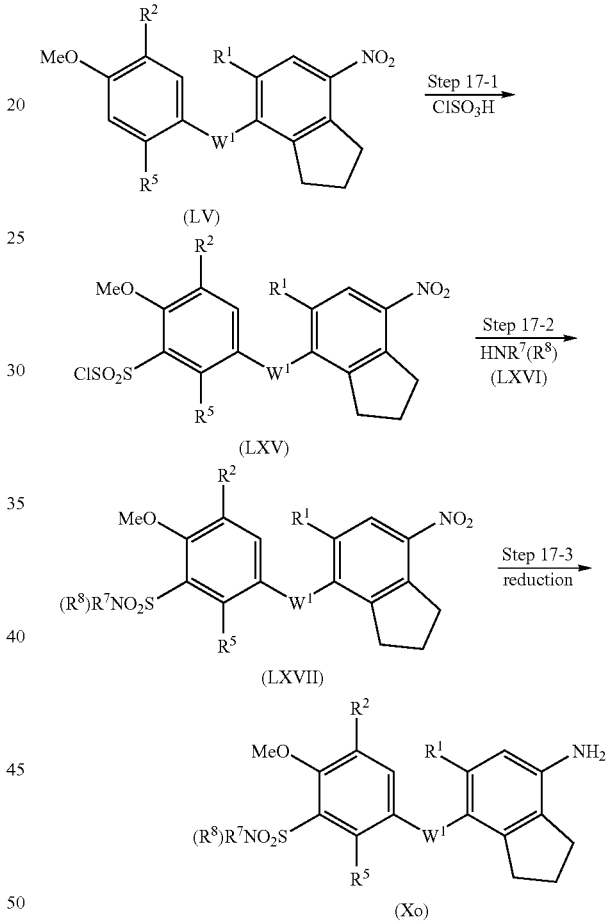

wherein $R^1$, $R^2$, $R^5$, $R^7$, $R^8$ and $W^1$ are as defined above.

(Step 17-1)

Chlorosulfonylation of a compound represented by general formula (LV) using chlorosulfonic acid without solvent or in an inert solvent such as methylene chloride affords a compound represented by general formula (LXV). The reaction is ordinarily carried out at 0° C. to 100° C. The reaction time varies depending on the starting materials, the solvent, the reaction temperature or the like, and is usually 1 hour to 3 days.

(Step 17-2)

Condensation of the compound (LXV) with a compound of general formula (LXVI) in the absence or presence of a base such as cesium carbonate, potassium carbonate, N,N-diisopropyl ethylamine, triethylamine, 2,6-lutidine or the like without solvent or in an inert solvent affords a compound represented by general formula (LXVII). The solvent employed in the reaction includes acetonitrile, N,N-dimethylformamide, tetrahydrofuran, methylene chloride, water and their mixed solvent. The reaction is ordinarily carried out at 0° C. to room temperature. The reaction time varies depending on the starting materials, the solvent, the reaction temperature or the like, and is usually 20 minutes to 24 hours.

(Step 17-3)

Catalytic hydrogenation of the compound (LXVII) using a catalyst such as palladium/carbon powder, platinum oxide or the like in an inert solvent under a pressure of 1 to 5 atmospheres affords a compound represented by general formula (Xo). The solvent employed in the reaction includes ethyl acetate, methanol, ethanol, tetrahydrofuran, water and their mixed solvent. The reaction is ordinarily carried out at room temperature to reflux temperature. The reaction time varies depending on the starting materials, the solvent, the reaction temperature or the like, and is usually 1 hour to 1 day.

Of the compounds (X) employed as a starting material in schemes 1 to 3 and 5, a compound represented by general formula (Xp) can be prepared by the method as illustrated in scheme 18.

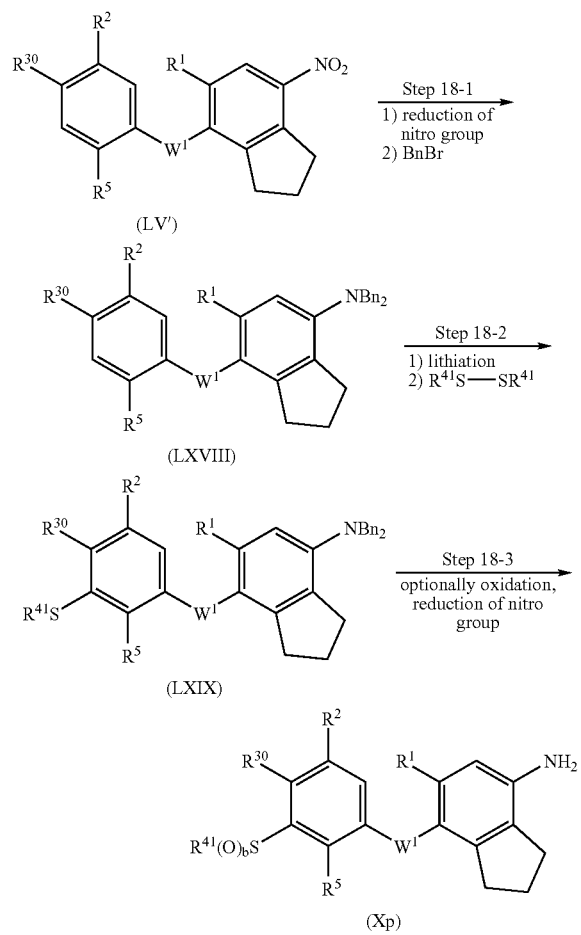

(Step 18-1)

A compound represented by general formula (LXVIII) can be prepared via reduction of the nitro group of a compound represented by general formula (LV'), and subsequent benzylation according to procedures analogous to those described in steps 10-2 and 10-3.

(Step 18-2)

The compound (LXVIII) is lithiated using a lithium reagent such as tert-butyl lithium or the like in an inert solvent such as tetrahydrofuran or the like, and then reacted with a disulfide compound to afford a compound represented by general formula (LXIX). The reaction is ordinarily carried out at −100° C. to room temperature. The reaction time varies depending on the starting materials, the solvent, the reaction temperature or the like, and is usually 1 hour to 1 day.

(Step 18-3)

The sulfur atom of the compound (LXIX) is oxidized, if required, with an oxidizing agent such as potassium permanganate, m-chloroperbenzoic acid, hydrogen peroxide, peracetic acid or the like in an inert solvent such as methylene chloride, tetrahydrofuran or the like, and thereafter catalytically hydrogenated using a catalyst such as palladium/carbon powder or the like in an inert solvent under a pressure of 1 to 5 atmospheres to afford a compound represented by general formula (Xp). The solvent employed in the catalytic hydrogenation reaction includes ethyl acetate, methanol, ethanol, tetrahydrofuran, water and their mixed solvent. The reaction is carried out ordinarily at room temperature to reflux temperature. The reaction time varies depending on the starting materials employed, the solvent, the reaction temperature or the like, and is usually 1 hour to 1 day.

Of the compounds (X) employed as a starting material in schemes 1 to 3 and 5, a compound represented by general formula (Xq) can be prepared by the method as illustrated in scheme 19.

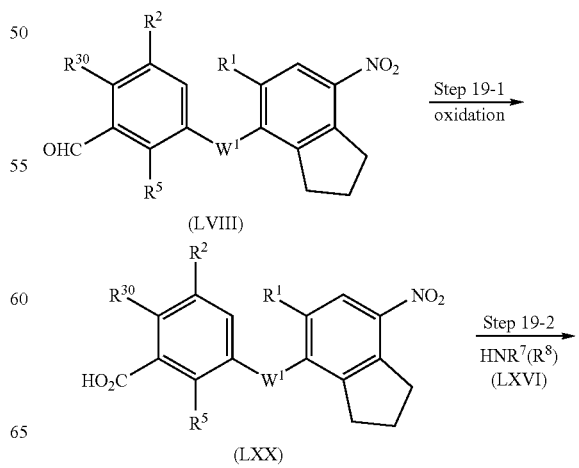

wherein $R^1$, $R^2$, $R^5$, $R^{30}$, $R^{41}$, $W^1$ and Bn are as defined above; b is 0 or an integer of 1 or 2.

-continued

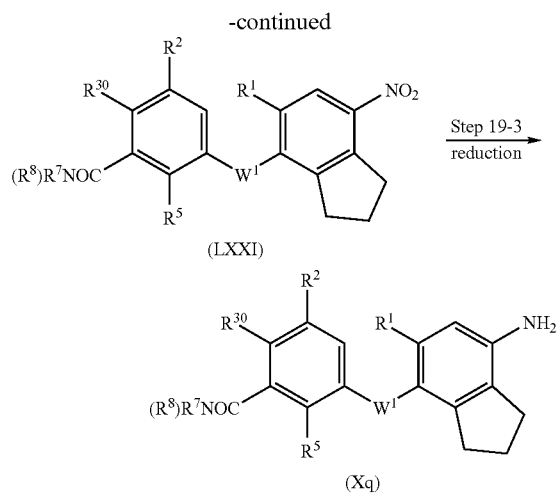

(LXXI)

(Xq)

wherein $R^1$, $R^2$, $R^5$, $R^7$, $R^8$, $R^{30}$ and $W^1$ are as defined above.

(Step 19-1)

Oxidation of a compound represented by general formula (LVIII) using sodium chlorite and 2-methyl-2-butene in an aqueous solution of tert-butanol/disodium hydrogen phosphate affords a compound of general formula (LXX). The reaction is ordinarily carried out at 0° C. to room temperature. The reaction time varies depending on the starting materials, the solvent, the reaction temperature or the like, and is usually 1 hour to 3 days.

(Step 19-2)

The compound (LXX) is reacted with a compound of general formula (LXVI) in the presence of a condensing reagent such as dicyclohexylcarbodiimide, 1-(3-dimethylaminopropyl)-3-ethylcarbodiimide hydrochloride, diethyl cyanophosphate, diphenylphosporylazide or the like in an inert solvent to afford a compound of general formula (LXXI). The solvent employed in the reaction includes acetonitrile, N,N-dimethylformamide, tetrahydrofuran, methylene chloride and their mixed solvent. The reaction is carried out ordinarily at 0° C. to room temperature. The reaction time varies depending on the starting materials employed, the solvent, the reaction temperature or the like, and is usually 1 to 24 hours.

(Step 19-3)

Catalytic hydrogenation of the compound (LXXI) using a catalyst such as palladium/carbon powder, platinum oxide or the like in an inert solvent under a pressure of 1 to 5 atmospheres affords a compound of general formula (Xq). The solvent employed in the reaction includes ethyl acetate, methanol, ethanol, tetrahydrofuran, water and their mixed solvent. The reaction is ordinarily carried out at room temperature to reflux temperature. The reaction time varies depending on the starting materials employed, the solvent, the reaction temperature or the like, and is usually 1 hour to 1 day.

Of the compounds (X) employed as a starting material in schemes 1 to 3 and 5, a compound represented by general formula (Xr) can be prepared by the method as illustrated in scheme 20.

SCHEME 20

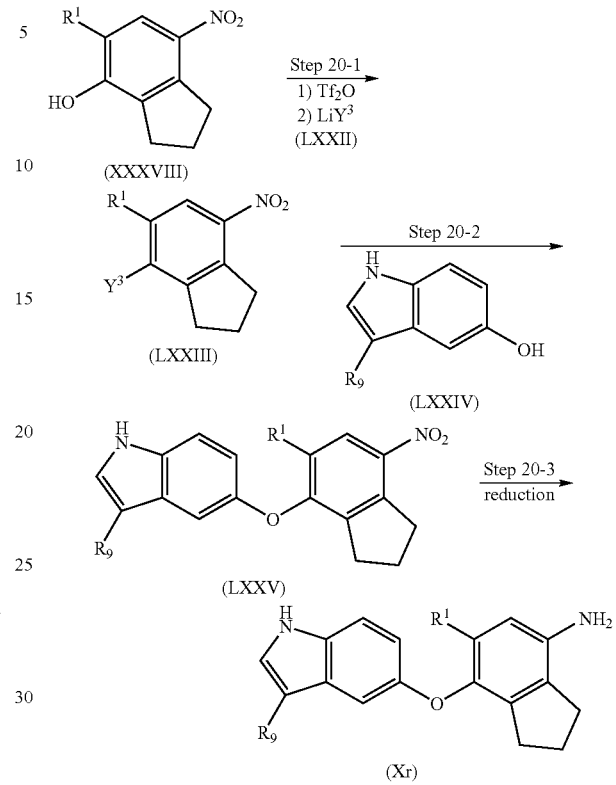

wherein $R^1$, $R^2$, $R^9$, $W^1$ and $Tf_2O$ are as defined above; $Y^3$ is a fluorine, chlorine, bromine or iodine atom.

(Step 20-1)

A compound of general formula (XXXVIII) is reacted with trifluoromethanesulfonic anhydride in the absence or presence of a base such as pyridine, N,N-diisopropylethylamine, triethylamine, 2,6-lutidine or the like in an inert solvent such as acetonitrile, N,N-dimethylformamide, tetrahydrofuran, methylene chloride and their mixed solvent to afford a trifluoromethanesulfonic acid ester. The reaction is ordinarily carried out at −20° C. to room temperature. The reaction time varies depending on the starting materials, the solvent, the reaction temperature or the like, and is usually 15 minutes to 1 day.

The trifluoromethanesulfonic acid ester is reacted with a lithium halide of general formula (LXXII) in an inert solvent such as dimethylsulfoxide, 1-methyl-2-pyrrolidone, acetonitrile, N,N-dimethylformamide and their mixed solvent to afford a compound of general formula (LXXIII). The reaction is ordinarily carried out at room temperature to reflux temperature. The reaction time varies depending on the starting materials, the solvent, the reaction temperature or the like, and is usually 1 hour to 1 day.

(Step 20-2)

The compound (LXXIII) is reacted with a compound of general formula (LXXIV) in the presence of a base such as potassium carbonate, sodium carbonate or the like in an inert solvent such as acetonitrile, N,N-dimethylformamide, tetrahydrofuran, methylene chloride and their mixed solvent to afford a compound of general formula (LXXV). The reaction is ordinarily carried out at room temperature to reflux temperature. The reaction time varies depending on the starting materials, the solvent, the reaction temperature or the like, and is usually 1 hour to 1 day.

(Step 20-3)

Catalytic hydrogenation of a compound represented by general formula (LXXV) using a catalyst such as palladium/carbon powder, platinum oxide or the like in an inert solvent under a pressure of 1 to 5 atmospheres affords a compound of general formula (Xr). The solvent employed in the reaction includes ethyl acetate, methanol, ethanol, tetrahydrofuran, water and their mixed solvent. The reaction is ordinarily carried out at room temperature to reflux temperature. The reaction time varies depending on the starting materials, the solvent, the reaction temperature or the like, and is usually 1 hour to 1 day.

The compounds represented by general formula (I) of the present invention and intermediates for preparing the compounds of the present invention can be isolated or purified, if required, according to conventional isolation or purification techniques well known to those in the art, such as crystallization, recrystallization, chromatography, preparative high performance liquid chromatography or the like.

The compounds of the present invention prepared in the above-mentioned schemes exhibit serum cholesterol lowering activities and/or triglyceride lowering activities, and are useful as a therapeutic or prophylactic agent for hyperlipidemia.

The compounds of the present invention can be used, if required, in combination with antihyperlipidemic agents other than thyroid hormone receptor ligands. Examples of such antihyperlipidemic agents include HMG-CoA reductase inhibitors, anion exchange resins, fibrates, MTP inhibitors, CETP inhibitors, nicotinic acid preparations, probucol and ACAT inhibitors. Examples of HMG-CoA reductase inhibitors which may be used in combination with compounds of the present invention include pravastatin, simvastatin, rosuvastatin, fluvastatin, atorvastatin, cerivastatin, nisvastatin and the like. Examples of anion exchange resins which may be used in combination with compounds of the present invention include cholestyramine, cholestipol and the like. Examples of fibrates which may be used in combination with compounds of the present invention include bezafibrate, fenofibrate, gemfibrozil, simfibrate, ciprofibrate and clinofibrate and the like. Examples of MTP (microsomal triglyceride transfer protein) inhibitors which may be used in combination with compounds of the present invention include BMS-201038, BMS-212122, R-103757 and the like. Examples of CETP (cholesteryl ester transfer protein) inhibitors which may be used in combination with compounds of the present invention include CETi-1, JTT-705, CP-529414 and the like. Examples of nicotinic acid preparations which may be used in combination with compounds of the present invention include nicotinic acid, tocopherol nicotinate, niceritrol, nicomol and the like. Examples of ACAT (acyl-CoA:cholesterol O-acyl transferase) inhibitors which may be used in combination with compounds of the present invention include avasimibe (CI-1011), eflucimibe (F-12511) and the like.

The compounds of the present invention exhibit thermogenic activities, and are useful as a therapeutic or prophylactic agent for obesity.

The compounds of the present invention can be used, if required, in combination with antiobesity agents other than thyroid hormone receptor ligands. Examples of such antiobesity agents include anorectic agents and β3-adrenoceptor agonists. Examples of anorectic agents include monoamine reuptake inhibitors, serotonergic agents, dopaminergic agents, neuropeptide Y antagonists, leptin or CCK-A (cholecystokinin-A) agonists. Examples of monoamine reuptake inhibitors which may be used in combination with compounds of the present invention include sibutramine, milnacipran, duloxetine, venlafaxine and the like. Examples of serotonergic agents which may be used in combination with compounds of the present invention include fenfluramine, dexfenfluramine and the like. Examples of dopaminergic agents which may be used in combination with compounds of the present invention include bromocriptine and the like. Examples of neuropeptide Y antagonists which may be used in combination with compounds of the present invention include CP-671906-01, J-115814 and the like. Examples of leptin which may be used in combination with compounds of the present invention include human recombinant leptin and the like. Examples of CCK-A agonists which may be used in combination with compounds of the present invention include GW-7178, SR-146131 and the like. Examples of β3-adrenoceptor agonists which may be used in combination with compounds of the present invention include KUC-7483, AJ-9677, LY-377604, SB-418790, N-5984 and the like.

The compounds of the present invention ameliorate obesity which is a risk factor of diabetes mellitus, and lower serum triglyceride. Furthermore, the compounds of the present invention improve glucose tolerance in peripheral tissues, and are useful as a therapeutic or prophylactic agent for diabetes mellitus, or diseases associated with diabetes mellitus.

The compounds of the present invention can be used, if required, in combination with antidiabetic agents other than thyroid hormone receptor ligands. Examples of such antidiabetic agents include α-glucosidase inhibitors, insulin sensitizers, insulin preparations, insulin secretion stimulants, biguanides, glucagon-like peptide 1, DPPIV inhibitors and SGLT inhibitors. Examples of α-glucosidase inhibitors which may be used in combination with compounds of the present invention include acarbose, miglitol, voglibose and the like. Examples of insulin sensitizers which may be used in combination with compounds of the present invention include pioglitazone, rosiglitazone, englitazone, darglitazone, isaglitazone, MCC-55, GI-262570, JTT-501 and the like. Examples of insulin preparations which may be used in combination with compounds of the present invention include genetically engineered human insulin, insulins extracted from bovine or swine pancreas or the like. Examples of insulin secretion stimulants which may be used in combination with compounds of the present invention include sulfonylureas such as tolbutamide, chlorpropamide, tolazamide, acetohexamide, glibenclamide, glipizide, gliclazide and the like; as well as mitiglinide (KAD-1229), nateglinide (AY-4116), glimepiride (Hoe490) and the like. Examples of biguanides which may be used in combination with compounds of the present invention include phenformin, metformin, butformin and the like. Examples of glucagon-like peptide 1 (GLP-1) include GLP-1 (1–36) amide, GLP-1 (7–36) amide, GLP-1 (7–37) and the like. Examples of DPPIV (dipeptidyl peptidase IV) inhibitors which may be used in combination with compounds of the present invention include P-32/98, NVP-DPP-728 and the like. Examples of SGLT (Na-dependent glucose cotransporter) inhibitors which may be used in combination with compounds of the present invention include compounds disclosed in WO01/16147, WO01/68660, WO01/27128, WO01/74834, WO01/74835, WO02/28872, WO02/44192, WO02/53573, WO02/64606, WO02/68439, WO02/68440, WO02/98893, EP850948, JP12/080041, JP11/21243 or JP09/188,625.

The compounds of the present invention exhibit antidepressive activities by stimulating cerebral thyroid hormone receptors, and are useful as a therapeutic or prophylactic agent for depression.

The compounds of the present invention can be used, if required, in combination with antidepressants other than thyroid hormone receptor ligands. Examples of such antidepressants include monoamine oxidase inhibitors such as phenelzine, tranylcypromine and the like; selective serotonin reuptake inhibitors such as paroxetine, fluoxetine, sertraline and the like; tricyclic antidepressants such as amoxapine, amitriptyline, perphenazine, desipramine, nortriptyline, doxepine, trimipramine, imipramine and the like.

The compounds of the present invention decrease peripheral vascular resistance and exhibit hypotensive activities, and are useful as a therapeutic or prophylactic agent for hypertension.

The compounds of the present invention can be used, if required, in combination with antihypertensive agents other than thyroid hormone receptor ligands. Example of such antihypertensive agents include calcium channel blockers such as diltiazem, nifedipine, verapamil, nicardipine, isradipine, bepridil, vatanidipine, azelnidipine, aranidipine, felodipine, cilnidipine, amlodipine, lercanidipine, nitrendipine, efonidipine, manidipine, benidipine, barnidipine, nisoldipine and the like; angiotensin converting enzyme inhibitors such as captopril, enalapril, quinapril, ramipril, benazepril, trandolapril, fosinopril, delapril, imidapril, cilazapril, temocapril, perindopril, omapatrilat, lisinopril and the like; angiotensin II inhibitors such as losartan, irbesartan, olemesartan medoxomil, candesartan cilexetil, telmisartan, eprosartan, valsartan and the like; α1-adrenoceptor antagonists such as bunazosin, urapidil amosulalol, doxazosin and the like; β1-adrenoceptor antagonists such as bisoprolol, bevantolol, betaxolol and the like; potassium channel openers such as pinacidil and the like; aldosterone antagonists such as torasemide, eplerenone and the like.

In the case of using a pharmaceutical composition comprising a compound represented by general formula (I) or a pharmaceutically acceptable salt thereof for a medical treatment, various dosage forms can be administered depending on their usages. Exemplary dosage forms include powders, granules, fine granules, dry syrups, tablets, capsules, injections, liquids, ointments, suppositories, poultices and the like, which are administered orally or parenterally.

Pharmaceutical compositions can be formulated by admixing, diluting or dissolving with appropriate pharmaceutical additives such as excipients, disintegrators, binders, lubricants, diluents, buffers, isotonic agents, preservatives, wetting agents, emulsifying agents, dispersing agents, stabilizing agents, solubilizing agents and the like, according to a conventional formulation procedure depending upon their dosage forms.

In the case of using a pharmaceutical composition of the present invention for a medical treatment, the dosage of a compound represented by general formula (I) or a pharmaceutically acceptable salt thereof is appropriately determined depending on the age, sex or body weight of the individual patient, the severity of the disease, the condition to be treated and the like. A typical dosage for oral administration is in the range of from about 0.1 μg to about 100 mg per day per adult human. A typical dosage for parenteral administration is in the range of from about 0.1 μg to about 30 mg per day per adult human. The dosages may be administered in single or divided doses, for example one to several times daily.

Where a compound represented by general formula (I) or a pharmaceutically acceptable salt thereof is used in combination with at least one selected from an antihyperlipidemic agent, an antiobesity agent, an antidiabetic agent, an antihypertensive agent and an antidepressant other than thyroid hormone receptor ligand, pharmaceutical compositions can be formulated by admixing separately each of active ingredients, or admixing concurrently both of active ingredients, with pharmaceutically acceptable additives such as excipients, disintegrators, binders, lubricants, diluents, buffers, isotonic agents, preservatives, wetting agents, emulsifying agents, dispersing agents, stabilizing agents, solubilizing agents and the like, and administered separately or concurrently in an oral or pareteral dosage form. Where separately formulated pharmaceutical compositions are used, the compositions may be mixed together with an appropriate diluent, and administered simultaneously. Alternatively, where separately formulated pharmaceutical compositions are used, the compositions may be administered separately, concurrently or at different intervals.

In a pharmaceutical combination comprising a compound represented by general formula (I) or a pharmaceutically acceptable salt thereof, and at least one selected from an anti-hyperlipidemic agent, an antiobesity agent, an antidiabetic agent, an antihypertensive agent and an antidepressant other than thyroid hormone receptor ligand, the dosage of each active ingredient may be appropriately determined depending on the age, sex or body weight of the individual patient, the severity of the disease, administration time, dosage form, administration method, combination of active ingredients and the like.

BEST MODE FOR CARRYING OUT THE INVENTION

The following examples, reference examples and test examples illustrate the invention in further detail. It is to be understood, however, that they are not to be construed as limiting the scope of the invention in any way.

REFERENCE EXAMPLE 1

5-Bromoindan-4-ol

To a solution of indan-4-ol (24.2 g) in dichloromethane (200 mL) was added diisopropylamine (2.55 mL). To the solution was added N-bromosuccinimide (32.07 g) in small portions under ice-cooling, and the mixture was stirred at room temperature overnight. Diluted sulphuric acid (pH1, 200 mL) was added to the reaction mixture, and the mixture was separated. The organic layer was washed with water and brine successively, and dried over anhydrous magnesium sulfate. The solvent was removed under reduced pressure. The residue was purified by column chromatography on silica gel (eluent: hexane/ethyl acetate=3/1–1/1) to give the title compound (31.1 g).

$^1$H-NMR (CDCl$_3$) δ ppm: 2.05–2.16 (2H, m), 2.83–2.95 (4H, m), 5.45 (1H, s), 6.69 (1H, d, J=8.0 Hz), 7.22 (1H, d, J=8.0 Hz).

REFERENCE EXAMPLE 2

5-Iodo-7-nitroindan-4-ol

To a solution of 5-iodoindan-4-ol (358 mg) in acetic acid (3 mL) was added water (0.5 mL). To the solution was added nitric acid (60%, 0.105 mL) in small portions under ice-cooling, and the mixture was stirred under ice-cooling for 20 min. After adding water (10 mL) and aqueous sodium sulfite (1.5 g/10 mL) successively, the mixture was extracted with ethyl acetate. The organic layer was washed with water, saturated sodium hydrogen carbonate and brine successively, and dried over anhydrous magnesium sulfate. The solvent was removed under reduced pressure. The residue was crystallized from a small amount of dichloromethane and hexane to give the title compound (70 mg).

$^1$H-NMR (CDCl$_3$) δ ppm: 2.13–2.22 (2H, m), 2.95–3.01 (2H, m), 3.35–3.44 (2H, m), 5.81 (1H, s), 8.40 (1H, s).

REFERENCE EXAMPLE 2-1

5-Bromo-7-nitroindan-4-ol

The title compound was prepared in a similar manner to those described in Reference Example 2 using 5-bromoindan-4-ol instead of 5-iodoindan-4-ol.

$^1$H-NMR (CDCl$_3$) δ ppm: 2.13–2.26 (2H, m), 2.95–3.02 (2H, m), 3.36–3.43 (2H, m), 6.04 (1H, s), 8.25 (1H, s).

REFERENCE EXAMPLE 2-2

5-Methyl-7-nitroindan-4-ol

The title compound was prepared in a similar manner to those described in Reference Example 2 using 5-methylindan-4-ol instead of 5-iodoindan-4-ol.

$^1$H-NMR (DMSO-d$_6$) δ ppm: 2.00–2.10 (2H, m), 2.20 (3H, s), 2.81–2.87 (2H, m), 3.21–3.28 (2H, m), 7.82 (1H, s), 10.01 (1H, s).

REFERENCE EXAMPLE 3

O-(5-methyl-7-nitroindan-4-yl) dimethylthiocarbamate

5-Methyl-7-nitroindan-4-ol (5.0 g) was dissolved in N,N-dimethylformamide (50 mL). After adding triethylenediamine (5.8 g) and dimethylthiocarbamoyl chloride (4.8 g) with stirring at room temperature, the mixture was stirred at 75° C. for 5 hours. The reaction mixture was cooled to room temperature. Water (100 mL) was added to the reaction mixture. The insoluble material was collected by filtration, washed with diethyl ether and dried to give the title compound (5.80 g).

$^1$H-NMR (CDCl$_3$) δ ppm: 2.00–2.35 (5H, m), 2.75–3.03 (2H, m), 3.30–3.55 (8H, m), 7.90–8.00 (1H, m).

REFERENCE EXAMPLE 4

S-(5-methyl-7-nitroindan-4-yl) dimethylthiocarbamate

O-(5-methyl-7-nitroindan-4-yl) dimethylthiocarbamate (5.0 g) was melted at 180° C. and stirred for 6 hours. The reaction mixture was cooled to room temperature to give the title compound (5.0 g).

$^1$H-NMR (CDCl$_3$) δ ppm: 2.05–2.30 (2H, m), 2.47 (3H, s), 2.90–3.30 (8H, m), 3.35–3.55 (2H, m), 7.85–7.95 (1H, m)

REFERENCE EXAMPLE 5

5-Methyl-7-nitroindan-4-thiol

A suspension of S-(5-methyl-7-nitroindan-4-yl) dimethylthiocarbamate (5.0 g) in a 2 mol/L aqueous solution of sodium hydroxide (30 mL) and methanol (30 mL) was stirred at 90° C. under an argon atmosphere for 6 hours. The reaction mixture was cooled to room temperature. The reaction mixture was acidified by 1 mol/L hydrochloric acid, and extracted with ethyl acetate. The organic layer was washed with brine and dried over anhydrous magnesium sulfate. The solvent was removed under reduced pressure. The residue was purified by column chromatography on silica gel (eluent: hexane/ethyl acetate=5/1–3/1) to give the title compound (1.87 g).

$^1$H-NMR (CDCl$_3$) δ ppm: 2.15–2.30 (2H, m), 2.38 (3H, s), 2.85–3.00 (2H, m), 3.35–3.50 (2H, m), 3.55 (1H, s), 7.86 (1H, s).

REFERENCE EXAMPLE 6

7-Hydroxy-6-methylindan-4-carbaldehyde

5-Methylindan-4-ol (4.50 g) and hexamethylenetetramine (4.26 g) were dissolved in trifluoroacetic acid (100 mL), and the mixture was stirred at 90° C. overnight. Water was added to the reaction mixture. After stirring for 30 min, the reaction mixture was extracted with ethyl acetate. The organic layer was washed with water, saturated sodium hydrogen carbonate and brine successively, and dried over anhydrous magnesium sulfate. The solvent was removed under reduced pressure to give the title compound (4.76 g).

$^1$H-NMR (CDCl$_3$) δ ppm: 2.10–2.40 (5H, m), 2.75–2.95 (2H, m), 3.20–3.40 (2H, m), 7.50 (1H, d, J=0.4 Hz), 9.88 (1H, s).

REFERENCE EXAMPLE 7

Bis[4-benzyloxy-3-(4-fluorobenzyl)phenyl]iodonium tetrafluoroborate

Fuming nitric acid (85 mL) was added to acetic anhydride (226 mL) under ice-cooling. To the reaction mixture was added iodine (76.1 g), and then added dropwise trifluoroacetic acid (175 mL). After stirring at room temperature for 1 hour, the mixture was evaporated under reduced pressure to dryness. To the residue were added acetic anhydride (500 mL) and 1-benzyloxy-2-(4-fluorobenzyl) benzene (391 g), then trifluoroacetic acid (100 mL) dropwise under ice-cooling. After stirring at 4° C. for 4 days, the reaction mixture was evaporated under reduced pressure to dryness. To the residue were added methanol (1000 mL), an aqueous solution of potassium metabisulfite (100 g/500 mL) and a 4 mol/L aqueous solution of sodium tetrafluoroborate (1250 mL) successively. The mixture was stirred for 2 hours. After the precipitate was aggregated, the supernatant was decanted. The residue was dissolved in dichloromethane (1000 mL), and the organic layer was washed with a 4.5 mol/L aqueous solution of sodium tetrafluoroborate (500 mL) and dried over anhydrous magnesium sulfate. The solvent was removed under reduced pressure. The residue was triturated with diethyl ether. The insoluble material was collected by filtration to give the title compound (263 g).

$^1$H-NMR (CDCl$_3$) δ ppm: 3.89 (4H, s), 5.03 (4H, s), 6.83–6.93 (6H, m), 7.03–7.07 (4H, m), 7.23–7.28 (4H, m), 7.31–7.39 (6H, m), 7.60 (2H, d, J=2.5 Hz), 7.80 (2H, dd, J=2.5, 8.9 Hz).

REFERENCE EXAMPLE 7-1

Bis(4-methoxyphenyl)iodonium tetrafluoroborate

The title compound was prepared in a similar manner to those described in Reference Example 7 using anisole instead of 1-benzyloxy-2-(4-fluorobenzyl)benzene.

¹H-NMR (CDCl₃) δ ppm: 3.83 (6H, s), 6.95 (4H, d, J=9.2 Hz), 7.91 (4H, d, J=9.2 Hz).

REFERENCE EXAMPLE 7-2

Bis(3-acetyl-2,4-dimethoxyphenyl)iodonium tetrafluoroborate

The title compound was prepared in a similar manner to those described in Reference Example 7 using 1-(2,6-dimethoxyphenyl)ethanone instead of 1-benzyloxy-2-(4-fluorobenzyl) benzene.

¹H-NMR (CDCl₃) δ ppm: 2.54 (6H, s), 3.87 (6H, s), 3.93 (6H, s), 6.77 (2H, d, J=9.1 Hz), 7.92 (2H, d, J=9.1 Hz).

REFERENCE EXAMPLE 8

4-(4-Methoxyphenoxy)-5-methyl-7-nitroindane

To a stirred suspension of 5-methyl-7-nitroindan-4-ol (6 g), bis(4-methoxyphenyl)iodonium tetrafluoroborate (17 g), and copper bronze (2 g) in dichloromethane (150 mL) was added triethylamine (5.6 mL) at room temperature. The mixture was stirred at room temperature for 5 days. The insoluble material was removed by filtration. The filtrate was evaporated under reduced pressure to dryness. The residue was purified by column chromatography on silicagel (eluent: hexane/ethyl acetate) to give the title compound (7.3 g).

¹H-NMR (CDCl₃) δ ppm: 1.99–2.13 (2H, m), 2.24 (3H, s), 2.65 (2H, t, J=7.6 Hz), 3.37 (2H, t, J=7.6 Hz), 3.77 (3H, s), 6.73 (2H, d, J=9.1 Hz), 6.81 (2H, d, J=9.1 Hz), 7.96 (1H, s).

REFERENCE EXAMPLE 8-1

4-(4-Benzyloxy-3-isopropylphenoxy)-5-methyl-7-nitroindane

The title compound was prepared in a similar manner to those described in Reference Example 8 using bis(4-benzyloxy-3-isopropylphenyl)iodonium tetrafluoroborate instead of bis(4-methoxyphenyl)iodonium tetrafluoroborate.

¹H-NMR (CDCl₃) δ ppm: 1.20 (6H, d, J=6.9 Hz), 2.05 (2H, t, J=7.5 Hz), 2.25 (3H, s), 2.64 (2H, t, J=7.6 Hz), 3.30–3.50 (3H, m), 5.03 (2H, s), 6.44 (1H, dd, J=8.8, 3.1 Hz), 6.70–6.90 (2H, m), 7.25–7.50 (5H, m), 7.96 (1H, d, J=0.6 Hz).

REFERENCE EXAMPLE 8-2

4-[4-benzyloxy-3-(4-fluorobenzyl)phenoxy]-5-methyl-7-nitroindane

The title compound was prepared in a similar manner to those described in Reference Example 8 using bis[4-benzyloxy-3-(4-fluorobenzyl)phenyl]iodonium tetrafluoroborate instead of bis(4-methoxyphenyl)iodonium tetrafluoroborate.

¹H-NMR (CDCl₃) δ ppm: 2.00–2.08 (2H, m), 2.22 (3H, s), 2.57–2.62 (2H, m), 3.33–3.38 (2H, m), 3.92 (2H, s), 4.99 (2H, s), 6.52 (1H, dd, J=3.0, 8.8 Hz), 6.63 (1H, d, J=3.0 Hz), 6.79 (1H, d, J=8.8 Hz), 6.87–6.93 (2H, m), 7.06–7.11 (2H, m), 7.25–7.37 (5H, m), 7.94 (1H, s).

REFERENCE EXAMPLE 8-3

4-(4-benzyloxy-3-isopropylphenoxy)-5-iodo-7-nitroindane

The title compound was prepared in a similar manner to those described in Reference Example 8 using 5-iodo-7-nitroindan-4-ol instead of 5-methyl-7-nitroindan-4-ol and using bis(4-benzyloxy-3-isopropylphenyl)iodonium tetrafluoroborate instead of bis(4-methoxyphenyl)iodonium tetrafluoroborate.

¹H-NMR (CDCl₃) δ ppm: 1.20 (6H, d, J=6.9 Hz), 1.97–2.08 (2H, m), 2.55–2.63 (2H, m), 3.30–3.41 (3H, m), 5.04 (2H, s), 6.49 (1H, dd, J=3.0, 8.8 Hz), 6.79 (1H, d, J=8.8 Hz), 6.86 (1H, d, J=3.0 Hz), 7.30–7.46 (5H, m), 8.53 (1H, s).

REFERENCE EXAMPLE 8-4

3-Chloro-6-[2-methoxy-5-(5-methyl-7-nitroindan-4-yloxy) benzyl]pyridazine

The title compound was prepared in a similar manner to those described in Reference Example 8 using bis[3-(6-chloropyridazin-3-ylmethyl)-4-methoxyphenyl]iodonium perchlorate instead of bis(4-methoxyphenyl)iodonium tetrafluoroborate.

¹H-NMR (CDCl₃) δ ppm: 2.00–2.10 (2H, m), 2.21 (3H, s), 2.57–2.64 (2H, m), 3.33–3.40 (2H, m), 3.78 (3H, s), 4.28 (2H, s), 6.59 (1H, dd, J=3.0, 8.9 Hz), 6.76 (1H, d, J=8.9 Hz), 6.80 (1H, d, J=3.0 Hz), 7.29 (1H, d, J=8.8 Hz), 7.37 (1H, d, J=8.8 Hz), 7.96 (1H, s).

REFERENCE EXAMPLE 8-5

4-(4-Benzyloxy-3-isopropylphenoxy)-5-bromo-7-nitroindane

The title compound was prepared in a similar manner to those described in Reference Example 8 using 5-bromo-7-nitroindan-4-ol instead of 5-methyl-7-nitroindan-4-ol and using bis(4-benzyloxy-3-isopropylphenyl)iodonium tetrafluoroborate instead of bis(4-methoxyphenyl)iodonium tetrafluoroborate.

¹H-NMR (CDCl₃) δ ppm: 1.20 (6H, d, J=6.9 Hz), 2.02–2.11 (2H, m), 2.63–2.70 (2H, m), 3.32–3.43 (3H, m), 5.05 (2H, s), 6.49 (1H, dd, J=3.0, 8.8 Hz), 6.78 (1H, d, J=8.8 Hz), 6.86 (1H, d, J=3.0 Hz), 7.30–7.47 (5H, m), 8.34 (1H, s).

REFERENCE EXAMPLE 8-6

5-Benzyloxy-8-(5-bromo-7-nitroindan-4-yloxy)-1,2,3,4-tetrahydronaphthalene

The title compound was prepared in a similar manner to those described in Reference Example 8 using bis(4-benzyloxy-5,6,7,8-tetrahydro-1-naphtyl)iodonium tetrafluoroborate instead of bis(4-methoxyphenyl)iodonium tetrafluoroborate.

¹H-NMR (CDCl₃) δ ppm: 1.73–1.78 (4H, m), 2.03–2.10 (2H, m), 2.50–2.92 (6H, m), 3.33–3.40 (2H, m), 5.00 (2H, s), 6.19 (1H, d, J=8.8 Hz), 6.55 (1H, d, J=8.8 Hz), 7.28–7.44 (5H, m), 8.34 (1H, s).

REFERENCE EXAMPLE 8-7

1-[2,6-Bis-benzyloxy-3-(5-methyl-7-nitroindan-4-yloxy) phenyl]ethanone

The title compound was prepared in a similar manner to those described in Reference Example 8 using bis(3-acetyl-2,4-dibenzyloxyphenyl)iodonium tetrafluoroborate instead of bis(4-methoxyphenyl)iodonium tetrafluoroborate.

¹H-NMR (CDCl₃) δ ppm: 2.03–2.12 (2H, m), 2.28 (3H, s), 2.45 (3H, s), 2.65–2.70 (2H, m), 3.35–3.42 (2H, m), 5.02 (2H, s), 5.17 (2H, s), 6.41 (1H, d, J=9.0 Hz), 6.54 (1H, d, J=9.0 Hz), 7.29–7.42 (10H, m), 7.98 (1H, s).

REFERENCE EXAMPLE 8-8

1-[2,6-Dimethoxy-3-(5-methyl-7-nitroindan-4-yloxy)phenyl]ethanone

The title compound was prepared in a similar manner to those described in Reference Example 8 using bis(3-acetyl-2,4-dimethoxyphenyl)iodonium tetrafluoroborate instead of bis(4-methoxyphenyl)iodonium tetrafluoroborate.

¹H-NMR (CDCl₃) δ ppm: 2.04–2.12 (2H, m), 2.28 (3H, s), 2.54 (3H, s), 2.63–2.67 (2H, m), 3.34–3.40 (2H, m), 3.76 (3H, s), 3.95 (3H, s), 6.40 (1H, d, J=9.0 Hz), 6.46 (1H, d, J=9.0 Hz), 7.98 (1H, s).

REFERENCE EXAMPLE 8-9

7-(4-Benzyloxy-3-isopropylphenoxy)-6-methylindan-4-carbaldehyde

The title compound was prepared in a similar manner to those described in Reference Example 8 using 7-hydroxy-6-methylindan-4-carbaldehyde instead of 5-methyl-7-nitroindan-4-ol and using bis(4-benzyloxy-3-isopropylphenyl)iodonium tetrafluoroborate instead of bis(4-methoxyphenyl)iodonium tetrafluoroborate.

¹H-NMR (CDCl₃) δ ppm: 1.19 (6H, d, J=7.0 Hz), 1.95–2.15 (2H, m), 2.25 (3H, s), 2.56 (2H, t, J=7.5 Hz), 3.25 (2H, t, J=7.5 Hz), 3.30–3.45 (1H, m), 5.02 (2H, s), 6.45 (1H, dd, J=8.7 Hz, 3.0 Hz), 6.76 (1H, d, J=8.7 Hz), 6.82 (1H, d, J=3.0 Hz), 7.25–7.50 (5H, m), 7.56 (1H, d, J=0.6 Hz), 10.09 (1H, s).

REFERENCE EXAMPLE 8-10

7-[4-Benzyloxy-3-(4-fluorobenzyl)phenoxy]-6-methylindan-4-carbaldehyde

The title compound was prepared in a similar manner to those described in Reference Example 8 using 7-hydroxy-6-methylindan-4-carbaldehyde instead of 5-methyl-7-nitroindan-4-ol and using bis[4-benzyloxy-3-(4-fluorobenzyl)phenyl]iodonium tetrafluoroborate instead of bis(4-methoxyphenyl)iodonium tetrafluoroborate.

¹H-NMR (CDCl₃) δ ppm: 1.95–2.15 (2H, m), 2.22 (3H, s), 2.54 (2H, t, J=7.6 Hz), 3.24 (2H, t, J=7.5 Hz), 3.91 (2H, s), 4.98 (2H, s), 6.54 (1H, dd, J=8.8 Hz, 3.2 Hz), 6.64 (1H, d, J=3.2 Hz), 6.78 (1H, d, J=8.8 Hz), 6.85–7.00 (2H, m), 7.05–7.15 (2H, m), 7.20–7.45 (5H, m), 7.55 (1H, s), 10.08 (1H, s).

REFERENCE EXAMPLE 9

2-methoxy-5-(5-methyl-7-nitroindan-4-yloxy)benzaldehyde 4-(4-methoxyphenoxy)-5-methyl-7-nitroindane (5.0 g) and dichloromethyl methyl ether (3.02 mL) were dissolved in dichloromethane (50 mL). To the solution was added dropwise titanium tetrachloride (3.67 mL) under ice-cooling with stirring. The reaction mixture was stirred at room temperature under an argon atmosphere for 20 hours. After adding ice water (300 mL), the reaction mixture was extracted with ethyl acetate. The organic layer was washed with a saturated aqueous solution of sodium hydrogen carbonate and brine successively, and dried over anhydrous magnesium sulfate. The solvent was removed under reduced pressure. The residue was triturated with hexane (50 mL) and diethyl ether (5 mL), and the insoluble material was collected by filtration and washed with hexane to give the title compound (4.37 g).

¹H-NMR (CDCl₃) δ ppm: 2.00–2.15 (2H, m), 2.22 (3H, s), 2.64 (2H, t, J=7.5 Hz), 3.39 (2H, t, J=7.5 Hz), 3.92 (3H, s), 6.97 (1H, d, J=9.0 Hz), 7.07–7.20 (2H, m), 7.97 (1H, s), 10.41 (1H, s).

REFERENCE EXAMPLE 10

2-Hydroxy-5-(5-methyl-7-nitroindan-4-yloxy)benzaldehyde

2-Methoxy-5-(5-methyl-7-nitroindan-4-yloxy) benzaldehyde (2.03 g) was dissolved in dichloromethane (80 mL). To the solution was added dropwise a 1 mol/L solution of boron trichloride in dichloromethane (20 mL) under ice-cooling with stirring. The reaction mixture was stirred at room temperature for 24 hours. To the reaction mixture was added dropwise methanol (10 mL) under ice-cooling with stirring. After adding diluted hydrochloric acid, the reaction mixture was extracted with ethyl acetate. The organic layer was washed with brine, and dried over anhydrous magnesium sulfate. The solvent was removed under reduced pressure to give the title compound (1.45 g).

¹H-NMR (CDCl₃) δ ppm: 2.00–2.15 (2H, m), 2.26 (3H, s), 2.68 (2H, t, J=7.6 Hz), 3.40 (2H, t, J=7.6 Hz), 6.87 (1H, d, J=3.1 Hz), 6.97 (1H, d, J=9.1 Hz), 7.11 (1H, dd, J=3.1 Hz, 9.1 Hz), 8.00 (1H, s), 9.78 (1H, s), 10.73 (1H, s).

REFERENCE EXAMPLE 10-1

2-Hydroxy-5-(5-methyl-7-nitroindan-4-yloxy)acetophenone

The title compound was prepared in a similar manner to those described in Reference Example 10 using 2-methoxy-5-(5-methyl-7-nitroindan-4-yloxy)acetophenone instead of 2-methoxy-5-(5-methyl-7-nitroindan-4-yloxy)benzaldehyde.

¹H-NMR (CDCl₃) δ ppm: 2.05–2.15 (2H, m), 2.26 (3H, s), 2.56 (3H, s), 2.63–2.70 (2H, m), 3.35–3.45 (2H, m), 6.88–6.95 (2H, m), 7.15–7.20 (1H, m), 7.99 (1H, s), 11.92 (1H, s).

REFERENCE EXAMPLE 11

2-Benzyloxy-5-(5-methyl-7-nitroindan-4-yloxy)benzaldehyde

A suspension of 2-hydroxy-5-(5-methyl-7-nitroindan-4-yloxy)benzaldehyde (3.20 g) and potassium carbonate (1.55 g) in N,N-dimethylformamide (25 mL) was stirred under ice-cooling. After adding dropwise benzyl bromide (1.34 mL), the mixture was stirred at room temperature for 24 hours. The reaction mixture was acidified with diluted hydrochloric acid and extracted with ethyl acetate. The organic layer was washed with brine, and dried over anhydrous magnesium sulfate. The solvent was removed under reduced pressure. The residue was purified by column chromatography on silica gel (eluent: hexane/ethyl acetate) to give the title compound (3.30 g).

¹H-NMR (CDCl₃) δ ppm: 2.00–2.15 (2H, m), 2.22 (3H, s), 2.64 (2H, t, J=7.5 Hz), 3.39 (2H, t, J=7.5 Hz), 5.17 (2H, s), 6.99–7.12 (2H, m), 7.16 (1H, d, J=3.0 Hz), 7.30–7.50 (5H, m), 7.97 (1H, s), 10.48 (1H, s).

REFERENCE EXAMPLE 11-1

2-Benzyloxy-5-(5-methyl-7-nitroindan-4-yloxy)acetophenone

The title compound was prepared in a similar manner to those described in Reference Example 11 using 2-hydroxy-5-(5-methyl-7-nitroindan-4-yloxy)acetophenone instead of 2-hydroxy-5-(5-methyl-7-nitroindan-4-yloxy)benzaldehyde.
$^1$H-NMR (CDCl$_3$) δ ppm: 2.03–2.12 (2H, m), 2.22 (3H, s), 2.58 (3H, s), 2.63–2.70 (2H, m), 3.35–3.42 (2H, m), 5.13 (2H, s), 6.90 (1H, dd, J=3.1, 9.0 Hz), 6.96 (1H, d, J=9.0 Hz), 7.17 (1H, d, J=3.1 Hz), 7.33–7.45 (5H, m), 7.96 (1H, s).

REFERENCE EXAMPLE 11-2

1-Benzyloxy-2-(4-fluorobenzyl)benzene

The title compound was prepared in a similar manner to those described in Reference Example 11 using 2-(4-fluorobenzyl) phenol instead of 2-hydroxy-5-(5-methyl-7-nitroindan-4-yloxy)benzaldehyde.
$^1$H-NMR (CDCl$_3$) δ ppm: 3.98 (2H, s), 5.04 (2H, s), 6.86–6.97 (4H, m), 7.06–7.20 (4H, m), 7.26–7.44 (5H, m).

REFERENCE EXAMPLE 11-3

4-(4-Benzyloxyphenoxy)-5-methyl-7-nitroindane

The title compound was prepared in a similar manner to those described in Reference Example 11 using 4-(5-methyl-7-nitroindan-4-yloxy)phenol instead of 2-hydroxy-5-(5-methyl-7-nitroindan-4-yloxy)benzaldehyde.
$^1$H-NMR (CDCl$_3$) δ ppm: 2.00–2.13 (2H, m), 2.24 (3H, s), 2.65 (2H, t, J=7.7 Hz), 3.37 (2H, t, J=7.5 Hz), 5.02 (2H, s), 6.65–6.80 (2H, m), 6.85–6.95 (2H, m), 7.28–7.46 (5H, m), 7.96 (1H, d, J=0.7 Hz).

REFERENCE EXAMPLE 12

[2-Benzyloxy-5-(5-methyl-7-nitroindan-4-yloxy)phenyl]methanol

To a suspension of sodium borohydride (340 mg) in tetrahydrofuran (10 mL) was added 2-benzyloxy-5-(5-methyl-7-nitroindan-4-yloxy)benzaldehyde (3.30 g) under ice-cooling. After adding dropwise methanol (1 mL) at room temperature, the mixture was stirred for 6 hours. The reaction mixture was acidified with diluted hydrochloric acid and extracted with ethyl acetate. The organic layer was washed with brine, and dried over anhydrous magnesium sulfate. The solvent was removed under reduced pressure to give the title compound (3.13 g).
$^1$H-NMR (CDCl$_3$) δ ppm: 1.98–2.15 (2H, m), 2.23 (3H, s), 2.66 (2H, t, J=7.5 Hz), 3.38 (2H, t, J=7.5 Hz), 4.68 (2H, s), 5.07 (2H, s), 6.63 (1H, dd, J=3.4 Hz, 8.8 Hz), 6.76–6.94 (2H, m), 7.20–7.54 (5H, m), 7.96 (1H, s).

REFERENCE EXAMPLE 13

4-(4-Benzyloxy-3-chloromethylphenoxy)-5-methyl-7-nitroindane

[2-benzyloxy-5-(5-methyl-7-nitroindan-4-yloxy)phenyl]methanol (2.48 g) was dissolved in diethyl ether. After adding dropwise thionyl chloride (5 mL) under ice-cooling with stirring, the mixture was stirred at room temperature for 6 hours. The reaction mixture was evaporated under reduced pressure to dryness. After adding water (10 mL), the residue was extracted with diethyl ether. The organic layer was washed with brine, and dried over anhydrous magnesium sulfate. The solvent was removed under reduced pressure to give the title compound (2.04 g).
$^1$H-NMR (CDCl$_3$) δ ppm: 1.98–2.17 (2H, m), 2.24 (3H, s), 2.66 (2H, t, J=7.5 Hz), 3.38 (2H, t, J=7.5 Hz), 4.63 (2H, s), 5.09 (2H, s), 6.63 (1H, dd, J=3.0 Hz, 8.9 Hz), 6.80–7.00 (2H, m), 7.24–7.60 (5H, m), 7.97 (1H, s).

REFERENCE EXAMPLE 14

[2-Benzyloxy-5-(5-methyl-7-nitroindan-4-yloxy)benzyl]triphenylphosphonium chloride A suspension of 4-(4-benzyloxy-3-chloromethylphenoxy)-5-methyl-7-nitroindane (2.04 g) and triphenylphosphine (1.39 g) in toluene (50 mL) was heated under reflux for 12 hours. The reaction mixture was allowed to cool to room temperature. Precipitate was collected by filtration, and washed with diethyl ether to give the title compound (2.50 g).
$^1$H-NMR (DMSO-d$_6$) δ ppm: 1.84–2.00 (2H, m), 2.03 (3H, s), 2.30–2.50 (2H, m), 3.18–3.40 (2H, m), 4.60 (2H, s), 4.96 (2H, d, J=14.8 Hz), 6.45 (1H, s), 6.89–8.15 (23H, m).

REFERENCE EXAMPLE 14-1

4-Methoxybenzyltriphenylphosphonium chloride

The title compound was prepared in a similar manner to those described in Reference Example 14 using 4-methoxybenzyl chloride instead of 4-(4-benzyloxy-3-chloromethylphenoxy)-5-methyl-7-nitroindane.
$^1$H-NMR (DMSO-d$_6$) δ ppm: 3.70 (3H, s), 5.09 (2H, d, J=14.7 Hz), 6.80 (2H, d, J=8.5 Hz), 6.85–6.95 (2H, m), 7.55–8.00 (15H, m).

REFERENCE EXAMPLE 14-2

(3-Methoxybenzyl)triphenylphosphonium bromide

The title compound was prepared in a similar manner to those described in Reference Example 14 using 3-methoxybenzyl bromide instead of 4-(4-benzyloxy-3-chloromethylphenoxy)-5-methyl-7-nitroindane.
$^1$H-NMR (DMSO-d$_6$) δ ppm: 3.56 (3H, s), 5.14 (2H, d, J=15.7 Hz), 6.40–6.70 (2H, m), 6.80–6.95 (1H, m), 7.10–7.25 (1H, m), 7.50–8.10 (15H, m).

REFERENCE EXAMPLE 14-3

(2-Methoxybenzyl)triphenylphosphonium bromide

The title compound was prepared in a similar manner to those described in Reference Example 14 using 2-methoxybenzyl bromide instead of 4-(4-benzyloxy-3-chloromethylphenoxy)-5-methyl-7-nitroindane.
$^1$H-NMR (DMSO-d$_6$) δ ppm: 3.20 (3H, s), 4.94 (2H, d, J=14.8 Hz), 6.75–6.90 (2H, m), 7.00–7.10 (1H, m), 7.23–7.35 (1H, m), 7.50–8.00 (15H, m).

REFERENCE EXAMPLE 14-4

(3-Fluoro-4-methoxybenzyl)triphenylphosphonium chloride

3-Fluoro-4-methoxyphenylmethanol was prepared in a similar manner to those described in Reference Example 12 using 3-fluoro-4-methoxybenzaldehyde instead of 2-benzyloxy-5-(5-methyl-7-nitroindan-4-yloxy)benzaldehyde.

3-Fluoro-4-methoxybenzyl chloride was prepared in a similar manner to those described in Reference Example 13 using 3-fluoro-4-methoxyphenylmethanol instead of [2-benzyloxy-5-(5-methyl-7-nitroindan-4-yloxy)phenyl]methanol.

The title compound was prepared in a similar manner to those described in Reference Example 14 using 3-fluoro-4-methoxybenzyl chloride instead of 4-(4-benzyloxy-3-chloromethylphenoxy)-5-methyl-7-nitroindane.

$^1$H-NMR (DMSO-d$_6$) δ ppm: 3.78 (3H, s), 5.19 (2H, d, J=15.3 Hz), 6.68–6.90 (2H, m), 7.00–7.15 (1H, m), 7.60–8.05 (15H, m).

REFERENCE EXAMPLE 15

3-{2-[2-Benzyloxy-5-(5-methyl-7-nitroindan-4-yloxy)phenyl]vinyl}furan

To a suspension of furfuryltriphenylphosphonium bromide (377 mg) in tetrahydrofuran (30 mL) was added potassium tert-butoxide (136 mg) at room temperature, and the mixture was stirred for 15 min. After adding 2-benzyloxy-5-(5-methyl-7-nitroindan-4-yloxy)benzaldehyde (377 mg), the mixture was stirred at room temperature for 6 hours. After adding dropwise diluted hydrochloric acid to make the mixture acidify fully, the reaction mixture was extracted with ethyl acetate. The organic layer was washed with brine, and dried over anhydrous magnesium sulfate. The solvent was removed under reduced pressure. The residue was purified by column chromatography on silica gel (eluent: hexane/ethyl acetate) to give the title compound (306 mg).

$^1$H-NMR (CDCl$_3$) δ ppm: 1.98–2.12 (2H, m), 2.20 (3H, s), 2.57–2.73 (2H, m), 3.30–3.42 (2H, m), 5.05 (2H, s), 6.07 (1H, d, J=1.6 Hz), 6.40 (1H, d, J=12.0 Hz), 6.56 (1H, d, J=12.0 Hz), 6.69 (1H, dd, J=3.1 Hz, 8.9 Hz), 6.75 (1H, d, J=3.1 Hz), 6.86 (1H, d, J=8.9 Hz), 7.10–7.55 (7H, m), 7.91 (1H, s).

REFERENCE EXAMPLE 15-1

4-{4-Methoxy-3-[2-(4-methoxyphenyl)vinyl]phenoxy}-5-methyl-7-nitroindane

The title compound was prepared in a similar manner to those described in Reference Example 15 using 4-methoxybenzyltriphenylphosphonium chloride instead of furfuryltriphenylphosphonium bromide.

$^1$H-NMR (CDCl$_3$) δ ppm: 1.90–2.10 (2H, m), 2.11 (3H, s), 2.54 (2H, t, J=7.5 Hz), 3.32 (2H, t, J=7.5 Hz), 3.76 (3H, s), 3.82 (3H, s), 6.40–6.90 (7H, m), 7.04 (2H, d, J=8.7 Hz), 7.84 (1H, s).

REFERENCE EXAMPLE 16

4-(7-Amino-5-methylindan-4-yloxy)-2-(tetrahydropyran-4-yl methyl)phenol

4-[2-Benzyloxy-5-(5-methyl-7-nitroindan-4-yloxy) benzylidene]tetrahydropyran (230 mg) was dissolved in ethanol (10 mL) and ethyl acetate (2 mL). After adding 10% Pd/C (50 mg) under ice-cooling, the mixture was stirred at room temperature under an atmospheric pressure of hydrogen for 24 hours. The insoluble material was removed by filtration. The filtrate was evaporated under reduced pressure to dryness. The residue was purified by column chromatography on silica gel (eluent: exane/ethyl acetate) to give the title compound (138 mg).

$^1$H-NMR (CDCl$_3$) δ ppm: 1.25–1.41 (2H, m), 1.49–1.64 (2H, m), 1.74–1.89 (1H, m), 1.94–2.13 (5H, m), 2.43–2.53 (2H, m), 2.60–2.75 (4H, m), 3.27–3.39 (2H, m), 3.48 (2H, br-s), 3.88–4.00 (2H, m), 4.97 (1H, br-s), 6.24–6.66 (4H, m).

REFERENCE EXAMPLE 16-1

4-(7-Amino-5-methylindan-4-yloxy)-2-[2-(tetrahydrofuran-3-yl)ethyl]phenol

The title compound was prepared in a similar manner to those described in Reference Example 16 using 3-{2-[2-benzyloxy-5-(5-methyl-7-nitroindan-4-yloxy)phenyl]vinyl}furan instead of 4-[2-benzyloxy-5-(5-methyl-7-nitroindan-4-yloxy)benzylidene]tetrahydropyran.

H-NMR (CDCl$_3$) δ ppm: 1.48–1.86 (3H, m), 1.94–2.34 (7H, m), 2.45–2.90 (6H, m), 3.30–4.10 (6H, m), 5.26 (1H, br-s), 6.30–6.80 (4H, m).

REFERENCE EXAMPLE 16-2

7-{4-Methoxy-3-[2-(4-methoxyphenyl)ethyl]phenoxy}-6-methylindan-4-ylamine

The title compound was prepared in a similar manner to those described in Reference Example 16 using 4-{4-methoxy-3-[2-(4-methoxyphenyl)vinyl]phenoxy}-5-methyl-7-nitroindane instead of 4-[2-benzyloxy-5-(5-methyl-7-nitroindan-4-yloxy)benzylidene]tetrahydropyran.

$^1$H-NMR (CDCl$_3$) δ ppm: 1.95–2.12 (5H, m), 2.55–2.92 (8H, m), 3.45 (2H, br-s), 3.76 (3H, s), 3.78 (3H, s), 6.40 (1H, s), 6.48–6.52 (2H, m), 6.69 (1H, d, J=8.7 Hz), 6.79 (2H, d, J=8.5 Hz), 7.06 (2H, d, J=8.5 Hz).

REFERENCE EXAMPLE 17

4-(7-Amino-5-methylindan-4-yloxy)-2-(1-methyl-2-phenylethyl)phenol

4-[4-Benzyloxy-3-(1-methyl-2-phenylvinyl)phenoxy]-5-methyl-7-nitroindane was prepared in a similar manner to those described in Reference Example 15 using 2-benzyloxy-5-(5-methyl-7-nitroindan-4-yloxy)acetophenone instead of 2-benzyloxy-5-(5-methyl-7-nitroindan-4-yloxy) benzaldehyde and using benzyltriphenylphosphonium chloride instead of furfuryltriphenylphosphonium bromide.

The title compound was prepared in a similar manner to those described in Reference Example 16 using 4-[4-benzyloxy-3-(1-methyl-2-phenylvinyl)phenoxy]-5-methyl-7-nitroindane instead of 4-[2-benzyloxy-5-(5-methyl-7-nitroindan-4-yloxy) benzylidene]tetrahydropyran.

$^1$H-NMR (CDCl$_3$) δ ppm: 1.20 (3H, d, J=6.9 Hz), 1.98–2.07 (2H, m), 2.06 (3H, s), 2.57–2.63 (2H, m), 2.67–2.75 (3H, m), 2.88–2.95 (1H, m), 3.27–3.35 (1H, m), 3.47 (2H, br-s), 4.44 (1H, br-s), 6.34 (1H, dd, J=3.0 Hz, 8.6 Hz), 6.42 (1H, s), 6.48(1H, d, J=8.6 Hz), 6.71 (1H, d, J=3.0 Hz), 7.06–7.26 (5H, m).

REFERENCE EXAMPLE 17-11

7-{4-Methoxy-3-[2-(3-methoxyphenyl)ethyl]phenoxy}-6-methylindan-4-ylamine

4-{4-Methoxy-3-[2-(3-methoxyphenyl)vinyl]phenoxy}-5-methyl-7-nitroindane was prepared in a similar manner to those described in Reference Example 15 using 2-methoxy-5-(5-methyl-7-nitroindan-4-yloxy)benzaldehyde instead of 2-benzyloxy-5-(5-methyl-7-nitroindan-4-yloxy)benzaldehyde and using (3-methoxybenzyl) triphenylphosphonium bromide instead of furfuryltriphenylphosphonium bromide.

The title compound was prepared in a similar manner to those described in Reference Example 16 using 4-{4-methoxy-3-[2-(3-methoxyphenyl)vinyl]phenoxy}-5-methyl-7-nitroindane instead of 4-[2-benzyloxy-5-(5-methyl-7-nitroindan-4-yloxy)benzylidene]tetrahydropyran.

$^1$H-NMR (CDCl$_3$) δ ppm: 1.90–2.15 (5H, m), 2.55–2.92 (8H, m), 3.45 (2H, br-s), 3.72–3.85 (6H, m), 6.35–6.90 (7H, m), 7.10–7.25 (1H, m).

REFERENCE EXAMPLE 17-2

7-{4-Methoxy-3-[2-(2-methoxyphenyl)ethyl]phenoxy}-6-methylindan-4-ylamine

4-{4-Methoxy-3-[2-(2-methoxyphenyl)vinyl]phenoxy}-5-methyl-7-nitroindane was prepared in a similar manner to those described in Reference Example 15 using 2-methoxy-5-(5-methyl-7-nitroindan-4-yloxy)benzaldehyde instead of 2-benzyloxy-5-(5-methyl-7-nitroindan-4-yloxy)benzaldehyde and using (2-methoxybenzyl)triphenylphosphonium bromide instead of furfuryltriphenylphosphonium bromide.

The title compound was prepared in a similar manner to those described in Reference Example 16 using 4-{4-methoxy-3-[2-(2-methoxyphenyl)vinyl]phenoxy}-5-methyl-7-nitroindane instead of 4-[2-benzyloxy-5-(5-methyl-7-nitroindan-4-yloxy) benzylidene]tetrahydropyran.

$^1$H-NMR (CDCl$_3$) δ ppm: 1.90–2.15 (5H, m), 2.55–2.92 (8H, m), 3.45 (2H, br-s), 3.75 (3H, s), 3.80 (3H, s), 6.40 (1H, d, J=4.5 Hz), 6.48 (1H, dd, J=8.8 Hz, 3.0 Hz), 6.62 (1H, d, J=3.0 Hz), 6.67 (1H, d, J=8.8 Hz), 6.75–6.95 (2H, m), 7.00–7.25 (2H, m).

REFERENCE EXAMPLE 17-3

7-{3-[2-(3-Fluoro-4-methoxyphenyl)ethyl]-4-methoxyphenoxy}-6-methylindan-4-ylamine 4-{3-[2-(3-Fluoro-4-methoxyphenyl)vinyl]-4-methoxyphenoxy}-5-methyl-7-nitroindane was prepared in a similar manner to those described in Reference Example 15 using 2-methoxy-5-(5-methyl-7-nitroindan-4-yloxy) benzaldehyde instead of 2-benzyloxy-5-(5-methyl-7-nitroindan-4-yloxy) benzaldehyde and using (3-fluoro-4-methoxybenzyl) triphenylphosphonium bromide instead of furfuryltriphenylphosphonium bromide.

The title compound was prepared in a similar manner to those described in Reference Example 16 using 4-{3-[2-(3-fluoro-4-methoxyphenyl)vinyl]-4-methoxyphenoxy}-5-methyl-7-nitroindane instead of 4-[2-benzyloxy-5-(5-methyl-7-nitroindan-4-yloxy)benzylidene]tetrahydropyran.

$^1$H-NMR (CDCl$_3$) δ ppm: 1.95–2.15 (5H, m), 2.55–2.90 (8H, m), 3.47 (2H, br-s), 3.77 (3H, s), 3.86 (3H, s), 6.40 (1H, s), 6.47–6.60 (2H, m), 6.69 (1H, d, J=8.5 Hz), 6.76–6.95 (3H, m).

REFERENCE EXAMPLE 18

4-[2-Benzyloxy-5-(5-methyl-7-nitroindan-4-yloxy) benzylidene]tetrahydropyran

To a suspension of [2-benzyloxy-5-(5-methyl-7-nitroindan-4-yloxy)benzyl]triphenylphosphonium chloride (559 mg) in dimethylsulfoxide (20 mL) was added sodium hydride (60%, 49 mg) at room temperature, the mixture was stirred for 15 min. After adding tetrahydro-4H-pyran-4-one (0.15 mL), the reaction mixture was stirred at room temperature for 6 hours. After adding dropwise diluted hydrochloric acid to make the mixture acidify fully, the reaction mixture was extracted with ethyl acetate. The organic layer was washed with brine, and dried over anhydrous magnesium sulfate. The solvent was removed-under reduced pressure. The residue was purified by column chromatography on silica gel (eluent: hexane/ethyl acetate) to give the title compound (230 mg).

$^1$H-NMR (CDCl$_3$) δ ppm: 1.96–2.11 (2H, m), 2.24 (3H, s), 2.30–2.46 (4H, m), 2.57–2.73 (2H, m), 3.30–3.42 (2H, m), 3.61 (2H, t, J=5.5 Hz), 3.75 (2H, t, J=5.5 Hz), 5.03 (2H, s), 6.34 (1H, s), 6.54 (1H, dd, J=3.1 Hz, 8.9 Hz), 6.65 (1H, d, J=3.1 Hz), 6.80 (1H, d, J=8.9 Hz), 7.23–7.50 (5H, m), 7.96 (1H, s).

REFERENCE EXAMPLE 19

7-[4-benzyloxy-3-(2-thiazol-2-ylethyl)phenoxy]-6-methylindan-4-ylamine

To a suspension of [2-benzyloxy-5-(5-methyl-7-nitroindan-4-yloxy)benzyl]triphenylphosphonium chloride (302 mg) in tetrahydrofuran (10 mL) was added potassium tert-butoxide (25 mg) at room temperature for 15 min. After adding 2-formylthiazole (47 mg), the reaction mixture was stirred at room temperature for 6 hours. After adding water, the reaction mixture was extracted with ethyl acetate. The organic layer was washed with brine, and dried over anhydrous magnesium sulfate. The solvent was removed under reduced pressure. The residue was purified by column chromatography on silica gel (eluent: hexane/ethyl acetate) to give olefin (80 mg). The olefin was dissolved in ethanol (10 mL) and ethyl acetate (2 mL). After adding 10% Pd/C (30 mg) under ice-cooling, the mixture was stirred at room temperature under an atmospheric pressure of hydrogen for 24 hours. The insoluble material was removed by filtration. The filtrate was evaporated under reduced pressure to dryness. The residue was purified by column chromatography on silica gel (eluent: hexane/ethyl acetate) to give the title compound (120 mg).

$^1$H-NMR (CDCl$_3$) δ ppm: 1.94–2.13 (5H, m), 2.61 (2H, t, J=7.4 Hz), 2.71 (2H, t, J=7.4 Hz), 3.08 (2H, t, J=7.4 Hz), 3.30 (2H, t, J=7.4 Hz), 3.45 (2H, br-s), 5.04 (2H, s), 6.39 (1H, s), 6.55–6.65 (2H, m), 6.75–6.85 (1H, m), 7.14 (1H, d, J=3.3 Hz), 7.20–7.54 (5H, m), 7.65 (1H, d, J=3.3 Hz).

REFERENCE EXAMPLE 20

4-(4-Benzyloxy-3-iodophenoxy)-5-methyl-7-nitroindane

To a solution of 4-(4-benzyloxyphenoxy)-5-methyl-7-nitroindane (3.21 g) in dichloromethane (15 mL) was added silver acetate (1.86 g). After adding iodine (2.60 g), the mixture was stirred under an argon atmosphere in the dark at room temperature for 2 days. The insoluble material was removed by filtration. The filtrate was washed with an aqueous solution of sodium sulfite (1.7 g/40 mL), a saturated aqueous solution of sodium hydrogen carbonate and brine successively, and dried over anhydrous magnesium sulfate. The solvent was removed under reduced pressure to give the title compound (4.18 g).

$^1$H-NMR (CDCl$_3$) δ ppm: 2.03–2.11 (2H, m), 2.23 (3H, s), 2.63–2.68 (2H, m), 3.34–3.40 (2H, m), 5.09 (2H, s), 6.70 (1H, dd, J=3.0, 9.0 Hz), 6.76 (1H, d, J=9.0 Hz), 7.30–7.45 (4H, m), 7.46–7.50 (2H, m), 7.97 (1H, s).

REFERENCE EXAMPLE 20-1

5-Iodoindan-4-ol

The title compound was prepared in a similar manner to those described in Reference Example 20 using indan-4-ol instead of 4-(4-benzyloxyphenoxy)-5-methyl-7-nitroindane.

$^1$H-NMR (CDCl$_3$) δ ppm: 2.03–2.12 (2H, m), 2.84–2.93 (4H, m), 5.22 (1H, s), 6.69 (1H, d, J=7.9 Hz), 7.41 (1H, d, J=7.9 Hz).

REFERENCE EXAMPLE 20-2

4-(4-Benzyloxy-3-iodo-phenoxy)-5-methyl-7-nitroindane

The title compound was prepared in a similar manner to those described in Reference Example 20 using 4-(4-benzyloxyphenoxy)-5-methyl-7-nitroindane instead of 4-(4-benzyloxyphenoxy)-5-methyl-7-nitroindane.

$^1$H-NMR (CDCl$_3$) δ ppm: 2.00–2.14 (2H, m), 2.23 (3H, s), 2.66 (2H, t, J=7.6 Hz), 3.39 (2H, t, J=7.6 Hz), 5.09 (2H, s), 6.66–6.80 (2H, m), 7.24–7.53 (6H, m), 7.97 (1H, s).

REFERENCE EXAMPLE 21

6-[2-Hydroxy-5-(5-methyl-7-nitroindan-4-yloxy)benzyl]-2H-pyridazine-3-one

A suspension of 3-chloro-6-[2-methoxy-5-(5-methyl-7-nitroindan-4-yloxy)benzyl]pyridazine (760 mg) and sodium acetate (50 mg)in acetic acid (10 mL) was heated at reflux temperature under an argon atmosphere for 2 hours. The reaction mixture was evaporated under reduced pressure to dryness. After adding water (15 mL), the residue was stirred for 30 min. The mixture was extracted with dichloromethane. The organic layer was washed with a saturated aqueous of sodium hydrogen carbonate and brine successively, and dried over anhydrous magnesium sulfate. The solvent was removed under reduced pressure to give 6-[2-methoxy-5-(5-methyl-7-nitroindan-4-yloxy)benzyl]-2H-pyridazine-3-one (707 mg).

To a solution of 6-[2-methoxy-5-(5-methyl-7-nitroindan-4-yloxy)benzyl]-2H-pyridazine-3-one (704 mg) in acetic acid (10 mL) was added hydrobromic acid (48%, 10 mL). The mixture was heated at reflux temperature under an argon atmosphere overnight. After adding water, the reaction mixture was extracted with dichloromethane. The organic layer was washed with water and brine successively, and dried over anhydrous magnesium sulfate. The solvent was removed under reduced pressure. The residue was crystallized from a small amount of ethyl acetate to give the title compound (270 mg).

$^1$H-NMR (CDCl$_3$) δ ppm: 2.03–2.10 (2H, m), 2.22 (3H, s), 2.59–2.66 (2H, m), 3.33–3.40 (2H, m), 3.87 (2H, s), 6.51 (1H, dd, J=3.0, 8.7 Hz), 6.66 (1H, d, J=3.0 Hz), 6.73 (1H, d, J=8.7 Hz), 6.86 (1H, d, J=9.6 Hz), 7.30 (1H, d, J=9.6 Hz), 7.97 (1H, s).

REFERENCE EXAMPLE 22

Dibenzyl[7-(4-benzyloxy-3-iodophenoxy)-6-methylindan-4-yl]amine

To a solution of 7-(4-benzyloxy-3-iodophenoxy)-6-methylindan-4-ylamine (3.80 g) in N,N-dimethylformamide (15 mL) were added benzyl bromide (2.30 mL) and potassium carbonate (2.67 g), and the mixture was stirred under an argon atmosphere at room temperature for 2 days. Adding water, the reaction mixture was extracted with ethyl acetate. The organic layer was washed with water and brine successively, and dried over anhydrous magnesium sulfate. The solvent was removed under reduced pressure. The residue was purified by column chromatography on silica gel (eluent: hexane/ethyl acetate=10/1) to give the title compound (4.50 g).

$^1$H-NMR (CDCl$_3$) δ ppm: 1.97–2.07 (2H, m), 2.01 (3H, s), 2.60–2.65 (2H, m), 2.93–2.98 (2H, m), 4.17 (4H, s), 5.07 (2H, s), 6.57 (1H, s), 6.65–6.76 (2H, m), 7.21–7.51 (16H, m).

REFERENCE EXAMPLE 23

Dibenzyl[7-(4-benzyloxy-3-trifluoromethylphenoxy)-6-methylindan-4-yl]amine

To a solution of dibenzyl[7-(4-benzyloxy-3-iodophenoxy)-6-methylindan-4-yl]amine (1.00 g) in N,N-dimethylformamide (8 mL) was added methyl difluoro(fluorosulfonyl)acetate (894 mg) After the reaction vessel was replaced with argon, CuI (235 mg) was added to the mixture, which was stirred under an argon atmosphere at 80° C. for 3 days. Adding water, the reaction mixture was extracted with ethyl acetate. The organic layer was washed with water, a saturated aqueous solution of sodium hydrogen carbonate and brine successively, and dried over anhydrous magnesium sulfate. The solvent was removed under reduced pressure. The residue was purified by column chromatography on silica gel (eluent: hexane/ethyl acetate=10/1) to give the title compound (718 mg).

$^1$H-NMR (CDCl$_3$) δ ppm: 1.98–2.05 (2H, m), 2.01 (3H, s), 2.58–2.65 (2H, m), 2.90–3.00 (2H, m), 4.17 (4H, s), 5.11 (2H, s), 6.58 (1H, s), 6.81 (1H, dd, J=3.0, 9.0 Hz), 6.91 (1H, d, J=9.0 Hz), 7.05 (1H, d, J=3.0 Hz), 7.17–7.45 (15H, m).

REFERENCE EXAMPLE 23-1

4-(4-Benzyloxy-3-isopropylphenoxy)-7-nitro-5-trifluoromethylindane

The title compound was prepared in a similar manner to those described in Reference Example 23 using 4-(4-benzyloxy-3-isopropylphenoxy)-5-iodo-7-nitroindane instead of dibenzyl[7-(4-benzyloxy-3-iodophenoxy)-6-methylindan-4-yl]amine.

$^1$H-NMR (CDCl$_3$) δ ppm: 1.19 (6H, d, J=6.9 Hz), 2.00–2.10 (2H, m), 2.43–2.48 (2H, m), 3.33–3.43 (3H, m), 5.05 (2H, s), 6.57 (1H, dd, J=3.0, 8.8 Hz), 6.81 (1H, d, J=8.8 Hz), 6.88 (1H, d, J=3.0 Hz), 7.30–7.44 (5H, m), 8.42 (1H, s).

REFERENCE EXAMPLE 24

1-[6-Benzyloxy-2-hydroxy-3-(5-methyl-7-nitroindan-4-yl oxy)phenyl]ethanone

To a solution of 1-[2,6-bisbenzyloxy-3-(5-methyl-7-nitroindan-4-yloxy)phenyl]ethanone (10.6 g) in dichloromethane (15 mL) was added a mixed solvent of trifluoroacetic acid/water/dimethylsulfide (7/3/1) (30 mL), and the mixture was stirred at room temperature for 12 hours. Adding water, the reaction mixture was extracted with dichloromethane. The organic layer was washed with water and a saturated aqueous solution of sodium hydrogen carbonate until the aqueous layer became weak alkaline, and dried over anhydrous magnesium sulfate. The solvent was removed under reduced pressure. The residue was crystallized from ethyl acetate and hexane to give the title compound (8.07 g).

$^1$H-NMR (CDCl$_3$) δ ppm: 2.03–2.10 (2H, m), 2.30 (3H, s), 2.62–2.68 (2H, m), 2.66 (3H, s), 3.32–3.37 (2H, m), 5.09 (2H, s), 6.31 (1H, d, J=9.0 Hz), 6.69 (1H, d, J=9.0 Hz), 7.35–7.42 (5H, m), 7.98 (1H, s), 13.58 (1H, s).

REFERENCE EXAMPLE 25

3-Benzyloxy-2-ethyl-6-(5-methyl-7-nitroindan-4-yloxy)phenol

To a solution of 1-[6-benzyloxy-2-hydroxy-3-(5-methyl-7-nitroindan-4-yloxy)phenyl]ethanone (1.081 g) in dichloromethane (18 mL) were added triethylsilane (0.955 mL) and trifluoroacetic acid (6 mL). The mixture was stirred at room temperature overnight. Adding water, the reaction mixture was stirred for 30 min and extracted with dichloromethane. The organic layer was washed with a saturated aqueous solution of sodium hydrogen carbonate and brine successively, and dried over anhydrous magnesium sulfate. The solvent was removed under reduced pressure. The residue was crystallized from dichloromethane and hexane to give the title compound (663 mg).

$^1$H-NMR (CDCl$_3$) δ ppm: 1.21 (3H, t, J=7.5 Hz), 2.03–2.11 (2H, m), 2.27 (3H, s), 2.59–2.65 (2H, m), 2.81 (2H, q, J=7.5 Hz), 3.33–3.38 (2H, m), 5.00 (2H, s), 5.72 (1H, s), 6.16 (1H, d, J=8.8 Hz), 6.28 (1H, d, J=8.8 Hz), 7.27–7.43 (5H, m), 7.97 (1H, s).

REFERENCE EXAMPLE 26

Ethyl 2-acetyl-3-benzyloxy-6-(5-methyl-7-nitroindan-4-yloxy)benzoate

To a solution of 1-[6-benzyloxy-2-hydroxy-3-(5-methyl-7-nitroindan-4-yloxy)phenyl]ethanone (1.50 g) in n-propanol (15 mL) was added ethyl carbazate (432 mg). The mixture was stirred under an argon atmosphere at 75° C. overnight and cooled to room temperature. Adding hexane (30 mL), the reaction mixture was stirred for 1 hour. The precipitate was filtrated to give ethyl N'-{1-[6-benzyloxy-2-hydroxy-3-(5-methyl-7-nitroindan-4-yloxy)phenyl]ethylidene}hydrazinecarboxate (1.16 g).

To a solution of ethyl N'-{1-[6-benzyloxy-2-hydroxy-3-(5-methyl-7-nitroindan-4-yloxy)phenyl]ethylidene}hydrazinecarboxate (1.16 g) in tetrahydrofuran (10 mL) was added lead tetraacetate (IV) (1.09 g). The mixture was stirred under an argon atmosphere at room temperature overnight. The insoluble material was removed by filtration. The filtrate was evaporated under reduced pressure to dryness. The residue was crystallized from a small amount of dichloromethane and hexane to give the title compound (416 mg).

$^1$H-NMR (CDCl$_3$) δ ppm: 1.33 (3H, t, J=7.1 Hz), 2.03–2.12 (2H, m), 2.25 (3H, s), 2.60–2.80 (2H, m), 2.62 (3H, s), 3.33–3.39 (2H, m), 4.34 (2H, q, J=7.1 Hz), 5.07 (2H, s), 6.46 (1H, d, J=9.1 Hz), 6.86 (1H, d, J=9.1 Hz), 7.30–7.41 (5H, m), 7.95 (1H, s).

REFERENCE EXAMPLE 27

Ethyl 2-acetyl-3-hydroxy-6-(5-methyl-7-nitroindan-4-yloxy)benzoate

Ethyl 2-acetyl-3-benzyloxy-6-(5-methyl-7-nitroindan-4-yloxy)benzoate (314 mg) was dissolved in trifluoroacetic acid/water/dimethylsulfide (95/5/10) (3 mL). The mixture was stood overnight at room temperature and evaporated under reduced pressure to dryness. Adding water, the residue was extracted with ethyl acetate. The organic layer was washed with a saturated aqueous solution of sodium hydrogen carbonate and brine successively, and dried over anhydrous magnesium sulfate. The solvent was removed under reduced pressure. The residue was purified by column chromatography on silica gel (eluent: hexane/ethyl acetate=5/1–3/1) to give the title compound (217 mg).

$^1$H-NMR (CDCl$_3$) δ ppm: 1.39 (3H, t, J=7.1 Hz), 2.03–2.12 (2H, m), 2.26 (3H, s), 2.37–2.92 (2H, m), 2.62 (3H, s), 3.32–3.42 (2H, m), 4.45 (2H, q, J=7.1 Hz), 6.87 (1H, d, J=9.1 Hz), 6.93 (1H, d, J=9.1 Hz), 7.96 (1H, s), 12.17 (1H, s).

REFERENCE EXAMPLE 27-1

4-(5-Iodo-7-nitroindan-4-yloxy)-2-isopropylphenol

The title compound was prepared in a similar manner to those described in Reference Example 27 using 4-(4-benzyloxy-3-isopropylphenoxy)-5-iodo-7-nitroindane instead of ethyl 2-acetyl-3-benzyloxy-6-(5-methyl-7-nitroindan-4-yloxy) benzoate.

$^1$H-NMR (CDCl$_3$) δ ppm: 1.23 (6H, d, J=6.9 Hz), 1.98–2.06 (2H, m), 2.57–2.63 (2H, m), 3.19 (1H, heptet, J=6.9 Hz), 3.32–3.35 (2H, m), 4.60 (1H, br-s), 6.44 (1H, dd, J=3.0, 8.6 Hz), 6.65 (1H, d, J=8.6 Hz), 6.80 (1H, d, J=3.0 Hz), 8.53 (1H, s).

REFERENCE EXAMPLE 28

7-(4-benzyloxy-3-isopropylphenoxy)-6-methylindan-4-yl formate 7-(4-benzyloxy-3-isopropylphenoxy)-6-methylindan-4-carbaldehyde (712 mg) was dissolved in dichloromethane (10 mL). To the solution were added sodium hydrogen carbonate (582 mg) and m-chloroperbenzoic acid (399 mg), and the resulting mixture was stirred at room temperature overnight. Adding water, the reaction mixture was extracted with ethyl acetate. The organic layer was washed with a saturated aqueous solution of sodium hydrogen carbonate and brine successively, and dried over anhydrous magnesium sulfate. The solvent was removed under reduced pressure to give the title compound (694 mg).

$^1$H-NMR (CDCl$_3$) δ ppm: 1.20 (6H, d, J=6.9 Hz), 1.95–2.05 (2H, m), 2.16 (3H, s), 2.67 (2H, t, J=7.3 Hz), 2.80 (2H, t, J=7.6 Hz), 3.30–3.55 (1H, m), 5.00 (2H, s), 6.40 (1H, dd, J=8.7 Hz, 2.8 Hz), 6.74 (1H, d, J=8.7 Hz), 6.81 (1H, s), 6.84 (1H, d, J=2.8 Hz), 7.20–7.55 (5H, m), 8.29 (1H, s).

REFERENCE EXAMPLE 28-1

7-[4-benzyloxy-3-(4-fluorobenzyl)phenoxy]-6-methylindan-4-yl formate

The title compound was prepared in a similar manner to those described in Reference Example 28 using 7-[4-benzyloxy-3-(4-fluorobenzyl)phenoxy]-6-methylindan-4-carbaldehyde instead of 7-(4-benzyloxy-3-isopropylphenoxy)-6-methyl-indan-4-carbaldehyde.

$^1$H-NMR (CDCl$_3$) δ ppm: 1.95–2.10 (2H, m), 2.14 (3H, s), 2.63 (2H, t, J=7.3 Hz), 2.79 (2H, t, J=7.6 Hz), 3.91 (2H, s), 4.97 (2H, s), 6.52 (1H, dd, J=8.8 Hz, 3.3 Hz), 6.64 (1H, d, J=3.3 Hz), 6.77 (1H, d, J=8.8 Hz), 6.80 (1H, s), 6.86–7.00 (2H, m), 7.05–7.15 (2H, m), 7.25–7.40 (5H, m), 8.28 (1H, s).

REFERENCE EXAMPLE 29

(4-fluorophenyl)-[2-hydroxy-5-(5-methyl-7-nitroindan-4-yloxy)phenyl]methanone 4-(4-methoxyphenoxy)-5-methyl-7-nitroindane (197 mg) and 4-fluorobenzoyl chloride (194 μL) were dissolved in dichloromethane (3.9 mL). Titanium tetrachloride (360 μL) was added dropwise to the solution under ice-cooling with stirring. The mixture was stirred under an argon atmosphere at room temperature for 15 hours. Adding water, the reaction mixture was extracted with ethyl acetate. The organic layer was washed with a saturated aqueous solution of sodium hydrogen carbonate, water and brine successively, and dried over anhydrous magnesium sulfate. The solvent was removed under reduced pressure. The residue was purified by column chromatography on silica gel (eluent: hexane/ethyl acetate=9/1) to give (4-fluorophenyl)-[2-methoxy-5-(5-methyl-7-nitroindan-4-yloxy)phenyl]methanone (155 mg).

The title compound was prepared in a similar manner to those described in Reference Example 5 using (4-fluorophenyl)-[2-methoxy-5-(5-methyl-7-nitroindan-4-yloxy)phenyl]methanone instead of 2-methoxy-5-(5-methyl-7-nitroindan-4-yloxy)benzaldehyde.

$^1$H-NMR (CDCl$_3$) δ ppm: 2.00–2.30 (5H, m), 2.66 (2H, t, J=7.6 Hz), 3.37 (2H, t, J=7.7 Hz), 6.90–7.30 (5H, m), 7.60–7.80 (2H, m), 7.94 (1H, d, J=0.7 Hz), 11.47 (1H, s).

REFERENCE EXAMPLE 30

2-methoxy-5-(5-methyl-7-nitroindan-4-yloxy)benzoic acid 2-methoxy-5-(5-methyl-7-nitroindan-4-yloxy)benzaldehyde (1.00 g) was dissolved in tert-butanol (24 mL). To the mixture was added 2-methyl-2-butene (6 mL) at room temperature with stirring. After adding sodium chlorite (553 mg) and an aqueous solution of sodium hydrogen phosphate (250 g/L, 12 mL), the mixture was stirred at room temperature for 2 days, and then extracted with ethyl acetate. The organic layer was washed with brine, and dried over anhydrous magnesium sulfate. The solvent was removed under reduced pressure to give the title compound (1.14 g).

$^1$H-NMR (CDCl$_3$) δ ppm: 2.03–2.13 (2H, m), 2.22 (3H, s), 2.65 (2H, t, J=7.7 Hz), 3.40 (2H, t, J=7.6 Hz), 4.07 (3H, s), 7.02 (1H, d, J=9.0 Hz), 7.08 (1H, dd, J=9.0, 3.2 Hz), 7.55 (1H, d, J=3.2 Hz), 7.98 (1H, s).

REFERENCE EXAMPLE 31

N-Cyclohexyl-2-methoxy-5-(5-methyl-7-nitroindan-4-yloxy) benzamide

2-Methoxy-5'-(5-methyl-7-nitroindan-4-yloxy)benzoic acid (100 mg), cyclohexylamine (37 μL), and triethylamine (61 μL) were dissolved in a mixed solvent of tetrahydrofuran (3 mL) and N,N-dimethylformamide (3 mL). Adding diethyl cyanophosphonate (66 μL) at room temperature with stirring, the mixture was stirred at room temperature for 16 hours. Adding water, the reaction mixture was extracted with ethyl acetate. The organic layer was washed with hydrochloric acid, water and brine successively, and dried over anhydrous magnesium sulfate. The solvent was removed under reduced pressure. The residue was purified by column chromatography on silica gel (eluent: hexane/ethyl acetate 3/1–1/1) to give the title compound (127 mg).

$^1$H-NMR (CDCl$_3$) δ ppm: 1.11–1.41 (5H, m), 1.47–1.67 (3H, m), 1.82–2.02 (4H, m), 2.13 (3H, s), 2.56 (2H, t, J=7.6 Hz), 3.28 (2H, t, J=7.5 Hz), 3.82–3.94 (4H, m), 6.82–6.88 (2H, m), 7.50–7.54 (1H, m), 7.76–7.86 (2H, m).

REFERENCE EXAMPLE 32

N-Cyclohexyl-2-hydroxy-5-(5-methyl-7-nitroindan-4-yloxy) benzamide

N-Cyclohexyl-2-methoxy-5-(5-methyl-7-nitroindan-4-yloxy)benzamide (40 mg) and lithium iodide (38 mg) were dissolved in 2,4,6-collidine (2 mL). The mixture was heated under reflux for 15 hours. Adding water, the reaction mixture was extracted with ethyl acetate. The organic layer was washed with 1 mol/L hydrochloric acid, water and brine successively, and dried over anhydrous magnesium sulfate. The solvent was removed under reduced pressure. The residue was purified by column chromatography on silica gel (eluent: hexane/ethyl acetate=3/1) to give the title compound (28 mg).

$^1$H-NMR (CDCl$_3$) δ ppm: 1.12–1.48 (5H, m), 1.62–1.82 (3H, m), 1.98–2.12 (4H, m), 2.26 (3H, s), 2.63 (2H, t, J=7.5 Hz), 3.36 (2H, t, J=7.5 Hz), 3.91–4.01 (1H, m), 6.09 (1H, d, J=7.6 Hz), 6.75 (1H, dd, J=8.9, 2.7 Hz), 6.88 (1H, d, J=8.9 Hz), 6.94 (1H, d, J=2.7 Hz), 7.95 (1H, s), 12.10 (1H, s).

REFERENCE EXAMPLE 33

3-{2-[2-Benzyloxy-5-(5-methyl-7-nitroindan-4-yloxy)phenyl]vinyl}cyclopentanone 4-(4-benzyloxy-3-iodo-phenoxy)-5-methyl-7-nitroindane (571 mg), 3-vinylcyclopentanone (197 μL), palladium acetate (II)(13 mg), triphenylphosphine (30 mg), and silver carbonate (189 mg) were stirred at 80° C. for 21 hours. To the reaction mixture were added water and ethyl acetate. The insoluble material was removed by filtration. The filtrate was extracted with ethyl acetate. The organic layer was washed with 1 mol/L hydrochloric acid, brine successively, and dried over anhydrous magnesium sulfate. The solvent was removed under reduced pressure. The residue was purified by column chromatography on silica gel (eluent: hexane/ethyl acetate=10/1–5/1) to give the title compound (155 mg).

¹H-NMR (CDCl₃) δ ppm: 1.73–1.84 (1H, m), 2.00–2.51 (10H, m), 2.66 (2H, t, J=7.9 Hz), 2.94–3.06 (1H, m), 3.38 (2H, t, J=7.4 Hz), 5.00–5.10 (2H, m), 6.20 (1H, dd, J=16.0, 7.4 Hz), 6.52 (1H, dd, J=8.7, 3.4 Hz), 6.77 (1H, dd, J=16.0, 0.8 Hz), 6.81 (1H, d, J=8.7 Hz), 6.97 (1H, d, J=3.4 Hz), 7.28–7.48 (5H, m), 7.97 (1H, s).

REFERENCE EXAMPLE 34

7-(4-Benzyloxy-3-iodophenoxy)-6-methylindan-4-ylamine

To a solution of 4-(4-benzyloxy-3-iodophenoxy)-5-methyl-7-nitroindane (4.18 g) in ethyl acetate (15 mL) was added 5% Pt/C (860 mg). The mixture was stirred under a hydrogen atmosphere at room temperature for 2 hours. The insoluble material was removed by filtration. The filtrate was evaporated under reduced pressure to dryness to give the title compound (3.89 g).

¹H-NMR (CDCl₃) δ ppm: 2.00–2.10 (2H, m), 2.06 (3H, s), 2.60–2.74 (4H, m), 5.06 (2H, s), 6.40 (1H, s), 6.67–6.75 (2H, m), 7.20–7.50 (6H, m).

REFERENCE EXAMPLE 34-1

4-(7-Amino-5-iodoindan-4-yloxy)-2-isopropylphenol

The title compound was prepared in a similar manner to those described in Reference Example 34 using 4-(5-iodo-7-nitroindan-4-yloxy)-2-isopropylphenol instead of 4-(4-benzyloxy-3-iodophenoxy)-5-methyl-7-nitroindane.

¹H-NMR (CDCl₃+CD₃OD) δ ppm: 1.19 (6H, d, J=6.9 Hz), 1.98–2.07 (2H, m), 2.63–2.73 (4H, m), 3.22 (1H, heptet, J=6.9 Hz), 6.37 (1H, dd, J=3.0, 8.7 Hz), 6.60 (1H, d, J=8.7 Hz), 6.76 (1H, d, J=3.0 Hz), 7.00 (1H, s).

REFERENCE EXAMPLE 34-2

7-(4-Benzyloxy-3-isopropylphenoxy)-6-trifluoromethylindan-4-ylamine

The title compound was prepared in a similar manner to those described in Reference Example 34 using 4-(4-benzyloxy-3-isopropylphenoxy)-7-nitro-5-trifluoromethylindane instead of 4-(4-benzyloxy-3-iodophenoxy)-5-methyl-7-nitroindane.

¹H-NMR (CDCl₃) δ ppm: 1.18 (6H, d, J=6.9 Hz), 1.99–2.07 (2H, m), 2.50–2.55 (2H, m), 2.68–2.73 (2H, m), 3.36 (1H, heptet, J=6.9 Hz), 3.62 (2H, br-s), 5.01 (2H, s), 6.48 (1H, dd, J=3.1, 8.8 Hz), 6.75 (1H, d, J=8.8 Hz), 6.81 (1H, s), 6.82 (1H, d, J=3.0 Hz), 7.27–7.44 (5H, m).

REFERENCE EXAMPLE 34-3

6-[5-(7-Amino-5-methylindan-4-yloxy)-2-hydroxybenzyl]-2H-pyridazine-3-one

The title compound was prepared in a similar manner to those described in Reference Example 34 using 6-[2-hydroxy-5-(5-methyl-7-nitroindan-4-yloxy)benzyl]-2H-pyridazine-3-one instead of 4-(4-benzyloxy-3-iodophenoxy)-5-methyl-7-nitroindane.

H-NMR (CDCl₃) δ ppm: 1.95–2.05 (2H, m), 2.02 (3H, s), 2.55–2.71 (4H, m), 3.85(2H, s), 6.40(1H, s), 6.47(1H, dd, J=3.0, 8.8 Hz), 6.59 (1H, d, J=3.0 Hz), 6.66 (1H, d, J=8.8 Hz), 6.83–6.90 (1H, m), 7.23–7.30 (1H, m).

REFERENCE EXAMPLE 34-4

7-(4-Benzyloxy-3-isopropylphenoxy)-6-bromoindan-4-ylamine

The title compound was prepared in a similar manner to those described in Reference Example 34 using 4-(4-benzyloxy-3-isopropylphenoxy)-5-bromo-7-nitroindane instead of 4-(4-benzyloxy-3-iodophenoxy)-5-methyl-7-nitroindane.

¹H-NMR (CDCl₃) δ ppm: 1.19 (6H, d, J=6.9 Hz), 2.00–2.10 (2H, m), 2.64–2.71 (4H, m), 3.36 (1H, heptet, J=6.9 Hz), 3.53 (2H, br-s), 5.00 (2H, s), 6.45 (1H, dd, J=3.0, 8.8 Hz), 6.75 (1H, d, J=8.8 Hz), 6.77 (1H, s), 6.85 (1H, d, J=3.0 Hz), 7.27–7.46 (5H, m).

REFERENCE EXAMPLE 34-5

7-(4-Benzyloxy-5,6,7,8-tetrahydronaphthalen-1-yloxy)-6-bromoindan-4-ylamine

The title compound was prepared in a similar manner to those described in Reference Example 34 using 5-benzyloxy-8-(5-bromo-7-nitroindan-4-yloxy)-1,2,3,4-tetrahydronaphthalene instead of 4-(4-benzyloxy-3-iodophenoxy)-5-methyl-7-nitroindane.

¹H-NMR (CDCl₃) δ ppm: 1.73–1.86 (4H, m), 2.00–2.10 (2H, m), 2.60–2.95 (8H, m), 3.52 (2H, br-s), 4.97 (2H, s), 6.16 (1H, d, J=8.8 Hz), 6.51 (1H, d, J=8.8 Hz), 6.76 (1H, s), 7.27–7.45 (5H, m).

REFERENCE EXAMPLE 34-6

[7-(3-acetyl-4-hydroxy-2-methoxyphenoxy)-6-methylindan-4-yl]amine

The title compound was prepared in a similar manner to those described in Reference Example 34 using 1-[6-hydroxy-2-methoxy-3-(5-methyl-7-nitroindan-4-yloxy)phenyl]ethanone instead of 4-(4-benzyloxy-3-iodophenoxy)-5-methyl-7-nitroindane.

¹H-NMR (CDCl₃) δ ppm: 2.03–2.12 (2H, m), 2.10 (3H, s), 2.62–2.75 (4H, m), 2.78 (3H, s), 3.48 (2H, br-s), 4.11 (3H, s), 6.42 (1H, s), 6.51 (1H, d, J=9.1 Hz), 6.64 (1H, d, J=9.1 Hz), 12.22 (1H, s).

REFERENCE EXAMPLE 34-7

4-(7-Amino-5-methylindan-4-yloxy)-2-ethyl-3-hydroxyphenyl trifluoromethanesulfonate The title compound was prepared in a similar manner to those described in Reference Example 34 using 2-ethyl-3-hydroxy-4-(7-amino-5-methylindan-4-yloxy)phenyl trifluoromethanesulfonate instead of 4-(4-benzyloxy-3-iodophenoxy)-5-methyl-7-nitroindane.

¹H-NMR (CDCl₃) δ ppm: 1.26 (3H, t, J=7.5 Hz), 2.00–2.10 (2H, m), 2.05 (3H, s), 2.58–2.75 (4H, m), 2.79 (2H, q, J=7.5 Hz), 6.25 (1H, d, J=9.0 Hz), 6.41 (1H, s), 6.60 (1H, d, J=9.0 Hz).

REFERENCE EXAMPLE 34-8

7-(4-Benzyloxy-3-isopropylphenoxy)-6-methylindan-4-ylamine

The title compound was prepared in a similar manner to those described in Reference Example 34 using 4-(4-benzyloxy-3-isopropylphenoxy)-5-methyl-7-nitroindane instead of 4-(4-benzyloxy-3-iodophenoxy)-5-methyl-7-nitroindane.

$^1$H-NMR (CDCl$_3$) δ ppm: 1.19 (6H, d, J=6.9 Hz), 1.98–2.10 (2H, m), 2.08 (3H, s), 2.63–2.75 (4H, m), 3.36 (1H, heptet, J=6.9 Hz), 3.45 (2H, br-s), 5.00(2H, s), 6.41 (1H, s), 6.41 (1H, dd, J=3.0, 8.9 Hz), 6.73 (1H, d, J=8.9 Hz), 6.81 (1H, d, J=3.0 Hz), 7.27–7.45 (5H, m).

REFERENCE EXAMPLE 34-9

7-(4-Benzyloxy-3-isopropyl-2-methoxyphenoxy)-6-methylindan-4-ylamine

The title compound was prepared in a similar manner to those described in Reference Example 34 using 4-(4-benzyloxy-3-isopropyl-2-methoxyphenoxy)-5-methyl-7-nitroindane instead of 4-(4-benzyloxy-3-iodophenoxy)-5-methyl-7-nitroindane.

$^1$H-NMR-(CDCl$_3$) δ ppm: 1.37 (6H, d, J=7.1 Hz), 2.00–2.12 (2H, m), 2.09 (3H, s), 2.63–2.75 (4H, m), 3.45 (2H, br-s), 3.65 (1H, heptet, J=7.1 Hz), 3.96 (3H, s), 4.96 (2H, s), 6.19 (1H, d, J=9.0 Hz), 6.42 (1H, s), 6.44 (1H, d, J=9.0 Hz), 7.27–7.45 (5H, m).

REFERENCE EXAMPLE 34-10

7-[4-benzyloxy-3-(4-fluorobenzyl)phenoxy]-6-methylindan-4-ylamine

The title compound was prepared in a similar manner to those described in Reference Example 34 using 4-[4-benzyloxy-3-(4-fluorobenzyl)phenoxy]-5-methyl-7-nitroindane instead of 4-(4-benzyloxy-3-iodophenoxy)-5-methyl-7-nitroindane.

$^1$H-NMR (CDCl$_3$) δ ppm: 1.97–2.08 (2H, m), 2.04 (3H, s), 2.57–2.74 (4H, m), 3.90 (2H, s), 4.95 (2H, s), 6.41 (1H, s), 6.53 (1H, dd, J=3.0, 8.8 Hz), 6.63 (1H, d, J=3.0 Hz), 6.76 (1H, d, J=8.8 Hz), 6.87–6.93 (2H, m), 7.07–7.15 (2H, m), 7.23–7.38 (5H, m).

REFERENCE EXAMPLE 34-11

[5-(7-Amino-5-methylindan-4-yloxy)-2-hydroxyphenyl]-(4-fluorophenyl)methanone

The title compound was prepared in a similar manner to those described in Reference Example 34 using (4-fluorophenyl)-[2-hydroxy-5-(5-methyl-7-nitroindan-4-yloxy)phenyl]methanone instead of 4-(4-benzyloxy-3-iodophenoxy)-5-methyl-7-nitroindane.

$^1$H-NMR (CDCl$_3$) δ ppm: 1.90–2.15 (5H, m), 2.55–2.80 (4H, m), 6.37 (1H, s), 6.90–7.20 (5H, m), 7.60–7.75 (2H, m), 11.30–11.50 (1H, br-s).

REFERENCE EXAMPLE 34-12

[7-(4-Methoxyphenoxy)-6-methylindan-4-yl]amine

The title compound was prepared in a similar manner to those described in Reference Example 34 using 4-(4-benzyloxy-3-isopropylphenoxy)-5-bromo-7-nitroindane instead of 4-(4-benzyloxy-3-iodophenoxy)-5-methyl-7-nitroindane.

$^1$H-NMR (CDCl$_3$) δ ppm: 1.95–2.15 (5H, m), 2.65 (2H, t, J=7.5 Hz), 2.71 (2H, t, J=7.3 Hz), 3.44 (2H, br-s), 3.75 (3H, s), 6.41 (1H, s), 6.65–6.85 (4H, m).

REFERENCE EXAMPLE 34-13

4-(7-Amino-5-methylindan-4-yloxy)-2-phenethylphenol

The title compound was prepared in a similar manner to those described in Reference Example 34 using 4-(5-methyl-7-nitroindan-4-yloxy)-2-phenethylphenol instead of 4-(4-benzyloxy-3-iodophenoxy)-5-methyl-7-nitroindane.

$^1$H-NMR (CDCl$_3$) δ ppm: 1.95–2.10 (5H, m), 2.55–2.95 (8H, m), 3.45 (2H, s), 4.31 (1H, s), 6.35–6.65 (4H, m), 7.10–7.35 (5H, m).

REFERENCE EXAMPLE 34-14

5-(7-Amino-5-methylindan-4-yloxy)-N-cyclohexyl-2-hydroxy benzamide

The title compound was prepared in a similar manner to those described in Reference Example 34 using N-cyclohexyl-2-hydroxy-5-(5-methyl-7-nitroindan-4-yloxy)benzamide instead of 4-(4-benzyloxy-3-iodophenoxy)-5-methyl-7-nitroindane.

$^1$H-NMR (CDCl$_3$) δ ppm: 1.16–1.84 (8H, m), 1.96–2.11 (7H, m), 2.64 (2H, t, J=7.7 Hz), 2.72 (2H, t, J=7.4 Hz), 3.35–3.61 (2H, br s), 3.87–4.01 (1H, m), 6.03 (1H, d, J=7.8 Hz), 6.42 (1H, s), 6.72 (1H, dd, J=9.3, 2.9 Hz), 6.82 (1H, d, J=9.3 Hz), 6.87 (1H, d, J=2.9 Hz), 11.92 (1H, s).

REFERENCE EXAMPLE 34-15

3-{2-[5-(7-Amino-5-methylindan-4-yloxy)-2-benzyloxyphenyl]ethyl}cyclopentanone

The title compound was prepared in a similar manner to those described in Reference Example 34 using 3-{2-[2-benzyloxy-5-(5-methyl-7-nitroindan-4-yloxy)phenyl]vinyl}cyclopentanone instead of 4-(4-benzyloxy-3-iodophenoxy)-5-methyl-7-nitroindane.

$^1$H-NMR (CDCl$_3$) δ ppm: 1.40–2.40 (14H, m), 2.56–2.75 (6H, m), 3.46 (2H, br-s), 5.00 (2H, s), 6.41 (1H, s), 6.50–6.54 (1H, m), 6.65 (1H, d, J=2.8 Hz), 6.76 (1H, d, J=8.8 Hz), 7.28–7.46 (5H, m).

REFERENCE EXAMPLE 35

7-(4-Benzyloxy-3-isopropylphenylsulfanyl)-6-methylindan-4-ylamine 4-(4-benzyloxy-3-isopropylphenylsulfanyl)-5-methyl-7-nitroindane was prepared in a similar manner to those described in Reference Example 8 using 5-methyl-7-nitroindan-4-thiol instead of 5-methyl-7-nitroindan-4-ol and using bis(4-benzyloxy-3-isopropylphenyl)iodonium tetrafluoroborate instead of bis(4-methoxyphenyl)iodonium tetrafluoroborate.

The title compound was prepared in a similar manner to those described in Reference Example 34 using 4-(4-benzyloxy-3-isopropylphenylsulfanyl)-5-methyl-7-nitroindane instead of 4-(4-benzyloxy-3-iodophenoxy)-5-methyl-7-nitroindane.

$^1$H-NMR (CDCl$_3$) δ ppm: 1.16 (6H, d, J=6.9 Hz), 1.95–2.15 (2H, m), 2.33 (3H, s), 2.68–2.82 (2H, m), 2.85–3.00 (2H, m), 3.25–3.40 (1H, m), 4.99 (2H, s), 6.49 (1H, s), 6.62 (1H, dd, J=8.5 Hz, 2.4 Hz), 6.70 (1H, d, J=8.5 Hz), 7.00 (H, d, J=2.4 Hz), 7.20–7.55 (5H, m).

REFERENCE EXAMPLE 36

1-[6-Benzyloxy-2-methoxy-3-(5-methyl-7-nitroindan-4-yloxy)phenyl]ethanone

To a solution of 1-[6-benzyloxy-2-hydroxy-3-(5-methyl-7-nitroindan-4-yloxy)phenyl]ethanone (10.0 g) in tetrahydrofuran (15 mL) was added cesium carbonate (7.53 g) under ice-cooling, and then was added dropwise methyl iodide (2.88 mL). After stirring at room temperature overnight, the reaction mixture was evaporated under reduced pressure to dryness. Adding ethyl acetate (30 mL), the mixture was stirred for 30 min. The insoluble material was removed by filtration. The filtrate was evaporated under reduced pressure to dryness to give the title compound (10.2 g).

$^1$H-NMR (CDCl$_3$) δ ppm: 2.03–2.10 (2H, m), 2.27 (3H, s), 2.55 (3H, s), 2.64–2.70 (2H, m), 3.33–3.40 (2H, m), 3.96 (3H, s), 5.01 (2H, s), 6.37 (1H, d, J=9.0 Hz), 6.51 (1H, d, J=9.0 Hz), 7.28–7.42 (5H, m), 7.98 (1H, s).

REFERENCE EXAMPLE 37

1-[3-(7-Amino-5-methylindan-4-yloxy)-6-benzyloxy-2-methoxyphenyl]ethanone

The title compound was prepared in a similar manner to those described in Reference Example 0.34 using 1-[6-benzyloxy-2-methoxy-3-(5-methyl-7-nitroindan-4-yloxy)phenyl]ethanone instead of 4-(4-benzyloxy-3-iodophenoxy)-5-methyl-7-nitroindane.

$^1$H-NMR (CDCl$_3$) δ ppm: 2.00–2.10 (2H, m), 2.08 (3H, s), 2.54 (3H, s), 2.63–2.74 (4H, m), 3.48 (2H, br-s), 4.00 (3H, s), 4.97 (2H, s), 6.36(1H, d, J=9.0 Hz), 6.42(1H, s), 6.46(1H, d, J=9.0 Hz), 7.27–7.35 (5H, m).

REFERENCE EXAMPLE 38

1-[6-Benzyloxy-3-(7-dibenzylamino-5-methylindan-4-yloxy)-2-methoxyphenyl]ethanone The title compound was prepared in a similar manner to those described in Reference Example 22 using 1-[3-(7-amino-5-methylindan-4-yloxy)-6-benzyloxy-2-methoxyphenyl]ethanone instead of 7-(4-benzyloxy-3-iodophenoxy)-6-methylindan-4-ylamine.

$^1$H-NMR (CDCl$_3$) δ ppm: 1.97–2.08 (2H, m), 2.04 (3H, s), 2.54 (3H, s), 2.63–2.67 (2H, m), 2.94–3.00 (2H, m), 3.99 (3H, s), 4.17 (4H, s), 4.98 (2H, s), 6.32 (1H, d, J=9.0 Hz), 6.47 (1H, d, J=9.0 Hz), 6.60 (1H, s), 7.20–7.40 (15H, m).

REFERENCE EXAMPLE 39

Dibenzyl[7-(4-benzyloxy-3-isopropenyl-2-methoxyphenoxy)-6-methylindan-4-yl]amine To a solution of 1-[6-benzyloxy-3-(7-dibenzylamino-5-methylindan-4-yloxy)-2-methoxyphenyl]ethanone (13.3 g) in tetrahydrofuran (100 mL) was added dropwise a 1.14 mol/L solution of methyllithium in diethyl ether (30 mL) under an argon atmosphere at −78° C. The mixture was stirred for 30 min, and then warmed up to room temperature gradually. To the dark-red reaction mixture was added a saturated aqueous solution of ammonium chloride (40 mL). The reaction mixture was stirred for 10 min. The organic solvent was evaporated under reduced pressure to dryness. The residue was extracted with ethyl acetate. The organic layer was washed with brine, and dried over anhydrous magnesium sulfate. The solvent was evaporated under reduced pressure to dryness to give 2-[6-benzyloxy-3-(7-dibenzylamino-5-methylindan-4-yloxy)-2-methoxyphenyl]-propane-2-ol (13.9 g).

2-[6-Benzyloxy-3-(7-dibenzylamino-5-methylindan-4-yloxy)-2-methoxyphenyl]-propane-2-ol (13.9 g) was dissolved in dichloromethane (100 mL). Adding concentrated hydrochloric acid (40 mL), the mixture was stirred for 20 min vigorously. The organic layer was separated, and the water layer was extracted with dichloromethane. The combined organic layers were washed with a 2 mol/L aqueous solution of sodium hydroxide and brine successively, and dried over anhydrous magnesium sulfate. The solvent was removed under reduced pressure. The residue was purified by column chromatography on silica gel (eluent: hexane/ethyl acetate=10/1–3/1) to give the title compound (7.97 g).

$^1$H-NMR (CDCl$_3$) δ ppm: 1.95–2.03 (2H, m), 2.05 (3H, d, J=9.0 Hz), 2.13 (3H, s), 2.65–2.70 (2H, m), 2.93–2.98 (2H, m), 3.93 (3H, s), 4.16 (4H, s), 4.98 (2H, s), 5.00 (1H, br-s), 5.35 (1H, br-s), 6.23 (1H, d, J=9.0 Hz), 6.45 (1H, d, J=9.0 Hz), 6.60 (1H, s), 7.20–7.40 (15H, m).

REFERENCE EXAMPLE 40

4-(4-Benzyloxy-3-isopropylphenoxy)-7-iodo-5-methylindane

To 7-(4-benzyloxy-3-isopropylphenoxy)-6-methylindan-4-ylamine (388 mg) were added concentrated hydrochloric acid (2.5 mL), water (5 mL) and toluene (3 mL). The mixture was heated to form a hydrochloride salt, and then cooled under ice-cooling. Adding an aqueous solution of sodium nitrite (76 mg) in water (1 mL), the mixture was stirred under ice-cooling for 5 min. Adding an aqueous solution of potassium iodide (1.66 g) in water (2.5 mL), the reaction mixture was stirred at room temperature for 10 min, then stirred at 100° C. for 10 min. Adding an aqueous solution of sodium sulfite (200 mg/20 mL) under ice-cooling, the reaction mixture was extracted with ethyl acetate. The organic layer was washed with, water, a saturated aqueous solution of sodium hydrogen carbonate and brine successively, and dried over anhydrous magnesium sulfate. The solvent was removed under reduced pressure. The residue was purified by column chromatography on silica gel (eluent: hexane/ethyl acetate=10/1) to give the title compound (244 mg).

$^1$H-NMR (CDCl$_3$) δ ppm: 1.19 (6H, d, J=6.9 Hz), 1.93–2.06 (2H, m), 2.12 (3H, s), 2.73–2.80 (2H, m), 2.83–2.90 (2H, m), 3.37 (1H, heptet, J=6.9 Hz), 5.01 (2H, s), 6.39 (1H, dd, J=3.0, 8.8 Hz), 6.74 (1H, d, J=8.8 Hz), 6.81 (1H, d, J=3.0 Hz), 7.28–7.47 (6H, m).

REFERENCE EXAMPLE 40-1

4-(4-Benzyloxy-3-isopropyl-2-methoxyphenoxy)-7-iodo-5-methylindane

The title compound was prepared in a similar manner to those described in Reference Example 40 using 7-(4-benzyloxy-3-isopropyl-2-methoxyphenoxy)-6-methylindan-4-ylamine instead of 7-(4-benzyloxy-3-isopropylphenoxy)-6-methylindan-4-ylamine.

$^1$H-NMR (CDCl$_3$) δ ppm: 1.37 (6H, d, J=7.1 Hz), 1.92–2.05 (2H, m), 2.14 (3H, s), 2.75–2.93 (4H, m), 3.64 (1H, heptet, J=7.1 Hz), 3.93 (3H, s), 4.97 (2H, s), 6.17 (1H, d, J=9.0 Hz), 6.45 (1H, d, J=9.0 Hz), 7.27–7.46 (6H, m).

REFERENCE EXAMPLE 40-2

4-[4-Benzyloxy-3-(4-fluorobenzyl)phenoxy]-7-iodo-5-methylindane

The title compound was prepared in a similar manner to those described in Reference Example 40 using 7-[4-benzyloxy-3-(4-fluorobenzyl)-phenoxy]-6-methylindan-4-ylamine instead of 7-(4-benzyloxy-3-isopropylphenoxy)-6-methylindan-4-ylamine.

$^1$H-NMR (CDCl$_3$) δ ppm: 1.93–2.05 (2H, m), 2.09 (3H, s), 2.70–2.90 (4H, m), 3.90(2H, s), 4.95(2H, s), 6.50(1H, dd, J=3.1, 8.8 Hz), 6.62 (1H, d, J=3.1 Hz), 6.76 (1H, d, J=8.8 Hz), 6.87–6.95 (2H, m), 7.05–7.15 (2H, m), 7.25–7.45 (6H, m).

REFERENCE EXAMPLE 41

7-(4-benzyloxy-3-isopropylphenoxy)-6-methylindan-4-carbonitrile 4-(4-benzyloxy-3-isopropylphenoxy)-7-iodo-5-methylindane (214 mg), potassium cyanide (60 mg), bis(dibenzylideneacetone)palladium (4 mg), 1,1'-bis(diphenylphosphino)ferrocene (8 mg), and 1-methyl-2-pyrrolidone (2 mL) were stirred under an argon atmosphere at 80° C. overnight. Adding water, the reaction mixture was extracted with ethyl acetate, washed with brine, and dried over anhydrous magnesium sulfate. The solvent was removed under reduced pressure. The residue was purified by thin layer chromatography on silica gel (developing solvent: hexane/ethyl acetate) to give the title compound (49 mg).

$^1$H-NMR (CDCl$_3$) δ ppm: 1.19 (6H, d, J=6.9 Hz), 2.00–2.10 (2H, m), 2.20 (3H, s), 2.56–2.63 (2H, m), 3.03–3.10 (2H, m), 3.38 (1H, heptet, J=6.9 Hz), 5.07 (2H, s), 6.43 (1H, dd, J=3.0, 8.8 Hz), 6.76 (1H, d, J=8.8 Hz), 6.80 (1H, d, J=3.0 Hz), 7.28–7.55 (6H, m).

REFERENCE EXAMPLE 41-1

7-(4-Benzyloxy-3-isopropyl-2-methoxyphenoxy)-6-methylindan-4-carbonitrile

The title compound was prepared in a similar manner to those described in Reference Example 41 using 4-(4-benzyloxy-3-isopropyl-2-methoxyphenoxy)-7-iodo-5-methylindane instead of 4-(4-benzyloxy-3-isopropylphenoxy)-7-iodo-5-methylindane.

$^1$H-NMR (CDCl$_3$) δ ppm: 1.37 (6H, d, J=7.1 Hz), 1.98–2.08 (2H, m), 2.23 (3H, s), 2.53–2.62 (2H, m), 3.03–3.08 (2H, m), 3.62 (1H, heptet, J=7.1 Hz), 3.90 (3H, s), 5.00 (2H, s), 6.25 (1H, d, J=9.0 Hz), 6.49 (1H, d, J=9.0 Hz), 7.27–7.45 (6H, m).

REFERENCE EXAMPLE 41-2

7-[4-Benzyloxy-3-(4-fluorobenzyl)phenoxy]-6-methylindan-4-carbonitrile

The title compound was prepared in a similar manner to those described in Reference Example 41 using 4-[4-benzyloxy-3-(4-fluorobenzyl)phenoxy]-7-iodo-5-methylindane instead of 4-(4-benzyloxy-3-isopropylphenoxy)-7-iodo-5-methylindane.

$^1$H-NMR (CDCl$_3$) δ ppm: 1.97–2.10 (2H, m), 2.16 (3H, s), 2.53–2.60 (2H, m), 2.98–3.08 (2H, m), 3.92 (2H, s), 4.98 (2H, s), 6.51 (1H, dd, J=3.1, 8.8 Hz), 6.63 (1H, d, J=3.1 Hz), 6.79 (1H, d, J=8.8 Hz), 6.87–6.96 (2H, m), 7.06–7.12 (2H, m), 7.25–7.45 (6H, m).

REFERENCE EXAMPLE 42

7-(4-Benzyloxy-3-isopropylphenoxy)-6-methylindan-4-carboxylic Acid

To a solution of 7-(4-benzyloxy-3-isopropylphenoxy)-6-methylindan-4-carbonitrile (49 mg) in ethanol (0.5 mL) was added sodium hydroxide (70 mg). The mixture was heated at reflux temperature under an argon atmosphere overnight. The reaction mixture was evaporated under reduced pressure to dryness. The residue was neutralized with 1 mol/L hydrochloric acid. Adding water, the mixture was extracted with ethylacetate. The organic layer was washed with brine, and dried over anhydrous magnesium sulfate. The solvent was removed under reduced pressure to give the title compound (52 mg).

$^1$H-NMR (CDCl$_3$) δ ppm: 1.20 (6H, d, J=6.9 Hz), 1.97–2.10 (2H, m), 2.22 (3H, s), 2.59–2.68 (2H, m), 3.26–3.34 (2H, m), 3.38 (1H, heptet, J=6.9 Hz), 5.02 (2H, s), 6.44 (1H, dd, J=3.0, 8.8 Hz), 6.76 (1H, d, J=8.8 Hz), 6.82 (1H, d, J=3.0 Hz), 7.30–7.50 (5H, m), 7.86 (1H, s).

REFERENCE EXAMPLE 42-1

7-(4-Benzyloxy-3-isopropyl-2-methoxyphenoxy)-6-methylindan-4-carboxylic Acid The title compound was prepared in a similar manner to those described in Reference Example 42 using 7-(4-benzyloxy-3-isopropyl-2-methoxyphenoxy)-6-methylindan-4-carbonitrile instead of 7-(4-benzyloxy-3-isopropylphenoxy)-6-methylindan-4-carbonitrile.

$^1$H-NMR (CDCl$_3$) δ ppm: 1.38 (6H, d, J=7.0 Hz), 1.96–2.10 (2H, m), 2.24 (3H, s), 2.56–2.72 (2H, m), 3.23–3.34 (2H, m), 3.64 (1H, heptet, J=7.0 Hz), 3.94 (3H, s), 4.99 (2H, s), 6.22 (1H, d, J=9.0 Hz), 6.48 (1H, d, J=9.0 Hz), 7.28–7.48 (5H, m), 7.86 (1H, s).

REFERENCE EXAMPLE 42-3

7-[4-Benzyloxy-3-(4-fluorobenzyl)phenoxy]-6-methylindan-4-carboxylic Acid

The title compound was prepared in a similar manner to those described in Reference Example 42 using 7-[4-benzyloxy-3-(4-fluorobenzyl)phenoxy]-6-methylindan-4-carbonitrile instead of 7-(4-benzyloxy-3-isopropylphenoxy) 6-methylindan-4-carbonitrile.

$^1$H-NMR (CDCl$_3$) δ ppm: 1.95–2.08 (2H, m), 2.19 (3H, s), 2.56–2.66 (2H, m), 3.23–3.33 (2H, m), 3.91 (2H, s), 4.97 (2H, s), 6.53 (1H, dd, J=3.0, 8.9 Hz), 6.65 (1H, d, J=3.0 Hz), 6.78 (1H, d, J=8.9 Hz), 6.86–6.96 (2H, m), 7.06–7.22 (2H, m), 7.27–7.48 (5H, m), 7.84 (1H, s).

REFERENCE EXAMPLE 43

4-Iodo-5-methyl-7-nitroindane

To a solution of 5-methyl-7-nitroindan-4-ol (2.78 g) in dichloromethane (20 mL) was added pyridine (3.15 mL). Adding dropwise trifluoromethanesulfonic anhydride (3.15 mL) under ice-cooling, the mixture was stirred at ambient temperature for 25 min. Adding water, the reaction mixture was acidified with 1 mol/L hydrochloric acid, and then extracted with dichloromethane. The organic layer was washed with a saturated aqueous solution of sodium hydrogen carbonate and brine successively, and dried over anhydrous magnesium sulfate. The reaction mixture was evaporated under reduced pressure to dryness to give 5-methyl-7-nitroindan-4-yl trifluoromethanesulfonate (4.40 g).

To a solution of 5-methyl-7-nitroindan-4-yl trifluoromethanesulfonate (3.02 g) in N,N-dimethylformamide (10 mL) was added lithium iodide mono hydrate (6.10 g). The mixture was stirred under an argon atmosphere at 150° C. for 7 hours. Adding water, the reaction mixture was extracted with ethyl acetate. The organic layer was washed with a 1 mol/L aqueous solution of sodium hydroxide, water and brine successively, and dried over anhydrous magnesium sulfate. The solvent was removed under reduced pressure to give the title compound (2.19 g).

$^1$H-NMR (CDCl$_3$) δ ppm: 2.12–2.20 (2H, m), 2.51 (3H, s), 3.00–3.06 (2H, m), 3.52–3.57 (2H, m), 7.84 (1H, s).

REFERENCE EXAMPLE 44

7-Iodo-6-methylindan-4-ylamine

The title compound was prepared in a similar manner to those described in Reference Example 34 using 4-iodo-5-methyl-7-nitroindane instead of 4-(4-benzyloxy-3-iodophenoxy)-5-methyl-7-nitroindane.

$^1$H-NMR (CDCl$_3$) δ ppm: 2.05–2.14 (2H, m), 2.33 (3H, s), 2.82–2.94 (4H, m), 6.47 (1H, s).

REFERENCE EXAMPLE 45

Dibenzyl(7-iodo-6-methylindan-4-yl)amine

The title compound was prepared in a similar manner to those described in Reference Example 22 using 7-iodo-6-methylindan-4-ylamine instead of 7-(4-benzyloxy-3-iodophenoxy)-6-methylindan-4-ylamine.

$^1$H-NMR (CDCl$_3$) δ ppm: 2.02–2.10 (2H, m), 2.29 (3H, s), 2.89–2.94 (2H, m), 3.12–3.16 (2H, m), 4.18 (4H, s), 6.60 (1H, s), 7.19–7.31 (10H, m).

REFERENCE EXAMPLE 46

(4-Benzyloxy-3-isopropylphenyl)-(7-dibenzylamino-5-methylindan-4-yl)methanol

To a solution of dibenzyl(7-iodo-6-methylindan-4-yl)amine (583 mg) in dry tetrahydrofuran (10 mL) was added a 1.48 mol/L solution of tert-butyllithium in n-pentane (1.30 mL) at −100° C. The mixture was stirred for 15 min. Adding dropwise 4-benzyloxy-3-isopropylbenzaldehyde (320 mg) in tetrahydrofuran (5 mL), the reaction mixture turned orange solution. The reaction mixture was stirred at ambient temperature for 15 min, and then warmed to room temperature. To the reaction mixture was added a saturated aqueous solution of ammonium chloride to quench the reaction. Adding brine, the mixture was extracted with ethyl acetate. The organic layer was dried over anhydrous magnesium sulfate. The solvent was removed under reduced pressure. The residue was purified by column chromatography on aminopropyl silica gel (eluent: hexane/ethyl acetate=3/1–1/1) to give the title compound (497 mg).

$^1$H-NMR (CDCl$_3$) δ ppm: 1.14–1.21 (6H, m), 1.90–2.05 (3H, m), 2.17 (3H, s), 2.65–2.72 (1H, m), 2.90–2.96 (3H, m), 3.34–3.43 (1H, m), 4.20 (4H, s), 5.06 (2H, s), 6.10–6.14 (1H, m), 6.53 (1H, s), 6.82 (1H, d, J=8.5 Hz), 6.94–6.98 (1H, m), 7.15–7.45 (15H, m).

REFERENCE EXAMPLE 47

(4-Benzyloxy-3-isopropylphenyl)-(7-dibenzylamino-5-methylindan-4-yl)methanone

To a solution of (4-benzyloxy-3-isopropylphenyl)-(7-dibenzylamino-5-methylindan-4-yl)methanol (497 mg) in dichloromethane (10 mL) was added manganese (IV) oxide (2.98 g) at room temperature for 3 days. The insoluble material was removed by filtration. The filtrate was evaporated under reduced pressure to dryness to give the title compound (436 mg).

$^1$H-NMR (CDCl$_3$) δ ppm: 1.24 (6H, d, J=6.9 Hz), 1.93–2.03 (2H, m), 2.06 (3H, s), 2.59–2.67 (2H, m), 2.92–2.99 (2H, m), 3.39 (1H, heptet, J=6.9 Hz), 4.28 (4H, s), 5.14 (2H, s), 6.54 (1H, s), 6.88 (1H, d, J=8.6 Hz), 7.22–7.46 (15H, m), 7.53 (1H, dd, J=2.1, 8.6 Hz), 7.83 (1H, d, J=2.1 Hz).

REFERENCE EXAMPLE 48

4-(7-Amino-5-methylindan-4-yloxy)-2-(4-fluorobenzyl)phenol

The title compound was prepared in a similar manner to those described in Reference Example 34 using 4-[4-benzyloxy-3-(4-fluorobenzyl)phenoxy]-5-methyl-7-nitroindane instead of 4-(4-benzyloxy-3-iodophenoxy)-5-methyl-7-nitroindane and using Pd/C instead of Pt/C.

$^1$H-NMR (CDCl$_3$) δ ppm: 1.97–2.08 (2H, m), 2.06 (3H, s), 2.60–2.64 (2H, m), 2.66–2.73 (2H, m), 3.46 (2H, br-s), 3.88 (2H, s), 4.49 (1H, br-s), 6.40 (1H, s), 6.47 (1H, dd, J=3.0, 8.7 Hz), 6.58 (1H, d, J=8.7 Hz), 6.60 (1H, d, J=3.0 Hz), 6.93–7.97 (2H, m), 7.12–7.17 (2H, m).

REFERENCE EXAMPLE 48-1

4-(7-Amino-5-methylindan-4-yloxy)-2-isopropylphenol

The title compound was prepared in a similar manner to those described in Reference Example 48 using 4-(4-benzyloxy-3-isopropylphenoxy)-5-methyl-7-nitroindane instead of 4-[4-benzyloxy-3-(4-fluorobenzyl)phenoxy]-5-methyl-7-nitroindane.

$^1$H-NMR (CDCl$_3$+CD$_3$OD) δ ppm: 1.19 (6H, d, J=6.9 Hz), 1.98–2.10 (2H, m), 2.08 (3H, s), 2.62–2.74 (4H, m), 3.22 (1H, heptet, J=6.9 Hz), 6.33 (1H, dd, J=3.0, 8.7 Hz), 6.43 (1H, s), 6.57 (1H, d, J=8.7 Hz), 6.73 (1H, d, J=3.0 Hz).

REFERENCE EXAMPLE 48-2

4-(7-Amino-5-methylindan-4-yloxy)-3-(2-cyclohexylethoxy)-2-ethylphenol

The title compound was prepared in a similar manner to those described in Reference Example 26 using 4-[4-benzyloxy-2-(2-cyclohexylethoxy)-3-ethylphenoxy]-5-methyl-7-nitroindane instead of 4-[4-benzyloxy-3-(4-fluorobenzyl)phenoxy]-5-methyl-7-nitroindane.

$^1$H-NMR (CDCl$_3$) δ ppm: 0.80–1.33 (5H, m), 1.21 (3H, t, J=7.4 Hz), 1.48–1.80 (8H, m), 1.95–2.10 (2H, m), 2.08

(3H, s), 2.57–2.78 (6H, m), 3.49 (2H, br-s), 4.13–4.20 (2H, m), 4.95 (1H, br-s), 6.07 (1H, d, J=8.8 Hz), 6.15 (1H, d, J=8.8 Hz), 6.43 (1H, s).

REFERENCE EXAMPLE 49

4-(7-Amino-5-methylindan-4-yloxy)-2-(1-hydroxyethyl)-3-hydroxymethylphenol

Ethyl 6-(7-amino-5-methylindan-4-yloxy)-2-acetyl-3-hydroxybenzoate was prepared in a similar manner to those described in Reference Example 34 using ethyl 2-acetyl-3-hydroxy-6-(5-methyl-7-nitroindan-4-yloxy)benzoate instead of 4-(4-benzyloxy-3-iodophenoxy)-5-methyl-7-nitroindane.

To a solution of ethyl 6-(7-amino-5-methylindan-4-yloxy)-2-acetyl-3-hydroxybenzoate (213 mg) in tetrahydrofuran (15 mL) were added lithium borohydride (390 mg) and ethanol (5 mL). The mixture was stirred at 60° C. for 4 days. To the reaction mixture was added water (10 mL). The mixture was acidified with an 10% aqueous solution of citric acid. To the mixture was added ethyl acetate (20 mL). The reaction mixture was stirred for 1 hour, and extracted with ethyl acetate (×3). The combined organic layers were washed with brine, and dried over anhydrous magnesium sulfate. The solvent was removed under reduced pressure. The residue was purified by thin layer chromatography on silica gel (developing solvent: hexane/ethyl acetate=1/1) to give the title compound (66 mg).

$^1$H-NMR (CDCl$_3$) δ ppm: 1.61 (3H, d, J=6.7 Hz), 1.98–2.08 (2H, m), 2.05 (3H, s), 2.40–2.73 (4H, m), 4.77 (1H, d, J=12.2 Hz), 4.86 (1H, d, J=12.2 Hz), 5.53 (1H, q, J=6.7 Hz), 6.29 (1H, d, J=8.9 Hz), 6.40 (1H, s), 6.64 (1H, d, J=8.9 Hz), 8.37 (1H, br-s).

REFERENCE EXAMPLE 50

4-(7-Amino-5-methylindan-4-yloxy)-2-ethyl-3-methylphenol

To a solution of 1-[-(7-amino-5-methylindan-4-yloxy)-6-benzyloxy-2-hydroxymethylphenyl]ethanol (40 mg) in dichloromethane (1 mL) was added triethylsilane (0.400 mL). Adding dropwise trifluoroacetic acid (1 mL), the mixture was stirred at room temperature overnight. The reaction mixture was evaporated to dryness. To the residue were added ethyl acetate (3 mL) and a saturated aqueous solution of sodium hydrogen carbonate (10 mL). The reaction mixture was stirred for 15 min, and extracted with ethyl acetate. The organic layer was washed with brine, and dried over anhydrous magnesium sulfate. The solvent was removed under reduced pressure. The residue was purified by thin layer chromatography on silica gel (developing solvent: hexane/ethyl acetate=1/1) to give the title compound (24 mg).

$^1$H-NMR (CDCl$_3$) δ ppm: 1.16 (3H, t, J=7.5 Hz), 1.98–2.07 (2H, m), 2.06 (3H, s), 2.34 (3H, s), 2.55–2.76 (6H, m), 6.09 (1H, d, J=8.7 Hz), 6.37 (1H, d, J=8.7 Hz), 6.43 (1H, s).

REFERENCE EXAMPLE 51

4-(7-Amino-5-methylindan-4-yloxy)-2-isopropyl-3-methoxy phenol

To a solution of dibenzyl[7-(4-benzyloxy-3-isopropenyl-2-methoxyphenoxy)-6-methylindan-4-yl]amine (7.97 g) in tetrahydrofuran (80 mL) was added 10% Pd/C (4.00 g). The mixture was stirred at room temperature under an atmospheric pressure of hydrogen overnight. The insoluble material was removed by filtration. The filtrate was evaporated under reduced pressure to dryness to give the title compound (4.33 g).

$^1$H-NMR (CDCl$_3$+CD$_3$OD) δ ppm: 1.38 (6H, d, J=7.1 Hz), 2.00–2.07 (2H, m), 2.10 (3H, s), 2.63–2.77 (4H, m), 3.54 (1H, heptet, J=7.1 Hz), 3.94 (3H, s), 6.09 (1H, d, J=8.8 Hz), 6.28 (1H, d, J=8.8 Hz), 6.50 (1H, s).

REFERENCE EXAMPLE 51-1

4-(7-Amino-5-methylindan-4-yloxy)-2-trifluoromethylphenol

The title compound was prepared in a similar manner to those described in Reference Example 51 using dibenzyl[7-(4-benzyloxy-3-trifluoromethylphenoxy)-6-methylindan-4-yl]amine instead of dibenzyl[7-(4-benzyloxy-3-isopropenyl-2-methoxyphenoxy)-6-methylindan-4-yl]amine.

$^1$H-NMR (CDCl$_3$+CD$_3$OD) δ ppm: 2.00–2.13 (2H, m), 2.06 (3H, s), 2.60–2.75 (4H, m), 6.44 (1H, s), 6.73–6.80 (2H, m), 6.93–6.97 (1H, m).

REFERENCE EXAMPLE 51-2

4-(7-Amino-5-methylindan-4-ylmethyl)-2-isopropylphenol

The title compound was prepared in a similar manner to those described in Reference Example 51 using (4-benzyloxy-3-isopropylphenyl)-(7-dibenzylamino-5-methylindan-4-yl) methanol instead of dibenzyl[7-(4-benzyloxy-3-isopropenyl-2-methoxyphenoxy)-6-methylindan-4-yl]amine.

$^1$H-NMR (CDCl$_3$+CD$_3$OD) δ ppm: 1.20 (6H, d, J=6.9 Hz), 2.03–2.08 (2H, m), 2.15 (3H, s), 2.70–2.75 (2H, m), 2.76–2.83 (2H, m), 3.21 (1H, heptet, J=6.9 Hz), 3.83 (2H, s), 6.42 (1H, s), 6.57–6.62 (2H, m), 6.94 (1H, s).

REFERENCE EXAMPLE 51-3

(7-Amino-5-methylindan-4-yl)-(4-hydroxy-3-isopropylphenyl)methanone

The title compound was prepared in a similar manner to those described in Reference Example 51 using (4-benzyloxy-3-isopropylphenyl)-(7-dibenzylamino-5-methylindan-4-yl)methanone instead of dibenzyl[7-(4-benzyloxy-3-isopropenyl-2-methoxyphenoxy)-6-methylindan-4-yl]amine.

$^1$H-NMR (CDCl$_3$+CD$_3$OD) δ ppm: 1.22 (6H, d, J=6.9 Hz), 1.97–2.05 (2H, m), 2.10 (3H, s), 2.58–2.73 (4H, m), 3.27 (1H, heptet, J=6.9 Hz), 6.40 (1H, s), 6.73 (1H, d, J=8.4 Hz), 7.43 (1H, dd, J=2.1, 8.4 Hz), 7.74 (1H, d, J=2.1 Hz).

EXAMPLE 1

Ethyl N-{7-[4-hydroxy-3-(tetrahydropyran-4-ylmethyl)phenoxy]-6-methylindan-4-yl}malonamate (compound 1)

4-(7-amino-5-methylindan-4-yloxy)-2-(tetrahydropyran-4-ylmethyl)phenol (43 mg) was dissolved in dichloromethane (5 mL), and pyridine (20 μL) was added thereto. To the solution was added dropwise ethyl malonyl chloride (19 μL) under ice-cooling with stirring, and the resulting mixture was stirred at room temperature for 3 hours. Adding diluted hydrochloric acid (5 mL), the reaction mixture was extracted with ethyl acetate. The organic layer was washed with a saturated aqueous solution of sodium hydrogen carbonate and brine successively, and dried over anhydrous magnesium sulfate. The solvent was removed under reduced pressure. The residue was purified by column chromatography on silica gel (eluent: hexane/ethyl acetate) to give the title compound (46 mg).

$^1$H-NMR (CDCl$_3$) δ ppm: 1.25–1.40 (5H, m), 1.50–1.70 (2H, m), 1.73–1.89 (1H, m), 1.98–2.11 (2H, m), 2.15 (3H, s), 2.48 (2H, d, J=7.2 Hz), 2.60–2.73 (2H, m), 2.83–2.94 (2H, m), 3.27–3.40 (2H, m), 3.49 (2H, s), 3.88–3.98-(2H, m), 4.27 (2H, q, J=7.1 Hz), 4.50 (1H, s), 6.48 (1H, dd, J=3.0 Hz, 8.6 Hz), 6.54 (1H, d, J=3.0 Hz), 6.62 (1H, d, J=8.6 Hz), 7.76 (1H, s), 9.21 (1H, s).

EXAMPLE 1-1

Ethyl N-(7-{4-hydroxy-3-[2-(tetrahydrofuran-3-yl) ethyl]phenoxy}-6-methylindan-4-yl)malonamate (Compound 2)

The title compound was prepared in a similar manner to those described in Example 1 using 4-(7-amino-5-methylindan-4-yloxy)-2-(tetrahydrofuran-4-ylethyl)phenol instead of 4-(7-amino-5-methylindan-4-yloxy)-2-(tetrahydropyran-4-yl methyl)phenol.

$^1$H-NMR (CDCl$_3$) δ ppm: 1.34 (3H, t, J=7.1 Hz), 1.48–1.85 (3H, m), 1.96–2.30 (7H, m), 2.46–2.75 (4H, m), 2.81–2.95 (2H, m), 3.30–3.57 (3H, m), 3.68–3.80 (1H, m), 3.82–3.95 (2H, m), 4.27 (2H, q, J=7.1 Hz), 4.90 (1H, br-s), 6.44 (1H, dd, J=2.9 Hz, 8.6 Hz), 6.54–6.70 (2H, m), 7.75 (1H, s), 9.21 (1H, s).

EXAMPLE 1-2

Ethyl N-{7-[4-hydroxy-3-(1-methyl-2-phenylethyl) phenoxy]-6-methylindan-4-yl}malonamate (Compound 3)

The title compound was prepared in a similar manner to those described in Example 1 using 4-(7-amino-5-methylindan-4-yloxy)-2-(1-methyl-2-phenylethyl)phenol instead of 4-(7-amino-5-methylindan-4-yloxy)-2-(tetrahydropyran-4-yl methyl)phenol.

$^1$H-NMR (CDCl$_3$) δ ppm: 1.20 (3H, d, J=6.9 Hz), 1.33 (3H, t, J=7.1 Hz), 1.98–2.10 (2H, m), 2.14 (3H, s), 2.57–2.65 (2H, m), 2.70–2.76 (1H, m), 2.82–2.95 (3H, m), 3.27–3.36 (1H, m), 3.49 (2H, s), 4.27 (2H, q, J=7.1 Hz), 4.58 (1H, br-s), 6.37 (1H, dd, J=3.0, 8.6 Hz), 6.56 (1H, d, J=8.6 Hz), 6.69 (1H, d, J=3.0 Hz), 7.05–7.25 (5H, m), 7.76 (1H, s), 9.20 (1H, s).

EXAMPLE 1-3

Ethyl N-[7-(4-hydroxy-3-isopropylphenoxy)-6-methylindan-4-yl]malonamate (Compound 4)

The title compound was prepared in a similar manner to those described in Example 1 using 4-(7-amino-5-methylindan-4-yloxy)-2-isopropylphenol instead of 4-(7-amino-5-methylindan-4-yloxy)-2-(tetrahydropyran-4-yl methyl)phenol.

$^1$H-NMR (CDCl$_3$) δ ppm: 1.21 (6H, d, J=6.9 Hz), 1.33 (3H, t, J=7.1 Hz), 1.95–2.10 (2H, m), 2.14 (3H, s), 2.60–2.75 (2H, m), 2.80–2.95 (2H, m), 3.10–3.25 (1H, m), 3.50 (2H, s), 4.27 (2H, q, J=7.1 Hz), 5.10 (1H, br-s), 6.32 (1H, dd, J=8.6, 3.0 Hz), 6.59 (1H, d, J=8.6 Hz), 6.76 (1H, d, J=3.0 Hz), 7.74 (1H, s), 9.20 (1H, s).

EXAMPLE 1-4

Ethyl N-{7-[3-(4-fluorobenzyl)-4-hydroxyphenoxy]-6-methylindan-4-yl}malonamate (Compound 5)

The title compound was prepared in a similar manner to those described in Example 1 using 4-(7-amino-5-methylindan-4-yloxy)-2-(4-fluorobenzyl)phenol instead of 4-(7-amino-5-methylindan-4-yloxy)-2-(tetrahydropyran-4-ylmethyl)phenol.

$^1$H-NMR (CDCl$_3$) δ ppm: 1.33 (3H, t, J=7.1 Hz), 1.97–2.09 (2H, m), 2.14 (3H, s), 2.57–2.68 (2H, m), 2.82–2.90 (2H, m), 3.49 (2H, s), 3.88 (2H, s), 4.27 (2H, q, J=7.1 Hz), 4.42 (1H, s), 6.50 (1H, dd, J=2.9, 8.7 Hz), 6.59 (1H, d, J=2.9 Hz), 6.64 (1H, d, J=8.7 Hz), 6.90–7.00 (2H, m), 7.10–7.17 (2H, m), 7.75 (1H, s), 9.19 (1H, s).

EXAMPLE 1-5

Ethyl N-[7-(4-hydroxy-3-isopropylphenoxy)-6-iodoindan-4-yl]malonamate (Compound 6)

The title compound was prepared in a similar manner to those described in Example 1 using 4-(7-amino-5-iodoindan-4-yloxy)-2-isopropylphenol instead of 4-(7-amino-5-methylindan-4-yloxy)-2-(tetrahydropyran-4-ylmethyl)phenol.

$^1$H-NMR (CDCl$_3$) δ ppm: 1.22 (6H, d, J=6.9 Hz), 1.34 (3H, t, J=7.1 Hz), 2.00–2.10(2H, m), 2.63–2.69(2H, m), 2.84–2.90(2H, m), 3.16 (1H, heptet, J=6.9 Hz), 3.50 (2H, s), 4.27 (2H, q, J=7.1 Hz), 4.52 (1H, s), 6.40 (1H, dd, J=3.0, 8.6 Hz), 6.61 (1H, d, J=8.6 Hz), 6.79 (1H, d, J=3.0 Hz), 8.41 (1H, s), 9.33 (1H, s).

EXAMPLE 1-6

Ethyl N-[7-(4-hydroxy-3-isopropylphenoxy)-6-iodoindan-4-yl]oxamate (Compound 7)

The title compound was prepared in a similar manner to those described in Example 1 using 4-(7-amino-5-iodoindan-4-yloxy)-2-isopropylphenol instead of 4-(7-amino-5-methylindan-4-yloxy)-2-(tetrahydropyran-4-ylmethyl)phenol and using ethyl oxalyl chloride instead of ethyl malonyl chloride.

$^1$H-NMR (CDCl$_3$) δ ppm: 1.22 (6H, d, J=6.9 Hz), 1.44 (3H, t, J=7.1 Hz), 2.00–2.10 (2H, m), 2.63–2.70 (2H, m), 2.83–2.90 (2H, m), 3.17 (1H, heptet, J=6.9 Hz), 4.43 (2H, q, J=7.1 Hz), 4.57 (1H, s), 6.41 (1H, dd, J=3.0, 8.6 Hz), 6.62 (1H, d, J=8.6 Hz), 6.80 (1H, d, J=3.0 Hz), 8.39 (1H, s), 8.67 (1H, s).

EXAMPLE 1-7

Ethyl N-{7-[4-hydroxy-3-(6-oxo-1,6-dihydropyridazine-3-ylmethyl)phenoxy]-6-methylindan-4-yl}malonamate (Compound 8)

The title compound was prepared in a similar manner to those described in Example 1 using 6-[5-(7-amino-5-methylindan-4-yloxy)-2-hydroxybenzyl]-2H-pyridazine-3-one instead of 4-(7-amino-5-methylindan-4-yloxy)-2-(tetrahydropyran-4-ylmethyl)phenol.

$^1$H-NMR (CDCl$_3$) δ ppm: 1.34 (3H, t, J=7.1 Hz), 1.98–2.08 (2H, m), 2.13 (3H, s), 2.58–2.67 (2H, m), 2.80–2.92 (2H, m), 3.50 (2H, s), 3.85 (2H, s), 4.27 (2H, q, J=7.1 Hz), 6.52 (1H, dd, J=3.0, 8.7 Hz), 6.59(1H, d, J=3.0 Hz), 6.70(1H, d, J=8.7 Hz), 6.85 (1H, d, J=9.7 Hz), 7.28 (1H, d, J=9.7 Hz), 7.65 (1H, s).

EXAMPLE 1-8

Ethyl N-[7-(4-hydroxy-3-trifluoromethylphenoxy)-6-methylindan-4-yl]malonamate (Compound 9)

The title compound was prepared in a similar manner to those described in Example 1 using 4-(7-amino-5-methylindan-4-yloxy)-2-trifluoromethylphenol instead of 4-(7-amino-5-methylindan-4-yloxy)-2-(tetrahydropyran-4-yl methyl)phenol $^1$H-NMR (CDCl$_3$) δ ppm: 1.34 (3H, t, J=7.1 Hz), 2.00–2.10 (2H, m), 2.10 (3H, s), 2.60–2.65 (2H, m), 2.83–2.90 (2H, m), 3.51 (2H, s), 4.27 (1H, q, J=7.1 Hz), 6.34 (1H, br-s), 6.66–6.73 (1H, m), 6.80–6.83 (1H, m), 6.98–7.02 (1H, m), 7.74 (1H, s), 9.31 (1H, s).

EXAMPLE 1-9

Ethyl N-[7-(4-hydroxy-3-trifluoromethylphenoxy)-6-methylindan-4-yl]oxamate (Compound 10)

The title compound was prepared in a similar manner to those described in Example 1 using 4-(7-amino-5-methylindan-4-yloxy)-2-trifluoromethylphenol instead of 4-(7-amino-5-methylindan-4-yloxy)-2-(tetrahydropyran-4-ylmethyl)phenol and using ethyl oxalyl chloride instead of ethyl malonyl chloride.

$^1$H-NMR (CDCl$_3$) δ ppm: 1.44 (3H, t, J=7.1 Hz), 2.05–2.13 (2H, m), 2.15 (3H, s), 2.64–2.70 (2H, m), 2.83–2.92 (2H, m), 4.43 (1H, q, J=7.1 Hz), 5.92 (1H, br-s), 6.78 (1H, dd, J=3.0, 8.9 Hz), 6.87 (1H, d, J=8.9 Hz), 6.97 (1H, d, J=3.0 Hz), 7.79 (1H, s), 8.72 (1H, br-s).

EXAMPLE 1-10

Ethyl N-[7-(4-hydroxy-3-isopropylbenzyl)-6-methylindan-4-yl]malonamate (Compound 11)

The title compound was prepared in a similar manner to those described in Example 1 using 4-(7-amino-5-methylindan-4-ylmethyl)-2-isopropylphenol instead of 4-(7-amino-5-methylindan-4-yloxy)-2-(tetrahydropyran-4-yl methyl)phenol.

$^1$H-NMR (CDCl$_3$) δ ppm: 1.21 (6H, d, J=6.9 Hz), 1.33 (3H, t, J=7.1 Hz), 2.02–2.12 (2H, m), 2.22 (3H, s), 2.80–2.93 (4H, m), 3.15 (1H, heptet, J=6.9 Hz), 3.48 (2H, s), 3.89 (2H, s), 4.26 (2H, q, J=7.1 Hz), 4.65 (1H, s), 6.55–6.63 (2H, m), 6.94 (1H, s), 7.73 (1H, s), 9.11 (1H, s).

EXAMPLE 1-11

Ethyl N-[7-(4-hydroxy-3-isopropylbenzoyl)-6-methylindan-4-yl]malonamate (Compound 12)

The title compound was prepared in a similar manner to those described in Example 1 using (7-amino-5-methylindan-4-ylmethyl)-(4-hydroxy-3-isopropylphenyl)methanone instead of 4-(7-amino-5-methylindan-4-yloxy)-2-(tetrahydropyran-4-ylmethyl)phenol.

$^1$H-NMR (CDCl$_3$) δ ppm: 1.25 (6H, d, J=6.9 Hz), 1.34 (3H, t, J=7.1 Hz), 2.00–2.10 (2H, m), 2.12 (3H, s), 2.65–2.72 (2H, m), 2.84–2.91 (2H, m), 3.23 (1H, heptet, J=6.9 Hz), 3.52 (2H, s), 4.28 (1H, q, J=7.1 Hz), 6.37 (1H, d, J=2.1 Hz), 6.72 (1H, d, J=8.3 Hz), 7.35 (1H, dd, J=2.1, 8.3 Hz), 7.85 (1H, s), 7.86 (1H, s), 9.41 (1H, s).

EXAMPLE 1-12

Ethyl N-[7-(4-hydroxy-3-isopropylbenzoyl)-6-methylindan-4-yl]oxamate (Compound 13)

The title compound was prepared in a similar manner to those described in Example 1 using (7-amino-5-methylindan-4-yl)-(4-hydroxy-3-isopropylphenyl)methanone instead of 4-(7-amino-5-methylindan-4-yloxy)-2-(tetrahydropyran-4-ylmethyl)phenol and using ethyl oxalyl chloride instead of ethyl malonyl chloride.

$^1$H-NMR (CDCl$_3$) δ ppm: 1.25 (6H, d, J=6.9 Hz), 1.45 (3H, t, J=7.1 Hz), 2.03–2.13 (2H, m), 2.17 (3H, s), 2.67–2.73 (2H, m), 2.83–2.90 (2H, m), 3.23 (1H, heptet, J=6.9 Hz), 4.44 (2H, q, J=7.1 Hz), 6.06 (1H, br-s), 6.75 (1H, d, J=8.3 Hz), 7.38 (1H, dd, J=2.0, 8.3 Hz), 7.85 (2H, s), 8.78 (1H, s).

EXAMPLE 1-13

Ethyl N-{7-[2-(2-cyclohexylethoxy)-3-ethyl-4-hydroxyphenoxy]-6-methylindan-4-yl}malonamate (Compound 14)

The title compound was prepared in a similar manner to those described in Example 1 using 4-(7-amino-5-methylindan-4-yloxy)-3-(2-cyclohexylethoxy)-2-ethylphenol instead of 4-(7-amino-5-methylindan-4-yloxy)-2-(tetrahydropyran-4-ylmethyl)phenol.

$^1$H-NMR (CDCl$_3$) δ ppm: 0.90–1.00 (2H, m), 1.10–1.30 (3H, m), 1.21 (3H, t, J=7.5 Hz), 1.34 (3H, t, J=7.1 Hz), 1.52–1.82 (8H, m), 2.01–2.08 (2H, m), 2.16 (3H, s), 2.63–2.70 (2H, m), 2.72 (2H, q, J=7.5 Hz), 2.85–2.91 (2H, m), 3.49 (2H, s), 4.13–4.19 (2H, m), 4.27 (2H, q, J=7.1 Hz), 4.54 (1H, s), 6.12 (1H, d, J=8.8 Hz), 6.30 (1H, d, J=8.8 Hz), 7.75 (1H, s), 9.19 (1H, s).

EXAMPLE 1-14

Ethyl N-[7-(3-ethyl-4-hydroxy-2-phenethyloxyphenoxy)-6-methylindan-4-yl]malonamate (Compound 15)

The title compound was prepared in a similar manner to those described in Example 1 using 4-(7-amino-5-methylindan-4-yloxy)-2-ethyl-3-phenethyloxyphenol instead of 4-(7-amino-5-methylindan-4-yloxy)-2-(tetrahydropyran-4-ylmethyl)phenol.

$^1$H-NMR (CDCl$_3$) δ ppm: 1.10 (3H, t, J=7.5 Hz), 1.34 (3H, t, J=7.1 Hz), 2.00–2.10 (2H, m), 2.15 (2H, s), 2.56 (2H, q, J=7.5 Hz), 2.62–2.68 (2H, m), 2.83–2.90 (2H, m), 3.15 (3H, t, J=7.2 Hz), 3.49 (2H, s), 4.27 (2H, q, J=7.1 Hz), 4.36 (2H, t, J=7.2 Hz), 4.60 (1H, s), 6.12 (1H, d, J=8.8 Hz), 6.30 (1H, d, J=8.8 Hz), 7.18–7.35 (5H, m), 7.76 (1H, s), 9.20 (1H, s).

EXAMPLE 1-15

Ethyl N-[7-(3-ethyl-4-hydroxy-2-methylphenoxy)-6-methylindan-4-yl]malonamate (Compound 16)

The title compound was prepared in a similar manner to those described in Example 1 using 4-(7-amino-5-methylindan-4-yloxy)-2-ethyl-3-methylphenol instead of 4-(7-amino-5-methylindan-4-yloxy)-2-(tetrahydropyran-4-ylmethyl)phenol.

$^1$H-NMR (CDCl$_3$) δ ppm-1.17 (3H, t, J=7.5 Hz), 1.33 (3H, t, J=7.1 Hz), 1.97–2.07 (2H, m), 2.14 (3H, s), 2.35 (3H, s), 2.55–2.70 (2H, m), 2.71 (2H, q, J=7.5 Hz), 2.83–2.89 (2H, m), 3.49 (2H, s), 4.27 (2H, q, J=7.1 Hz), 4.63 (1H, s), 6.10 (1H, d, J=8.8 Hz), 6.41 (1H, d, J=8.8 Hz), 7.74 (1H, s), 9.18 (1H, s.)

EXAMPLE 1-16

Ethyl N-[7-(4-hydroxy-3-isopropyl-2-methoxyphenoxy)-6-methylindan-4-yl]malonamate (Compound 17)

The title compound was prepared in a similar manner to those described in Example 1 using 4-(7-amino-5-methylindan -4-yloxy)-2-isopropyl-3-methoxyphenol instead of 4-(7-amino-5-methylindan-4-yloxy)-2-(tetrahydropyran-4-yl methyl)phenol.

$^1$H-NMR (CDCl$_3$) δ ppm: 1.33 (3H, t, J=7.1 Hz), 1.39 (6H, d, J=7.1 Hz), 1.98–2.05 (2H, m), 2.13 (3H, s), 2.63–2.68 (2H, m), 2.83–2.88 (2H, m), 3.50 (2H, s), 3.56 (1H, heptet, J=7.1 Hz), 3.94 (3H, s), 4.27 (2H, q, J=7.1 Hz), 5.32 (1H, s), 6.06 (1H, d, J=8.8 Hz), 6.26 (1H, d, J=8.8 Hz), 7.72 (1H, s), 9.23 (1H, s).

EXAMPLE 1-17

Ethyl N-[7-(3-acetyl-4-hydroxy-2-methoxyphenoxy)-6-methylindan-4-yl]oxamate (Compound 18)

The title compound was prepared in a similar manner to those described in Example 1 using [7-(3-acetyl-4-hydroxy-2-methoxyphenoxy)-6-methylindan-4-yl]amine instead of 4-(7-amino-5-methylindan-4-yloxy)-2-(tetrahydropyran-4-yl methyl)phenol and using ethyl oxalyl chloride instead of ethyl malonyl chloride.

$^1$H-NMR (CDCl$_3$) δ ppm: 1.45 (3H, t, J=7.1 Hz), 2.03–2.13 (2H, m), 2.22 (3H, s), 2.64–2.70 (2H, m), 2.78 (3H, s), 2.85–2.93 (2H, m), 4.11 (3H, s), 4.43 (2H, q, J=7.1 Hz), 6.54 (1H, d, J=9.1 Hz), 6.63 (1H, d, J=9.1 Hz), 7.82 (1H, s), 8.69 (1H, s), 12.27 (1H, s).

EXAMPLE 1-18

Ethyl N-[7-(3-ethyl-2-hydroxy-4-trifluoromethanesulfonyloxy phenoxy)-6-methylindan-4-yl]malonamate (Compound 19)

The title compound was prepared in a similar manner to those described in Example 1 using 4-(7-amino-5-methylindan-4-yloxy)-2-ethyl-3-hydroxyphenyl trifluoromethanesulfonate instead of 4-(7-amino-5-methylindan-4-yloxy)-2-(tetrahydropyran-4-ylmethyl)phenol.

$^1$H-NMR (CDCl$_3$) δ ppm: 1.23–1.30 (3H, m), 1.34 (3H, t, J=7.1 Hz), 2.03–2.16 (2H, m), 2.15 (3H, s), 2.63–2.68 (2H, m), 2.75–2.82 (2H, m), 2.86–2.93 (2H, m), 3.50 (2H, s), 4.27 (2H, q, J=7.1 Hz), 6.19 (1H, s), 6.26 (1H, d, J=9.0 Hz), 6.61 (1H, d, J=9.0 Hz), 7.83 (1H, s), 9.31 (1H, s).

EXAMPLE 1-19

Ethyl N-{7-[3-(4-fluorobenzoyl)-4-hydroxyphenoxy]-6-methylindan-4-yl}malonamate (Compound 20)

The title compound was prepared in a similar manner to those described in Example 1 using [5-(7-amino-5-methylindan-4-yloxy)-2-hydroxyphenyl]-(4-fluorophenyl) methanone instead of 4-(7-amino-5-methylindan-4-yloxy)-2-(tetrahydropyran-4-ylmethyl)phenol.

$^1$H-NMR (CDCl$_3$) δ ppm: 1.34 (3H, t, J=7.2 Hz), 1.95–2.20 (5H, m), 2.67 (2H, t, J=7.5 Hz), 2.87 (2H, t, J=7.5 Hz), 3.49 (2H, s), 4.15–4.40 (2H, m), 6.90–7.25 (5H, m), 7.60–7.90 (3H, m), 9.25 (1H, s), 11.43 (1H, s).

EXAMPLE 1-20

Ethyl N-[7-(4-hydroxy-3-phenethylphenoxy)-6-methylindan-4-yl]malonamate (Compound 21)

The title compound was prepared in a similar manner to those described in Example 1 using 4-(7-amino-5-methylindan-4-yloxy)-2-phenethylphenol instead of 4-(7-amino-5-methylindan-4-yloxy)-2-(tetrahydropyran-4-ylmethyl)phenol.

$^1$H-NMR (CDCl$_3$) δ ppm: 1.33 (3H, t, J=7.2 Hz), 1.95–2.10 (2H, m), 2.11 (3H, s) 2.62 (2H, t, J=7.5 Hz), 2.75–2.95 (6H, m), 3.50 (2H, s), 4.27 (2H, q, J=7.2 Hz), 4.89 (1H, s), 6.45 (1H, dd, J=8.6, 3.0 Hz), 6.52 (1H, d, J=3.0 Hz), 6.62 (1H, d, J=8.6 Hz), 7.10–7.30 (5H, m), 7.73 (1H, s), 9.20 (1H, s).

REFERENCE EXAMPLE 52

Ethyl N-(7-{4-methoxy-3-[2-(4-methoxyphenyl) ethyl]phenoxy}-6-methylindan-4-yl)malonamate The title compound was prepared in a similar manner to those described in Example 1-using 7-{4—methoxy-3-[2-(4-methoxyphenyl)ethyl]phenoxy}-6-methylindan-4-ylamine instead of 4-(7-amino-5-methylindan-4-yloxy)-2-(tetrahydropyran-4-ylmethyl)phenol.

$^1$H-NMR (CDCl$_3$) δ ppm: 1.34 (3H, t, J=7.1 Hz), 1.96–2.10 (2H, m), 2.12 (3H, s), 2.62 (2H, t, J=7.5 Hz), 2.73–2.94 (6H, m), 3.50 (2H, s), 3.77 (3H, s), 3.78 (3H, s), 4.27 (2H, q, J=7.1 Hz), 6.48–6.60 (2H, m), 6.70 (1H, d, J=8.9 Hz), 6.79 (2H, d, J=8.6 Hz), 7.06 (2H, d, J=8.6 Hz), 7.74 (1H, s), 9.20 (1H, s).

REFERENCE EXAMPLE 52-1

Ethyl N-[7-(4-benzyloxy-3-iodophenoxy)-6-methylindan-4-yl]malonamate

The title compound was prepared in a similar manner to those described in Example 1 using 7-(4-benzyloxy-3-iodophenoxy)-6-methylindan-4-ylamine instead of 4-(7-amino-5-methylindan-4-yloxy)-2-(tetrahydropyran-4-yl methyl)phenol.

$^1$H-NMR (CDCl$_3$) δ ppm: 1.34 (3H, t, J=7.1 Hz), 2.01–2.15 (2H, m), 2.14 (3H, s), 2.63–2.77 (2H, m), 2.86–2.97 (2H, m), 3.50 (2H, s), 4.28 (2H, q, J=7.1 Hz), 5.07 (2H, s), 6.67–6.80 (2H, m), 7.25–7.58 (6H, m), 7.79 (1H, s), 9.23 (1H, s).

REFERENCE EXAMPLE 52-2

Ethyl N-(7-{4-methoxy-3-[2-(3-methoxyphenyl) ethyl]phenoxy}-6-methylindan-4-yl)malonamate The title compound was prepared in a similar manner to those described in Example 1 using 7-{4-methoxy-3-[2-(3-methoxyphenyl)ethyl]phenoxy}-6-methylindan-4-ylamine instead of 4-(7-amino-5-methylindan-4-yloxy)-2-(tetrahydropyran-4-ylmethyl)phenol.

$^1$H-NMR (CDCl$_3$) δ ppm: 1.34 (3H, t, J=7.1 Hz), 1.96–2.10 (2H, m), 2.13 (3H, s), 2.63 (2H, t, J=7.5 Hz), 2.75–2.95 (6H, m), 3.49 (2H, s), 3.77 (3H, s), 3.78 (3H, s), 4.27 (2H, q, J=7.1 Hz), 6.48–6.60 (2H, m), 6.65–6.80 (4H, m), 7.10–7.25 (1H, m), 7.75 (1H, s), 9.18 (1H, s).

REFERENCE EXAMPLE 52-3

Ethyl N-(7-{4-methoxy-3-[2-(2-methoxyphenyl)ethyl]phenoxy}-6-methylindan-4-yl)malonamate The title compound was prepared in a similar manner to those described in Example 1 using 7-{4-methoxy-3-[2-(2-methoxyphenyl)ethyl]phenoxy}-6-methylindan-4-ylamine instead of 4-(7-amino-5-methylindan-4-yloxy)-2-(tetrahydropyran-4-ylmethyl)phenol.

$^1$H-NMR (CDCl$_3$) δ ppm: 1.34 (3H, t, J=7.1 Hz), 1.96–2.10 (2H, m), 2.13 (3H, s), 2.63 (2H, t, J=7.4 Hz), 2.75–2.95 (6H, m), 3.49 (2H, s), 3.76 (3H, s), 3.79 (3H, s), 4.27 (2H, q, J=7.1 Hz), 6.49 (1H, dd, J=8.8 Hz, 3.0 Hz), 6.60 (1H, d, J=3.0 Hz), 6.68 (1H, d, J=8.8 Hz), 6.76–6.89 (2H, m), 7.05 (1H, dd, J=7.7 Hz, 1.5 Hz), 7.10–7.20 (1H, m), 7.75 (1H, s), 9.18 (1H, s).

REFERENCE EXAMPLE 52-4

Ethyl N-(7-{4-methoxy-3-[2-(3-fluoro-4-methoxyphenyl)ethyl]phenoxy}-6-methylindan-4-yl)malonamate The title compound was prepared in a similar manner to those described in Example 1 using 7-{3-[2-(3-fluoro-4-methoxyphenyl)ethyl]-4-methoxyphenoxy}-6-methylindan-4-ylamine instead of 4-(7-amino-5-methylindan-4-yloxy)-2-(tetrahydropyran-4-ylmethyl)phenol.

$^1$H-NMR (CDCl$_3$) δ ppm: 1.34 (3H, t, J=7.1 Hz), 1.96–2.10 (2H, m), 2.13 (3H, s), 2.62 (2H, t, J=7.5 Hz), 2.70–2.95 (6H, m), 3.49 (2H, s), 3.78 (3H, s), 3.86 (3H, s), 4.27 (2H, q, J=7.1 Hz), 6.45–6.60 (2H, m), 6.70 (1H, d, J=8.7 Hz), 6.80–6.95 (3H, m), 7.75 (1H, s), 9.19 (1H, s).

REFERENCE EXAMPLE 52-5

Ethyl N-[7-(4-methoxyphenoxy)-6-methylindan-4-yl]malonamate

The title compound was prepared in a similar manner to those described in Example 1 using [7-(4-methoxyphenoxy)-6-methylindan-4-yl]amine instead of 4-(7-amino-5-methylindan-4-yloxy)-2-(tetrahydropyran-4-ylmethyl) phenol.

$^1$H-NMR (CDCl$_3$) δ ppm: 1.34 (3H, t, J=7.1 Hz), 1.96–2.12 (2H, m), 2.16 (3H, s), 2.68 (2H, t, J=7.4 Hz), 2.88 (2H, t, J=7.4 Hz), 3.49 (2H, s), 3.76 (3H, s), 4.27 (2H, q, J=7.1 Hz), 6.68–6.82 (4H, m), 7.77 (1H, s), 9.20 (1H, s)

EXAMPLE 2

Ethyl N-{7-[3-ethyl-2-(4-fluorobenzyloxy)-4-trifluoro-methanesulfonyloxyphenoxy]-6-methylindan-4-yl}malonamate (Compound 22)

To a solution of ethyl N-[7-(3-ethyl-2-hydroxy-4-trifluoromethanesulfonyloxyphenoxy)-6-methylindan-4-yl]malonamate (22 mg), 4-fluorobenzylalcohol (9 μL) and triphenylphosphine (22 mg) in tetrahydrofuran (1 mL) was added diethyl azodicarboxylate (37 μL) under ice-cooling. After being stirred under an argon atmosphere at room temperature for 2 days, the reaction mixture was purified by thin layer chromatography on silica gel (developing solvent: hexane/ethyl acetate=2/1) to give the title compound (24 mg).

$^1$H-NMR (CDCl$_3$) δ ppm: 1.18 (3H, t, J=7.5 Hz), 1.34 (3H, t, J=7.2 Hz), 2.06–2.15 (2H, m), 2.19 (3H, s), 2.65–2.76 (4H, m), 2.87–2.93 (2H, m), 3.51 (2H, s), 4.28 (2H, q, J=7.2 Hz), 5.19 (2H, s), 6.35 (1H, d, J=9.2 Hz), 6.83 (1H, d, J=9.2 Hz), 7.01–7.10 (2H, m), 7.43–7.48 (2H, m), 7.84 (1H, s), 9.30 (1H, s)

REFERENCE EXAMPLE 53

4-[4-Benzyloxy-2-(2-cyclohexylethoxy)-3-ethylphenoxy]-5-methyl-7-nitroindane

The title compound was prepared in a similar manner to those described in Example 2 using 3-benzyloxy-2-ethyl-6-(5-methyl-7-nitroindan-4-yloxy)phenol instead of ethyl N-[7-(3-ethyl-2-hydroxy-4-trifluoromethanesulfonyloxyphenoxy)-6-methylindan-4-yl]malonamate and using 2-cyclohexylethanol instead of 4-fluorobenzylalcohol.

$^1$H-NMR (CDCl$_3$) δ ppm: 0.87–1.00 (2H, m), 1.10–1.27 (–3H, m), 1.20 (3H, t, J=7.4 Hz), 1.45–1.85 (8H, m), 1.98–2.08 (2H, m), 2.27 (3H, s), 2.57–2.63 (2H, m), 2.78 (2H, q, J=7.4 Hz), 3.33–3.38 (2H, m), 4.07–4.13 (2H, m), 5.01 (2H, s), 6.25 (1H, d, J=8.9 Hz), 6.47 (1H, d, J=8.9 Hz), 7.27–7.45 (5H, m), 7.96 (1H, s)

REFERENCE EXAMPLE 54

4-(7-Amino-5-methylindan-4-yloxy)-2-ethyl-3-phenethyloxy phenol 4-(4-benzyloxy-3-ethyl-2-phenethyloxyphenoxy)-5-methyl-7-nitroindane was prepared in a similar manner to those described in Example 2 using 3-benzyloxy-2-ethyl-6-(5-methyl-7-nitroindan-4-yloxy)phenol instead of ethyl N-[7-(3-ethyl-2-hydroxy-4-trifluoromethanesulfonyloxyphenoxy)-6-methylindan-4-yl]malonamate and using 2-phenylethanol instead of 4-fluorobenzylalcohol.

The title compound was prepared in a similar manner to those described in Reference Example 48 using 4-(4-benzyloxy-3-ethyl-2-phenethyloxyphenoxy)-5-methyl-7-nitroindane instead of 4-[4-benzyloxy-3-(4-fluorobenzyl)phenoxy]-5-methyl-7-nitroindane.

$^1$H-NMR (CDCl$_3$) δ ppm: 1.10 (3H, t, J=7.5 Hz), 1.97–2.07 (2H, m), 2.08 (3H, s), 2.56 (2H, q, J=7.5 Hz), 2.60–2.74 (4H, m), 3.15 (2H, t, J=7.2 Hz), 3.49 (2H, br-s), 4.37 (2H, t, J=7.2 Hz), 4.64 (1H, br-s), 6.11 (1H, d, J=8.8 Hz), 6.22 (1H, d, J=8.8 Hz), 6.42 (1H, s), 7.18–7.34 (5H, m)

EXAMPLE 3

Ethyl N-[7-(3-ethyl-4-hydroxy-2-methylphenoxy)-6-methylindan-4-yl]oxamate (Compound 23)

To 4-(7-amino-5-methylindan-4-yloxy)-2-ethyl-3-methylphenol (12 mg) was added diethyl oxalate (150 mg), and the mixture was stirred under an argon atmosphere at 120° C. for 3 hours. The reaction mixture was purified by thin layer chromatography on silica gel (developing solvent: hexane/ethyl acetate=2/1) to give the title compound (15 mg).

$^1$H-NMR (CDCl$_3$) δ ppm: 1.17 (3H, t, J=7.5 Hz), 1.44 (3H, t, J=7.1 Hz), 1.99–2.10 (2H, m), 2.16 (3H, s), 2.35 (3H, s), 2.55–2.70 (2H, m), 2.72 (2H, q, J=7.5 Hz), 2.83–2.88 (2H, m), 4.42 (2H, q, J=7.1 Hz), 4.68 (1H, s), 6.11 (1H, d, J=8.7 Hz), 6.43 (1H, d, J=8.7 Hz), 7.77 (1H, s), 8.68 (1H, s)

REFERENCE EXAMPLE 55

Ethyl N-(7-{4-methoxy-3-[2-(4-methoxyphenyl)ethyl]phenoxy}-6-methylindan-4-yl)oxamate The title compound was prepared in a similar manner to those described in Example 3 using 7-{4-methoxy-3-[2-(4-methoxyphenyl)ethyl]phenoxy}-6-methylindan-4-ylamine instead of 4-(7-amino-5-methylindan-4-yloxy)-2-ethyl-3-methylphenol.

$^1$H-NMR (CDCl$_3$) δ ppm: 1.46 (3H, t, J=7.1 Hz), 1.96–2.10 (2H, m), 2.14 (3H, s), 2.62 (2H, t, J=7.5 Hz), 2.73–2.94 (6H, m), 3.778 (3H, s), 3.782 (3H, s), 4.43 (2H, q, J=7.1 Hz), 6.45–6.60 (2H, m), 6.65–6.75 (1H, m), 6.79 (–2H, d, J=8.5 Hz), 7.05 (2H, d, J=8.5 Hz), 7.77 (1H, s), 8.68 (1H, s)

REFERENCE EXAMPLE 55-1

Ethyl N-(7-{4-methoxy-3-[2-(3-methoxyphenyl)ethyl]phenoxy}-6-methylindan-4-yl)oxamate The title compound was prepared in a similar manner to those described in Example 3 using 7-{4-methoxy-3-[2-(3-methoxyphenyl)ethyl]phenoxy}-6-methylindan-4-ylamine instead of 4-(7-amino-5-methylindan-4-yloxy)-2-ethyl-3-methylphenol.

$^1$H-NMR (CDCl$_3$) δ ppm: 1.45 (3H, t, J=7.1 Hz), 1.96–2.10 (2H, m), 2.14 (3H, s), 2.62 (2H, t, J=7.5 Hz), 2.73–2.94 (6H, m), 3.77 (3H, s), 3.78 (3H, s), 4.44 (2H, q, J=7.1 Hz), 6.45–6.90 (6H, m), 7.10–7.25 (1H, m), 7.78 (1H, s), 8.69 (1H, s)

REFERENCE EXAMPLE 55-2

Ethyl N-(7-{4-methoxy-3-[2-(2-methoxyphenyl)ethyl]phenoxy}-6-methylindan-4-yl)oxamate The title compound was prepared in a similar manner to those described in Example 3 using 7-{4-methoxy-3-[2-(2-methoxyphenyl)ethyl]phenoxy}-6-methylindan-4-ylamine instead of 4-(7-amino-5-methylindan-4-yloxy)-2-ethyl-3-methylphenol.

$^1$H-NMR (CDCl$_3$) δ ppm: 1.45 (3H, t, J=7.1 Hz), 1.96–2.10 (2H, m), 2.14 (3H, s), 2.63 (2H, t, J=7.5 Hz), 2.73–2.94 (6H, m), 3.77 (3H, s), 3.79 (3H, s), 4.44 (2H, q, J=7.1 Hz), 6.49 (1H, dd, J=8.8 Hz, 3.0 Hz), 6.58 (1H, d, J=3.0 Hz), 6.69 (1H, d, J=8.8 Hz), 6.76–6.89 (2H, m), 7.03 (1H, dd, J=7.6 Hz, 1.6 Hz), 7.10–7.20 (1H, m), 7.77 (1H, s), 8.68 (1H, s)

REFERENCE EXAMPLE 55-3

Ethyl N-(7-{4-methoxy-3-[2-(3-fluoro-4-methoxyphenyl)ethyl]phenoxy}-6-methylindan-4-yl)oxamate The title compound was prepared in a similar manner to those described in Example 3 using 7-{3-[2-(3-fluoro-4-methoxyphenyl)ethyl]-4-methoxyphenoxy}-6-methylindan-4-yl amine instead of 4-(7-amino-5-methylindan-4-yloxy)-2-ethyl-3-methylphenol.

$^1$H-NMR (CDCl$_3$) δ ppm: 1.45 (3H, t, J=7.1 Hz), 1.96–2.10 (2H, m), 2.14 (3H, s), 2.62 (2H, t, J=7.4 Hz), 2.70–2.95 (6H, m), 3.78 (3H, s), 3.86 (3H, s), 4.43 (2H, q, J=7.1 Hz), 6.50 (1H, d, J=3.0 Hz), 6.54 (1H, dd, J=8.8 Hz, 3.0 Hz), 6.70 (1H, d, J=8.8 Hz), 6.75–6.95 (3H, m), 7.77 (1H, s), 8.69 (1H, s)

REFERENCE EXAMPLE 55-4

Ethyl N-[7-(4-benzyloxy-3-isopropylphenylsulfanyl)-6-methylindan-4-yl]oxamate

The title compound was prepared in a similar manner to those described in Example 3 using 7-(4-benzyloxy-3-isopropyl phenylsulfanyl)-6-methylindan-4-ylamine instead of 4-(7-amino-5-methylindan-4-yloxy)-2-ethyl-3-methylphenol.

$^1$H-NMR (CDCl$_3$) δ ppm: 1.16 (6H, d, J=6.9 Hz), 1.44 (3H, t, J=7.1 Hz), 2.00–2.18 (2H, m), 2.43 (3H, s), 2.85–3.03 (4H, m), 3.25–3.42 (1H, m), 4.43 (2H, q, J=7.1 Hz), 5.01 (2H, s), 6.60–6.80 (2H, m), 7.02 (1H, d, J=2.3 Hz), 7.25–7.55 (5H, m), 7.95 (1H, s), 8.73 (1H, s)

REFERENCE EXAMPLE 55-5

Ethyl N-[7-(4-methoxyphenoxy)-6-methylindan-4-yl]oxamate

The title compound was prepared in a similar manner to those described in Example 3 using [7-(4-methoxyphenoxy)-6-methylindan-4-yl]amine instead of 4-(7-amino-5-methylindan-4-yloxy)-2-ethyl-3-methylphenol.

$^1$H-NMR (CDCl$_3$) δ ppm: 1.44 (3H, t, J=7.2 Hz), 2.00–2.15 (2H, m), 2.18 (3H, s), 2.69 (2H, t, J=7.4 Hz), 2.87 (2H, t, J=7.4 Hz), 3.76 (3H, s), 4.43 (2H, q, J=7.2 Hz), 6.65–6.85 (4H, m), 7.79 (1H, s), 8.68 (1H, s)

EXAMPLE 3-1

Ethyl N-(7-{4-hydroxy-3-[2-(tetrahydrofuran-3-yl)ethyl]phenoxy}-6-methylindan-4-yl)oxamate
(Compound 24)

The title compound was prepared in a similar manner to those described in Example 3 using 4-(7-amino-5-methylindan-4-yloxy)-2-(tetrahydrofuran-4-ylethyl)phenol instead of 4-(7-amino-5-methylindan-4-yloxy)-2-ethyl-3-methylphenol.

$^1$H-NMR (CDCl$_3$) δ ppm: 1.30–1.80 (6H, m), 1.94–2.34 (7H, m), 2.45–2.75 (4H, m), 2.80–2.90 (2H, m), 3.30–3.45 (1H, m), 3.65–4.00 (3H, m), 4.43 (2H, q, J=7.1 Hz), 4.72 (1H, br-s), 6.45 (1H, dd, J=8.6 Hz, 3.0 Hz), 6.55–6.70 (2H, m), 7.77 (1H, s), 8.69 (1H, s).

EXAMPLE 3-2

Ethyl N-{7-[4-hydroxy-3-(tetrahydropyran-4-ylmethyl)phenoxy]-6-methylindan-4-yl}oxamate
(Compound 25)

The title compound was prepared in a similar manner to those described in Example 3 using 4-(7-amino-5-methylindan-4-yloxy)-2-(tetrahydropyran-4-ylmethyl)phenol instead of 4-(7-amino-5-methylindan-4-yloxy)-2-ethyl-3-methylphenol.

$^1$H-NMR (CDCl$_3$) δ ppm: 1.15–1.65 (7H, m), 1.75–1.90 (1H, m), 1.95–2.15 (5H, m), 2.40–2.55 (2H, m), 2.60–2.78

(2H, m), 2.80–2.95 (2H, m), 3.27–3.43 (2H, m), 3.88–4.05 (2H, m), 4.35–4.65 (3H, m), 6.40–6.80 (3H, m), 7.78 (1H, s), 8.69 (1H, s)

EXAMPLE 3-3

Ethyl N-[7-(4-hydroxy-3-isopropylphenoxy)-6-methylindan-4-yl]oxamate (Compound 26)

The title compound was prepared in a similar manner to those described in Example 3 using 4-(7-amino-5-methylindan-4-yloxy)-2-isopropylphenol instead of 4-(7-amino-5-methylindan-4-yloxy)-2-ethyl-3-methylphenol.

$^1$H-NMR (CDCl$_3$) δ ppm: 1.21 (6H, d, J=6.9 Hz), 1.44 (3H, t, J=7.1 Hz), 2.00–2.15 (2H, m), 2.17 (3H, s), 2.60–2.75 (2H, m), 2.80–2.95 (2H, m), 3.10–3.25 (1H, m), 4.42 (2H, q, J=7.1 Hz), 4.65–4.85 (1H, br-s), 6.35 (1H, dd, J=8.6, 3.0 Hz), 6.60 (1H, d, J=8.6 Hz), 6.76 (1H, d, J=3.0 Hz), 7.78 (1H, s), 8.69 (1H, s)

EXAMPLE 3-4

Ethyl N-{7-[4-hydroxy-3-(6-oxo-1,6-dihydropyridazin-3-ylmethyl)phenoxy]-6-methylindan-4-yl}oxamate (Compound 27)

The title compound was prepared in a similar manner to those described in Example 3 using 6-[5-(7-amino-5-methylindan-4-yloxy)-2-hydroxybenzyl]-2H-pyridazine-3-one instead of 4-(7-amino-5-methylindan-4-yloxy)-2-ethyl-3-methylphenol.

$^1$H-NMR (CDCl$_3$) δ ppm: 1.44 (3H, t, J=7.1 Hz), 2.00–2.10 (2H, m), 2.15 (3H, s), 2.60–2.70 (2H, m), 2.83–2.90 (2H, m), 3.88 (2H, s), 4.43 (2H, q, J=7.1 Hz), 6.54 (1H, dd, J=3.0, 8.7 Hz), 6.64 (1H, d, J=3.0 Hz), 6.75 (1H, d, J=8.7 Hz), 6.93 (1H, d, J=9.7 Hz), 7.26 (1H, d, J=9.7 Hz), 7.52 (1H, br-s), 7.75 (1H, s), 8.70 (1H, s)

EXAMPLE 3-5

Ethyl N-[7-(4-hydroxy-3-isopropylbenzyl)-6-methylindan-4-yl ]oxamate (Compound 28)

The title compound was prepared in a similar manner to those described in Example 3 using 4-(7-amino-5-methylindan-4-ylmethyl)-2-isopropylphenol instead of 4-(7-amino-5-methylindan-4-yloxy)-2-ethyl-3-methylphenol.

$^1$H-NMR (CDCl$_3$) δ ppm: 1.22 (6H, d, J=6.9 Hz), 1.44 (3H, t, J=7.1 Hz), 2.05–2.13 (2H, m), 2.25 (3H, s), 2.82–2.92 (4H, m), 3.15 (1H, heptet, J=6.9 Hz), 3.90 (2H, s), 4.42 (1H, q, J=7.1 Hz), 4.56 (1H, s), 6.55–6.63 (2H, m), 6.94 (1H, br-s), 7.77 (1H, s), 8.68 (1H—, br-s).

EXAMPLE 3-6

Ethyl N-{7-[2-(2-cyclohexylethoxy)-3-ethyl-4-hydroxyphenoxy]-6-methylindan-4-yl}oxamate (Compound 29)

The title compound was prepared in a similar manner to those described in Example 3 using 4-(7-amino-5-methylindan-4-yloxy)-3-(2-cyclohexylethoxy)-2-ethylphenol instead of 4-(7-amino-5-methylindan-4-yloxy)-2-ethyl-3-methylphenol.

$^1$H-NMR (CDCl$_3$) δ ppm: 0.91–0.99 (2H, m), 1.10–1.28 (3H, m), 1.21 (3H, t, J=7.5 Hz), 1.44 (3H, t, J=7.1 Hz), 1.50–1.80 (8H, m), 2.03–2.10 (2H, m), 2.19 (3H, s), 2.64–2.70 (2H, m), 2.72 (2H, q, J=7.5 Hz), 2.83–2.88 (2H, m), 4.13–4.19 (2H, m), 4.42 (2H, q, J=7.1 Hz), 4.58 (1H, s), 6.13 (1H, d, J=8.8 Hz), 6.31 (1H, d, J=8.8 Hz), 7.78 (1H, s), 8.68 (1H, s)

EXAMPLE 3-7

Ethyl N-[7-(3-ethyl-4-hydroxy-2-phenethyloxyphenoxy)-6-methylindan-4-yl]oxamate (Compound 30)

The title compound was prepared in a similar manner to those described in Example 3 using 4-(7-amino-5-methylindan-4-yloxy)-2-ethyl-3-phenethyloxyphenol instead of 4-(7-amino-5-methylindan-4-yloxy)-2-ethyl-3-methylphenol.

$^1$H-NMR (CDCl$_3$) δ ppm: 1.10 (3H, t, J=7.5 Hz), 1.44 (3H, t, J=7.1 Hz), 2.02–2.09 (2H, m), 2.19 (3H, s), 2.56 (2H, q, J=7.5 Hz), 2.62–2.68 (2H, m), 2.82–2.89 (2H, m), 3.14 (2H, t, J=7.1 Hz), 4.36 (2H, t, J=7.1 Hz), 4.43 (2H, q, J=7.1 Hz), 4.46 (1H, s), 6.14 (1H, d, J=8.8 Hz), 6.32 (1H, d, J=8.8 Hz), 7.18–7.25 (1H, m), 7.25–7.35 (4H, m), 7.79 (1H, s), 8.68 (1H, s)

EXAMPLE 3-8

Ethyl N-[7-(4-hydroxy-3-isopropyl-2-methoxyphenoxy)-6-methylindan-4-yl]oxamate (Compound 31)

The title compound was prepared in a similar manner to those described in Example 3 using [7-(4-hydroxy-3-isopropyl-2-methoxyphenoxy)-6-methylindan-4-yl]amine instead of 4-(7-amino-5-methylindan-4-yloxy)-2-ethyl-3-methylphenol.

$^1$H-NMR (CDCl$_3$) δ ppm: 1.39 (3H, t, J=7.1 Hz), 1.44 (6H, d, J=7.1 Hz), 2.02–2.10 (2H, m), 2.20 (3H, s), 2.65–2.71 (2H, m), 2.83–2.90 (2H, m), 3.56 (1H, heptet, J=7.1 Hz), 3.95 (3H, s), 4.37–4.46 (2H, m), 6.13 (1H, d, J=8.8 Hz), 6.27 (1H, d, J=8.8 Hz), 7.79 (1H, s), 8.68 (1H, s)

EXAMPLE 3-9

Ethyl N-[7-(4-hydroxy-3-phenethylphenoxy)-6-methylindan-4-yl]oxamate (Compound 32)

The title compound was prepared in a similar manner to those described in Example 3 using 4-(7-amino-5-methylindan-4-yloxy)-2-phenethylphenol instead of 4-(7-amino-5-methylindan-4-yloxy)-2-ethyl-3-methylphenol.

$^1$H-NMR (CDCl$_3$) δ ppm: 1.44 (3H, t, J=7.1 Hz), 2.06 (2H, t, J=7.4 Hz), 2.14 (3H, s), 2.63 (2H, t, J=7.5 Hz), 2.80–2.95 (6H, m), 4.23 (1H, s), 4.43 (2H, q, J=7.1 Hz), 6.40–6.55 (2H, m), 6.63 (1H, d, J=8.6 Hz), 7.10–7.30 (5H, m), 7.77 (1H, s), 8.67 (1H, s)

EXAMPLE 3-10

Ethyl N-[7-(3-cyclohexylcarbamoyl-4-hydroxyphenoxy)-6-methylindan-4-yl]oxamate (Compound 33)

The title compound was prepared in a similar manner to those described in Example 3 using 5-(7-amino-5-methylindan-4-yloxy)-N-cyclohexyl-2-hydroxybenzamide instead of 4-(7-amino-5-methylindan-4-yloxy)-2-ethyl-3-methylphenol.

$^1$H-NMR (CDCl$_3$) δ ppm: 1.14–1.83 (11H, m), 1.97–2.13 (4H, m), 2.19 (3H, s), 2.66 (2H, t, J=7.5 Hz), 2.87 (2H, t, J=7.3 Hz), 3.89–4.01 (1H, m), 4.43 (2H, q, J=7.2 Hz), 6.07

(1H, d, J=7.7 Hz), 6.75 (1H, dd, J=8.7, 2.8 Hz), 6.80–6.90 (2H, m), 7.78 (1H, s), 8.69 (1H, s), 12.01 (1H, s)

EXAMPLE 4

Ethyl N-{7-[4-hydroxy-3-(2-thiazol-2-ylethyl)phenoxy]-6-methylindan-4-yl}malonamate (Compound 34)

7-[4-Benzyloxy-3-(2-thiazol-2-ylethyl)phenoxy]-6-methylindan-4-ylamine (43 mg) was dissolved in dichloromethane (5 mL), and pyridine (23 μL) was added to the mixture. Ethyl malonyl chloride (16 μL) was added dropwise to the mixture under ice-cooling with stirring, then the mixture was stirred at room temperature for 3 hours. Adding diluted hydrochloric acid (5 mL), the reaction mixture was extracted with ethyl acetate. The organic layer was washed with a saturated aqueous solution of sodium hydrogen carbonate and brine successively, and dried over anhydrous magnesium sulfate. The solvent was removed under reduced pressure. The residue was purified by column chromatography on silica gel (eluent: hexane/ethyl acetate) to give a benzyloxy ethyl malonamate. The benzyloxy ethyl malonamate was dissolved in a mixed solvent of trifluoroacetic acid/water/dimethylsulfide (95/5/10, 5 mL). The mixture was stood at room temperature for 12 hours. The solvent was removed under reduced pressure, and the residue was purified by column chromatography on silica gel (eluent: hexane/ethyl acetate) to give the title compound (23 mg).

$^1$H-NMR (CDCl$_3$) δ ppm: 1.34 (3H, t, J=7.1 Hz), 1.98–2.11 (2H, m), 2.15 (3H, s), 2.66 (2H, t, J=7.4 Hz), 2.88 (2H, t, J=7.4 Hz), 3.07–3.13 (2H, m), 3.33–3.43 (2H, m), 3.49 (2H, s), 3.76 (3H, s), 4.27 (2H, q, J=7.1 Hz), 6.53 (1H, dd, J=3.0 Hz, 8.7 Hz), 6.58 (H, d, J=3.0 Hz), 6.77 (1H, d, J=8.7 Hz), 7.24 (1H, d, J=3.4 Hz), 7.66 (1H, d, J=3.4 Hz), 7.75 (1H, s), 9.18 (1H, s)

EXAMPLE 4-1

Ethyl N-[7-(4-hydroxy-3-isopropylphenoxy)-6-trifluoromethylindan-4-yl]malonamate (Compound 35)

The title compound was prepared in a similar manner to those described in Example 4 using 7-(4-benzyloxy-3-isopropylphenoxy)-6-trifluoromethylindan-4-ylamine instead of 7-[4-benzyloxy-3-(2-thiazol-2-ylethyl)phenoxy]-6-methylindan-4-ylamine.

$^1$H-NMR (CDCl$_3$) δ ppm: 1.20 (6H, d, J=6.9 Hz), 1.34 (3H, t, J=7.1 Hz), 2.00–2.06 (2H, m), 2.48–2.54 (2H, m), 2.87–2.93 (2H, m), 3.18 (1H, heptet, J=6.9 Hz), 3.52 (2H, s), 4.27 (2H, q, J=7.1 Hz), 5.00 (1H, s), 6.43 (1H, dd, J=3.0, 8.6 Hz), 6.62 (1H, d, J=8.6 Hz), 6.79 (1H, d, J=3.0 Hz), 8.24 (1H, s), 9.45 (1H, s)

EXAMPLE 4-2

Ethyl N-[7-(4-hydroxy-3-isopropylphenoxy)-6-trifluoromethylindan-4-yl]oxamate (Compound 36)

The title compound was prepared in a similar manner to those described in Example 4 using 7-(4-benzyloxy-3-isopropylphenoxy)-6-trifluoromethylindan-4-ylamine instead of 7-[4-benzyloxy-3-(2-thiazol-2-ylethyl)phenoxy]-6-methylindan-4-ylamine and using ethyl oxalyl chloride instead of ethyl malonyl chloride.

$^1$H-NMR (CDCl$_3$) δ ppm: 1.21 (6H, d, J=6.9 Hz), 1,45 (3H, t, J=7.1 Hz), 2.02–2.10 (2H, m), 2.50–2.57 (2H, m), 2.86–2.93 (2H, m), 3.17 (1H, heptet, J=6.9 Hz), 4.44 (2H, q, J=7.1 Hz), 4.66 (1H, s), 6.46 (1H, dd, J=3.0, 8.6 Hz), 6.63 (1H, d, J=8.6 Hz), 6.80 (1H, d, J=3.0 Hz), 8.24 (1H, s), 8.75 (1H, s)

EXAMPLE 4-3

Ethyl N-[6-bromo-7-(4-hydroxy-3-isopropylphenoxy)indan-4-yl]malonamate (Compound 37)

The title compound was prepared in a similar manner to those described in Example 4 using 7-(4-benzyloxy-3-isopropylphenoxy)-6-bromoindan-4-ylamine instead of 7-[4-benzyloxy-3-(2-thiazol-2-ylethyl)phenoxy]-6-methylindan-4-ylamine.

$^1$H-NMR (CDCl$_3$) δ ppm: 1.22 (6H, d, J=6.9 Hz), 1.34 (3H, t, J=7.2 Hz), 2.02–2.10 (2H, m), 2.67–2.74 (2H, m), 2.83–2.89 (2H, m), 2.87 (1H, heptet, J=6.9 Hz), 3.50 (2H, s), 4.27 (2H, q, J=7.2 Hz), 4.50 (1H, s), 6.41 (1H, dd, J=3.0, 8.6 Hz), 6.61 (1H, d, J=8.6 Hz), 6.80 (1H, d, J=3.0 Hz), 8.25 (1H, s), 9.36 (1H, s)

EXAMPLE 4-4

Ethyl N-[6-bromo-7-(4-hydroxy-5,6,7,8-tetrahydronaphthalen-1-yloxy)indan-4-yl]malonamate (Compound 38)

The title compound was prepared in a similar manner to those described in Example 4 using 7-(4-benzyloxy-5,6,7,8-tetrahydronaphthalen-1-yloxy)-6-bromoindan-4-ylamine instead of 7-[4-benzyloxy-3-(2-thiazol-2-ylethyl)phenoxy]-methylindan-4-ylamine.

$^1$H-NMR (CDCl$_3$) δ ppm: 1.34 (3H, t, J=7.1 Hz), 1.77–1.88 (4H, m), 2.01–2.09 (2H, m), 2.60–2.78 (4H, m), 2.78–2.94 (4H, m), 3.49 (2H, s), 4.27 (2H, q, J=7.1 Hz), 4.54 (1H, s), 6.11 (1H, d, J=8.7 Hz), 6.43 (1H, d, J=8.7 Hz), 8.22 (1H, s), 9.34 (1H, s)

EXAMPLE 4-5

Ethyl N-[6-bromo-7-(4-hydroxy-5,6,7,8-tetrahydronaphthalen-1-yloxy)indan-4-yl]oxamate (Compound 39)

The title compound was prepared in a similar manner to those described in Example 4 using 7-(4-benzyloxy-5,6,7,8-tetrahydronaphthalen-1-yloxy)-6-bromoindan-4-ylamine instead of 7-[4-benzyloxy-3-(2-thiazol-2-ylethyl)phenoxy]-6-methylindan-4-ylamine and using ethyl oxalyl chloride instead of ethyl malonyl chloride.

$^1$H-NMR (CDCl$_3$) δ ppm: 1.44 (3H, t, J=7.1 Hz), 1.76–1.90 (4H, m), 2.03–2.13 (2H, m), 2.57–2.92 (8H, m), 4.43 (2H, q, J=7.1 Hz), 4.60 (1H, br-s), 6.12 (1H, d, J=8.7 Hz), 6.45 (1H, d, J=8.7 Hz), 8.21 (1H, s), 8.70 (1H, s)

EXAMPLE 4-6

Ethyl N-[7-(4-hydroxy-3-iodophenoxy)-6-methylindan-4-yl]oxamate (Compound 40)

The title compound was prepared in a similar manner to those described in Example 4 using [7-(4-benzyloxy-3-iodophenoxy)-6-methylindan-4-yl]amine instead of 7-[4-benzyloxy-3-(2-thiazol-2-ylethyl)phenoxy]-6-methylindan-4-ylamine and using ethyl oxalyl chloride instead of ethyl malonyl chloride.

¹H-NMR (CDCl₃) δ ppm: 1.44 (3H, t, J=7.1 Hz), 2.03–2.13 (2H, m), 2.16 (3H, s), 2.65–2.72 (2H, m), 2.84–2.92 (2H, m), 4.43 (2H, q, J=7.1 Hz), 5.05 (1H, s), 6.71 (1H, dd, J=2.9, 8.9 Hz), 6.87 (1H, d, J=8.9 Hz), 7.07 (1H, d, J=2.9 Hz), 7.80 (1H, s), 8.69 (1H, br-s)

EXAMPLE 5

Ethyl N-[7-(4-hydroxy-3-iodophenoxy)-6-methylindan-4-yl]malonamate (Compound 41)

The title compound was prepared in a similar manner to those described in Reference Example 27 using ethyl N-[7-(4-benzyloxy-3-iodophenoxy)-6-methylindan-4-yl]malonamate instead of ethyl 2-acetyl-3-benzyloxy-6-(5-methyl-7-nitroindan-4-yloxy)benzoate.
¹H-NMR (CDCl₃) δ ppm: 1.34 (3H, t, J=7.1 Hz), 2.02–2.12 (2H, m), 2.14 (3H, s), 2.64–2.70 (2H, m), 2.84–2.91 (2H, m), 3.50 (2H, s), 4.27 (2H, q, J=7.1 Hz), 5.05 (1H, s), 6.71 (1H, dd, J=2.9, 8.9 Hz), 6.86 (1H, d, J=8.9 Hz), 7.06 (1H, d, J=2.9 Hz), 7.78 (1H, s), 9.24 (1H, s)

EXAMPLE 5-1

Ethyl N-[7-(4-hydroxy-3-isopropylphenylsulfanyl)-6-methylindan-4-yl]oxamate (Compound 42)

The title compound was prepared in a similar manner to those described in Reference Example 27 using ethyl N-[7-(4-benzyloxy-3-isopropylphenylsulfanyl)-6-methylindan-4-yl]oxamate instead of ethyl 2-acetyl-3-benzyloxy-6-(5-methyl-7-nitroindan-4-yloxy)benzoate.
¹H-NMR (CDCl₃) δ ppm: 1.19 (6H, d, J=6.9 Hz), 1.44 (3H, t, J=7.1 Hz), 2.00–2.18 (2H, m), 2.42 (3H, s), 2.84–3.00 (4H, m), 3.05–3.20 (1H, m), 4.43 (2H, q, J=7.1 Hz), 4.63 (1H, s), 6.52–6.68 (2H, m), 7.00 (1H, d, J=2.2 Hz), 7.94 (1H, s), 8.72 (1H, s)

REFERENCE EXAMPLE 56

Ethyl N-(7-{3-[2-(4-fluorophenyl)acetyl]-4-methoxyphenoxy}-6-methylindan-4-yl)malonamate Ethyl N-[7-(4-methoxyphenoxy)-6-methylindan-4-yl]malonamate (100 mg) and 4-fluorophenylacetic acid (60 mg) were dissolved in dichloromethane (261 μL). To the solution was added dropwise trifluoromethanesulfonic anhydride (66 μL) at room temperature with stirring. The mixture was stirred at room temperature for 15 hours. Adding water, the reaction mixture was extracted with diethyl ether. The organic layer was washed with water, a saturated aqueous solution of sodium hydrogen carbonate and brine successively, and dried over anhydrous magnesium sulfate. The solvent was removed under reduced pressure. The residue was purified by column chromatography on silica gel (eluent: hexane/ethyl acetate=2/1) to give the title compound (74 mg).
¹H-NMR (CDCl₃) δ ppm: 1.34 (3H, t, J=7.1 Hz), 2.00–2.10 (2H, m), 2.12 (3H, s), 2.62 (2H, t, J=7.5 Hz), 2.87 (2H, t, J=7.4 Hz), 3.49 (2H, s), 3.88 (3H, s), 4.23 (2H, s), 4.27 (2H, q, J=7.1 Hz), 6.80–7.20 (7H, m), 7.78 (1H, s), 9.18 (1H, s)

REFERENCE EXAMPLE 56-1

1-[2-methoxy-5-(5-methyl-7-nitroindan-4-yloxy)phenyl]ethanone

The title compound was prepared in a similar manner to those described in Reference Example 56 using 4-(4-methoxyphenoxy)-5-methyl-7-nitroindane instead of ethyl N-[7-(4-methoxyphenoxy)-6-methylindan-4-yl]malonamate and using acetic acid instead of 4-fluorophenylacetic acid.
¹H-NMR (CDCl₃) δ ppm: 2.00–2.15 (2H, m), 2.23 (3H, s), 2.60 (3H, s), 2.64 (2H, t, J=7.6 Hz), 3.38 (2H, t, J=7.6 Hz), 3.89 (3H, s), 6.85–7.00 (2H, m), 7.17 (1H, d, J=3.0 Hz), 7.97 (1H, s)

REFERENCE EXAMPLE 56-2

1-[2-methoxy-5-(5-methyl-7-nitroindan-4-yloxy)phenyl]-2-phenylethanone

The title compound was prepared in a similar manner to those described in Reference Example 56 using 4-(4-methoxyphenoxy)-5-methyl-7-nitroindane instead of ethyl N-[7-(4-methoxyphenoxy)-6-methylindan-4-yl]malonamate and using phenylacetic acid instead of 4-fluorophenylacetic acid.
¹H-NMR (CDCl₃) δ ppm: 1.95–2.10 (2H, m), 2.19 (3H, s), 2.57 (2H, t, J=7.5 Hz), 3.36 (2H, t, J=7.5 Hz), 3.90 (3H, s), 4.27 (2H, s), 6.85–7.05 (3H, m), 7.10–7.35 (5H, m), 7.94 (1H, s)

REFERENCE EXAMPLE 56-3

Ethyl N-[7-(3-acetyl-4-methoxyphenoxy)-6-methylindan-4-yl]malonamate

The title compound was prepared in a similar manner to those described in Reference Example 56 using acetic acid instead of 4-fluorophenylacetic acid.
¹H-NMR (CDCl₃) δ ppm: 1.34 (3H, t, J=7.1 Hz), 2.02–2.10 (2H, m), 2.14 (3H, s), 2.58 (3H, s), 2.63–2.69 (2H, m), 2.87–2.92 (2H, m), 3.49 (2H, s), 3.87 (3H, s), 4.27 (2H, q, J=7.1 Hz), 6.83–6.90 (2H, m), 7.17 (1H, d, J=3.0 Hz), 7.79 (1H, s), 9.18 (1H, s)

REFERENCE EXAMPLE 56-4

Ethyl N-(7-{3-[2-(4-fluorophenyl)acetyl]-4-methoxyphenoxy}-6-methylindan-4-yl)oxamate The title compound was prepared in a similar manner to those described in Reference Example 56 using ethyl N-[7-(4-methoxyphenoxy)-6-methylindan-4-yl]oxamate instead of ethyl N-[7-(4-methoxyphenoxy)-6-methylindan-4-yl]malonamate.
¹H-NMR (CDCl₃) δ ppm: 1.44 (3H, t, J=7.1 Hz), 2.00–2.10 (2H, m), 2.13 (3H, s), 2.63 (2H, t, J=7.5 Hz), 2.86 (2H, t, J=7.4 Hz), 3.88 (3H, s), 4.23 (2H, s), 4.43 (2H, q, J=7.1 Hz), 6.80–7.20 (7H, m), 7.79 (1H, s), 8.67 (1H, s)

REFERENCE EXAMPLE 57

4-(4-methoxy-3-phenethylphenoxy)-5-methyl-7-nitroindane

The title compound was prepared in a similar manner to those described in Reference Example 25 using 1-[2-methoxy-5-(5-methyl-7-nitroindan-4-yloxy)phenyl]-2-phenylethanone instead of 1-[6-benzyloxy-2-hydroxy-3-(5-methyl-7-nitroindan-4-yloxy)phenyl]ethanone.
¹H-NMR (CDCl₃) δ ppm: 1.95–2.15 (2H, m), 2.19 (3H, s), 2.56 (2H, t, J=7.6 Hz), 2.80–2.95 (4H, m), 3.36 (2H, t, J=7.5 Hz), 3.80 (3H, s), 6.50 (1H, d, J=3.1 Hz), 6.55 (1H, dd, J=8.8, 3.1 Hz), 6.73 (1H, d, J=8.8 Hz), 7.05–7.30 (5H, m), 7.94 (1H, s)

REFERENCE EXAMPLE 57-1

Ethyl N-(7-{3-[2-(4-fluorophenyl)ethyl]-4-methoxyphenoxy}-6-methylindan-4-yl)oxamate The title compound was prepared in a similar manner to those described in Reference Example 25 using ethyl N-(7-{3-[2-(4-fluorophenyl)acetyl]-4-methoxyphenoxy}-6-methylindan-4-yl)oxamate instead of 1-[6-benzyloxy-2-hydroxy-3-(5-methyl-7-nitroindan-4-yloxy)phenyl]ethanone.

$^1$H-NMR (CDCl$_3$) δ ppm: 1.45 (3H, t, J=7.1 Hz), 2.00–2.10 (2H, m), 2.14 (3H, s), 2.60 (2H, t, J=7.6 Hz), 2.75–2.95 (6H, m), 3.77 (3H, s), 4.43 (2H, q, J=7.1 Hz), 6.40–7.15 (7H, m), 7.77 (1H, s), 8.68 (1H, s)

EXAMPLE 6

Ethyl N-[7-(3-acetyl-4-hydroxyphenoxy)-6-methylindan-4-yl]malonamate (Compound 43)

To a solution of ethyl N-[7-(3-acetyl-4-methoxyphenoxy)-6-methylindan-4-yl]malonamate (268 mg) in dichloromethane (15 mL) was added a 1 mol/L solution of boron trichloride in dichloromethane (1.9 mL) under ice-cooling, and the mixture was stirred at room temperature for 3 days. Ethanol was added to the reaction mixture, and the solvent was removed under reduced pressure. The residue was purified by column chromatography on silica gel (eluent: hexane/ethyl acetate=3/1–1/1) to give the title compound (183 mg).

$^1$H-NMR (CDCl$_3$) δ ppm: 1.34 (3H, t, J=7.1 Hz), 2.03–2.11 (2H, m), 2.17 (3H, s), 2.54 (3H, s), 2.65–2.72 (2H, m), 2.86–2.94 (2H, m), 3.50 (2H, s), 4.27 (2H, q, J=7.1 Hz), 6.87 (1H, d, J=3.0 Hz), 6.94 (1H, dd, J=3.0, 9.1 Hz), 7.15 (1H, d, J=3.0 Hz), 7.82 (1H, s), 9.24 (1H, s), 11.85 (1H, s)

EXAMPLE 6-1

Ethyl N-(7-{3-[2-(4-fluorophenyl)acetyl]-4-hydroxyphenoxy}-6-methylindan-4-yl)malonamate (Compound 44)

The title compound was prepared in a similar manner to those described in Example 6 using ethyl N-(7-{3-[2-(4-fluorophenyl)acetyl]-4-methoxyphenoxy}-6-methylindan-4-yl) malonamate instead of ethyl N-[7-(3-acetyl-4-methoxyphenoxy)-6-methylindan-4-yl]malonamate.

$^1$H-NMR (CDCl$_3$) δ ppm: 1.34 (3H, t, J=7.1 Hz), 1.96–2.16 (5H, m), 2.59 (2H, t, J=7.4 Hz), 2.91 (2H, t, J=7.4 Hz), 3.52 (2H, s), 4.07 (2H, s), 4.29 (2H, q, J=7.1 Hz), 6.86–7.12 (7H, m), 7.84 (1H, s), 9.30 (1H, s), 11.76 (1H, s)

REFERENCE EXAMPLE 58

1-[6-hydroxy-2-methoxy-3-(5-methyl-7-nitroindan-4-yloxy)phenyl]ethanone

The title compound was prepared in a similar manner to those described in Example 6 using 1-[2,6-dimethoxy-3-(5-methyl-7-nitroindan-4-yloxy)phenyl]ethanone instead of ethyl N-[7-(3-acetyl-4-methoxyphenoxy)-6-methylindan-4-yl]malonamate.

$^1$H-NMR (CDCl$_3$) δ ppm: 2.03–2.10 (2H, m), 2.30 (3H, s), 2.57–2.63 (2H, m), 2.78 (3H, s), 3.34–3.39 (2H, m), 4.09 (3H, s), 6.59 (1H, d, J=9.1 Hz), 6.67 (1H, d, J=9.1 Hz), 7.98 (1H, s), 12.38 (1H, s)

REFERENCE EXAMPLE 59

2-Acetyl-3-methoxy-4-(5-methyl-7-nitroindan-4-yloxy)phenyl trifluoromethanesulfonate To a solution of 1-[6-hydroxy-2-methoxy-3-(5-methyl-7-nitroindan-4-yloxy)phenyl]ethanone (4.12 g) in dichloromethane (40 mL) was added pyridine (2.6 mL). Trifluoromethanesulfonic anhydride (2.55 mL) was added dropwise to the mixture under ice-cooling, and the mixture was stirred at ambient temperature for 1 hour. Adding water, the reaction mixture was acidified with 1 mol/L hydrochloric acid, and extracted with dichloromethane. The organic layer was washed with 1 mol/L hydrochloric acid, water, a saturated aqueous solution of sodium hydrogen carbonate and brine successively, and dried over anhydrous magnesium sulfate. The solvent was removed under reduced pressure. The residue was purified by column chromatography on silica gel (eluent: hexane/ethyl acetate=10/1–3/1) to give the title compound (1.892 g).

$^1$H-NMR (CDCl$_3$) δ ppm: 2.08–2.18 (2H, m), 2.26 (3H, s), 2.64 (3H, s), 2.67–2.76 (2H, m), 3.37–3.45 (2H, m), 4.06 (3H, s), 6.47 (1H, d, J=9.1 Hz), 6.91 (1H, d, J=9.1 Hz), 8.01 (1H, s)

REFERENCE EXAMPLE 60

2-Acetyl-3-hydroxy-4-(5-methyl-7-nitroindan-4-yloxy)phenyl trifluoromethanesulfonate The title compound was prepared in a similar manner to those described in Example 6 using 2-acetyl-3-methoxy-4-(5-methyl-7-nitroindan-4-yloxy)phenyl trifluoromethanesulfonate instead of ethyl N-[7-(3-acetyl-4-methoxyphenoxy)-6-methylindan-4-yl]malonamate.

$^1$H-NMR (CDCl$_3$) δ ppm: 2.06–2.15 (2H, m), 2.27 (3H, s), 2.66–2.73 (2H, m), 2.80 (3H, s), 3.35–3.43 (2H, m), 6.64 (1H, d, J=9.0 Hz), 6.76 (1H, d, J=9.0 Hz), 7.99 (1H, s), 12.63 (1H, s)

REFERENCE EXAMPLE 61

2-Ethyl-3-hydroxy-4-(5-methyl-7-nitroindan-4-yloxy)phenyl trifluoromethanesulfonate To a solution of 2-acetyl-3-hydroxy-4-(5-methyl-7-nitroindan-4-yloxy)phenyl trifluoromethanesulfonate (477 mg) in dichloromethane (5 mL) were added triethylsilane (0.960 mL) and trifluoroacetic acid (5 mL), and the mixture was stirred at room temperature overnight. Adding water, the reaction mixture was stirred for 1 hour and extracted with dichloromethane. The organic layer was washed with water, a saturated aqueous solution of sodium hydrogen carbonate and brine successively, and dried over anhydrous magnesium sulfate. The solvent was removed under reduced pressure. The residue was crystallized from dichloromethane and hexane to give the title compound (274 mg).

$^1$H-NMR (CDCl$_3$) δ ppm: 1.27 (3H, t, J=7.5 Hz), 2.07–2.15 (2H, m), 2.25 (3H, s), 2.65–2.70 (2H, m), 2.82 (2H, q, J=7.5 Hz), 3.36–3.44 (2H, m), 5.97 (1H, s), 6.25 (1H, d, J=9.0 Hz), 7.67 (1H, d, J=9.0 Hz), 7.80 (1H, s)

EXAMPLE 7

Ethyl N-[7-(3-ethyl-4-hydroxyphenoxy)-6-methylindan-4-yl]malonamate (Compound 45)

The title compound was prepared in a similar manner to those described in Reference Example 25 using ethyl N-[7-(3-acetyl-4-hydroxyphenoxy)-6-methylindan-4-yl]malonamate instead of 1-[6-benzyloxy-2-hydroxy-3-(5-methyl-7-nitroindan-4-yloxy)phenyl]ethanone.

$^{1}$H-NMR (CDCl$_{3}$) δ ppm: 1.19 (3H, t, J=7.5 Hz), 1.33 (3H, t, J=7.1 Hz), 2.00–2.10 (2H, m), 2.14 (3H, s), 2.57 (2H, q, J=7.5 Hz), 2.65–2.70 (2H, m), 2.85–2.90 (2H, m), 3.49 (2H, s), 4.27 (2H, q, J=7.1 Hz), 4.86 (1H, s), 6.41 (1H, dd, J=3.0, 8.7 Hz), 6.59–6.66 (2H, m), 7.74 (1H, s), 9.19 (1H, s)

EXAMPLE 7-1

Ethyl N-[7-(3-ethyl-4-hydroxy-2-methoxyphenoxy)-6-methylindan-4-yl]oxamate (Compound 46)

The title compound was prepared in a similar manner to those described in Reference Example 25 using ethyl N-[7-(3-acetyl-4-hydroxy-2-methoxyphenoxy)-6-methylindan-4-yl]oxamate instead of 1-[6-benzyloxy-2-hydroxy-3-(5-methyl-7-nitroindan-4-yloxy)phenyl]ethanone.

$^{1}$H-NMR (CDCl$_{3}$) δ ppm: 1.22 (3H, t, J=7.5 Hz), 1.44 (3H, t, J=7.1 Hz), 2.00–2.10 (2H, m), 2.19 (3H, s), 2.64–2.7–7 (4H, m), 2.83–2.88 (2H, m), 3.98 (3H, s), 4.42 (2H, q, J=7.1 Hz), 4.76 (1H, s), 6.14 (1H, d, J=8.8 Hz), 6.34 (1H, d, J=8.8 Hz), 7.78 (1H, s), 8.68 (1H, s)

EXAMPLE 8

Ethyl N-(7-{3-[2-(4-fluorophenyl)ethyl]-4-hydroxyphenoxy}-6-methylindan-4-yl)malonamate (Compound 47)

The title compound was prepared in a similar manner to those described in Reference Example 25 using ethyl N-(7-{3-[2-(4-fluorophenyl)acetyl]-4-hydroxyphenoxy}-6-methylindan-4-yl)malonamate instead of 1-[6-benzyloxy-2-hydroxy-3-(5-methyl-7-nitroindan-4-yloxy)phenyl]ethanone.

$^{1}$H-NMR (CDCl$_{3}$) δ ppm: 1.34 (3H, t, J=7.1 Hz), 2.00–2.09 (2H, m), 2.12 (3H, s), 2.60 (2H, t, J=7.5 Hz), 2.76–2.94 (6H, m), 3.50 (2H, s), 4.27 (2H, q, J=7.1 Hz), 4.33 (1H, s), 6.40–6.54 (2H, m), 6.58–6.66 (1H, m), 6.88–6.98 (2H, m), 7.03–7.13 (2H, m), 7.75 (1H, s), 9.20 (1H, s)

REFERENCE EXAMPLE 62

Ethyl {[7-(4-benzyloxy-3-isopropylphenoxy)-6-methylindan-4-carbonyl]amino}acetate Thionyl chloride (0.16 mL) was added to 7-(4-benzyloxy-3-isopropylphenoxy)-6-methylindan-4-carboxylic acid (47 mg), and the mixture was stirred at room temperature for 10 min. The reaction mixture was evaporated under reduced pressure to dryness. Toluene (1 mL) was added to the residue, and the solvent was evaporated under reduced pressure to dryness. To the reaction mixture was added N,N-dimethylformamide (2 mL), and the resulting mixture was added to a suspension of glycine ethyl ester hydrochloric acid (47 mg) and triethylamine (90 μL) in N,N-dimethylformamide (3 mL) under ice-cooling. The reaction mixture was stirred at room temperature for 20 min. Adding 1 mol/L hydrochloric acid, the reaction mixture was extracted with ethyl acetate 3 times. The organic layer was washed with brine, and dried over anhydrous magnesium sulfate. The solvent was removed under reduced pressure. The residue was purified by thin layer chromatography on silica gel (developing solvent: hexane/ethyl acetate=3/1) to give the title compound (39 mg).

$^{1}$H-NMR (CDCl$_{3}$) δ ppm: 1.20 (6H, d, J=6.9 Hz), 1.33 (3H, t, J=7.1 Hz), 1.97–2.07 (2H, m), 2.20 (3H, s), 2.58–2.66 (2H, m), 3.16–3.21 (2H, m), 3.37 (1H, heptet, J=6.9 Hz), 4.24 (2H, d, J=4.9 Hz), 4.27 (2H, q, J=7.1 Hz), 5.02 (2H, s), 6.42 (1H, dd, J=3.0, 8.8 Hz), 6.47 (1H, t, J=4.9 Hz), 6.75 (1H, d, J=8.8 Hz), 6.80 (1H, d, J=3.0 Hz), 7.30–7.46 (6H, m)

REFERENCE EXAMPLE 62-1

Ethyl {[7-(4-benzyloxy-3-isopropyl-2-methoxyphenoxy)-6-methylindan-4-carbonyl]amino}acetate The title compound was prepared in a similar manner to those described in Reference Example 62 using 7-(4-benzyloxy-3-isopropyl-2-methoxyphenoxy)-6-methylindan-4-carboxylic acid instead of 7-(4-benzyloxy-3-isopropylphenoxy)-6-methylindan-4-carboxylic acid.

$^{1}$H-NMR (CDCl$_{3}$) δ ppm: 1.33 (6H, d, J=7.1 Hz), 1.37 (3H, t, J=7.0 Hz), 1.97–2.07 (2H, m), 2.21 (3H, s), 2.57–2.65 (2H, m), 3.13–3.20 (2H, m), 3.64 (1H, heptet, J=7.0 Hz), 3.95 (3H, s), 4.24 (2H, d, J=5.0 Hz), 4.28 (2H, d, J=7.1 Hz), 4.98 (2H, s), 6.17 (1H, d, J=9.0 Hz), 6.46 (1H, d, J=9.0 Hz), 6.47 (1H, br-s), 7.27–7.47 (6H, m)

REFERENCE EXAMPLE 62-2

Ethyl ({7-[4-benzyloxy-3-(4-fluorobenzyl)phenoxy]-6-methylindan-4-carbonyl}amino)acetate The title compound was prepared in a similar manner to those described in Reference Example 62 using 7-[4-benzyloxy-3-(4-fluorobenzyl)phenoxy]-6-methylindan-4-carboxylic acid instead of 7-(4-benzyloxy-3-isopropylphenoxy)-6-methylindan-4-carboxylic acid.

$^{1}$H-NMR (CDCl$_{3}$) δ ppm: 1.32 (3H, t, J=7.2 Hz), 1.97–2.07 (2H, m), 2.16 (3H, s), 2.57–2.63 (2H, m), 3.13–3.19 (2H, m), 3.90 (2H, s), 4.23 (2H, d, J=5.0 Hz), 4.27 (2H, q, J=7.2 Hz), 4.97 (2H, s), 6.47 (3H, br-t, J=4.8 Hz), 6.52 (1H, dd, J=3.0, 8.8 Hz), 6.62 (1H, d, J=3.0 Hz), 6.78 (1H, d, J=8.8 Hz), 6.88–6.93 (2H, m), 7.05–7.13 (2H, m), 7.26–7.45 (6H, m)

EXAMPLE 9

Ethyl {[7-(4-hydroxy-3-isopropylphenoxy)-6-methylindan-4-carbonyl]amino}acetate (Compound 48)

The title compound was prepared in a similar manner to those described in Reference Example 27 using ethyl {[7-(4-benzyloxy-3-isopropylphenoxy)-6-methylindan-4-carbonyl]amino}acetate instead of ethyl 2-acetyl-3-benzyloxy-6-(5-methyl-7-nitroindan-4-yloxy)benzoate.

$^{1}$H-NMR (CDCl$_{3}$) δ ppm: 1.21 (6H, d, J=6.9 Hz), 1.32 (3H, t, J=7.1 Hz), 1.97–2.07 (2H, m), 2.18 (3H, s), 2.57–2.64 (2H, m), 3.13–3.23 (3H, m), 4.24 (2H, d, J=5.0 Hz), 4.27 (2H, q, J=7.1 Hz), 4.98 (1H, s), 6.33 (1H, dd, J=3.0, 8.6 Hz), 6.49 (1H, br-t, J=4.9 Hz), 6.59 (1H, d, J=8.6 Hz), 6.75 (1H, d, J=3.0 Hz), 7.43 (1H, s)

EXAMPLE 9-1

Ethyl {[7-(4-benzyloxy-3-isopropyl-2-methoxyphenoxy)-6-methylindan-4-carbonyl]amino}acetate (Compound 49)

The title compound was prepared in a similar manner to those described in Reference Example 27 using ethyl {[7-

(4-benzyloxy-3-isopropyl-2-methoxyphenoxy)-6-methylindan-4-carbonyl]amino}acetate instead of ethyl 2-acetyl-3-benzyloxy-6-(5-methyl-7-nitroindan-4-yloxy)benzoate.

$^1$H-NMR (CDCl$_3$) δ ppm: 1.32 (3H, t, J=7.1 Hz), 1.39 (6H, d, J=7.1 Hz), 1.95–2.06 (2H, m), 2.19 (3H, s), 2.57–2.64 (2H, m), 3.10–3.20 (2H, m), 3.56 (1H, heptet, J=7.1 Hz), 3.94 (3H, s), 4.24 (2H, d, J=5.0 Hz), 4.27 (2H, d, J=7.1 Hz), 5.12 (1H, s), 6.06 (1H, d, J=8.8 Hz), 6.25 (1H, d, J=8.8 Hz), 6.49 (1H, br-t, J=4.8 Hz), 7.44 (1H, s)

EXAMPLE 9-2

Ethyl ({7-[3—(4-fluorobenzyl)-4-hydroxyphenoxy]-6-methylindan-4-carbonyl}amino)acetate
(Compound 50)

The title compound was prepared in a similar manner to those described in Reference Example 27 using ethyl ({7-[4-benzyloxy-3-(4-fluorobenzyl)phenoxy]-6-methylindan-4-carbonyl}amino)acetate instead of ethyl 2-acetyl-3-benzyloxy-6-(5-methyl-7-nitroindan-4-yloxy)benzoate.

$^1$H-NMR (CDCl$_3$) δ ppm: 1.32 (3H, t, J=7.2 Hz), 1.95–2.05 (2H, m), 2.14 (3H, s), 2.56–2.63 (2H, m), 3.11–3.18 (2H, m), 3.88 (2H, s), 4.23 (2H, d, J=5.0 Hz), 4.26 (2H, q, J=7.2 Hz), 5.36 (1H, s), 6.42 (1H, dd, J=3.0, 8.7 Hz), 6.50 (1H, br-t, J=4.8 Hz), 6.57 (1H, d, J=3.0 Hz), 6.63 (1H, d, J=8.7 Hz), 6.93–6.98 (2H, m), 7.12–7.17 (2H, m), 7.41 (1H, s)

EXAMPLE 10

Ethyl N-(7-{4-hydroxy-3-[2-(3-oxocyclopentyl)ethyl]phenoxy}-6-methylindan-4-yl)malonamate
(Compound 51)

Ethyl N-(7-{4-benzyloxy-3-[2-(3-oxocyclopentyl)ethyl]phenoxy}-6-methylindan-4-yl)malonamate was prepared in a similar manner to those described in Example 1 using 3-{2-[5-(7-amino-5-methylindan-4-yloxy)-2-benzyloxyphenyl]ethyl}cyclopentanone instead of 4-(7-amino-5-methylindan-4-yloxy)-2-(tetrahydropyran-4-ylmethyl)phenol.

The title compound was prepared in a similar manner to those described in Reference Example 27 using ethyl N-(7-{4-benzyloxy-3-[2-(3-oxocyclopentyl)ethyl]phenoxy}-6-methylindan-4-yl)malonamate instead of ethyl 2-acetyl-3-benzyloxy-6-(5-methyl-7-nitroindan-4-yloxy)benzoate.

$^1$H-NMR (CDCl$_3$) δ ppm: 1.33 (3H, t, J=7.3 Hz), 1.48–2.23 (12H, m), 2.24–2.48 (2H, m), 2.53–2.73 (4H, m), 2.87 (2H, t, J=7.3 Hz), 3.50 (2H, s), 4.27 (2H, q, J=7.0 Hz), 5.77 (1H, s), 6.35–6.46 (1H, m), 6.50–6.70 (2H, m), 7.72 (1H, s), 9.24 (1H, s)

EXAMPLE 11

Ethyl N-(7-{4-hydroxy-3-[2-(3-oxocyclopentyl)ethyl]phenoxy}-6-methylindan-4-yl)oxamate
(Compound 52)

Ethyl N-(7-{4-benzyloxy-3-[2-(3-oxocyclopentyl)ethyl]phenoxy}-6-methylindan-4-yl)oxamate was prepared in a similar manner to those described in Example 3 using 3-{2-[5-(7-amino-5-methylindan-4-yloxy)-2-benzyloxyphenyl]ethyl}cyclopentanone instead of 4-(7-amino-5-methylindan-4-yloxy)-2-ethyl-3-methylphenol.

The title compound was prepared in a similar manner to those described in Reference Example 27 using ethyl N-(7-{4-benzyloxy-3-[2-(3-oxocyclopentyl)ethyl]phenoxy}-6-methylindan-4-yl)oxamate instead of ethyl 2-acetyl-3-benzyloxy-6-(5-methyl-7-nitroindan-4-yloxy)benzoate.

$^1$H-NMR (CDCl$_3$) δ ppm: 1.44 (3H, t, J=7.1 Hz), 1.50–1.91 (4H, m), 2.00–2.47 (10H, m), 2.56–2.72 (4H, m), 2.87 (2H, t, J=7.5 Hz), 4.43 (2H, q, J=7.1 Hz), 4.65 (1H, s), 6.45 (1H, dd, J=8.6, 3.0 Hz), 6.56–6.65 (2H, m), 7.77 (1H, s), 8.69 (1H, s)

EXAMPLE 12

N-{7-[4-hydroxy-3-(tetrahydropyran-4-ylmethyl)phenoxy]-6-methylindan-4-yl}malonamic acid
(Compound 53)

To ethyl N-{7-[4-hydroxy-3-(tetrahydropyran-4-ylmethyl)phenoxy]-6-methylindan-4-yl}malonamate (50 mg) were added methanol (10 mL) and a 1 mol/L aqueous solution of sodium hydroxide (8 mL), and the mixture was stirred under an argon atmosphere at 50° C. for 30 min. Adding water (20 mL), the reaction mixture was washed with diethyl ether (10 mL) twice. Adding 1 mol/L hydrochloric acid (20 mL) and brine (10 mL), the aqueous layer was extracted with ethyl acetate (10 mL) twice. The organic layer was dried over anhydrous magnesium sulfate and evaporated under reduced pressure to dryness to give the title compound (45 mg).

$^1$H-NMR (DMSO-d$_6$) δ ppm: 1.05–1.30 (2H, m), 1.35–1.49 (2H, m), 1.64–1.80 (1H, m), 1.86–2.00 (2H, m), 2.06 (3H, s), 2.38 (2H, d, J=7.1 Hz), 2.40–2.60 (2H, m), 2.70–2.88 (2H, m), 3.10–3.50 (4H, m), 3.70–3.90 (2H, m), 6.39 (1H, dd, J=3.0 Hz, 8.7 Hz), 6.47 (1H, d, J=3.0 Hz), 6.66 (1H, d, J=8.7 Hz), 7.38 (1H, s), 8.88 (1H, s), 9.50 (1H, s), 12.20–13.00 (1H, br-s)

REFERENCE EXAMPLE 63

7-(4-benzyloxy-3-isopropylphenoxy)-6-methylindan-4-ol

The title compound was prepared in a similar manner to those described in Example 12 using 7-(4-benzyloxy-3-isopropylphenoxy)-6-methylindan-4-yl formate instead of ethyl N-{7-[4-hydroxy-3-(tetrahydropyran-4-ylmethyl)phenoxy]-6-methylindan-4-yl}malonamate.

$^1$H-NMR (CDCl$_3$) δ ppm: 1.19 (6H, d, J=6.9 Hz), 1.95–2.09 (2H, m), 2.11 (3H, s) 2.60–2.72 (2H, m), 2.77–2.89 (2H, m), 3.30–3.45 (1H, m), 5.00 (2H, s), 6.40 (1H, dd, J=8.7 Hz, 3.1 Hz), 6.53 (1H, s), 6.73 (1H, d, J=8.7 Hz), 6.80 (1H, d, J=3.1 Hz), 7.25–7.50 (5H, m)

REFERENCE EXAMPLE 63-1

7-[4-benzyloxy-3-(4-fluorobenzyl)phenoxy]-6-methylindan-4-ol

The title compound was prepared in a similar manner to those described in Example 12 using 7-[4-benzyloxy-3-(4-fluorobenzyl)phenoxy]-6-methylindan-4-yl formate instead of ethyl N-{7-[4-hydroxy-3-(tetrahydropyran-4-ylmethyl)phenoxy]-6-methylindan-4-yl}malonamate.

$^1$H-NMR (CDCl$_3$) δ ppm: 1.95–2.15 (5H, m), 2.63 (2H, t, J=7.5 Hz), 2.79 (2H, t, J=7.5 Hz), 3.90 (2H, s), 4.95 (2H, s), 6.45–6.55 (2H, m), 6.62 (1H, d, J=3.3 Hz), 6.76 (1H, d, J=8.9 Hz), 6.86–6.96 (2H, m), 7.05–7.15 (2H, m), 7.25–7.45 (5H, m)

REFERENCE EXAMPLE 64

Ethyl [7-(4-benzyloxy-3-isopropylphenoxy)-6-methylindan-4-yloxy]acetate

The title compound was prepared in a similar manner to those described in Reference Example 11 using 7-(4-benzyloxy-3-isopropylphenoxy)-6-methylindan-4-ol instead of 2-hydroxy-5-(5-methyl-7-nitroindan-4-yloxy)benzaldehyde and using ethyl bromoacetate instead of benzyl bromide.

$^1$H-NMR (CDCl$_3$) δ ppm: 1.19 (6H, d, J=6.9 Hz), 1.31 (3H, t, J=7.0 Hz), 1.95–2.09-(2H, m), 2.13 (3H, s), 2.60–2.72 (2H, m), 2.87–2.99 (2H, m), 3.30–3.45 (1H, m), 4.28 (2H, q, J=7.0 Hz), 4.63 (2H, s), 5.00 (2H, s), 6.39 (1H, dd, J=8.8 Hz, 3.0 Hz), 6.45 (1H, s), 6.73 (1H, d, J=8.8 Hz), 6.80 (1H, d, J=3.0 Hz), 7.25–7.50 (5H, m)

REFERENCE EXAMPLE 64-1

Ethyl {7-[4-benzyloxy-3-(4-fluorobenzyl)phenoxy]-6-methylindan-4-yloxy}acetate

The title compound was prepared in a similar manner to those described in Reference Example 11 using 7-[4-benzyloxy-3-(4-fluorobenzyl)phenoxy]-6-methylindan-4-ol instead of 2-hydroxy-5-(5-methyl-7-nitroindan-4-yloxy) benzaldehyde and using ethyl bromoacetate instead of benzyl bromide.

$^1$H-NMR (CDCl$_3$) δ ppm: 1.31 (3H, t, J=7.2 Hz), 1.95–2.05 (2H, m), 2.10 (3H, s), 2.55–2.66 (2H, m), 2.85–2.96 (2H, m), 3.90 (2H, s), 4.28 (2H, q, J=7.2 Hz), 4.62 (2H, s), 4.95 (2H, s), 6.43 (1H, s), 6.50 (1H, dd, J=8.8 Hz, 3.0 Hz), 6.62 (1H, d, J=3.0 Hz), 6.76 (1H, d, J=8.8 Hz), 6.85–6.95 (2H, m), 7.05–7.15 (2H, m), 7.25–7.40 (5H, m)

EXAMPLE 13

Ethyl [7-(4-hydroxy-3-isopropylphenoxy)-6-methylindan-4-yloxy]acetate (Compound 54)

The title compound was prepared in a similar manner to those described in Reference Example 27 using ethyl [7-(4-benzyloxy-3-isopropylphenoxy)-6-methylindan-4-yloxy]acetate instead of ethyl 2-acetyl-3-benzyloxy-6-(5-methyl-7-nitroindan-4-yloxy)benzoate.

$^1$H-NMR (CDCl$_3$) δ ppm: 1.21 (6H, d, J=7.0 Hz), 1.31 (3H, t, J=7.2 Hz), 1.95–2.09 (2H, m), 2.12 (3H, s), 2.58–2.69 (2H, m), 2.85–2.95 (2H, m), 3.10–3.25 (1H, m), 4.28 (2H, q, J=7.2 Hz), 4.63 (2H, s), 6.33 (1H, dd, J=8.7 Hz, 3.0 Hz), 6.44 (1H, s), 6.58 (1H, d, J=8.7 Hz), 6.74 (1H, d, J=3.0 Hz)

EXAMPLE 13-1

Ethyl {7-[3-(4-fluorobenzyl)-4-hydroxyphenoxy]-6-methylindan-4-yloxy}acetate (Compound 55)

The title compound was prepared in a similar manner to those described in Reference Example 27 using ethyl {7-[3-(4-fluorobenzyl)-4-hydroxyphenoxy]-6-methylindan-4-yloxy}acetate instead of ethyl 2-acetyl-3-benzyloxy-6-(5-methyl-7-nitroindan-4-yloxy)benzoate.

$^1$H-NMR (CDCl$_3$) δ ppm: 1.31 (3H, t, J=7.0 Hz), 1.95–2.05 (2H, m), 2.10 (3H, s), 2.55–2.66 (2H, m), 2.85–2.95 (2H, m), 3.88 (2H, s), 4.28 (2H, q, J=7.0 Hz), 4.55 (1H, s), 4.62 (2H, s), 6.43 (1H, s), 6.47 (1H, dd, J=8.6 Hz, 3.0 Hz), 6.58 (1H, d, J=3.0 Hz), 6.63 (1H, d, J=8.6 Hz), 6.90–7.03 (2H, m), 7.10–7.20 (2H, m)

EXAMPLE 14

N-(7-{4-hydroxy-3-[2-(tetrahydrofuran-3-yl)ethyl]phenoxy}-6-methylindan-4-yl)malonamic acid (Compound 56)

The title compound was prepared in a similar manner to those described in Example 12 using ethyl N-(7-{4-hydroxy-3-[2-(tetrahydrofuran-3-yl)ethyl]phenoxy}-6-methylindan-4-yl)malonamate instead of ethyl N-{7-[4-hydroxy-3-(tetrahydropyran-4-ylmethyl)phenoxy]-6-methylindan-4-yl}malonamate.

$^1$H-NMR (DMSO-d$_6$) δ ppm: 1.40–1.70 (3H, m), 1.90–2.20 (7H, m), 2.76–2.91 (6H, m), 3.20–3.31 (1H, m), 3.44 (2H, s), 3.55–3.85 (3H, m), 6.43 (1H, dd, J=3.1 Hz, 8.7 Hz), 6.59(1H, d, J=3.1 Hz), 6.72 (1H, d, J=8.7 Hz), 7.44 (1H, s), 8.97 (1H, s), 9.54 (1H, s), 12.50–12.80 (1H, br-s)

EXAMPLE 14-1

N-(7-{4-hydroxy-3-[2-(tetrahydrofuran-3-yl)ethyl]phenoxy}-6-methylindan-4-yl)oxamic acid (Compound 57)

The title compound was prepared in a similar manner to those described in Example 12 using ethyl N-(7-{4-hydroxy-3-[2-(tetrahydrofuran-3-yl)ethyl]phenoxy}-6-methylindan-4-yl)oxamate instead of ethyl N-{7-[4-hydroxy-3-(tetrahydropyran-4-ylmethyl)phenoxy]-6-methylindan-4-yl}malonamate.

$^1$H-NMR (DMSO-d$_6$) δ ppm: 1.40–1.70 (3H, m), 1.90–2.20 (7H, m), 2.76–2.91 (6H, m), 3.20–3.35 (1H, m), 3.60–3.90 (3H, m), 6.36–6.50 (1H, m), 6.62 (1H, d, J=3.0 Hz), 6.72 (1H, d, J=8.7 Hz), 7.28 (1H, s), 9.00 (1H, s), 10.21 (1H, s)

EXAMPLE 14-2

N-{7-[4-hydroxy-3-(1-methyl-2-phenylethyl)phenoxy]-6-methylindan-4-yl}malonamic acid (Compound 58)

The title compound was prepared in a similar manner to those described in Example 12 using ethyl N-{7-[4-hydroxy-3-(1-methyl-2-phenylethyl)phenoxy]-6-methylindan-4-yl}malonamate instead of ethyl N-[7-[4-hydroxy-3-(tetrahydropyran-4-ylmethyl)phenoxy]-6-methylindan-4-yl]malonamate.

$^1$H-NMR (CDCl$_3$) δ ppm: 1.20 (3H, d, J=6.8 Hz), 1.95–2.05 (2H, m), 2.13 (3H, s), 2.55–2.63 (2H, m), 2.70–2.95 (4H, m), 3.27–3.37 (1H, m), 3.56 (2H, s), 6.35 (1H, dd, J=2.7, 8.6 Hz), 6.55 (1H, d, J=8.6 Hz), 6.70 (1H, d, J=2.7 Hz), 7.05–7.25 (5H, m), 7.57 (1H, s), 8.60 (1H, s)

EXAMPLE 14-3

N-{7-[4-hydroxy-3-(tetrahydropyran-4-ylmethyl)phenoxy]-6-methylindan-4-yl}oxamic acid (Compound 59)

The title compound was prepared in a similar manner to those described in Example 12 using ethyl N-{7-[4-hydroxy-3-(tetrahydropyran-4-ylmethyl)phenoxy]-6-methylindan-4-yl}oxamate instead of ethyl N-{7-[4-hydroxy-3-(tetrahydropyran-4-ylmethyl)phenoxy]-6-methylindan-4-yl}malonamate.

¹H-NMR (DMSO-d₆) δ ppm: 1.05–1.30 (2H, m), 1.35–1.55 (2H, m), 1.64–1.80 (1H, m), 1.86–2.00 (2H, m), 2.06 (3H, s), 2.39 (2H, d, J=7.1 Hz), 2.45–2.65 (2H, m), 2.70–2.88 (2H, m), 3.10–3.50 (2H, m), 3.70–3.90 (2H, m), 6.40 (1H, dd, J=2.9 Hz, 8.7 Hz), 6.49 (1H, d, J=2.9 Hz), 6.67 (1H, d, J=8.7 Hz), 7.22 (1H, s), 8.91 (1H, s), 8.97 (1H, s), 1–3.80–14.40 (1H—, br-s)

EXAMPLE 14-4

N-{7-[4-hydroxy-3-(2-thiazol-2-ylethyl)phenoxy]-6-methylindan-4-yl}malonamic acid (Compound 60)

The title compound was prepared in a similar manner to those described in Example 12 using ethyl N-{7-[4-hydroxy-3-(2-thiazole-2-ylethyl)phenoxy]-6-methylindan-4-yl}malonamate instead of ethyl N-{7-[4-hydroxy-3-(tetrahydropyran-4-ylmethyl)phenoxy]-6-methylindan-4-yl}malonamate.

¹H-NMR (DMSO-d₆) δ ppm: 1.83–2.15 (5H, m), 2.70–2.85 (4H, m), 2.90 (2H, t, J=7.5 Hz), 3.20 (2H, t, J=7.5 Hz), 3.51 (2H, s), 6.33–7.88 (6H, m), 9.05 (1H, s), 9.46 (1H, s)

EXAMPLE 14-5

N-[7-(4-hydroxy-3-isopropylphenoxy)-6-methylindan-4-yl]malonamic acid (Compound 61)

The title compound was prepared in a similar manner to those described in Example 12 using ethyl N-[7-(4-hydroxy-3-isopropylphenoxy)-6-methylindan-4-yl]malonamate instead of ethyl N-{7-[4-hydroxy-3-(tetrahydropyran-4-ylmethyl)phenoxy]-6-methylindan-4-yl}malonamate.

¹H-NMR (CD₃OD) δ ppm: 1.14 (6H, d, J=6.9 Hz), 1.90–2.10 (2H, m), 2.11 (3H, s), 2.55–2.65 (2H, m), 2.80–2.90 (2H, m), 3.15–3.30 (1H, m), 3.47 (2H, s), 6.32 (1H, dd, J=8.7, 3.0 Hz), 6.55–6.70 (2H, m), 7.30 (1H, s)

EXAMPLE 14-6

N-[7-(4-hydroxy-3-isopropylphenoxy)-6-methylindan-4-yl]oxamic acid (Compound 62)

The title compound was prepared in a similar manner to those described in Example 12 using ethyl N-[7-(4-hydroxy-3-isopropylphenoxy)-6-methylindan-4-yl]oxamate instead of ethyl N-{7-[4-hydroxy-3-(tetrahydropyran-4-ylmethyl)phenoxy]-6-methylindan-4-yl}malonamate.

¹H-NMR (CD₃OD) δ ppm: 1.13 (6H, d, J=6.9 Hz), 1.95–2.10 (2H, m), 2.13 (3H, s), 2.55–2.70 (2H, m), 2.80–2.95 (2H, m), 3.15–3.35 (1H, m), 6.33 (1H, dd, J=8.7, 3.0 Hz), 6.55–6.65 (2H, m), 7.42 (1H, s)

EXAMPLE 14-7

N-{7-[3-(4-fluorobenzyl)-4-hydroxyphenoxy]-6-methylindan-4-yl}malonamic acid (Compound 63)

The title compound was prepared in a similar manner to those described in Example 12 using ethyl N-{7-[3-(4-fluorobenzyl)-4-hydroxyphenoxy]-6-methylindan-4-yl}malonamate instead of ethyl N-{7-[4-hydroxy-3-(tetrahydropyran-4-ylmethyl)phenoxy]-6-methylindan-4-yl}malonamate.

¹H-NMR (DMSO-d₆) δ ppm: 1.84–1.92 (2H, m), 2.03 (3H, s), 2.72–2.77 (2H, m), 3.26–3.33 (2H, m), 3.38 (2H, s), 3.79 (2H, s), 6.39 (1H, dd, J=3.0, 8.7 Hz), 6.54 (1H, d, J=3.0 Hz), 6.69 (1H, d, J=8.7 Hz), 7.03–7.09 (2H, m), 7.17–7.23 (2H, m), 7.36 (1H, s), 9.08 (1H, s), 9.48 (1H, s), 12.60 (1H, s)

EXAMPLE 14-8

N-[7-(4-hydroxy-3-isopropylphenoxy)-6-iodoindan-4-yl]malonamic acid (Compound 64)

The title compound was prepared in a similar manner to those described in Example 12 using ethyl N-[7-(4-hydroxy-3-isopropylphenoxy)-6-iodoindan-4-yl]malonamate instead of ethyl N-{7-[4-hydroxy-3-(tetrahydropyran-4-ylmethyl)phenoxy]-6-methylindan-4-yl}malonamate.

¹H-NMR (CDCl₃+CD₃OD) δ ppm: 1.19 (6H, d, J=6.9 Hz), 1.95–2.05 (2H, m), 2.60–2.65 (2H, m), 2.81–2.87 (2H, m), 3.24 (1H, heptet, J=6.9 Hz), 3.47 (2H, s), 6.38 (1H, dd, J=3.0, 8.6 Hz), 6.62 (1H, d, J=8.6 Hz), 6.77 (1H, d, J=3.0 Hz), 8.27 (1H, s)

EXAMPLE 14-9

N-[7-(4-hydroxy-3-isopropylphenoxy)-6-trifluoromethylindan-4-yl]malonamic acid (Compound 65)

The title compound was prepared in a similar manner to those described in Example 12 using ethyl N-[7-(4-hydroxy-3-isopropylphenoxy)-6-trifluoromethylindan-4-yl]malonamate instead of ethyl N-{7-[4-hydroxy-3-(tetrahydropyran-4-ylmethyl)phenoxy]-6-methylindan-4-yl}malonamate.

¹H-NMR (CDCl₃+CD₃OD) δ ppm: 1.18 (6H, d, J=6.9 Hz), 1.96–2.05 (2H, m), 2.45–2.53 (2H, m), 2.83–2.90 (2H, m), 3.23 (1H, heptet, J=6.9 Hz), 3.50 (2H, s), 6.43 (1H, dd, J=3.0, 8.6 Hz), 6.62 (1H, d, J=8.6 Hz), 6.78 (1H, d, J=3.0 Hz), 8.15 (1H, s)

EXAMPLE 14-10

N-{7-[4-hydroxy-3-(6-oxo-1,6-dihydropyridazin-3-ylmethyl) phenoxy]-6-methylindan-4-yl}malonamic acid (Compound 66)

The title compound was prepared in a similar manner to those described in Example 12 using ethyl N-{7-[4-hydroxy-3-(6-oxo-1,6-dihydropyridazin-3-ylmethyl)phenoxy]-6-methylindan-4-yl}malonamate instead of ethyl N-{7-[4-hydroxy-3-(tetrahydropyran-4-ylmethyl)phenoxy]-6-methylindan-4-yl}malonamate.

¹H-NMR (CDCl₃+CD₃OD) δ ppm: 1.96–2.08 (2H, m), 2.13 (3H, s), 2.57–2.64 (2H, m), 2.82–2.88 (2H, m), 3.48 (2H, s), 3.86 (2H, s), 6.52 (1H, dd, J=3.0, 8.7 Hz), 6.57 (1H, d, J=3.0 Hz), 6.70 (1H, d, J=8.7 Hz), 6.85 (1H, d, J=9.7 Hz), 7.30 (1H, d, J=9.7 Hz), 7.58 (1H, s)

EXAMPLE 14-11

N-[6-bromo-7-(4-hydroxy-3-isopropylphenoxy)indan-4-yl]malonamic acid (Compound 67)

The title compound was prepared in a similar manner to those described in Example 12 using ethyl N-[6-bromo-7-(4-hydroxy-3-isopropylphenoxy)indan-4-yl]malonamate instead of ethyl N-{7-[4-hydroxy-3-(tetrahydropyran-4-ylmethyl)phenoxy]-6-methylindan-4-yl}malonamate.

¹H-NMR (CDCl₃) δ ppm: 1.22 (6H, d, J=6.9 Hz), 2.02–2.10 (2H, m), 2.66–2.73 (2H, m), 2.79–2.85 (2H, m), 3.16 (1H, heptet, J=6.9 Hz), 3.56 (2H, s), 4.43 (1H, br-s), 6.41 (1H, dd, J=3.0, 8.6 Hz), 6.61 (1H, d, J=8.6 Hz), 6.80 (1H, d, J=3.0 Hz), 8.11 (1H, s), 8.48 (1H, br-s)

EXAMPLE 14-12

N-[6-bromo-7-(4-hydroxy-5,6,7,8-tetrahydronaphthalen-1-yl oxy)indan-4-yl]malonamic acid (Compound 68)

The title compound was prepared in a similar manner to those described in Example 12 using ethyl N-[6-bromo-7-(4-hydroxy-5,6,7,8-tetrahydronaphthalen-1-yloxy)indan-4-yl]malonamate instead of ethyl N-{7-[4-hydroxy-3-(tetrahydropyran-4-ylmethyl)phenoxy]-6-methylindan-4-yl}malonamate.

$^1$H-NMR (CDCl$_3$+CD$_3$OD) δ ppm: 1.74–1.85 (4H, m), 1.98–2.07 (2H, m), 2.62–2.73 (4H, m), 2.77–2.89 (4H, m), 3.48 (2H, s), 6.09 (1H, d, J=8.6 Hz), 6.42 (1H, d, J=8.6 Hz), 8.12 (1H, s)

EXAMPLE 14-13

N-[7-(4-hydroxy-3-iodophenoxy)-6-methylindan-4-yl]malonamic acid (Compound 69)

The title compound was prepared in a similar manner to those described in Example 12 using ethyl N-[7-(4-hydroxy-3-iodophenoxy)-6-methylindan-4-yl]malonamate instead of ethyl N-{7-[4-hydroxy-3-(tetrahydropyran-4-ylmethyl)phenoxy]-6-methylindan-4-yl}malonamate.

$^1$H-NMR (CDCl$_3$+CD$_3$OD) δ ppm: 1.99–2.10 (0.2H, m), 2.14 (3H, s), 2.63–2.70 (2H, m), 2.83–2.90 (2H, m), 3.48 (2H, s), 6.66 (1H, dd, J=2.9, 8.8 Hz), 6.78 (1H, d, J=8.8 Hz), 7.10 (1H, d, J=2.9 Hz), 7.66 (1H, s)

EXAMPLE 14-14

N-[7-(4-hydroxy-3-trifluoromethylphenoxy)-6-methylindan-4-yl]malonamic acid (Compound 70)

The title compound was prepared in a similar manner to those described in Example 12 using ethyl N-[7-(4-hydroxy-3-trifluoromethylphenoxy)-6-methylindan-4-yl]malonamate instead of ethyl N-{7-[4-hydroxy-3-(tetrahydropyran-4-ylmethyl)phenoxy]-6-methylindan-4-yl}malonamate.

$^1$H-NMR (CDCl$_3$+CD$_3$OD) δ ppm: 1.95–2.05 (2H, m), 2.10 (3H, s), 2.60–2.65 (2H, m), 2.81–2.89 (2H, m), 3.56 (2H, s), 6.74 (1H, dd, J=2.9, 8.9 Hz), 6.81 (1H, d, J=8.9 Hz), 6.94 (1H, d, J=2.9 Hz), 7.35 (1H, s)

EXAMPLE 14-15

N-[7-(3-ethyl-4-hydroxyphenoxy)-6-methylindan-4-yl]malonamic acid (Compound 71)

The title compound was prepared in a similar manner to those described in Example 12 using ethyl N-[7-(3-ethyl-4-hydroxyphenoxy)-6-methylindan-4-yl]malonamate instead of ethyl N-{7-[4-hydroxy-3-(tetrahydropyran-4-ylmethyl)phenoxy]-6-methylindan-4-yl}malonamate.

$^1$H-NMR (CDCl$_3$+CD$_3$OD) δ ppm: 1.17 (3H, t, J=7.5 Hz), 1.95–2.08 (2H, m), 2.14 (3H, s), 2.57 (2H, q, J=7.5 Hz), 2.62–2.70 (2H, m), 2.80–2.90 (2H, m), 3.37 (2H, s), 6.38 (1H, dd, J=3.0, 8.6 Hz), 6.58–6.64 (2H, m), 7.57 (1H, s)

EXAMPLE 14-16

N-[7-(4-hydroxy-3-isopropylbenzyl)-6-methylindan-4-yl]malonamic acid (Compound 72)

The title compound was prepared in a similar manner to those described in Example 12 using ethyl N-[7-(4-hydroxy-3-isopropylbenzyl)-6-methylindan-4-yl]malonamate instead of ethyl N-{7-[4-hydroxy-3-(tetrahydropyran-4-ylmethyl)phenoxy]-6-methylindan-4-yl}malonamate.

$^1$H-NMR (CDCl$_3$+CD$_3$OD) δ ppm: 1.21 (6H, d, J=6.9 Hz), 2.00–2.10 (2H, m), 2.21 (3H, s), 2.77–2.86 (4H, m), 3.16 (1H, heptet, J=6.9 Hz), 3.53 (2H, s), 3.88 (2H, s), 6.54–6.60 (2H, m), 6.95 (1H, s), 7.51 (1H, s), 8.49 (1H, s)

EXAMPLE 14-17

N-[7-(4-hydroxy-3-isopropylbenzoyl)-6-methylindan-4-yl]malonamic acid (Compound 73)

The title compound was prepared in a similar manner to those described in Example 12 using ethyl N-[7-(4-hydroxy-3-isopropylbenzoyl)-6-methylindan-4-yl]malonamate instead of ethyl N-{7-[4-hydroxy-3-(tetrahydropyran-4-ylmethyl)phenoxy]-6-methylindan-4-yl}malonamate.

$^1$H-NMR (CDCl$_3$+CD$_3$OD) δ ppm: 1.22 (6H, d, J=6.9 Hz), 1.98–2.07 (2H, m), 2.15 (3H, s), 2.64–2.69 (2H, m), 2.83–2.90 (2H, m), 3.27 (1H, heptet, J=6.9 Hz), 3.50 (2H, s), 6.73 (1H, d, J=8.3 Hz), 7.37 (1H, dd, J=1.9, 8.3 Hz), 7.73 (1H, s), 7.78 (1H, d, J=1.8 Hz)

EXAMPLE 14-18

N-{7-[2-(2-cyclohexylethoxy)-3-ethyl-4-hydroxyphenoxy]-6-methylindan-4-yl}malonamic acid (Compound 74)

The title compound was prepared in a similar manner to those described in Example 12 using ethyl N-{7-[2-(2-cyclohexylethoxy)-3-ethyl-4-hydroxyphenoxy]-6-methylindan-4-yl}malonamate instead of ethyl N-{7-[4-hydroxy-3-(tetrahydropyran-4-ylmethyl)phenoxy]-6-methylindan-4-yl}malonamate.

$^1$H-NMR (CDCl$_3$+CD$_3$OD) δ ppm: 0.82–0.92 (2H, m), 1.00–1.22 (3H, m), 1.13 (3H, t, J=7.5 Hz), 1.00–1.22 (3H, m), 1.43–1.73 (8H, m), 1.90–1.98 (2H, m), 2.08 (3H, s), 2.53–2.58 (2H, m), 2.72–2.78 (2H, m), 3.41 (2H, s), 4.03–4.10 (2H, m), 6.00 (1H, d, J=8.8 Hz), 6.22 (1H, d, J=8.8 Hz), 7.54 (1H, s)

EXAMPLE 14-19

N-[7-(3-ethyl-4-hydroxy-2-phenethyloxyphenoxy)-6-methylindan-4-yl]malonamic acid (Compound 75)

The title compound was prepared in a similar manner to those described in Example 12 using ethyl N-[7-(3-ethyl-4-hydroxy-2-phenethyloxyphenoxy)-6-methylindan-4-yl]malonamate instead of ethyl N-{7-[4-hydroxy-3-(tetrahydropyran-4-ylmethyl)phenoxy]-6-methylindan-4-yl}malonamate.

$^1$H-NMR (CDCl$_3$) δ ppm: 1.05–1.13 (3H, m), 1.93–2.05 (2H, m), 2.15 (3H, s), 2.50–2.68 (4H, m), 2.73–2.85 (2H, m), 3.10–3.18 (2H, m), 3.55 (2H, s), 4.30–4.40 (2H, m), 6.11 (1H, d, J=8.6 Hz), 6.30 (1H, d, J=8.6 Hz), 7.17–7.30 (5H, m), 7.56 (1H, s), 8.51(1H, s)

EXAMPLE 14-20

N-[7-(3-ethyl-4-hydroxy-2-methylphenoxy)-6-methylindan-4-yl]malonamic acid (Compound 76)

The title compound was prepared in a similar manner to those described in Example 12 using ethyl N-[7-(3-ethyl-4-hydroxy-2-methylphenoxy)-6-methylindan-4-yl]malonamate instead of ethyl N-{7-[4-hydroxy-3-(tetrahydropyran-4-ylmethyl)phenoxy]-6-methylindan-4-yl}malonamate.

$^1$H-NMR (CDCl$_3$+CD$_3$OD) δ ppm: 1.16 (3H, t, J=7.5 Hz), 1.97–2.06 (2H, m), 2.15 (3H, s), 2.34 (3H, s), 2.56–2.65 (2H, m), 2.72 (2H, q, J=7.5 Hz), 2.82–2.88 (2H, m), 3.47 (2H, s), 6.09 (1H, d, J=8.7 Hz), 6.44 (1H, d, J=8.7 Hz), 7.54 (1H, s)

EXAMPLE 14-21

N-[7-(4-hydroxy-3-isopropyl-2-methoxyphenoxy)-6-methylindan-4-yl]malonamic acid (Compound 77)

The title compound was prepared in a similar manner to those described in Example 12 using ethyl N-[7-(4-hydroxy-3-isopropyl-2-methoxyphenoxy)-6-methylindan-4-yl]malonamate instead of ethyl N-{7-[4-hydroxy-3-(tetrahydropyran-4-ylmethyl)phenoxy]-6-methylindan-4-yl}malonamate.

$^1$H-NMR (CDCl$_3$+CD$_3$OD) δ ppm: 1.38 (6H, d, J=7.1 Hz), 1.95–2.05 (2H, m), 2.16 (3H, s), 2.62–2.68 (2H, m), 2.79–2.86 (2H, m), 3.45 (2H, s), 3.54 (1H, heptet, J=7.1 Hz), 3.94 (3H, s), 6.07 (1H, d, J=8.8 Hz), 6.27 (1H, d, J=8.8 Hz), 7.62 (1H, s)

EXAMPLE 14-22

N-[7-(4-hydroxy-3-isopropyl-2-methoxyphenoxy)-6-methylindan-4-yl]oxamic acid (Compound 78)

The title compound was prepared in a similar manner to those described in Example 12 using ethyl N-[7-(4-hydroxy-3-isopropyl-2-methoxyphenoxy)-6-methylindan-4-yl]oxamate instead of ethyl N-{7-[4-hydroxy-3-(tetrahydropyran-4-ylmethyl)phenoxy]-6-methylindan-4-yl}malonamate.

$^1$H-NMR (CDCl$_3$+CD$_3$OD) δ ppm: 1.39 (6H, d, J=7.1 Hz), 1.99–2.10 (2H, m), 2.20 (3H, s), 2.63–2.72 (2H, m), 2.80–2.92 (2H, m), 3.54 (1H, heptet, J=7.1 Hz), 3.94 (3H, s), 6.09 (1H, d, J=8.8 Hz), 6.29 (1H, d, J=8.8 Hz), 7.73 (1H, s)

EXAMPLE 14-23

N-{7-[3-ethyl-2-(4-fluorobenzyloxy)-4-hydroxyphenoxy]-6-methylindan-4-yl}malonamic acid (Compound 79)

The title compound was prepared in a similar manner to those described in Example 12 using ethyl N-{7-[3-ethyl-2-(4-fluorobenzyloxy)-4-trifluoromethanesulfonyloxyphenoxy]-6-methylindan-4-yl}malonamate instead of ethyl N-{7-[4-hydroxy-3-(tetrahydropyran-4-ylmethyl)phenoxy]-6-methylindan-4-yl}malonamate.

$^1$H-NMR (CDCl$_3$+CD$_3$OD) δ ppm: 1.16 (3H, t, J=7.5 Hz), 2.01–2.08 (2H, m), 2.20 (3H, s), 2.63–2.71 (2H, m), 2.68 (2H, q, J=7.5 Hz), 2.81–2.85 (2H, m), 3.56 (2H, s), 5.13 (2H, s), 6.18 (1H, d, J=8.8 Hz), 6.36 (1H, d, J=8.8 Hz), 7.03–7.08 (2H, m), 7.43–7.49 (2H, m), 7.59 (1H, s), 8.40 (1H, s)

EXAMPLE 14-24

N-{7-[3-ethyl-4-hydroxy-2-(pyridin-3-ylmethoxy)phenoxy]-6-methylindan-4-yl}malonamic acid (Compound 80)

The title compound was prepared in a similar manner to those described in Example 12 using ethyl N-{7-[3-ethyl-4-hydroxy-2-(pyridin-3-ylmethoxy)phenoxy]-6-methylindan-4-yl}malonamate instead of ethyl N-{7-[4-hydroxy-3-(tetrahydropyran-4-ylmethyl)phenoxy]-6-methylindan-4-yl}malonamate.

$^1$H-NMR (CDCl$_3$+CD$_3$OD) δ ppm: 1.16 (3H, t, J=7.6 Hz), 2.00–2.07 (2H, m), 2.19 (3H, s), 2.64–2.73 (4H, m), 2.92–2.98 (2H, m), 3.48 (2H, s), 5.20 (2H, s), 6.18 (1H, d, J=8.8 Hz), 6.37 (1H, d, J=8.8 Hz), 7.35–7.40 (1H, m), 7.60 (1H, s), 7.93–7.98 (1H, m), 7.48–7.55 (1H, m), 8.62–8.68 (1H, m)

EXAMPLE 14-25

{[7-(4-hydroxy-3-isopropylphenoxy)-6-methylindan-4-carbonyl]amino}acetic acid (Compound 81)

The title compound was prepared in a similar manner to those described in Example 12 using ethyl {[7-(4-hydroxy-3-isopropylphenoxy)-6-methylindan-4-carbonyl]amino}acetate instead of ethyl N-{7-[4-hydroxy-3-(tetrahydro-pyran-4-ylmethyl)phenoxy]-6-methylindan-4-yl}malonamate.

$^1$H-NMR (CDCl$_3$+CD$_3$OD) ppm: 1.19 (6H, d, J=6.9 Hz), 1.95–2.05 (2H, m), 2.19 (3H, s), 2.57–2.63 (2H, m), 3.12–3.18 (2H, m), 3.23 (1H, heptet, J=6.9 Hz), 4.20 (2H, s), 6.34 (1H, dd, J=3.0, 8.6 Hz), 6.61 (1H, d, J=8.6 Hz), 6.73 (1H, d, J=3.0 Hz), 7.43 (1H, s)

EXAMPLE 14-26

{[7-(4-hydroxy-3-isopropyl-2-methoxyphenoxy)-6-methylindan-4-carbonyl]amino}acetic acid (Compound 82)

The title compound was prepared in a similar manner to those described in Example 12 using ethyl {[7-(4-hydroxy-3-isopropyl-2-methoxyphenoxy)-6-methylindan-4-carbonyl]amino}acetate instead of ethyl N-{7-[4-hydroxy-3-(tetrahydropyran-4-ylmethyl)phenoxy]-6-methylindan-4-yl}malonamate.

$^1$H-NMR (CDCl$_3$+CD$_3$OD) δ ppm: 1.38 (6H, d, J=7.1 Hz), 1.96–2.05 (2H, m), 2.20 (3H, s), 2.57–2.63 (2H, m), 3.10–3.16 (2H, m), 3.54 (1H, heptet, J=7.1 Hz), 3.93 (3H, s), 4.13 (2H, s), 6.07 (1H, d, J=8.8 Hz), 6.30 (1H, d, J=8.8 Hz), 7.43 (1H, s)

EXAMPLE 14-27

({7-[3-(4-fluorobenzyl)-4-hydroxyphenoxy]-6-methylindan-4-carbonyl}amino)acetic acid (Compound 83)

The title compound was prepared in a similar manner to those described in Example 12 using ethyl ({7-[3-(4-fluorobenzyl)-4-hydroxyphenoxy]-6-methylindan-4- carbonyl}amino)acetate instead of ethyl N-{7-[4-hydroxy-3-(tetrahydropyran-4-ylmethyl)phenoxy]-6-methylindan-4-yl}malonamate.

$^1$H-NMR (CDCl$_3$+CD$_3$OD) δ ppm: 1.93–2.05 (2H, m), 2.16 (3H, s), 2.53–2.62 (2H, m), 3.10–3.17 (2H, m), 3.88 (2H, s), 4.18 (2H, s), 6.44 (1H, dd, J=3.0, 8.7 Hz), 6.52 (1H, d, J=3.0 Hz), 6.67 (1H, d, J=8.7 Hz), 6.90–6.97 (2H, m), 7.13–7.20 (2H, m), 7.40 (1H, s)

EXAMPLE 14-28

N-[7-(4-hydroxy-3-isopropylphenoxy)-6-methylindan-4-yloxy]acetic acid (Compound 84)

The title compound was prepared in a similar manner to those described in Example 12 using ethyl N-[7-(4-hydroxy-3-isopropylphenoxy)-6-methylindan-4-yloxy]acetate instead of ethyl N-{7-[4-hydroxy-3-(tetrahydro-pyran-4-ylmethyl)phenoxy]-6-methylindan-4-yl}malonamate.

$^1$H-NMR (DMSO-d$_6$) δ ppm: 1.10 (6H, d, J=6.9 Hz), 1.85–2.00 (2H, m), 2.04 (3H, s), 2.40–2.60 (2H, m), 2.70–2.90 (2H, m), 3.05–3.22 (1H, m), 4.65 (2H, s), 6.23 (1H, dd, J=3.0 Hz, 8.6 Hz), 6.52–6.75 (3H, m), 8.86 (1H, s), 12.80–13.10 (1H, br-s)

EXAMPLE 14-29

N-{7-[3-(4-fluorobenzyl)-4-hydroxyphenoxy]-6-methylindan-4-yloxy}acetic acid (Compound 85)

The title compound was prepared in a similar manner to those described in Example 12 using ethyl N-{7-[3-(4-fluorobenzyl)-4-hydroxyphenoxy]-6-methylindan-4-yloxy}acetate instead of ethyl N-{7-[4-hydroxy-3-(tetrahydropyran 4-ylmethyl)phenoxy]-6-methylindan-4-yl}malonamate.

$^1$H-NMR (DMSO-d$_6$) δ ppm: 1.80–1.98 (2H, m), 2.02 (3H, s), 2.40–2.60 (2H, m), 2.70–2.90 (2H, m), 3.78 (2H, s), 4.65 (2H, s), 6.36 (1H, dd, J=3.1 Hz, 8.8 Hz), 6.51 (1H, d, J=3.1 Hz), 6.56 (1H, s), 6.68 (2H, d, J=8.8 Hz), 7.00–7.14 (2H, m), 7.15–7.30 (2H, m), 9.05 (1H, s), 12.70–13.10 (1H, br-s)

EXAMPLE 14-30

N-{7-[3-(4-fluorobenzoyl)-4-hydroxyphenoxy]-6-methylindan-4-yl}malonamic acid (Compound 86)

The title compound was prepared in a similar manner to those described in Example 12 using ethyl N-{7-[3-(4-fluorobenzoyl)-4-hydroxyphenoxy]-6-methylindan-4-yl}malonamate instead of ethyl N-{7-[4-hydroxy-3-(tetrahydropyran-4-ylmethyl)phenoxy]-6-methylindan-4-yl}malonamate.

$^1$H-NMR (CDCl$_3$) δ ppm: 1.95–2.20 (5H, m), 2.66 (2H, t, J=7.4 Hz), 2.83 (2H, t, J=7.4 Hz), 3.57 (2H, s), 6.90–7.25 (5H, m), 7.50–7.80 (3H, m), 8.66 (1H, s), 11.44 (1H, s)

EXAMPLE 14-31

N-(7-{3-[2-(4-fluorophenyl)ethyl]-4-hydroxyphenoxy}-6-methylindan-4-yl)malonamic acid (Compound 87)

The title compound was prepared in a similar manner to those described in Example 12 using ethyl N-(7-{3-[2-(4-fluorophenyl)ethyl]-4-hydroxyphenoxy}-6-methylindan-4-yl) malonamate instead of ethyl N-{7-[4-hydroxy-3-(tetrahydropyran-4-ylmethyl)phenoxy]-6-methylindan-4-yl}malonamate.

$^1$H-NMR (CD$_3$OD) δ ppm: 1.90–2.10 (5H, m), 2.51 (2H, t, J=7.4 Hz), 2.72–2.90 (6H, m), 3.46 (2H, s), 6.26 (1H, d, J=3.0 Hz), 6.43 (1H, dd, J=8.7, 3.0 Hz), 6.64 (1H, d, J=8.7 Hz), 6.85–6.95 (2H, m), 7.02–7.12 (2H, m), 7.28 (1H, s).

EXAMPLE 14-32

N-[7-(4-hydroxy-3-phenethylphenoxy)-6-methylindan-4-yl]malonamic acid (Compound 88)

The title compound was prepared in a similar manner to those described in Example 12 using ethyl N-[7-(4-hydroxy-3-phenethylphenoxy)-6-methylindan-4-yl]malonamate instead of ethyl N-{7-[4-hydroxy-3-(tetrahydropyran-4-ylmethyl)phenoxy]-6-methylindan-4-yl}malonamate.

$^1$H-NMR (CD$_3$OD) δ ppm: 1.90–2.10 (5H, m), 2.52 (2H, t, J=7.4 Hz), 2.75–2.90 (6H, m), 3.46 (2H, s), 6.31 (1H, d, J=3.0 Hz), 6.42 (1H, dd, J=8.7, 3.0 Hz), 6.64 (1H, d, J=8.7 Hz), 7.05–7.25 (5H, m), 7.28 (1H, s).

EXAMPLE 14-33

N-(7-{4-hydroxy-3-[2-(3-oxocyclopentyl)ethyl]phenoxy}-6-methylindan-4-yl)malonamic acid (Compound 89)

The title compound was prepared in a similar manner to those described in Example 12 using ethyl N-(7-{4-hydroxy-3-[2-(3-oxocyclopentyl)ethyl]phenoxy}-6-methylindan-4-yl) malonamate instead of ethyl N-{7-[4-hydroxy-3-(tetrahydropyran-4-ylmethyl)phenoxy]-6-methylindan-4-yl}malonamate.

$^1$H-NMR (CD$_3$OD) δ ppm: 1.26–2.38 (14H, m), 2.52–2.66 (4H, m), 2.84 (2H, t, J=7.3 Hz), 3.47 (2H, s), 6.42 (1H, dd, J=8.5, 3.1 Hz), 6.52 (1H, d, J=3.1 Hz), 6.63 (1H, d, J=8.5 Hz), 7.30 (1H, s).

EXAMPLE 15

N-(7-{4-hydroxy-3-[2-(4-hydroxyphenyl)ethyl]phenoxy}-6-methylindan-4-yl}malonamic acid (Compound 90)

Ethyl N-(7-{4-methoxy-3-[2-(4-methoxyphenyl)ethyl] phenoxy}-6-methylindan-4-yl)malonamate (40 mg) was dissolved in dichloromethane (5 mL). Adding dropwise a 1 mol/L solution of boron tribromide in dichloromethane (1 mL) under dry ice/acetone-cooling, the solution was stirred at room temperature for 24 hours. To the reaction mixture was added dropwise methanol (5 mL) under ice-cooling with stirring. Adding diluted hydrochloric acid, the reaction mixture was extracted with ethyl acetate. The organic layer was washed with brine, and dried over anhydrous magnesium sulfate. The solvent was removed under reduced pressure. To the residue were added methanol (5 mL) and a 1 mol/L aqueous solution of sodium hydroxide (5 mL), and the mixture was stirred under an argon atmosphere at 50° C. for 30 min. The reaction mixture was evaporated under reduced pressure to dryness and water (10 mL) was added thereto. The mixture was washed with diethyl ether (10 mL) twice. To the aqueous layer were added 1 mol/L hydrochloric acid (20 mL) and brine (10 mL), and the aqueous layer was extracted with ethyl acetate (10 mL) twice. The organic layer was dried over anhydrous magnesium sulfate and evaporated-under reduced pressure to dryness to give the title compound (20 mg).

¹H-NMR (DMSO-d₆) δ ppm: 1.85–1.98 (2H, m), 2.02 (3H, s), 2.40–2.60 (2H, m), 2.60–2.80 (6H, m), 6.36 (1H, dd, J=3.0 Hz, 8.6 Hz), 6.43 (1H, d, J=3.0 Hz), 6.55–6.74 (3H, m), 6.92 (2H, d, J=8.4 Hz), 7.36 (1H, s), 8.94 (1H, s), 9.08 (1H, s), 9.47 (1H, s), 12.61 (1H, s).

REFERENCE EXAMPLE 65

4-(5-methyl-7-nitroindan-4-yloxy)-2-phenethylphenol

The title compound was prepared in a similar manner to those described in Example 15 using 4-(4-methoxy-3-phenethylphenoxy)-5-methyl-7-nitroindan instead of ethyl N-(7-{4-methoxy-3-[2-(4-methoxyphenyl)ethyl]phenoxy}-6-methylindan-4-yl)malonamate.

¹H-NMR (CDCl₃) δ ppm: 1.97–2.10 (2H, m), 2.19 (3H, s), 2.56 (2H, t, J=7.6 Hz), 2.82–2.94 (4H, m), 3.36 (2H, t, J=7.5 Hz), 4.56 (1H, s), 6.44–6.53 (2H, m), 6.66 (1H, d, J=8.5 Hz), 7.08–7.30 (5H, m), 7.94 (1H, s).

REFERENCE EXAMPLE 65-1

4-(5-methyl-7-nitroindan-4-yloxy)phenol

The title compound was prepared in a similar manner to those described in Example 15 using 4-(4-methoxyphenoxy)-5-methyl-7-nitroindane instead of ethyl N-(7-{4-methoxy-3-[2-(4-methoxyphenyl)ethyl]phenoxy}-6-methylindan-4-yl) malonamate.

¹-NMR (CDCl₃) δ ppm: 2.02–2.12 (2H, m), 2.24 (3H, s), 2.65 (2H, t, J=7.5 Hz), 3.37 (2H, t, J=7.5 Hz), 4.66 (1H, s), 6.64–6.79 (4H, m), 7.96 (1H, s).

EXAMPLE 16

N-(7-{4-hydroxy-3-[2-(4-hydroxyphenyl)ethyl]phenoxy}-6-methylindan-4-yl)oxamic acid
(Compound 91)

The title compound was prepared in a similar manner to those described in Example 15 using ethyl N-(7-{4-hydroxy-3-[2-(4-hydroxyphenyl)ethyl]phenoxy}-6-methylindan-4-yl) oxamate instead of ethyl N-(7-{4-methoxy-3-[2-(4-methoxyphenyl)ethyl]phenoxy}-6-methylindan-4-yl) malonamate.

¹H-NMR (CD₃OD) δ ppm: 1.90–2.15 (2H, m), 2.07 (3H, s), 2.40–2.60 (2H, m), 2.63–2.95 (6H, m), 6.25 (1H, d, J=2.8 Hz), 6.43 (1H, dd, J=8.7 Hz, 2.8 Hz), 6.55–6.75 (3H, m), 6.88 (2H, d, J=8.5 Hz), 7.31 (1H, s).

EXAMPLE 16-1

N-(7-{4-hydroxy-3-[2-(3-hydroxyphenyl)ethyl]phenoxy}-6-methylindan-4-yl}malonamic acid
(Compound 92)

The title compound was prepared in a similar manner to those described in Example 15 using ethyl N-(7-{4-methoxy-3-[2-(3-methoxyphenyl)ethyl]phenoxy}-6-methylindan-4-yl) malonamate instead of ethyl N-(7-{4-methoxy-3-[2-(4-methoxyphenyl)ethyl]phenoxy}-6-methylindan-4-yl) malonamate.

¹H-NMR (CD₃OD) δ ppm: 1.90–2.15 (5H, m), 2.45–2.60 (2H, m), 2.70–2.90 (6H, m), 3.20–3.40 (2H, m), 6.32 (1H, d, J=3.0 Hz), 6.42 (1H, dd, J=8.6 Hz, 3.0 Hz), 6.50–6.70 (4H, m), 6.95–7.10 (1H, m), 7.27 (1H, s).

EXAMPLE 16-2

N-(7-{4-hydroxy-3-[2-(3-hydroxyphenyl)ethyl]phenoxy}-6-methylindan-4-yl)oxamic acid
(Compound 93)

The title compound was prepared in a similar manner to those described in Example 15 using ethyl N-(7-{4-methoxy-3-[2-(3-methoxyphenyl)ethyl]phenoxy}-6-methylindan-4-yl) oxamate instead of ethyl N-(7-{4-methoxy-3-[2-(4-methoxyphenyl)ethyl]phenoxy}-6-methylindan-4-yl) malonamate.

¹H-NMR (CD₃OD) δ ppm: 1.90–2.15 (5H, m), 2.45–2.60 (2H, m), 2.70–2.90 (6H, m), 6.20–6.70 (6H, m), 6.95–7.10 (1H, m), 7.31 (1H, s).

EXAMPLE 16-3

N-(7-{4-hydroxy-3-[2-(2-hydroxyphenyl)ethyl]phenoxy}-6-methylindan-4-yl}malonamic acid
(Compound 94)

The title compound was prepared in a similar manner to those described in Example 15 using ethyl N-(7-{4-methoxy-3-[2-(2-methoxyphenyl)ethyl]phenoxy}-6-methylindan-4-yl) malonamate instead of ethyl N-(7-{4-methoxy-3-[2-(4-methoxyphenyl)ethyl]phenoxy}-6-methylindan-4-yl) malonamate.

¹H-NMR (DMSO-d₆) δ ppm: 1.80–1.98 (2H, m), 2.02 (3H, s), 2.40–2.60 (2H, m), 2.60–2.90 (6H, m), 3.20–3.50 (2H, m), 6.36 (1H, dd, J=3.0 Hz, 8.6 Hz), 6.45 (1H, d, J=3.0 Hz), 6.58–6.85 (3H, m), 6.88–7.05 (2H, m), 7.36 (1H, s), 8.92 (1H, s), 9.18 (1H, s), 9.48 (1H, s), 12.62 (1H, s).

EXAMPLE 16-4

N-(7-{4-hydroxy-3-[2-(2-hydroxyphenyl)ethyl]phenoxy}-6-methylindan-4-yl)oxamic acid
(Compound 95)

The title compound was prepared in a similar manner to those described in Example 15 using ethyl N-(7-{4-methoxy-3-[2-(2-methoxyphenyl)ethyl]phenoxy}-6-methylindan-4-yl) oxamate instead of ethyl N-(7-{4-methoxy-3-[2-(4-methoxyphenyl)ethyl]phenoxy}-6-methylindan-4-yl) malonamate.

¹H-NMR (DMSO-d₆) δ ppm: 1.80–1.98 (2H, m), 2.05 (3H, s), 2.40–2.60 (2H, m), 2.60–2.90 (6H, m), 6.37 (1H, dd, J=3.0 Hz, 8.6 Hz), 6.47 (1H, d, J=3.0 Hz), 6.60–6.80 (3H, m), 6.90–7.05 (2H, m), 7.21 (1H, s), 8.96 (1H, s), 9.19 (1H, s), 10.13 (1H, s), 13.9–14.4 (1H, br-s).

EXAMPLE 16-5

N-(7-{3-[2-(3-fluoro-4-hydroxyphenyl)ethyl]-4-hydroxyphenoxy}-6-methylindan-4-yl)malonamic acid (Compound 96)

The title compound was prepared in a similar manner to those described in Example 15 using ethyl N-(7-{4-methoxy-3-[2-(3-fluoro-4-methoxyphenyl)ethyl]phenoxy}-6-methylindan-4-yl)malonamate instead of ethyl N-(7-{4- methoxy-3-[2-(4-methoxyphenyl)ethyl]phenoxy}-6-methylindan-4-yl)malonamate.

¹H-NMR (CD₃OD) δ ppm: 1.90–2.15 (5H, m), 2.45–2.60 (2H, m), 2.67–2.95 (6H, m), 3.47 (2H, s), 6.26 (1H, d, J=3.0 Hz), 6.43 (1H, dd, J=8.7 Hz, 3.0 Hz), 6.60–6.80 (4H, m), 7.27 (1H, s).

EXAMPLE 16-6

N-(7-{3-[2-(3-fluoro-4-hydroxyphenyl)ethyl]-4-hydroxyphenoxy}-6-methylindan-4-yl)oxamic acid
(Compound 97)

The title compound was prepared in a similar manner to those described in Example 15 using ethyl N-(7-{4-methoxy-3-[2-(3-fluoro-4-methoxyphenyl)ethyl]phenoxy}-6-methylindan-4-yl)oxamate instead of ethyl N-(7-{4-methoxy-3-[2-(4-methoxyphenyl)ethyl]phenoxy}-6-methylindan-4-yl) malonamate.

¹H-NMR (CD₃OD) δ ppm: 1.90–2.20 (5H, m), 2.40–2.60 (2H, m), 2.67–2.95 (6H, m), 6.25 (1H, d, J=2.9 Hz), 6.44 (1H, dd, J=8.7 Hz, 2.9 Hz), 6.55–6.90 (4H, m), 7.31 (1H, s).

EXAMPLE 16-7

Ethyl N-(7-{3-[2-(4-fluorophenyl)ethyl]-4-hydroxyphenoxy}-6-methylindan-4-yl)oxamate
(Compound 98)

The title compound was prepared in a similar manner to those described in Example 15 using ethyl N-(7-{3-[2-(4-fluorophenyl)ethyl]-4-methoxyphenoxy}-6-methylindan-4-yl) oxamate instead of ethyl N-(7-{4-methoxy-3-[2-(4-methoxyphenyl)ethyl]phenoxy}-6-methylindan-4-yl) malonamate.

¹H-NMR (CD₃OD) δ ppm: 1.85–2.00 (5H, m), 2.30–2.50 (2H, m), 2.60–2.90 (6H, m), 6.10–6.60 (4H, m), 6.70–7.05 (3H, m), 7.54 (1H, s).

EXAMPLE 17

N-[6-bromo-7-(4-hydroxy-3-isopropylphenoxy)indan-4-yl]oxamic acid (Compound 99)

Ethyl N-[7-(4-benzyloxy-3-isopropylphenoxy)-6-trifluoromethylindan-4-yl]oxamate was prepared in a similar manner to that described in Example 1 using 7-(4-benzyloxy-3-isopropylphenoxy)-6-bromoindan-4-ylamine instead of 4-(7-amino-5-methylindan-4-yloxy)-2-(tetrahydropyran-4-ylmethyl)phenol.

Ethyl N-[6-bromo-7-(4-hydroxy-3-isopropylphenoxy)indan-4-yl]oxamate was prepared in a similar manner to those described in Reference Example 27 using ethyl N-[7-(4-benzyloxy-3-isopropylphenoxy)-6-bromoindan-4-yl]malonamate instead of ethyl 2-acetyl-3-benzyloxy-6-(5-methyl-7-nitroindan-4-yloxy)benzoate.

The title compound was prepared in a similar manner to those described in Example 12 using ethyl N-[6-bromo-7-(4-hydroxy-3-isopropylphenoxy)indan-4-yl]oxamate instead of ethyl N-{7-[4-hydroxy-3-(tetrahydropyran-4-ylmethyl)phenoxy]-6-methylindan-4-yl}malonamate.

¹H-NMR (CDCl₃) δ ppm: 1.22 (6H, d, J=6.9 Hz), 2.00–2.20 (2H, m), 2.65–2.95 (4H, m), 3.10–3.25 (1H, m), 6.41 (1H, dd, J=8.6, 3.0 Hz), 6.62 (1H, d, J=8.6 Hz), 6.80 (1H, d, J=3.0 Hz), 8.20 (1H, s), 8.79 (1H, s).

EXAMPLE 18

N-(7-{3-[(4-fluorophenyl)hydroxymethyl]-4-hydroxyphenoxy}-6-methylindan-4-yl)malonamic acid
(Compound 100)

The title compound was prepared in a similar manner to those described in Reference Example 12 using N-{7-[3-(4-fluorobenzoyl)-4-hydroxyphenoxy]-6-methylindan-4-yl}malonamic acid instead of 2-benzyloxy-5-(5-methyl-7-nitroindan-4-yloxy)benzaldehyde.

¹H-NMR (CDCl₃) δ ppm: 1.90–2.20 (5H, m), 2.50–2.70 (2H, m), 2.75–2.85 (2H, m), 3.53 (2H, s), 5.89 (1H, s), 6.38 (1H, d, J=2.6 Hz), 6.55–6.65 (1H, m), 6.76 (1H, d, J=8.8 Hz), 6.90–7.10 (2H, m), 7.25–7.45 (2H, m), 7.57 (1H, s), 8.45–8.55 (1H, br-s).

EXAMPLE 19

N-[7-(4-hydroxy-3-isobutylphenoxy)-6-methylindan-4-yl]malonamic acid (Compound 101)

The title compound was prepared in a similar manner to those described in Reference Example 56, Example 6-1, Example 8, and Example 14-31 using isobutylic acid instead of 4-fluorophenylacetic acid successively.

¹H-NMR (CD₃OD) δ ppm: 0.86 (6H, d, J=6.6 Hz), 1.80–2.20 (6H, m), 2.37 (2H, d, J=7.1 Hz), 2.63 (2H, t, J=7.3 Hz), 2.85 (2H, t, J=7.4 Hz), 3.46 (2H, s), 6.40–6.46 (2H, m), 6.62 (1H, d, J=8.8 Hz), 7.31 (1H, s).

EXAMPLE 19-1

N-{7-[4-hydroxy-3-(3-methylbutyl)-phenoxy]-6-methylindan-4-=yl}malonamic acid
(Compound 102)

The title compound was prepared in a similar manner to those described in Reference Example 56, Example 6-1, Example 8 and Example 14-31 using isovaleric acid instead of 4-fluorophenylacetic acid successively.

¹H-NMR (CD₃OD) δ ppm: 0.91 (6H, d, J=6.6 Hz), 1.35–1.60 (3H, m), 1.90–2.20 (5H, m), 2.45–2.70 (4H, m), 2.85 (2H, t, J=7.6 Hz), 3.46 (2H, s), 6.39 (1H, dd, J=8.7, 3.0 Hz), 6.50 (1H, d, J=3.0 Hz), 6.61 (1H, d, J=8.7 Hz), 7.30 (1H, s).

EXAMPLE 19-2

N-(7-{3-[2-(3,4-difluorophenyl)ethyl]-4-hydroxyphenoxy}-6-methylindan-4-yl)malonamic acid
(Compound 103)

The title compound was prepared in a similar manner to those described in Reference Example 56, Example 6-1, Example 8, and Example 14-31 using 3,4-difluorophenylacetic acid instead of 4-fluorophenylacetic acid successively.

¹H-NMR (CD₃OD) δ ppm: 1.90–2.15 (5H, m), 2.51 (2H, t, J=7.4 Hz), 2.70–2.95 (6H, m), 3.40–3.60 (2H, m), 6.20–6.50 (2H, m), 6.60–6.70 (1H, m), 6.80–7.15 (3H, m), 7.28 (1H, s).

EXAMPLE 19-3

N-(7-{3-[2-(2,6-dichlorophenyl)ethyl]-4-hydroxyphenoxy}-6-methylindan-4-yl)malonamic acid
(Compound 104)

The title compound was prepared in a similar manner to those described in Reference Example 56, Example 6-1, Example 8, and Example 14-31 using 2,6-dichlorophenylacetic acid instead of 4-fluorophenylacetic acid successively.

$^1$H-NMR (CD$_3$OD) δ ppm: 1.90–2.15 (5H, m), 2.59 (2H, t, J=7.4 Hz), 2.75–2.90 (4H, m), 3.19 (2H, t, J=7.6 Hz), 3.47 (2H, s), 6.30 (1H, d, J=2.8 Hz), 6.43 (1H, dd, J=8.8, 2.8 Hz), 6.63 (1H, d, J=8.8 Hz), 7.05–7.35 (4H, m).

EXAMPLE 19-4

N-{7-[4-hydroxy-3-(2-phenylpropyl)phenoxy]-6-methylindan-4-yl}malonamic acid (Compound 105)

The title compound was prepared in a similar manner to those described in Reference Example 56, Example 6-1, Example 8 and Example 14-31 using 2-phenylpropionic acid instead of 4-fluorophenylacetic acid successively.

$^1$H-NMR (CD$_3$OD) δ ppm: 1.10–1.30 (3H, m), 1.80–2.10 (5H, m), 2.30–2.55 (2H, m), 2.60–2.90 (4H, m), 3.00–3.15 (1H, m), 3.47 (2H, s), 6.15 (1H, d, J=2.8 Hz), 6.42 (1H, dd, J=8.5, 2.8 Hz), 6.62 (1H, d, J=8.5 Hz), 7.00–7.35 (6H, m).

EXAMPLE 19-5

N-(7-{3-[2-(2-chlorophenyl)ethyl]-4-hydroxyphenoxy}-6-methylindan-4-yl)malonamic acid (Compound 106)

The title compound was prepared in a similar manner to those described in Reference Example 56, Example 6-1, Example 8, and Example 14-31 using 2-chlorophenylacetic acid instead of 4-fluorophenylacetic acid successively.

$^1$H-NMR (CD$_3$OD) δ ppm: 1.94–2.03 (2H, m), 2.05 (3H, s), 2.53 (2H, t, J=7.4 Hz), 2.78–2.88-(4H, m), 2.95–3.02 (2H, m), 3.46 (2H, s), 6.28 (1H, d, J=3.0 Hz), 6.42 (1H, dd, J=8.7, 3.0 Hz), 6.64 (1H, d, J=8.7 Hz), 7.04–7.20 (3H, m), 7.22–7.36 (2H, m).

EXAMPLE 19-6

N-(7-{3-[2-(3-chlorophenyl)ethyl]-4-hydroxyphenoxy}-6-methylindan-4-yl)malonamic acid (Compound 107)

The title compound was prepared in a similar manner to those described in Reference Example 56, Example 6-1, Example 8, and Example 14-31 using 3-chlorophenylacetic acid instead of 4-fluorophenylacetic acid successively.

$^1$H-NMR (CD$_3$OD) δ ppm: 1.93–2.02 (2H, m), 2.04 (3H, s), 2.51 (2H, t, J=7.4 Hz), 2.75–2.90 (6H, m), 3.46 (2H, s), 6.27 (1H, d, J=2.9 Hz), 6.53 (1H, dd, J=8.6, 2.9 Hz), 6.65 (1H, d, J=8.6 Hz), 6.96–7.21 (4H, m), 7.28 (1H, m).

EXAMPLE 19-7

N-(7-{3-[2-(4-chlorophenyl)ethyl]-4-hydroxyphenoxy}-6-methylindan-4-yl)malonamic acid (Compound 108)

The title compound was prepared in a similar manner to those described in Reference Example 56, Example 6-1, Example 8, and Example 14-31 using 4-chlorophenylacetic acid instead of 4-fluorophenylacetic acid successively.

$^1$H-NMR (CD$_3$OD) δ ppm: 1.93–2.05 (5H, m), 2.50 (2H, t, J=7.3 Hz), 2.74–2.88 (6H, m), 3.46 (2H, s), 6.23 (1H, d, J=3.0 Hz), 6.44 (1H, dd, J=8.7, 3.0 Hz), 6.64 (1H, d, J=8.7 Hz), 7.01–7.07 (2H, m), 7.12–7.20 (2H, m), 7.28 (1H, s).

EXAMPLE 19-8

N-(7-{3-[2-(2,4-difluorophenyl)ethyl]-4-hydroxyphenoxy}-6-methylindan-4-yl)malonamic acid (Compound 109)

The title compound was prepared in a similar manner to those described in Reference Example 56, Example 6-1, Example 8, and Example 14-31 using 2,4-difluorophenylacetic acid instead of 4-fluorophenylacetic acid successively.

$^1$H-NMR (CD$_3$OD) δ ppm: 1.94–2.02 (2H, m), 2.04 (3H, s), 2.51 (2H, t, J=7.5 Hz), 2.75–2.91 (6H, m), 3.45 (2H, s), 6.24 (1H, d, J=3.0 Hz), 6.42 (1H, dd, J=8.6, 3.0 Hz), 6.63 (1H, d, J=8.6 Hz), 6.72–6.84 (2H, m), 7.01–7.09 (1H, m), 7.29 (1H, s).

EXAMPLE 19-9

N-{7-[4-hydroxy-3-(3-phenylpropyl)phenoxy]-6-methylindan-yl}malonamic acid (Compound 110)

The title compound was prepared in a similar manner to those described in Reference Example 56, Example 6-1, Example 8, and Example 14-31 using hydrocinnamic acid instead of 4-fluorophenylacetic acid successively.

$^1$H-NMR (CD$_3$OD) δ ppm: 1.75–2.20 (7H, m), 2.45–2.90 (8H, m), 3.47 (2H, s), 6.40–6.70 (3H, m), 7.00–7.40 (6H, m).

EXAMPLE 19-10

N-{7-[3-(2-cyclohexylethyl)-4-hydroxyphenoxy]-6-methylindan-4-yl}malonamic acid (Compound 111)

The title compound was prepared in a similar manner to those described in Reference Example 56, Example 6-1, Example 8, and Example 14-31 using cyclohexylacetic acid instead of 4-fluorophenylacetic acid successively.

$^1$H-NMR (CD$_3$OD) δ ppm: 0.80–1.00 (2H, m), 1.09–1.50 (6H, m), 1.55–1.80 (5H, m), 1.92–2.07 (2H, m), 2.12 (3H, s), 2.45–2.57 (2H, m), 2.63 (2H, t, J=7.3 Hz), 2.85 (2H, t, J=7.2 Hz), 3.46 (2H, s), 6.41 (1H, dd, J=8.6, 3.0 Hz), 6.46 (1H, d, J=3.0 Hz), 6.62 (1H, d, J=8.6 Hz), 7.31 (1H, s).

EXAMPLE 19-11

N-{7-[4-hydroxy-3-(2-naphthalen-1-ylethyl)phenoxy]-6-methylindan-4-yl}malonamic acid (Compound 112)

The title compound was prepared in a similar manner to those described in Reference Example 56, Example 6-1, Example 8, and Example 14-31 using naphthalen-1-ylacetic acid instead of 4-fluorophenylacetic acid successively.

$^1$H-NMR (CD$_3$OD) δ ppm: 1.84–2.10 (5H, m), 2.40–2.55 (2H, m), 2.70–3.00 (4H, m), 3.20–3.50 (4H, m), 6.29 (1H, d, J=2.8 Hz), 6.41 (1H, dd, J=8.9, 2.8 Hz), 6.68 (1H, d, J=8.9 Hz), 7.12–7.88 (7H, m), 8.19 (1H, d, J=7.5 Hz).

EXAMPLE 19-12

N-{7-[4-hydroxy-3-(2-naphthalen-2-ylethyl)phenoxy]-6-methylindan-4-yl}malonamic acid (Compound 113)

The title compound was prepared in a similar manner to those described in Reference Example 56, Example 6-1, Example 8, and Example 14-31 using naphthalen-2-ylacetic acid instead of 4-fluorophenylacetic acid successively.

¹H-NMR (CD₃OD) δ ppm: 1.70–1.85 (2H, m), 1.89 (3H, s), 2.30–2.40 (2H, m), 2.65–2.80 (2H, m), 2.91 (2H, t, J=7.4 Hz), 3.02 (2H, t, J=7.4 Hz), 3.20–3.40 (2H, m), 6.21 (1H, d, J=3.3 Hz), 6.42 (1H, dd, J=9.1, 3.3 Hz), 6.66 (1H, d, J=9.1 Hz), 7.13–7.31 (2H, m), 7.33–7.55 (3H, m), 7.60–7.85 (3H, m).

EXAMPLE 20

Sodium N-[7-(4-hydroxy-3-isopropylphenoxy)-6-methylindan-4-yl]oxamate (Compound 114)

N-[7-(4-hydroxy-3-isopropylphenoxy)-6-methylindan-4-yl]oxamic acid (2.25 g) was dissolved in ethanol (20 mL). Adding a 1 mol/L aqueous solution of sodium hydroxide (6.09 mL), the mixture was stirred for 5 min. The reaction mixture was evaporated under reduced pressure to dryness. Adding water (0.115 mL) and diisopropyl ether (20 mL), the residue was stirred for 3 hours. The precipitate was filtrated to give the title compound (2.4 g).

¹H-NMR (DMSO-d₆) δ ppm: 1.11 (6H, d, J=6.9 Hz), 1.92–2.00 (2H, m), 2.06 (3H, s), 2.50–2.58 (2H, m), 2.75–2.82 (2H, m), 3.15 (1H, heptet, J=6.9 Hz), 6.26 (1H, dd, J=3.0, 8.7 Hz), 6.64 (1H, d, J=8.7 Hz), 6.66 (1H, d, J=3.0 Hz), 7.72 (1H, s), 8.95 (1H, s), 9.75 (1H, s).

The compounds as illustrated in the following table 1 can be prepared using suitable reagents according to the procedures as described in Examples, Reference Examples and Schemes 1–20a, as well as their modified procedures well known to those skilled in the art.

TABLE 1

Compound 115

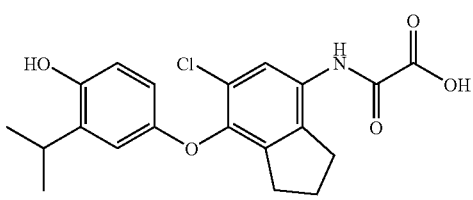

Compound 116

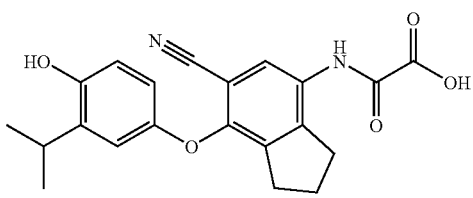

Compound 117

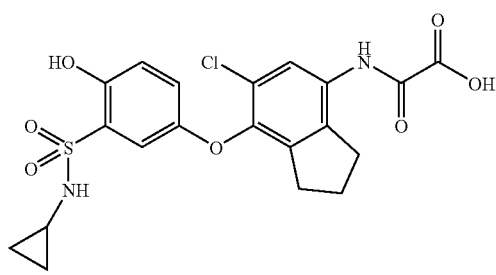

Compound 118

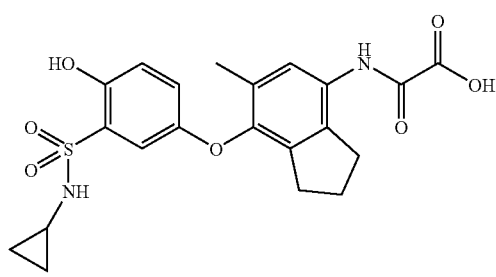

TABLE 1-continued
Compound 119
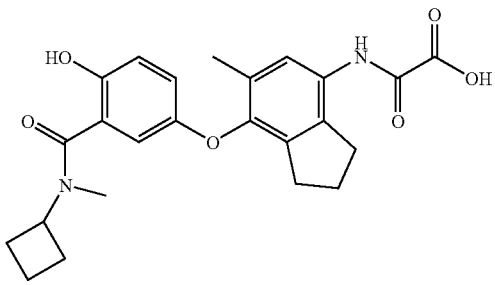
Compound 120
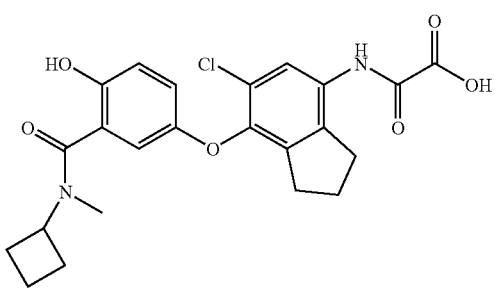
Compound 121
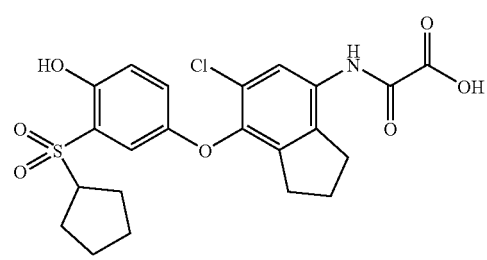
Compound 122
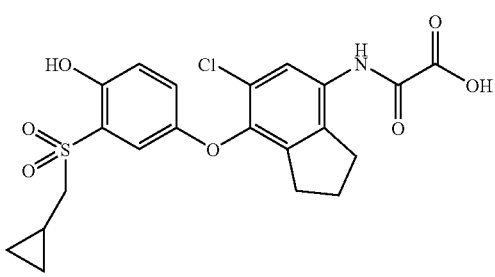
Compound 123
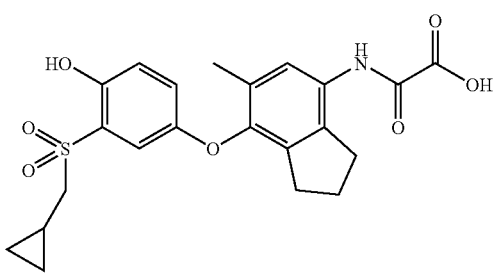

TABLE 1-continued
Compound 124
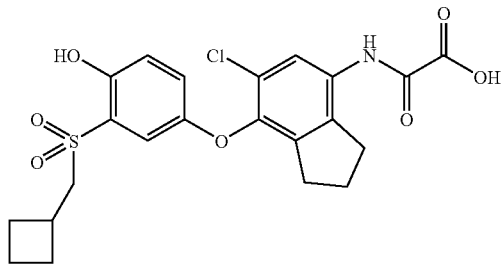
Compound 125
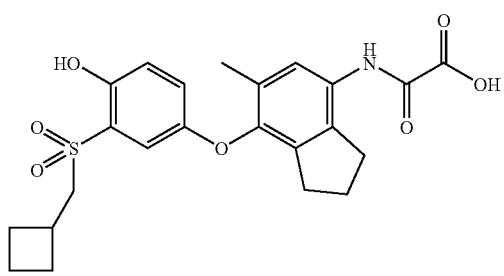
Compound 126
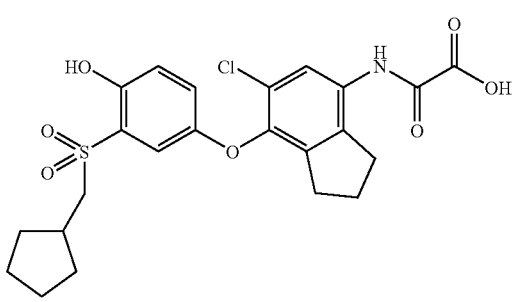
Compound 127
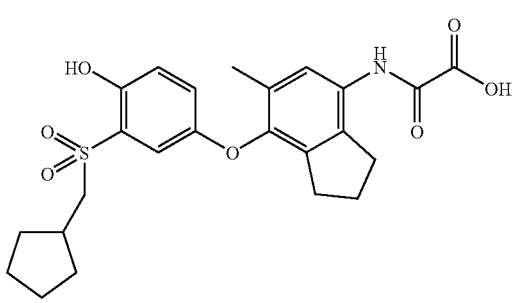
Compound 128
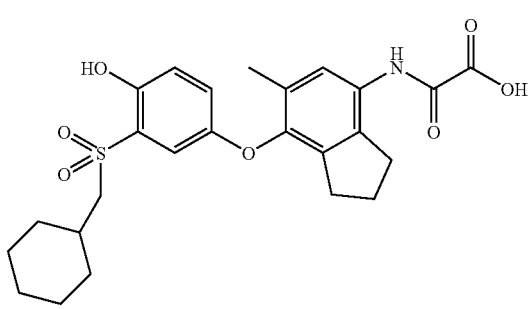

TABLE 1-continued
Compound 129
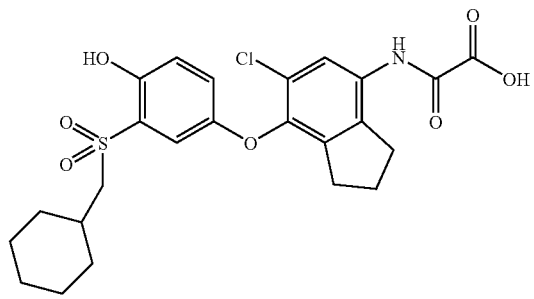
Compound 130
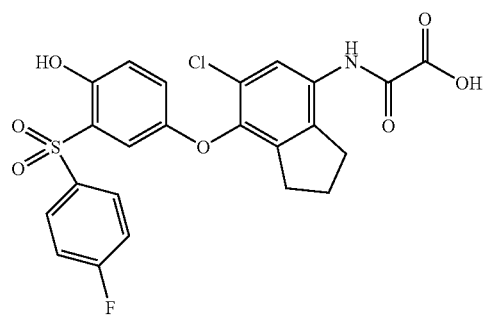
Compound 131
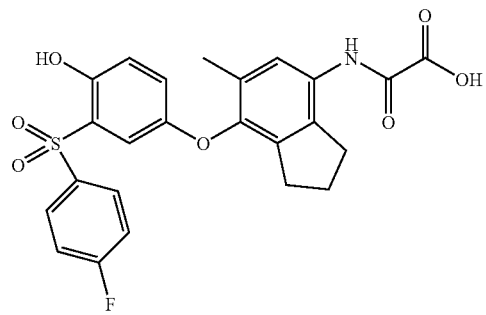
Compound 132
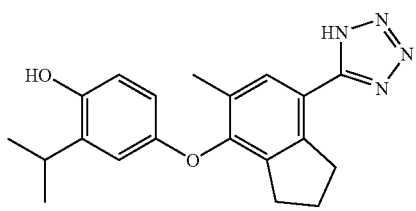
Compound 133
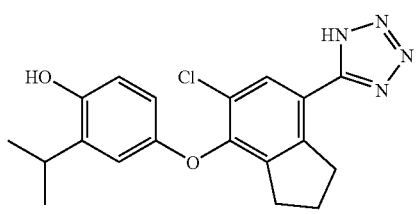

TABLE 1-continued
Compound 134
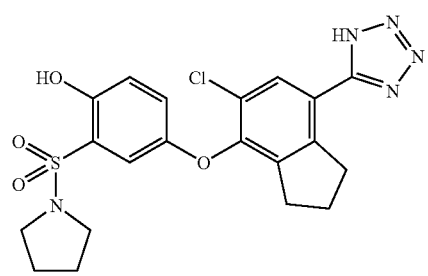
Compound 135
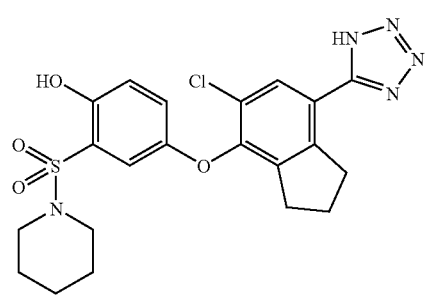
Compound 136
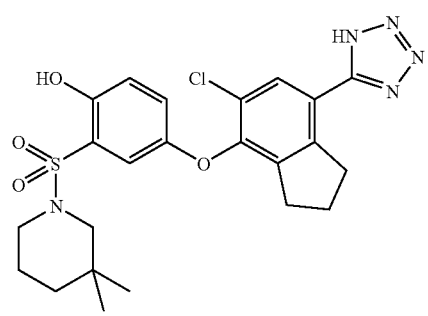
Compound 137
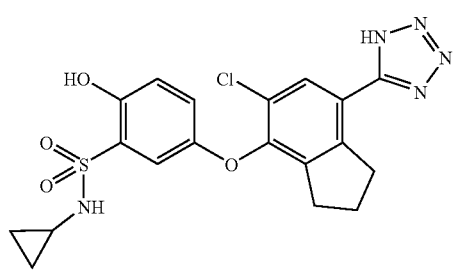
Compound 138
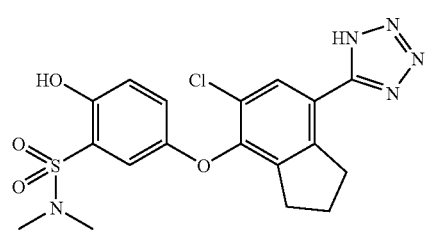

TABLE 1-continued
Compound 139
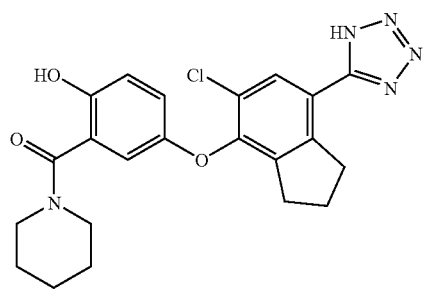
Compound 140
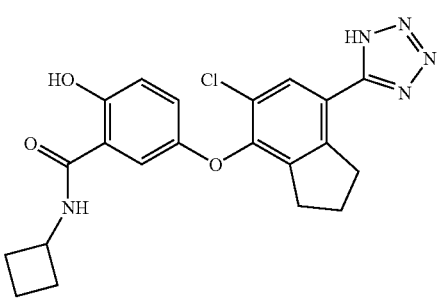
Compound 141
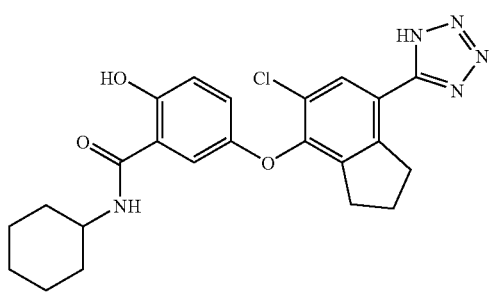
Compound 142
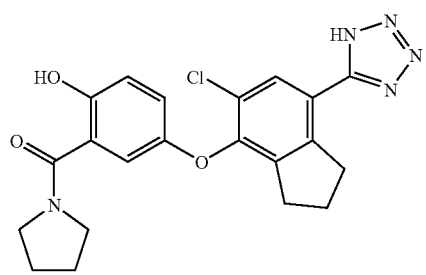
Compound 143
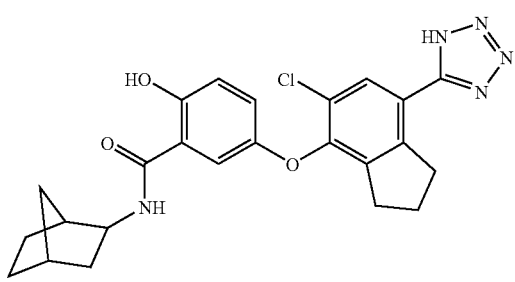
Compound 144
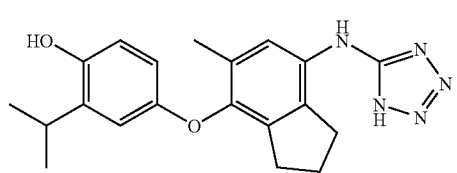

TABLE 1-continued
Compound 145
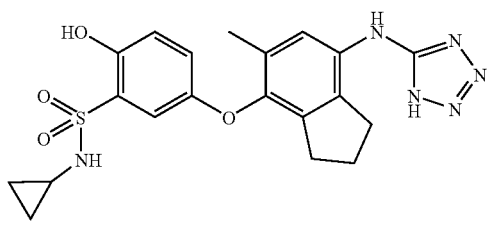
Compound 146
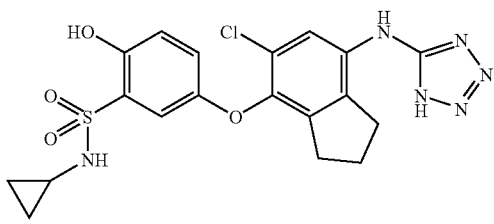
Compound 147
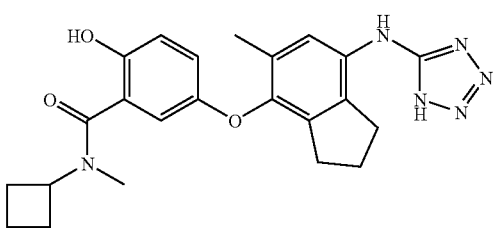
Compound 148
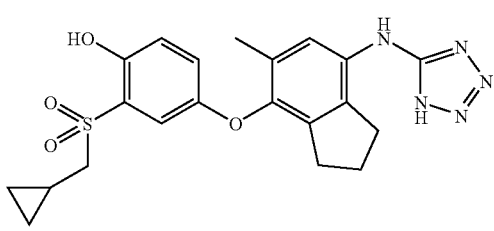
Compound 149
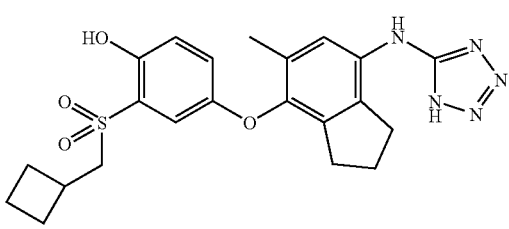
Compound 150
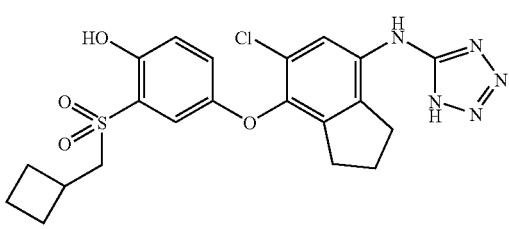
Compound 151
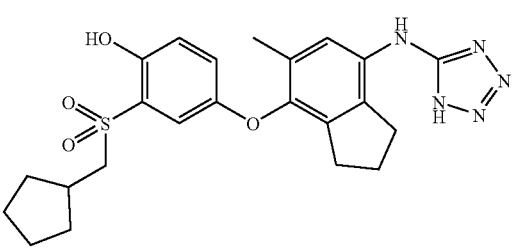

TABLE 1-continued
Compound 152 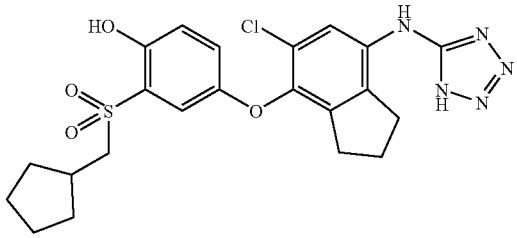
Compound 153 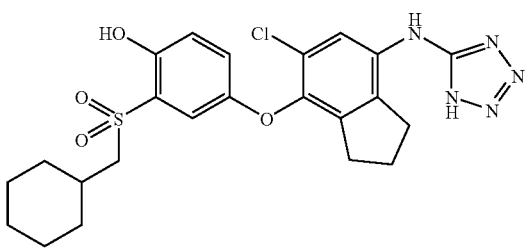
Compound 154 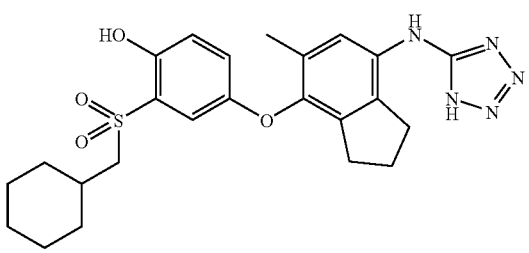
Compound 155 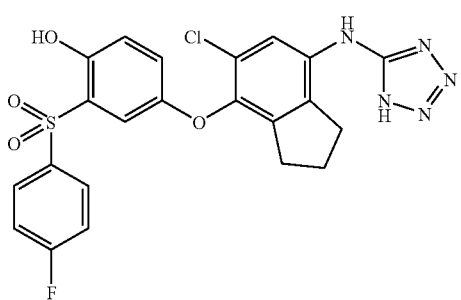
Compound 156 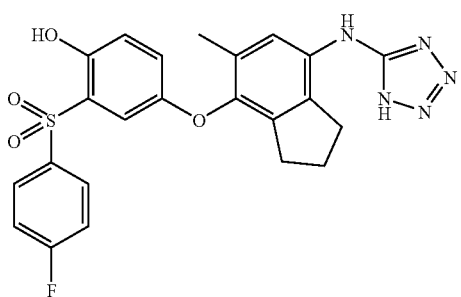
Compound 157 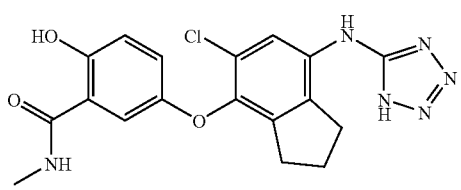

TABLE 1-continued
Compound 158
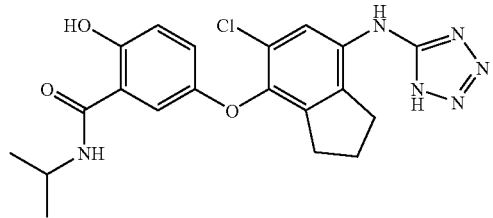
Compound 159
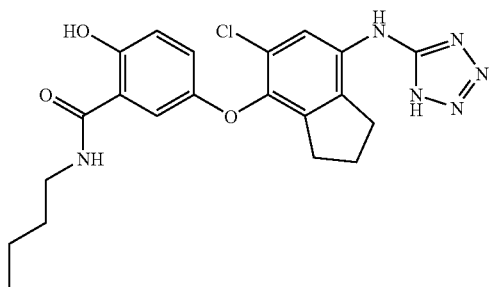
Compound 160
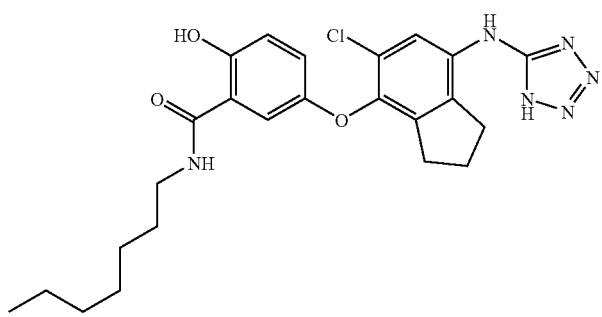
Compound 161
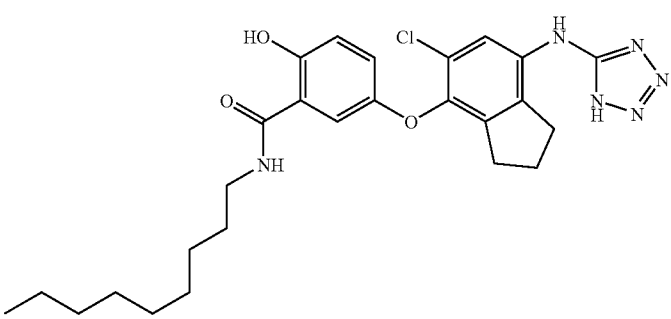
Compound 162
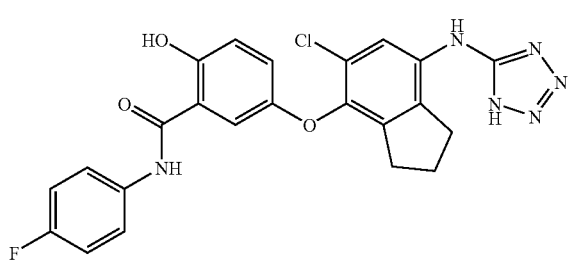

TABLE 1-continued
Compound 163 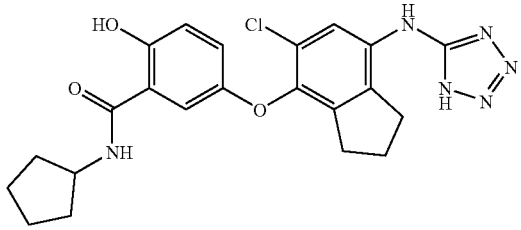
Compound 164 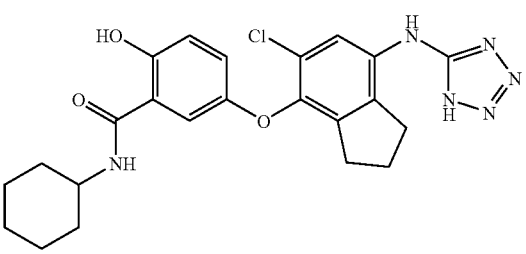
Compound 165 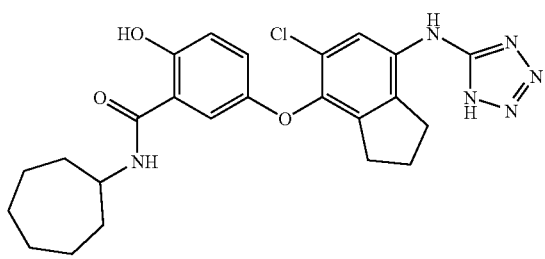
Compound 166 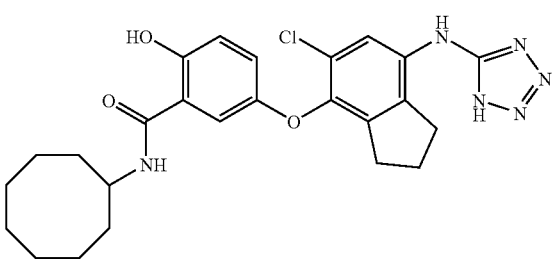
Compound 167 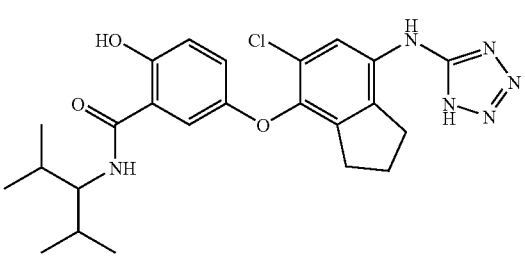
Compound 168 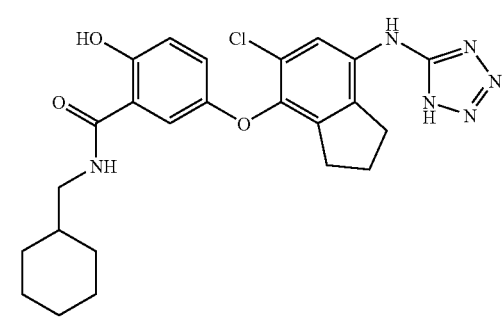

TABLE 1-continued
Compound 169 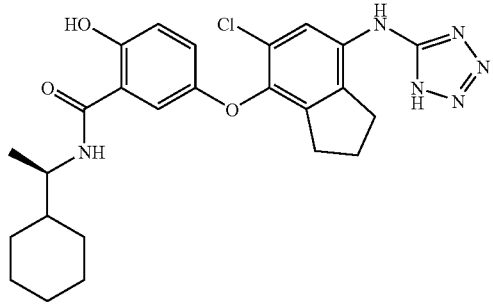
Compound 170 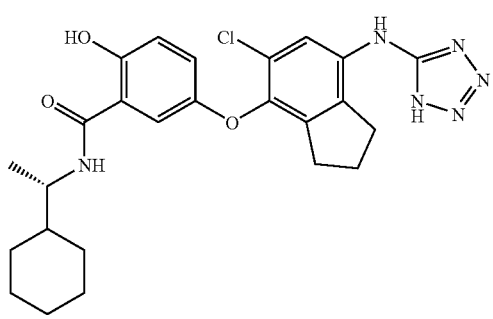
Compound 171 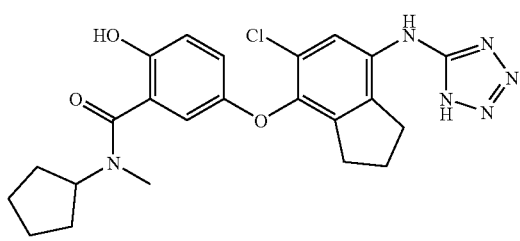
Compound 172 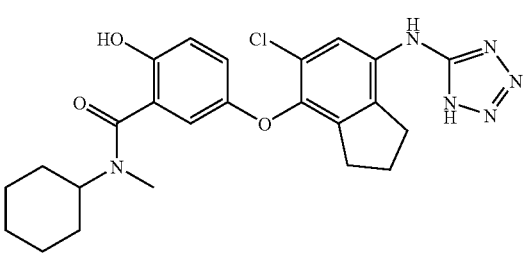
Compound 173 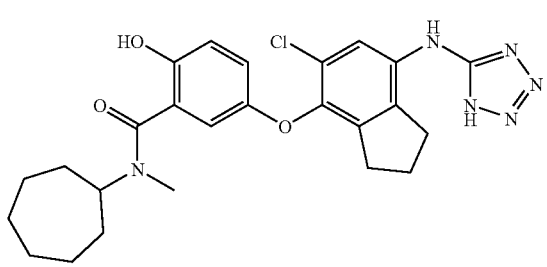

TABLE 1-continued
Compound 174 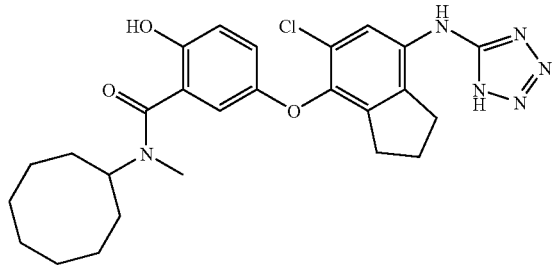
Compound 175 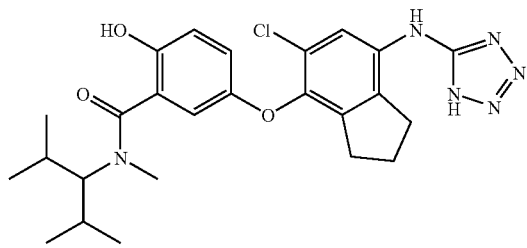
Compound 176 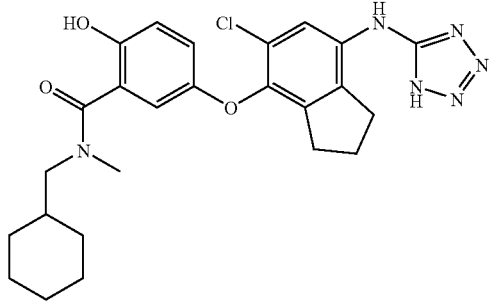
Compound 177 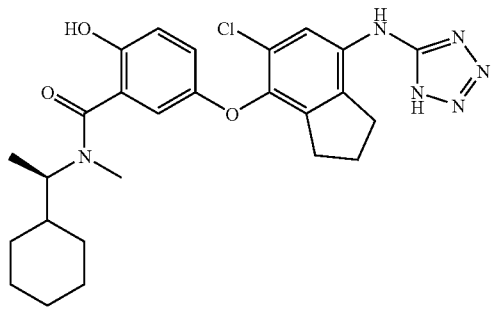
Compound 178 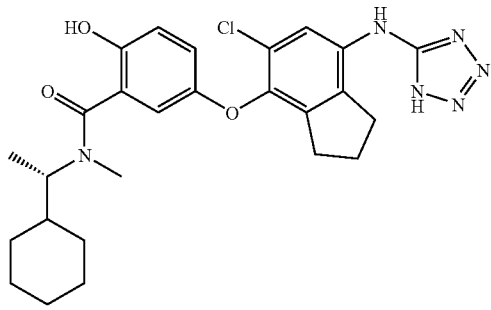

TABLE 1-continued
Compound 179 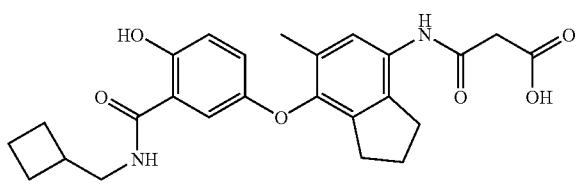
Compound 180 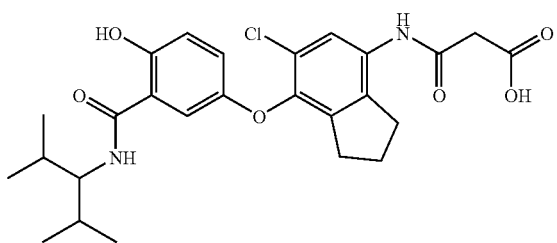
Compound 181 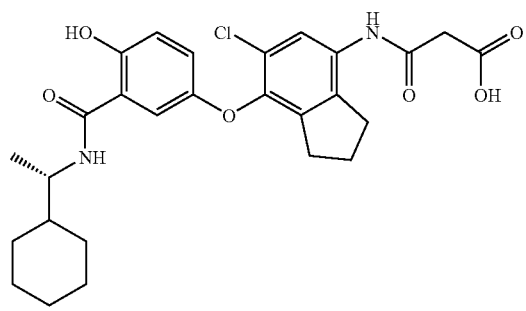
Compound 182 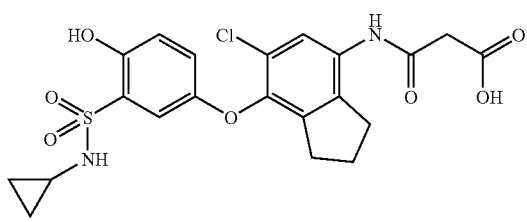
Compound 183 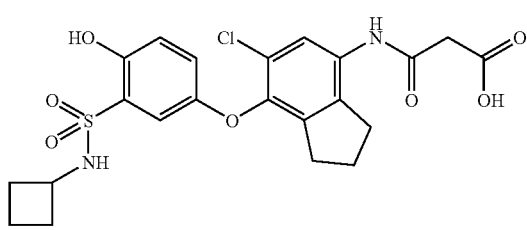
Compound 184 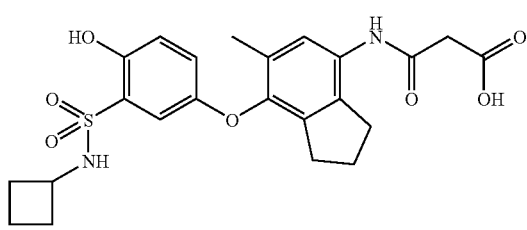

TABLE 1-continued

Compound 185

Compound 186

Compound 187

Compound 188

Compound 189

Compound 190

Compound 191

TABLE 1-continued
Compound 192
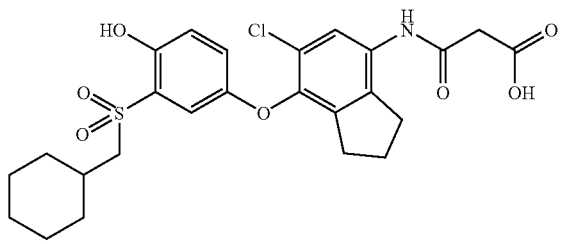
Compound 193
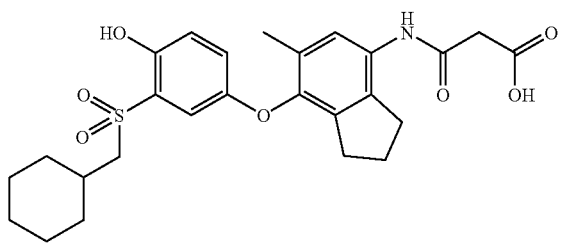
Compound 194
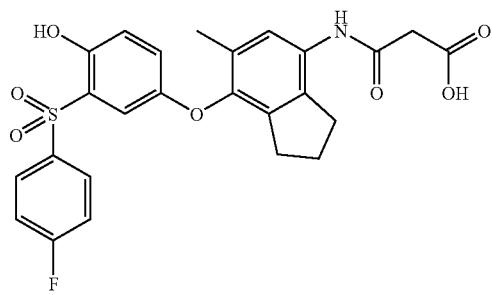
Compound 195
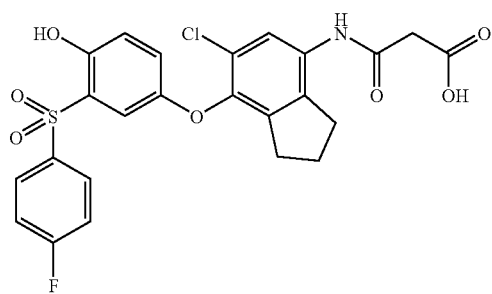
Compound 196
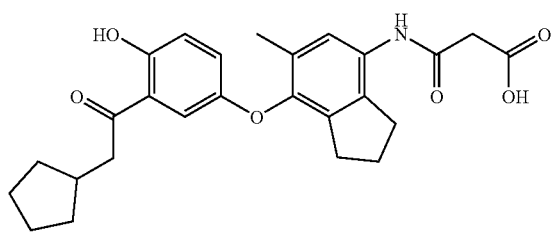
Compound 197
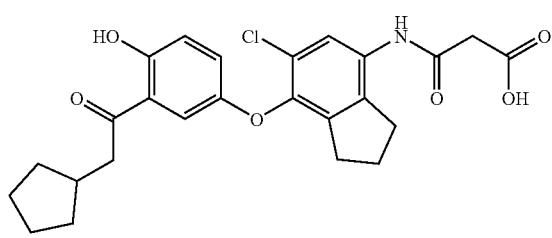

TABLE 1-continued
Compound 198
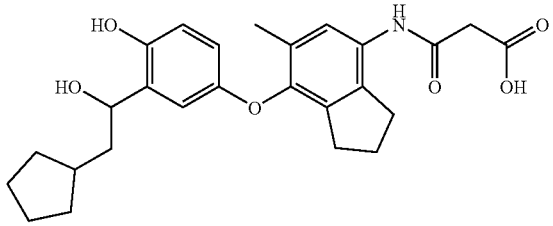
Compound 199
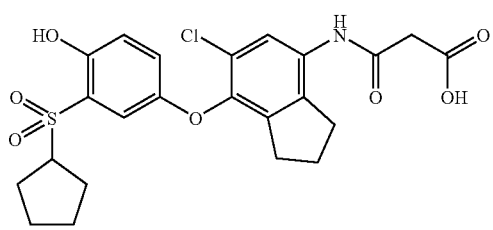
Compound 200
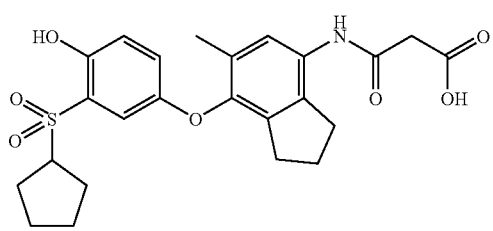
Compound 201
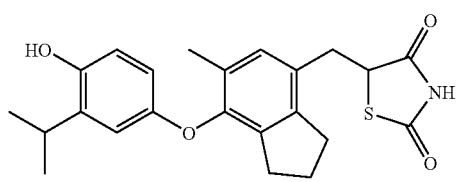
Compound 202
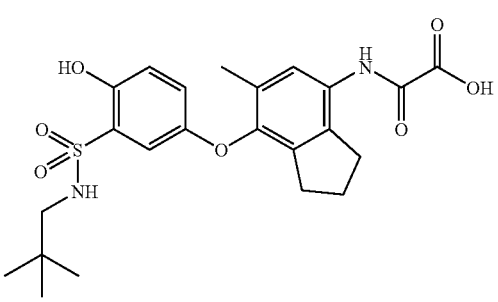
Compound 203
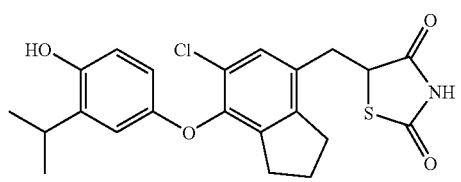

TABLE 1-continued
Compound 204
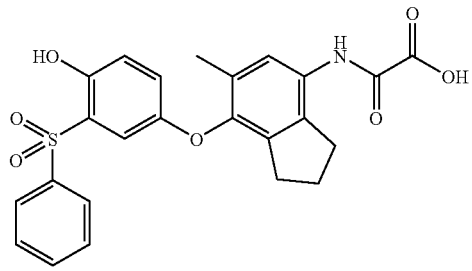
Compound 205
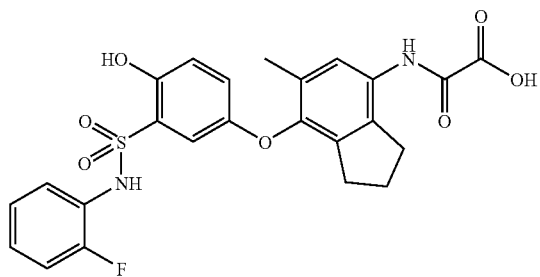
Compound 206
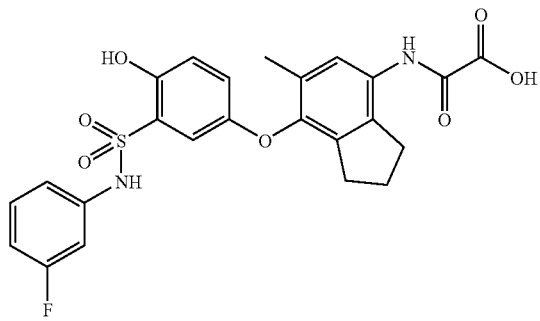
Compound 207
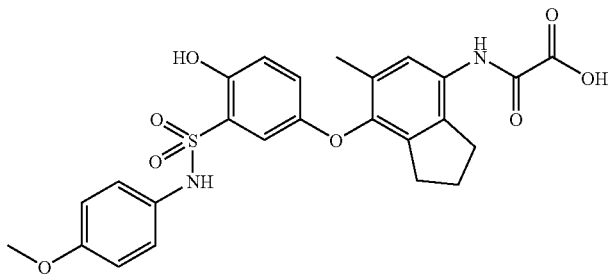
Compound 208
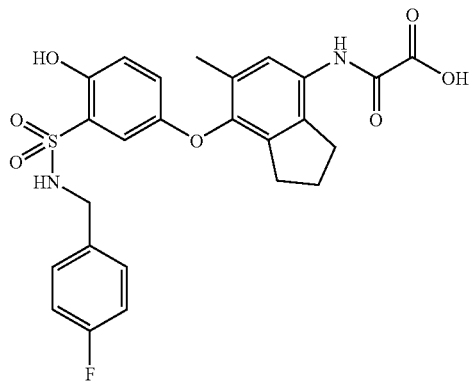

TABLE 1-continued
Compound 209
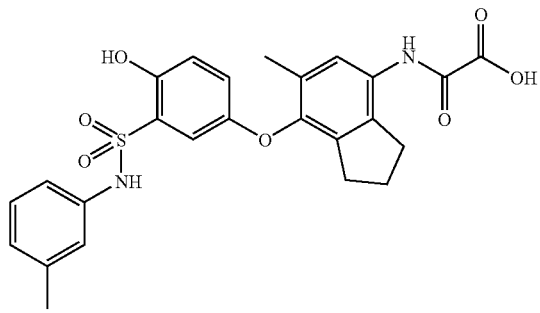
Compound 210
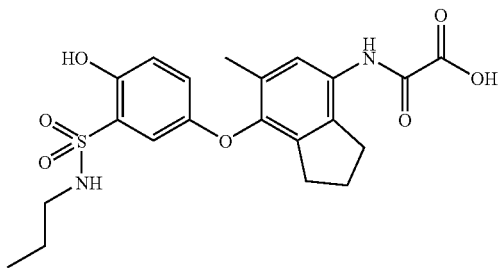
Compound 211
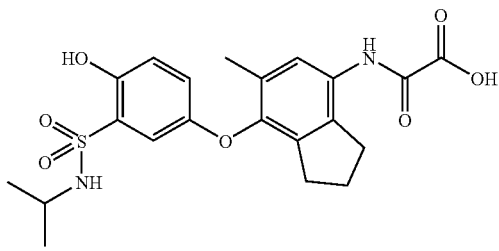
Compound 212
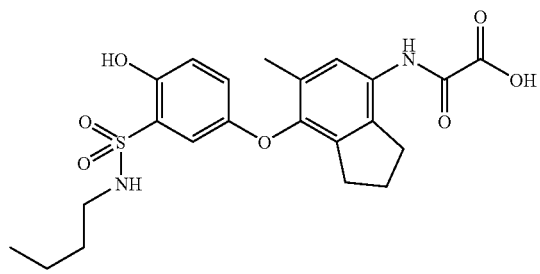
Compound 213
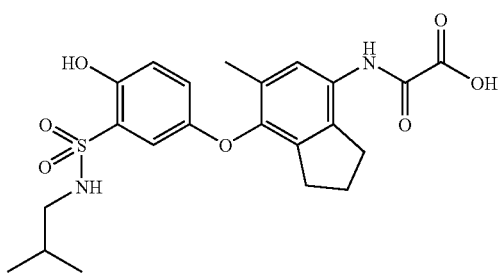

TABLE 1-continued
Compound 214
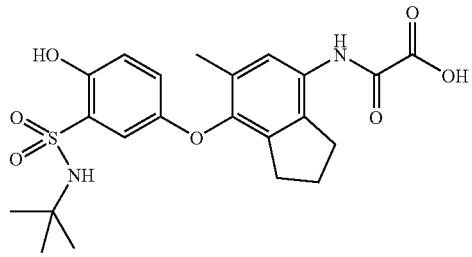
Compound 215
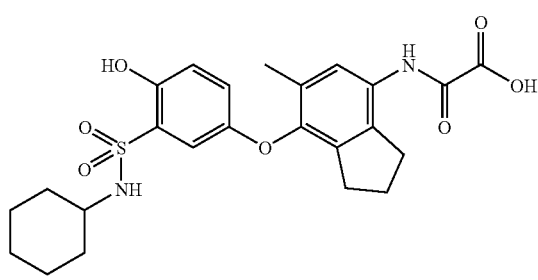
Compound 216
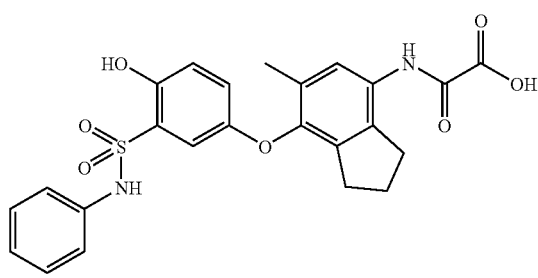
Compound 217
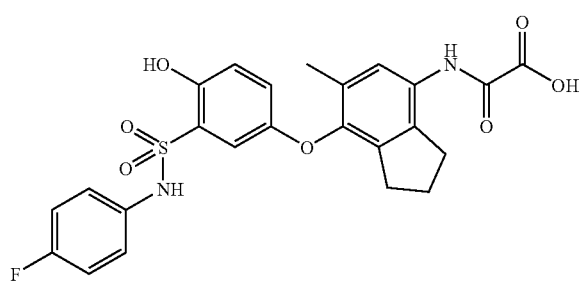
Compound 218
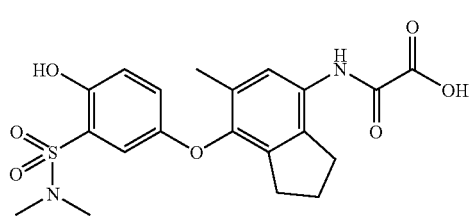
Compound 219
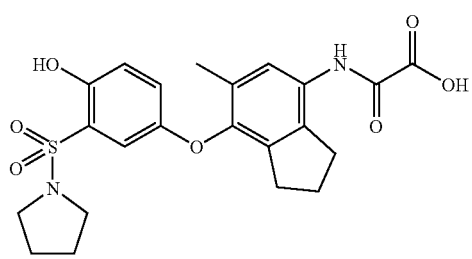

TABLE 1-continued
Compound 220
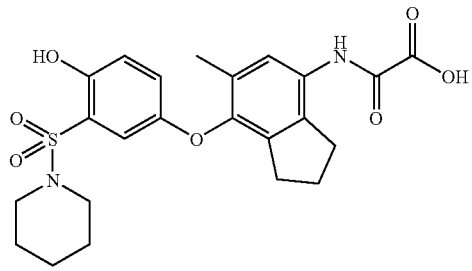
Compound 221
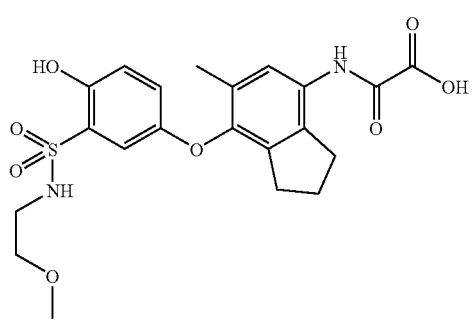
Compound 222
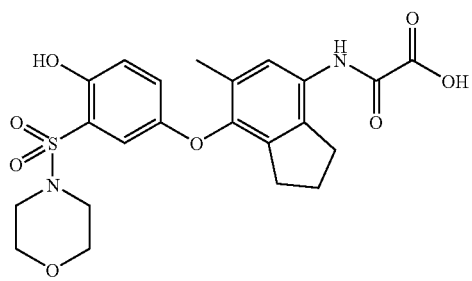
Compound 223
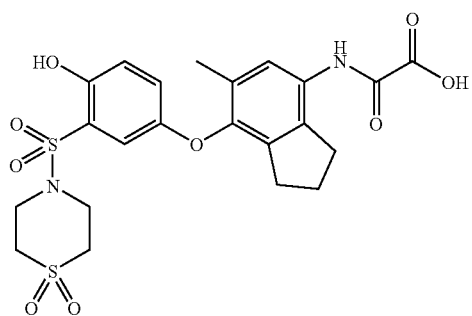
Compound 224
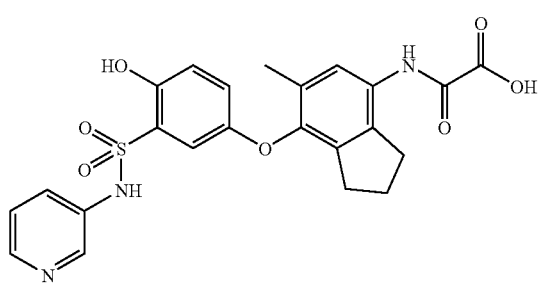

TABLE 1-continued
Compound 225
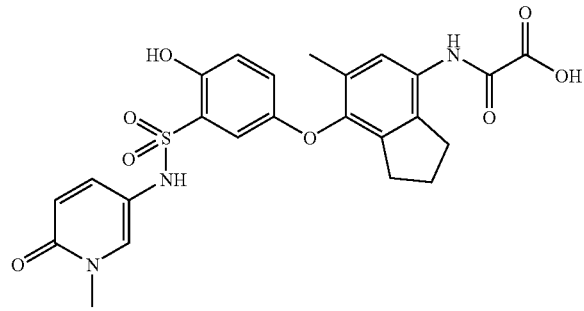
Compound 226
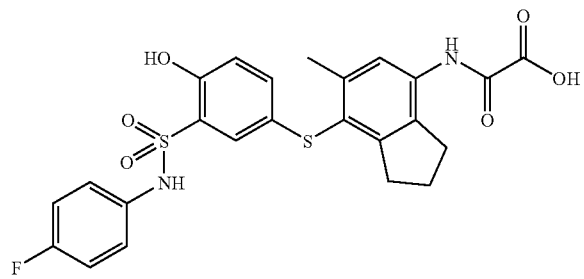
Compound 227
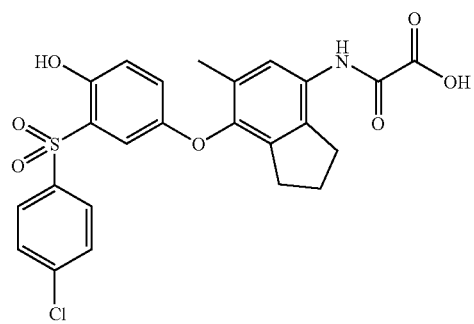
Compound 228
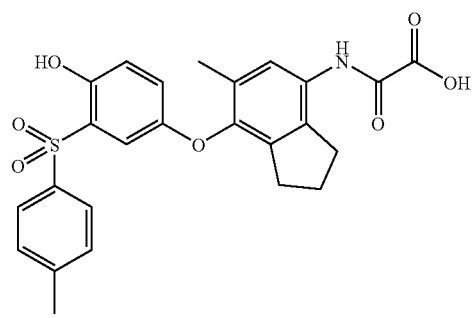
Compound 229
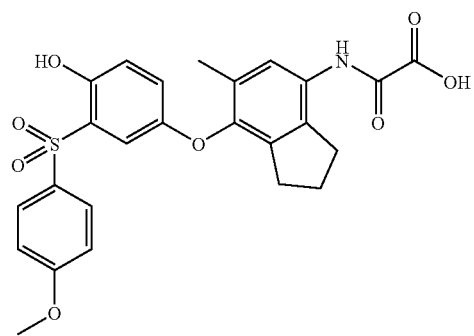

TABLE 1-continued
Compound 230
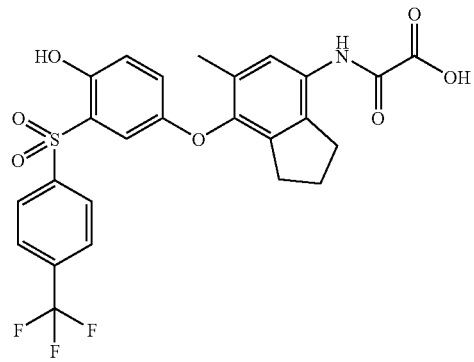
Compound 231
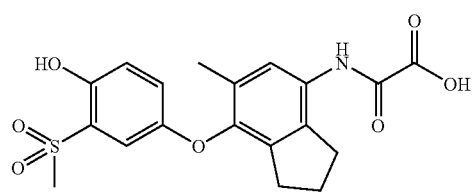
Compound 232
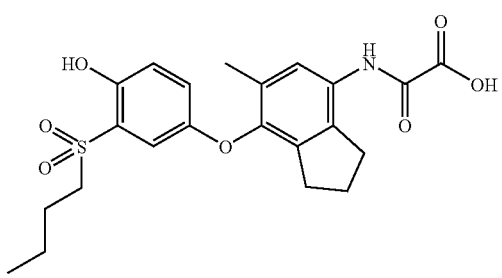
Compound 233
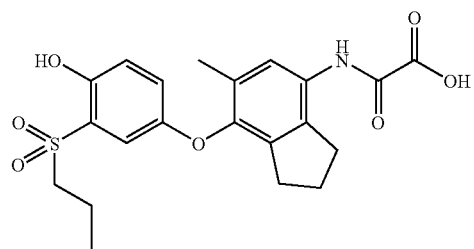
Compound 234
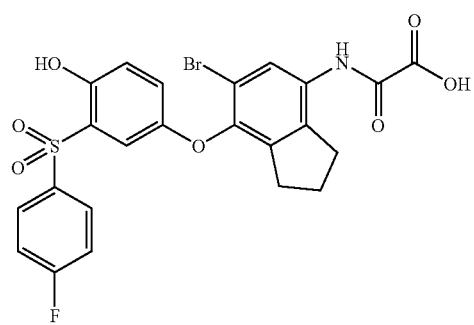

TABLE 1-continued
Compound 235 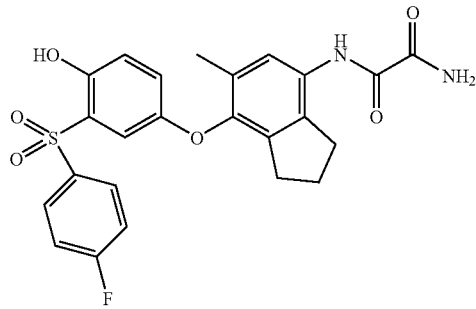
Compound 236 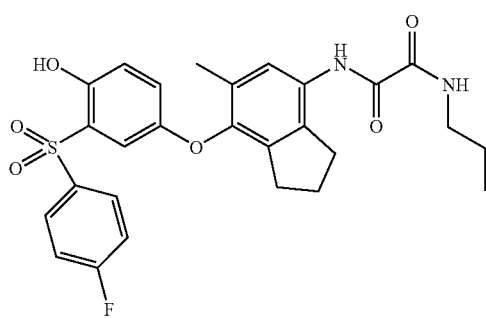
Compound 237 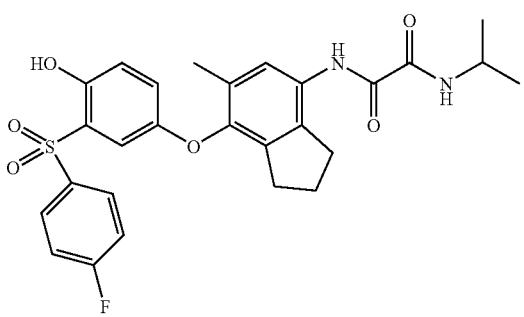
Compound 238 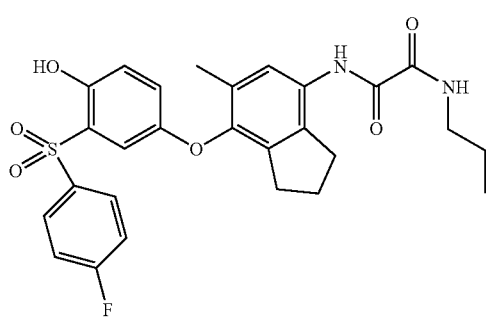
Compound 239 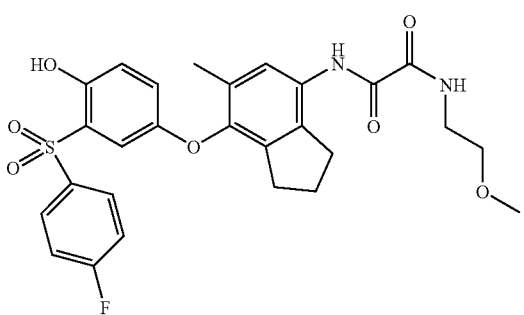

TABLE 1-continued
Compound 240
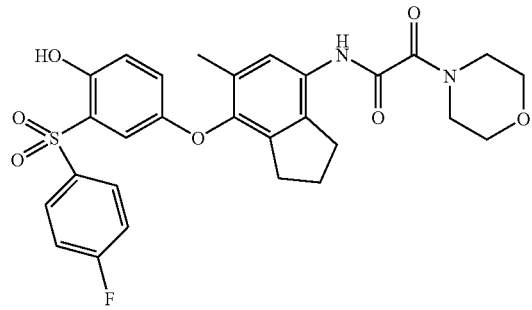
Compound 241
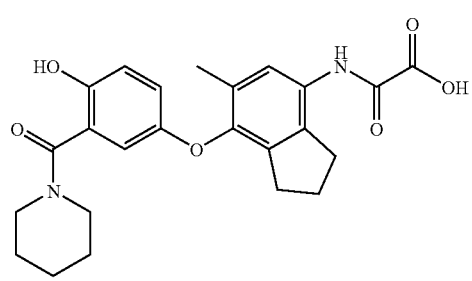
Compound 242
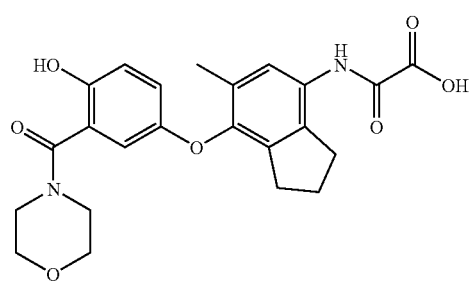
Compound 243
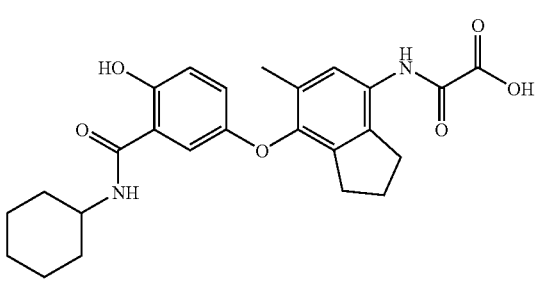
Compound 244
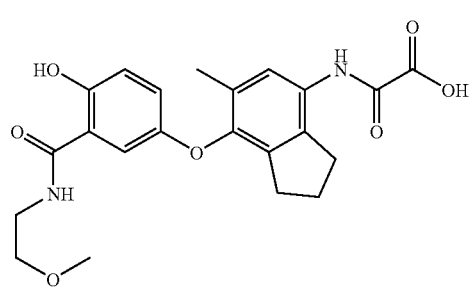

TABLE 1-continued
Compound 245 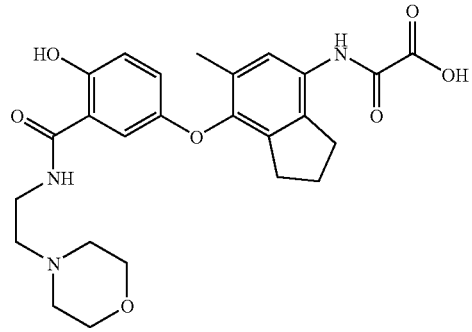
Compound 246 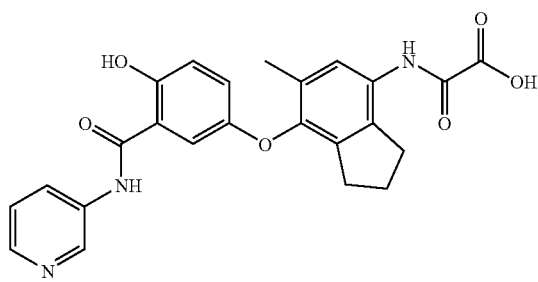
Compound 247 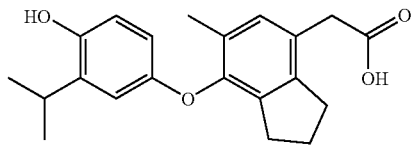
Compound 248 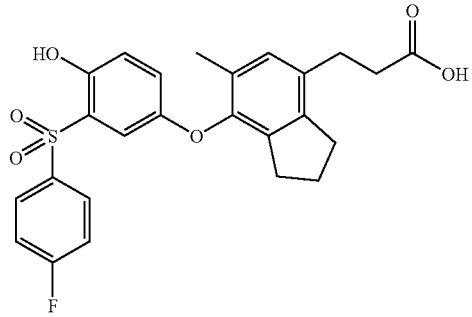
Compound 249 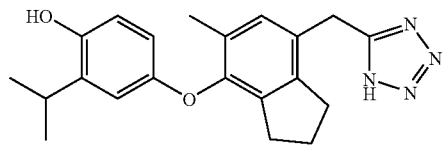
Compound 250 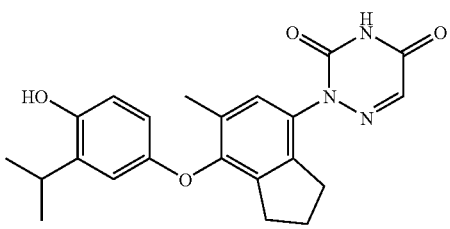

TABLE 1-continued
Compound 251 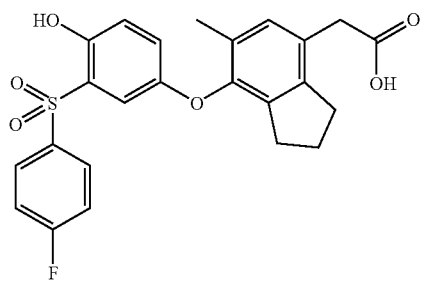
Compound 252 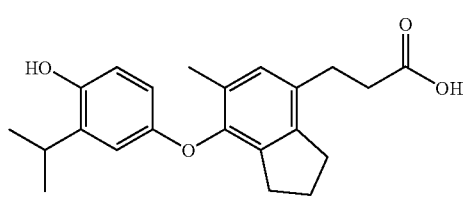
Compound 253 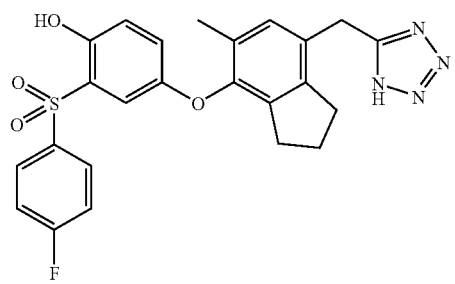
Compound 254 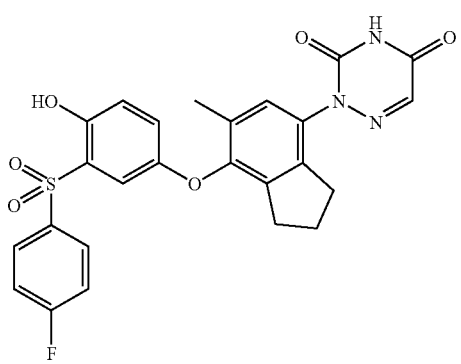
Compound 255 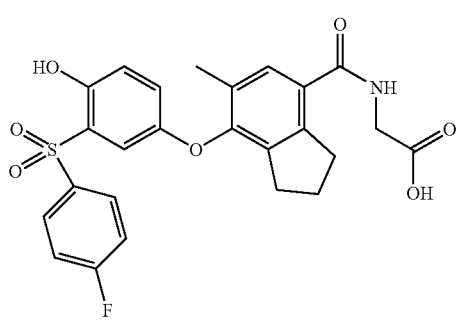

TABLE 1-continued
Compound 256
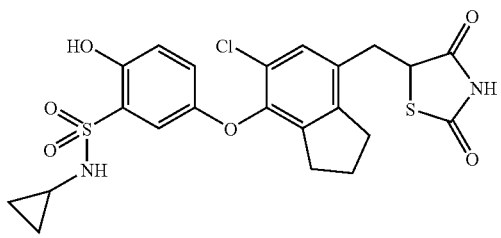
Compound 257
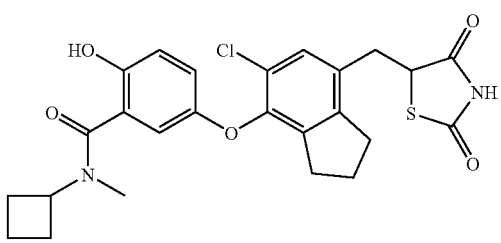
Compound 258
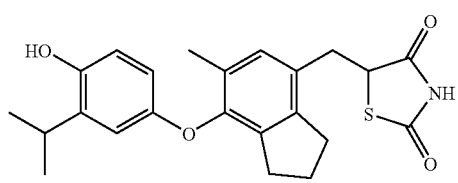
Compound 259
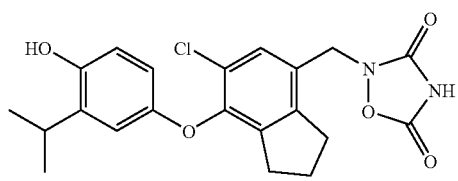
Compound 260
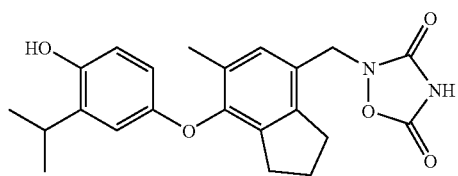
Compound 261
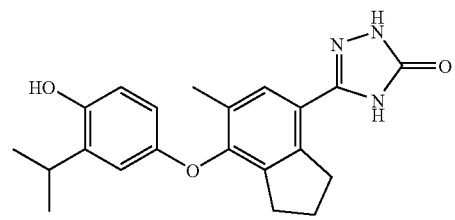
Compound 262
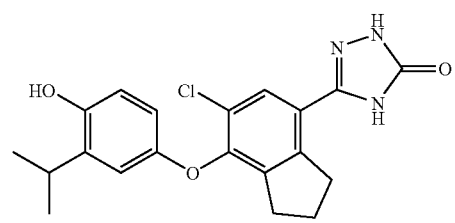

TABLE 1-continued
Compound 263
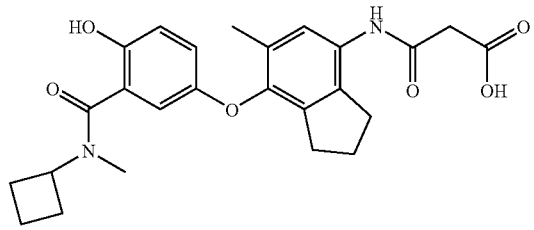
Compound 264
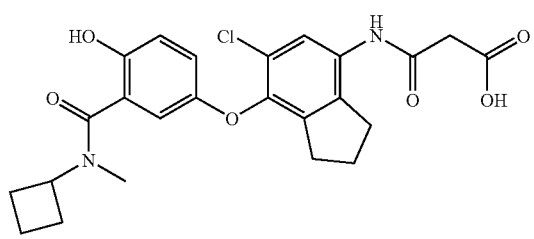
Compound 265
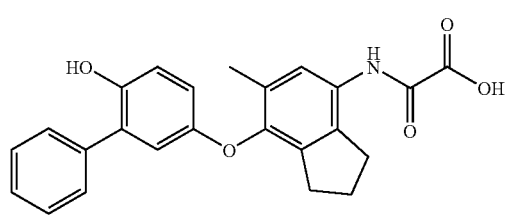
Compound 266
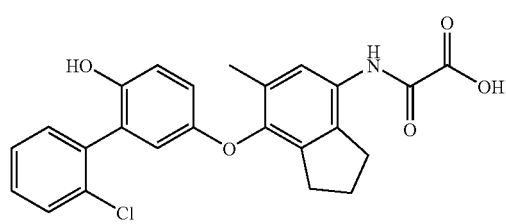
Compound 267
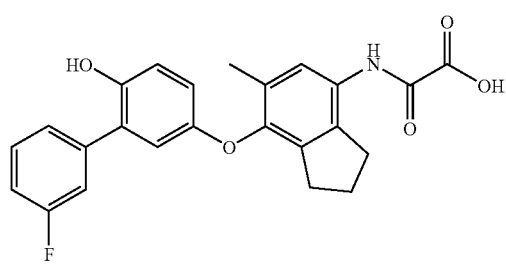
Compound 268
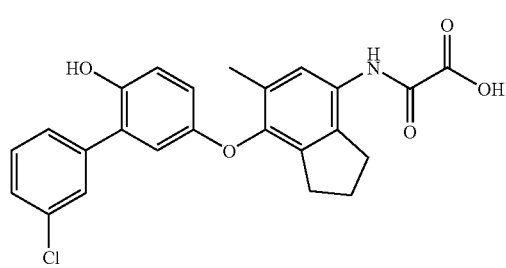

TABLE 1-continued
Compound 269 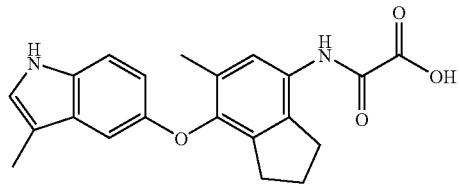
Compound 270 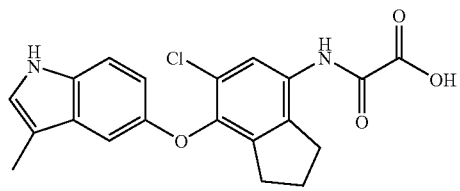
Compound 271 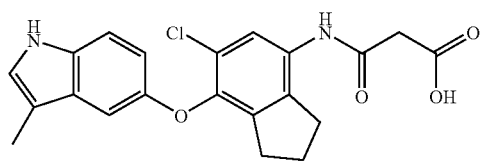
Compound 272 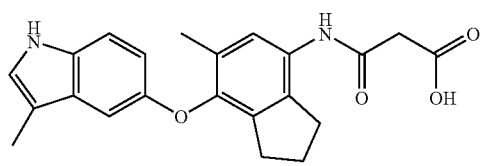
Compound 273 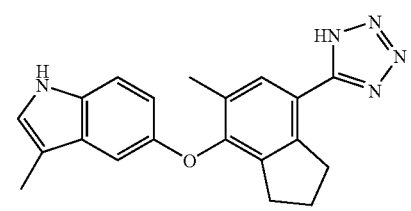
Compound 274 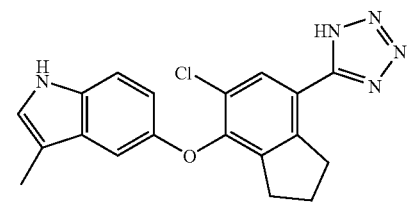
Compound 275 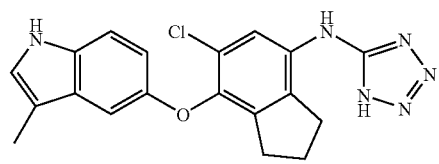
Compound 276 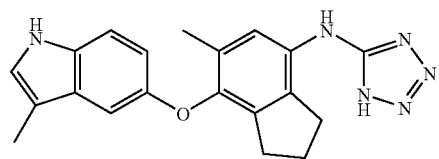

TABLE 1-continued
Compound 277 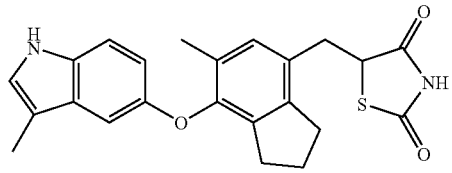
Compound 278 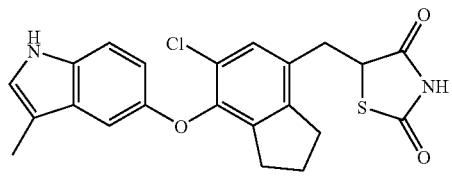
Compound 279 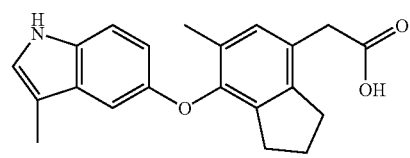
Compound 280 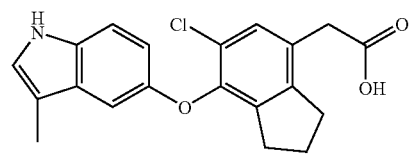
Compound 281 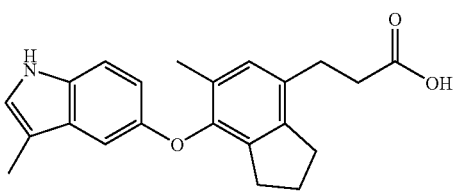
Compound 282 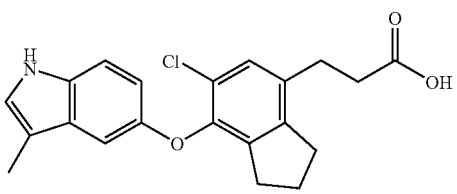
Compound 283 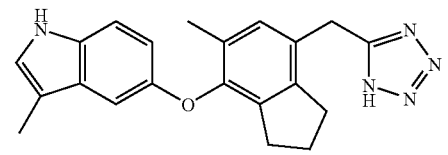
Compound 284 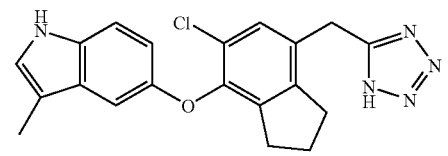

TABLE 1-continued
Compound 285 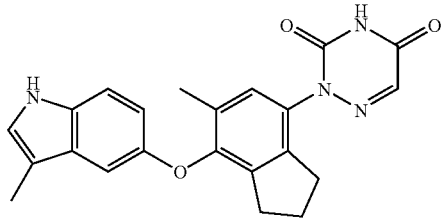
Compound 286 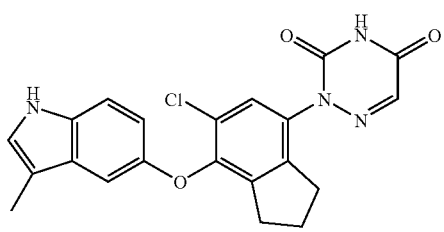
Compound 287 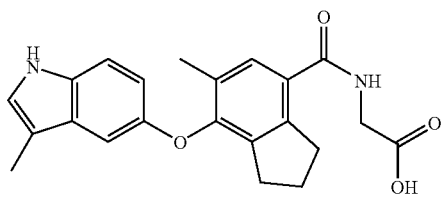
Compound 288 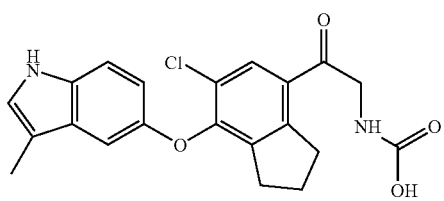
Compound 289 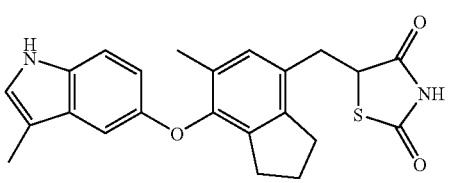
Compound 290 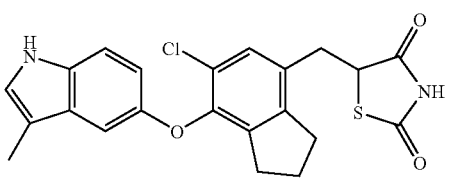
Compound 291 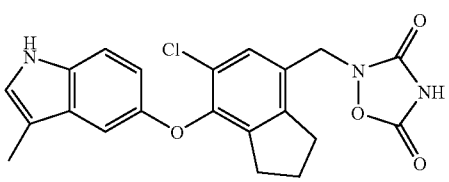
Compound 292 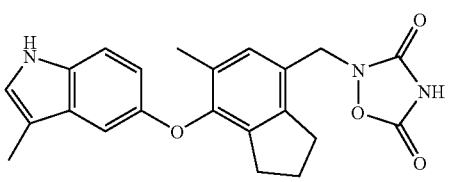

TABLE 1-continued
Compound 293 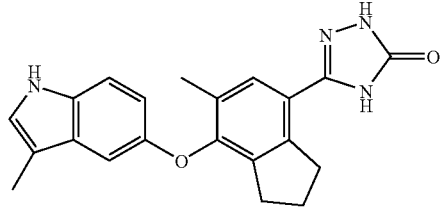
Compound 294 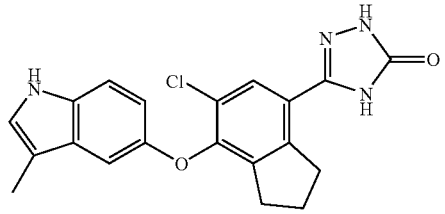
Compound 295 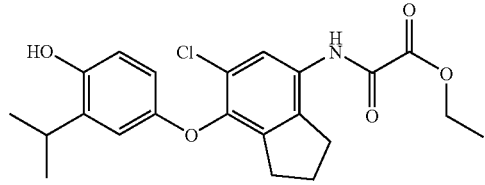
Compound 296 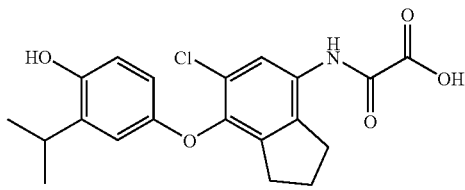
Compound 297 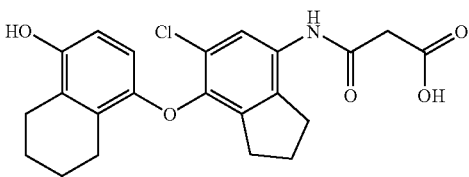
Compound 298 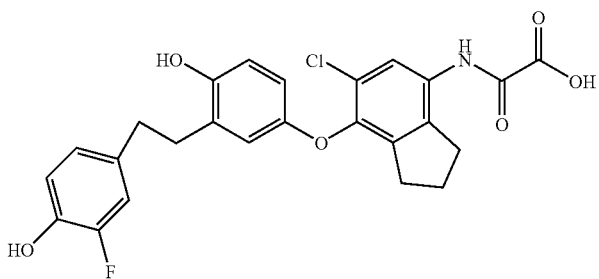
Compound 299 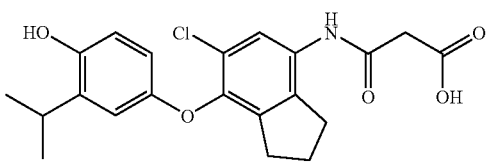

TABLE 1-continued
Compound 300
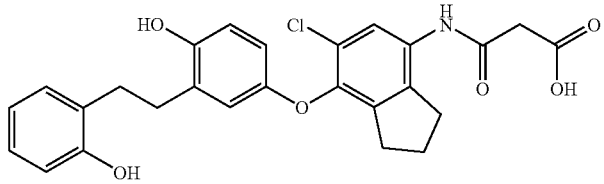
Compound 301
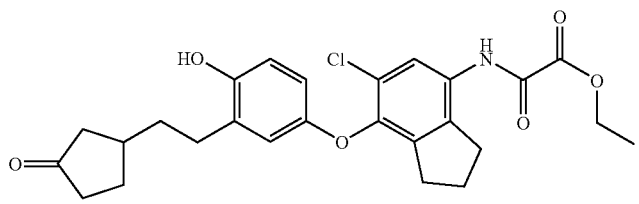
Compound 302
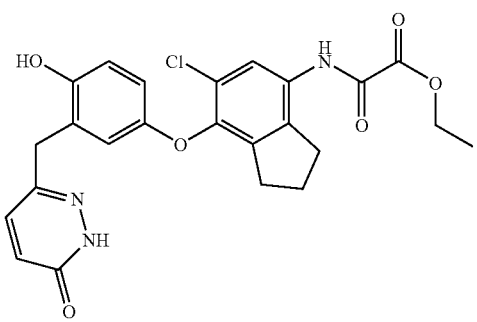
Compound 303
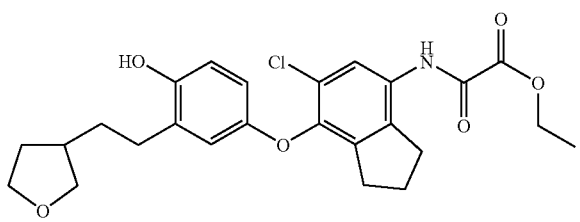
Compound 304
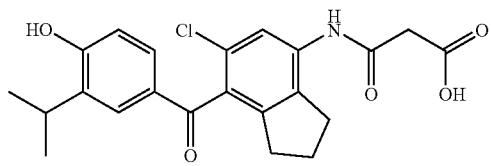
Compound 305
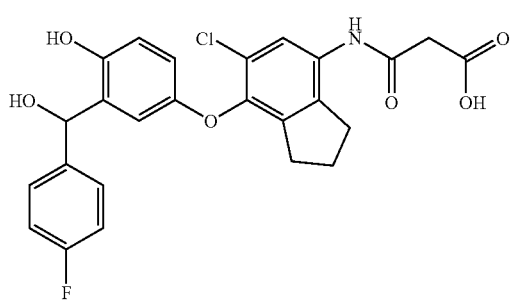

TABLE 1-continued
Compound 306
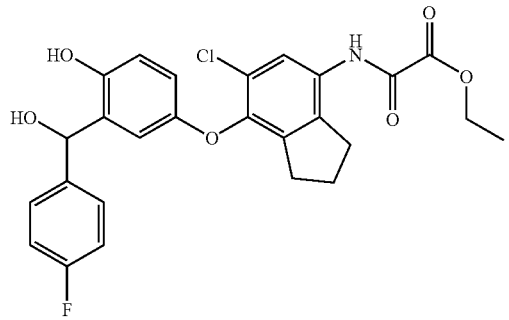
Compound 307
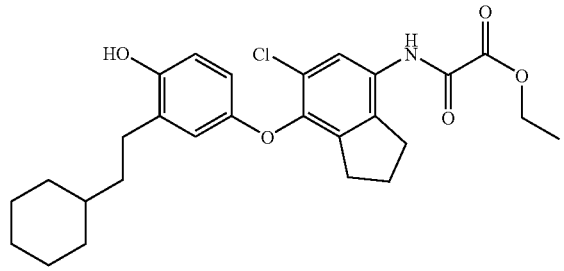
Compound 308
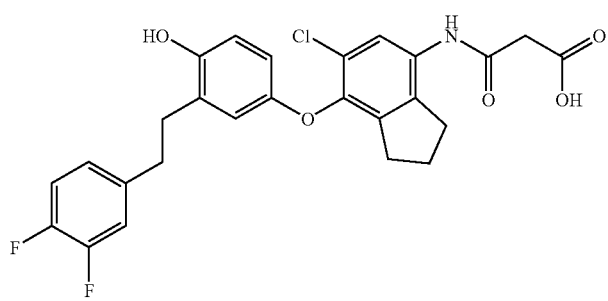
Compound 309
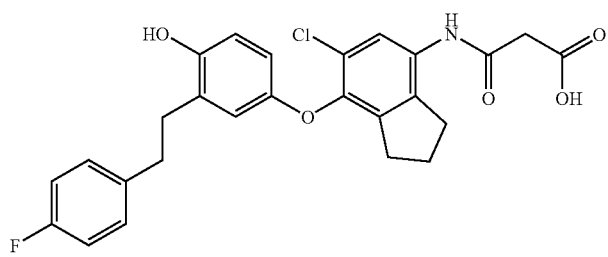
Compound 310
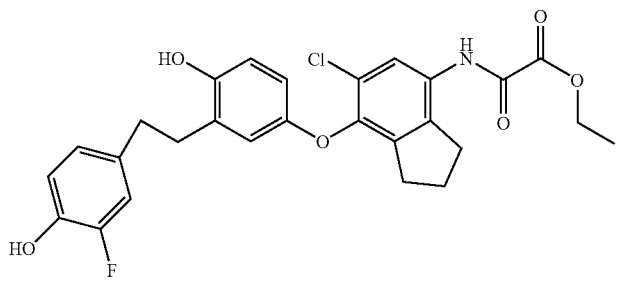

TABLE 1-continued
Compound 311
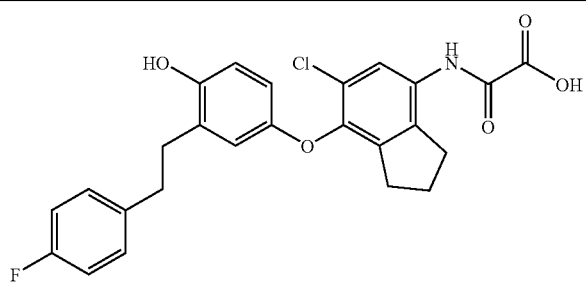
Compound 312
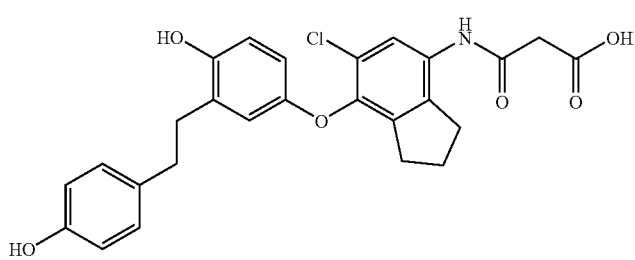
Compound 313
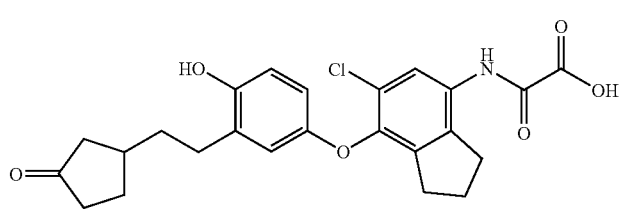
Compound 314
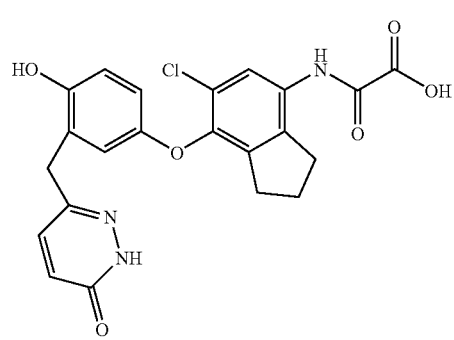
Compound 315
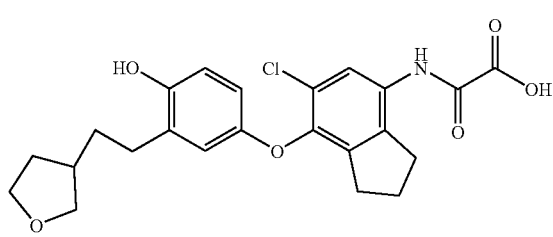
Compound 316
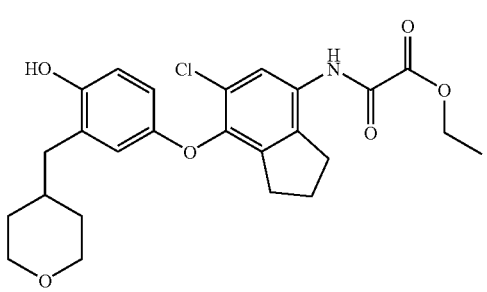

TABLE 1-continued
Compound 317
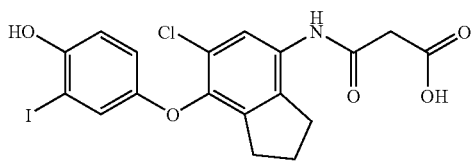
Compound 318
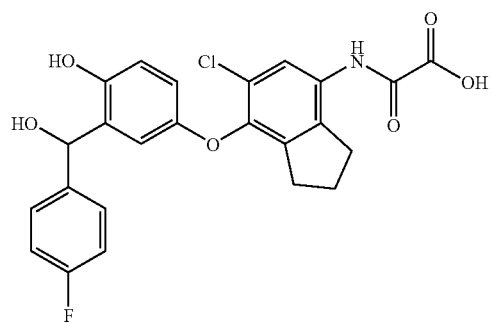
Compound 319
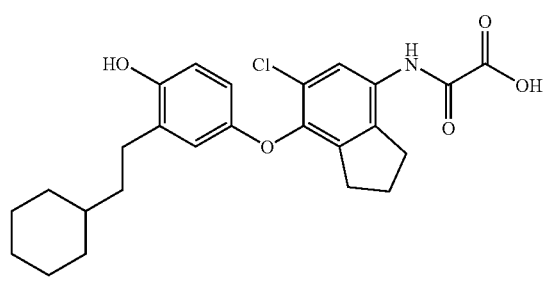
Compound 320
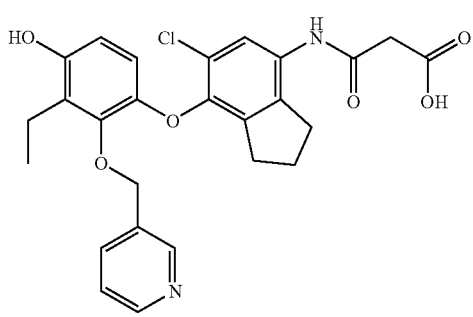
Compound 321
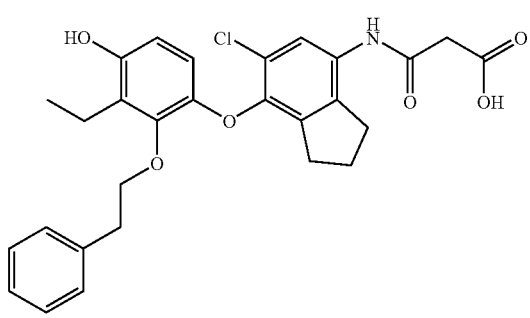

TABLE 1-continued
Compound 322
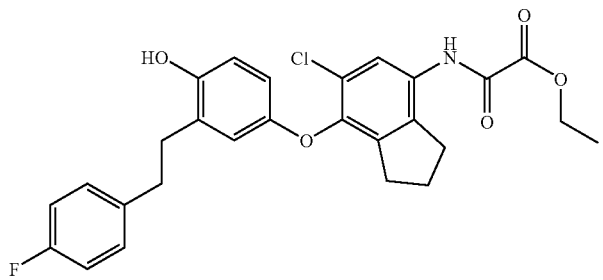
Compound 323
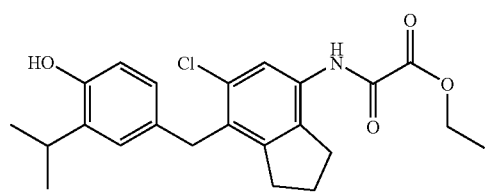
Compound 324
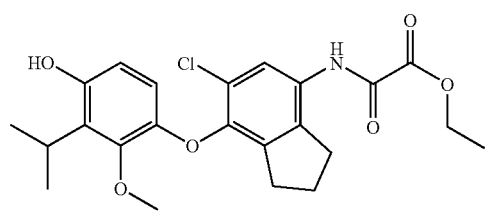
Compound 325
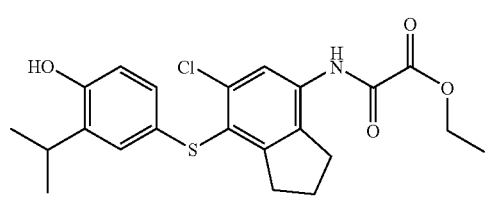
Compound 326
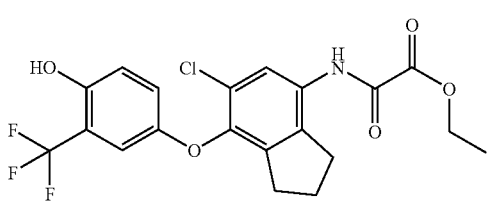
Compound 327
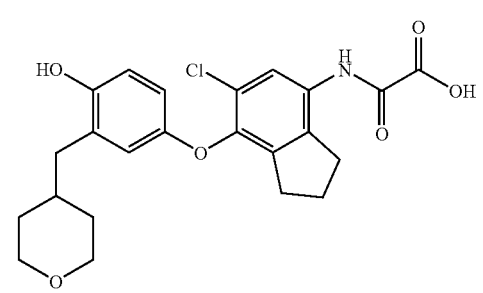
Compound 328
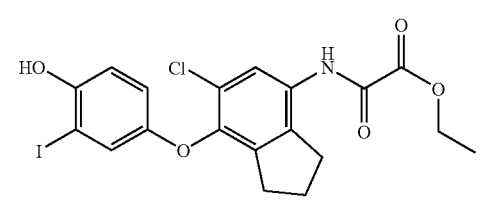

TABLE 1-continued
Compound 329
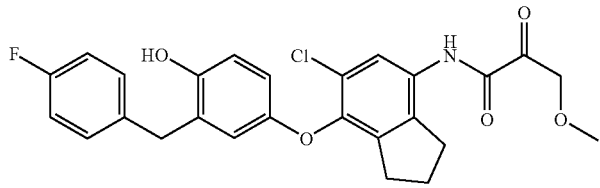
Compound 330
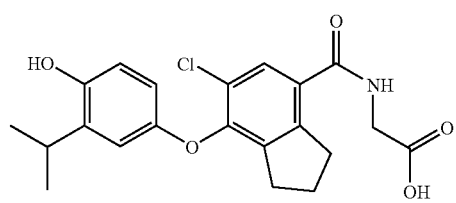
Compound 331
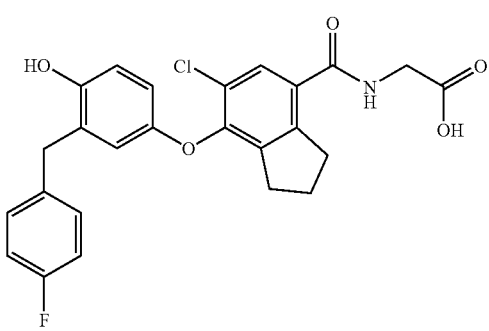
Compound 332
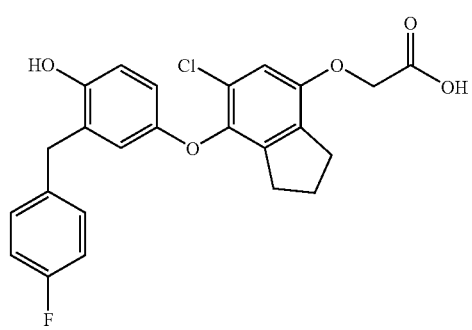
Compound 333
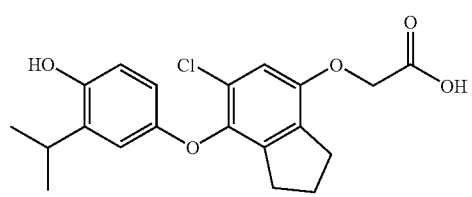
Compound 334
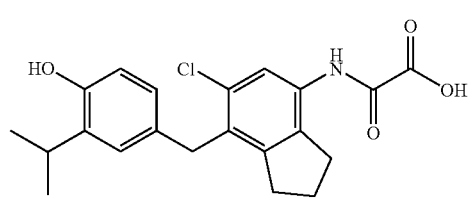

TABLE 1-continued

Compound 335

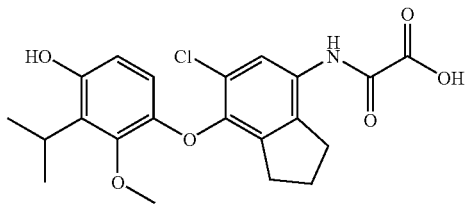

Compound 336

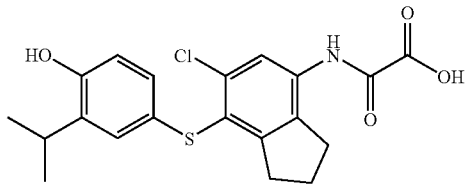

Compound 337

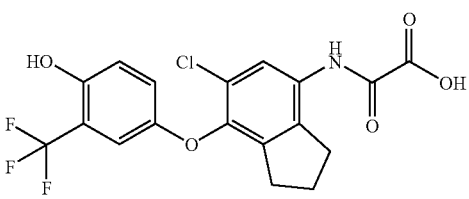

Compound 338

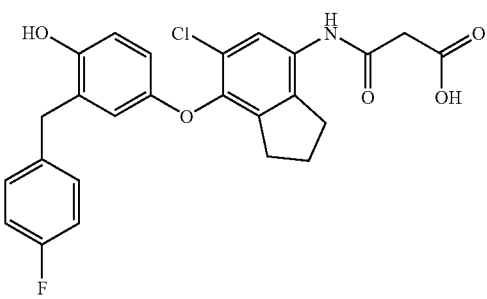

Compound 339

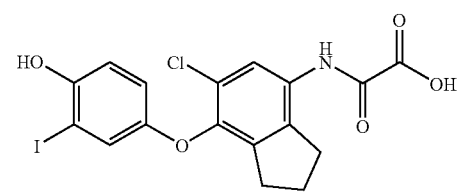

Compound 340

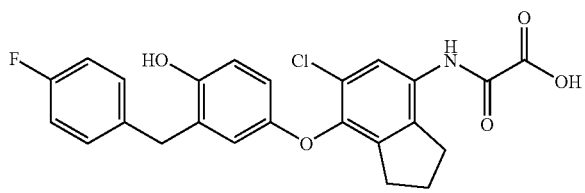

TEST EXAMPLE 1

Receptor Binding Assay

Recombinant human thyroid hormone receptors α and β were expressed in insect cells (Miyamoto, T. et al., J. Biol. Chem., 272 (12) 7752–7758, (1997)), and each receptor was mixed with appropriate concentrations of said compounds and L-3,5,3'-[125I]-Triiodothyronine ([125I]-T3, 0.95 nM, 160 Ci/mmol, [125I]-T3(NEN) was diluted with L-3,5,3'-Triiodothyronine (Sigma)) in a buffer containing 0.4 M KCl, 1 mM $MgCl_2$, 10 mM Tris-HCl and 1 mM dithiothreitol (pH 8.0). Each 0.5 mL of the mixture was incubated in a glass tube in an ice bath, for 16–48 hours. At the end of the incubation, 500 μl of an ion exchange resin (Muromachi Kagaku, Dowex 1-X8, 80 mg/ml, suspended in the above buffer) was added to each test tube, and stirred. The stirring was repeated after the sedimentation of the resin at the bottom of the tube, followed by another stirring as well. The tubes were centrifuged at 1000 rpm for 5 minutes at 1° C. by a centrifuge separator (KUBOTA, 8800). A portion of the supernatant (500 μl) was transferred to another tube, and the radioactivity was measured using γ-ray detector. The radioactivities detected reflect the quantity of [125I]-T3 bound to the soluble thyroid hormone receptor. The amount of the recombinant thyroid hormone receptor in the experiment was used in a range in which the radioactivities of T3 binding showed a concentration-dependent increase in the amount of the receptor.

The Kd value of T3 to the respective receptor subtype was determined according to the Scatchard analyses of the binding data obtained in the various [125I]-T3 concentrations. The Kd values of T3 to the α and β receptors were 0.268 nM and 0.304 nM respectively, in these experimental conditions.

The Ki values of each compound were calculated by the following equation.

$$Ki(nM)=[IC50]/(1+Kd/0.95)$$

wherein IC50 represents the concentration of the compound which inhibits [125I]-T3 binding by 50%.

TABLE 2

| Compound No. | Ki value for β receptor (nM) | Ki value for α receptor (nM) |
|---|---|---|
| 31 | 13.7 | 368.5 |
| 61 | 7.8 | 172.3 |
| 67 | 1.2 | 69.3 |
| 68 | 5.4 | 263.3 |
| 80 | 35.3 | 3438.0 |
| 90 | 57.6 | 10000.0 |
| 94 | 53.5 | 10000.0 |
| 97 | 3.6 | 147.7 |

TEST EXAMPLE 2

Cholesterol-lowering Activities

High cholesterol diets (CLEA Japan, CE2, 1.5% cholesterol, 0.5% cholic acid) were fed to rats (Wistar, male, 5 weeks old) for 1 week beforehand. Test compounds (3 to 30000 nmol/kg) suspended in a vehicle containing 5% ethanol (Wako Pure Chemical), 0.5% sodium carboxymethylcellulose (Wako Pure Chemical), were administered orally to the rats (5 ml/kg), once daily for 14 days. Rats were fed with high cholesterol diets continuously during the treatment. On the next day of the final dosing, whole blood was collected from the abdominal aorta of the rat under an ether anesthesia, and the serum was obtained by the centrifugation of the clotted blood. Cholesterol concentrations in the sera were determined using a commercial kit (Cholesterol C-test Wako, Wako Pure Chemical). The averaged serum cholesterol value of the rats fed with normal diet (CLEA Japan, CE2) was subtracted from the value in the vehicle-treated rats fed with high cholesterol diet, and the difference was regarded as 100%. The dosage which lowers the serum cholesterol level by 50% was shown as ED50 in the following table 3.

TABLE 3

| Compound No. | Serum cholesterol lowering effects (ED50, nmol/kg) |
|---|---|
| 61 | 37 |
| 67 | 300 |

TEST EXAMPLE 3

Toxicity Test

The compounds suspended in a vehicle (5% ethanol, 0.5% sodium carboxymethycellulose, Wako Pure Chemical) were administered orally to rats (5 ml/kg), once daily for 14 days, and the resultant mortality was estimated. The results were shown in the following table 4. The compounds of the present invention were demonstrated to be highly safe, as no death was observed in rats dosed with the following amount of the compounds.

TABLE 4

| Compound No. | Dose (nmol/kg) | Death |
|---|---|---|
| 61 | 30000 | 0/5 |
| 67 | 30000 | 0/5 |

INDUSTRIAL APPLICABILITY

The compounds represented by general formula (I) have a high affinity to human thyroid hormone receptors and are highly selective to TRβ. Therefore, the compounds of the present invention are useful for treating or preventing metabolic function disorders or diseases associated with the expression of T3 regulated genes, and are suitable for a medicament with less cardiac toxicities in the treatment or prevention of hyperlipidemia, atherosclerosis, obesity, diabetes mellitus, fatty liver, liver cirrhosis, liver cancer or hypothyroidism.

The invention claimed is:

1. A compound represented by general formula (I):

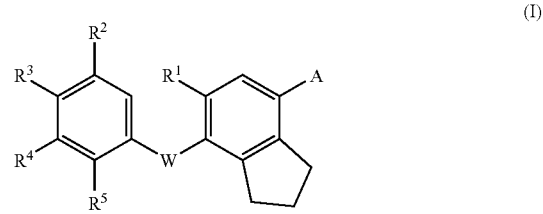

(I)

wherein
W is —O—;
R$^1$ is a halogen atom, a lower alkyl group, a halo-lower alkyl group, a lower alkoxy group or —CN;
R$^2$ is a hydrogen atom;
R$^3$ is a hydroxy group or an acyloxy group;
R$^4$ is a hydrogen atom, a halogen atom, an alkyl group, a halo-lower alkyl group, a substituted alkyl group, an aryl group, an aralkyl group, an alkoxy group, a substituted alkoxy group, an alkanoyl group, an aroyl group, —CONR$^7$(R$^8$), —S(O)$_m$R$^9$ or —SO$_2$NR$^7$(R$^8$), or R$^3$ and R$^4$ are bonded together to form —NH—CH=(R$^9$)—;
R$^5$ is a hydrogen atom, a halogen atom, an alkyl group, a substituted alkyl group, a hydroxy group, an alkoxy group, a substituted alkoxy group or an aralkyloxy group; m is 0 or an integer of 1 or 2;
R$^6$ is a hydrogen atom or a lower alkyl group;
each of R$^7$ and R$^8$ is independently a hydrogen atom, an alkyl group, a substituted alkyl group, a cycloalkyl group, an aryl group or a heteroaryl group, or R$^7$ and R[8], together with the nitrogen atom to which they are bonded, form a cyclic amine;

R[9] is an alkyl group, a substituted alkyl group, a cycloalkyl group, an aryl group or a heteroaryl group;

A represents
—N(R[6])CO—A[1]—COR[10],

R[10] is a hydroxy group, a lower alikoxy group or —NR[11](R[12]);

each of R[11] and R[12] is independently a hydrogen atom, a lower alkyl group or a substituted lower alkyl group, or R[11] and R[12], together with the nitrogen atom to which they are bonded, form a cyclic amine;

A[1] is an alkylene group, an alkenylene group or a bond;

a prodrug thereof, or a pharmaceutically acceptable salt thereof.

2. The compound according to claim 1, wherein R[1] is a halogen atom or a lower alkyl group, or a pharmaceutically acceptable salt thereof.

3. The compound according to claim 1, wherein R[4] is an alkyl group, a substituted alkyl group, an aralkyl group, an alkanoyl group or an aroyl group, or a pharmaceutically acceptable salt thereof.

4. The compound according to claim 1, wherein R[1] is a halogen atom or a lower alkyl group; and R[4] is an alkyl group, a substituted alkyl group, an aralkyl group, an alkanoyl group or an aroyl group, or a pharmaceutically acceptable salt thereof.

5. The compound according to claim 1, selected from the group consisting of ethyl N-[6-bromo-7-(4-hydroxy-3-isopropylphenoxy)indan-4-yl]oxamate;

N-[6-bromo-7-(4-hydroxy-3-isopropylphenoxy)indan-4-yl]malonamic acid;

ethyl N-[7-(4-hydroxy-3-isopropylphenoxy)-6-methylindan-4-yl]oxamate;

N-[7-(4-hydroxy-3-isopropylphenoxy)-6-methylindan-4-yl]malonamic acid;

N-[7-(4-hydroxy-3-isopropylphenoxy)-6-methylindan-4-yl]oxamic acid;

N-(7-{3-[(4-fluorophenyl)hydroxymethyl]-4-hydroxyphenoxy}-6-methylindan-4-yl)malonamic acid;

N-[6-bromo-7-(4-hydroxy-3-isopropylphenoxy)indan-4-yl]oxamic acid;

N-(7-{3-[2-(4-fluorophenyl)ethyl]-4-hydroxyphenoxy}-6-methylindan-4-yl)oxamic acid;

N-(7-{3-[2-(3,4-difluorophenyl)ethyl]-4-hydroxy-phenoxy}-6-methylindan-4-yl)malonamic acid;

N-(7-{3-[2-(4-fluorophenyl)ethyl]-4-hydroxyphenoxy}-6-methylindan-4-yl)malonamic acid;

N-{7-[3-(2-cyclohexylethyl)-4-hydroxyphenoxy]-6-methylindan-4-yl}oxamic acid;

N-{7-[3-ethyl-4-hydroxy-2-(pyridin-3-ylmethoxy)phenoxy]-6-methylindan-4-yl}malonamic acid;

N-[7-(3-ethyl-4-hydroxy-2-phenethyloxyphenoxy)-6-methylindan-4-yl]malonamic acid;

N-(7-{4-hydroxy-3-[2-(3-oxocyclopentyl)ethyl]phenoxy}-6-methylindan-4-yl)oxamic acid;

N-(7-{4-hydroxy-3-[2-(4-hydroxyphenyl)ethyl]phenoxy}-6-methylindan-4-yl)malonamic acid;

N-(7-{4-hydroxy-3-[2-(2-hydroxyphenyl)ethyl]phenoxy}-6-methylindan-4-yl)malonamic acid;

ethyl N-{7-[4-hydroxy-3-(6-oxo-1,6-dihydropyridazin-3-ylmethyl)phenoxy]-6-methylindan-4-yl}oxamate;

N-{7-[4-hydroxy-3-(6-oxo-1,6-dihydropyridazin-3-ylmethyl)phenoxy]-6-methylindan-4-yl}oxamic acid;

ethyl N-[7-(4-hydroxy-3-isopropyl-2-methoxyphenoxy)-6-methylindan-4-yl]oxamate;

N-(7-[4-hydroxy-3-[2-(tetrahydro furan-3-yl)ethyl]phenoxy}-6-methylindan-4-yl)oxamic acid;

N-(7-{3-[2-(3-fluoro-4-hydroxyphenyl)ethyl]-4-hydroxyphenoxy}-6-methylindan-4-yl)oxamic acid;

ethyl N-(7-{4-hydroxy-3-[2-(3-oxocyclopentyl)ethyl]phenoxy}-6-methylindan-4-yl)oxamate;

ethyl N-[7-(4-hydroxy-3-iodophenoxy)-6-methylindan-4-yl]oxamate;

N-[7-(4-hydroxy-3-iodophenoxy)-6-methylindan-4-yl]oxamic acid;

N-[7-(4-hydroxy-3-iodophenoxy)-6-methylindan-4-yl]malonamic acid;

ethyl N-{7-[3-(4-fluorobenzyl)-4-hydroxyphenoxy]-6-methylindan-4-yl}oxamate;

N-{7-[3-(4-fluorobenzyl)-4-hydroxyphenoxy]-6-methylindan-4-yl}oxamic acid;

N-{7-[3-(4-fluorobenzyl)-4-hydroxyphenoxy]-6-methylindan-4-yl}malonamic acid;

N-{7-[4-hydroxy-3-(tetrahydropyran-4-ylmethyl)phenoxy]-6-methylindan-4-yl}oxamic acid;

N-[7-(4-hydroxy-3-isopropyl-2-methoxyphenoxy)-6-methylindan-4-yl]oxamic acid;

ethyl N-[7-(4-hydroxy-3-trifluoromethylphenoxy)-6-methylindan-4-yl]oxamate;

N-[7-(4-hydroxy-3-trifluoromethylphenoxy)-6-methylindan-4-yl]oxamic acid;

ethyl N-[7-(4-hydroxy-3-isopropylphenoxy)-6-trifluoromethylindan-4-yl]oxamate;

N-[7-(4-hydroxy-3-isopropylphenoxy)-6-trifluoromethylindan-4-yl]oxamic acid;

ethyl N-[7-(4-hydroxy-3-isopropylphenoxy)-6-iodoindan-4-yl]oxamate;

N-[7-(4-hydroxy-3-isopropylphenoxy)-6-iodoindan-4-yl]oxamic acid;

N-[7-(4-hydroxy-3-isopropylphenoxy)-6-trifluoromethylindan-4-yl]malonamic acid;

N-[7-(4-hydroxy-3-isopropylphenoxy)-6-iodoindan-4-yl]malonamic acid;

or a pharmaceutically acceptable salt thereof.

6. A pharmaceutical composition which comprises, as an active ingredient, a compound according to claim 1 or a pharmaceutically acceptable salt thereof and a pharmaceutically acceptable carrier.

7. A pharmaceutical combination comprising a compound according to claim 1 or a pharmaceutically acceptable salt thereof and at least one member selected from the group consisting of an antihyperlipidemic agent, an antiobesity agent, an antidiabetic agent and an antihypertensive agent other than a thyroid hormone receptor ligand.

8. A method for treating hyperlipidemia, atherosclerosis, obesity, diabetes mellitus, or hypothyroidism, which comprises administering an effective amount of a compound according to claim 1 or a pharmaceutically acceptable salt thereof.

* * * * *